(12) United States Patent
Rigo

(10) Patent No.: US 11,299,737 B1
(45) Date of Patent: Apr. 12, 2022

(54) COMPOUNDS AND METHODS FOR MODULATING SMN2

(71) Applicant: Ionis Pharmaceuticals, Inc., Carlsbad, CA (US)

(72) Inventor: Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/356,961

(22) Filed: Jun. 24, 2021

Related U.S. Application Data

(63) Continuation of application No. 17/187,018, filed on Feb. 26, 2021.

(60) Provisional application No. 62/983,545, filed on Feb. 28, 2020.

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/322* (2013.01); *C12N 2310/3341* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,751,219 A | 6/1988 | Kempen et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,176,996 A | 1/1993 | Hogan et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,294,564 A | 3/1994 | Karapiperis et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |

(Continued)

FOREIGN PATENT DOCUMENTS

| | | |
|---|---|---|
| EP | 1133993 | 9/2001 |
| EP | 1910395 | 10/2012 |

(Continued)

OTHER PUBLICATIONS

Agrawal et al., "Modified oligonucleotides and therapeutic and diagnostic agents" Curr Opin Biotechn (1995) 6: 12-19.

(Continued)

*Primary Examiner* — Tracy Vivlemore
(74) *Attorney, Agent, or Firm* — McNeill Baur PLLC

(57) ABSTRACT

Provided are compounds, methods, and pharmaceutical compositions for modulating SMN2 RNA and/or protein in a cell or subject. Such compounds, methods, and pharmaceutical compositions are useful to ameliorate at least one symptom of a neurodegenerative disorder. Such symptoms include reduced muscle strength; inability or reduced ability to sit upright, to stand, and/or walk; reduced neuromuscular activity; reduced electrical activity in one or more muscles; reduced respiration; inability or reduced ability to eat, drink, and/or breathe without assistance; loss of weight or reduced weight gain; and/or decreased survival.

32 Claims, No Drawings

Specification includes a Sequence Listing.

(56) References Cited

U.S. PATENT DOCUMENTS

| | | |
|---|---|---|
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,627,274 A | 5/1997 | Kole et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,172,216 B1 | 1/2001 | Bennett et al. |
| 6,210,892 B1 | 4/2001 | Bennett et al. |
| 6,214,986 B1 | 4/2001 | Bennett et al. |
| 6,268,490 B1 | 7/2001 | Imanishi et al. |
| 6,300,319 B1 | 10/2001 | Manoharan |
| 6,376,508 B1 | 4/2002 | Li et al. |
| 6,383,812 B1 | 5/2002 | Chen et al. |
| 6,426,220 B1 | 7/2002 | Bennett et al. |
| 6,525,031 B2 | 2/2003 | Manoharan et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,620,916 B1 | 9/2003 | Takahara et al. |
| 6,660,720 B2 | 12/2003 | Manoharan |
| 6,670,461 B1 | 12/2003 | Wengel et al. |
| 6,753,423 B1 | 6/2004 | Cook et al. |
| 6,770,633 B1 | 8/2004 | Robbins et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 6,962,906 B2 | 11/2005 | Efimov et al. |
| 6,998,259 B1 | 2/2006 | Davis et al. |
| 7,015,315 B1 | 3/2006 | Cook et al. |
| 7,034,009 B2 | 4/2006 | Pavco et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,582,744 B2 | 9/2009 | Manoharan et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,838,657 B2 | 11/2010 | Singh et al. |
| 7,851,615 B2 | 12/2010 | Manoharan et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,110,560 B2 | 2/2012 | Singh et al. |
| 8,124,745 B2 | 2/2012 | Allerson et al. |
| 8,137,695 B2 | 3/2012 | Rozema et al. |
| 8,153,365 B2 | 4/2012 | Wengel et al. |
| 8,158,601 B2 | 4/2012 | Chen et al. |
| 8,183,002 B2 | 5/2012 | Adamczyk et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,361,977 B2 | 1/2013 | Baker et al. |
| 8,394,932 B2 | 3/2013 | Melki et al. |
| 8,404,862 B2 | 3/2013 | Manoharan et al. |
| 8,435,491 B2 | 5/2013 | Wang et al. |
| 8,440,803 B2 | 5/2013 | Swayze et al. |
| 8,450,467 B2 | 5/2013 | Manoharan et al. |
| 8,501,805 B2 | 8/2013 | Seth et al. |

(56) References Cited

U.S. PATENT DOCUMENTS

| | | |
|---|---|---|
| 8,501,930 B2 | 8/2013 | Rozema et al. |
| 8,530,640 B2 | 9/2013 | Seth et al. |
| 8,541,548 B2 | 9/2013 | Rozema et al. |
| 8,546,556 B2 | 10/2013 | Seth et al. |
| 8,552,163 B2 | 10/2013 | Lee et al. |
| 8,586,559 B2 | 11/2013 | Singh et al. |
| 8,609,065 B2 | 12/2013 | Kuik-Romeijn et al. |
| RE44,779 E | 2/2014 | Imanishi et al. |
| 8,779,128 B2 | 7/2014 | Hanson et al. |
| 8,796,437 B2 | 8/2014 | Swayze et al. |
| 8,802,642 B2 | 8/2014 | Singh et al. |
| 8,828,956 B2 | 9/2014 | Manoharan et al. |
| 8,946,183 B2 | 2/2015 | Baker et al. |
| 8,962,269 B2 | 2/2015 | Melki et al. |
| 8,980,853 B2 | 3/2015 | Bennett et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,161,948 B2 | 10/2015 | Hanson et al. |
| 9,181,549 B2 | 11/2015 | Prakash et al. |
| 9,217,147 B2 | 12/2015 | Singh et al. |
| 9,290,760 B2 | 3/2016 | Rajeev et al. |
| 9,476,042 B2 | 10/2016 | Singh et al. |
| 9,518,259 B2 | 12/2016 | Rigo et al. |
| 9,717,750 B2 | 8/2017 | Bennett et al. |
| 9,765,338 B2 | 9/2017 | Bennett et al. |
| 9,862,946 B2 | 1/2018 | Hanson et al. |
| 9,926,559 B2 | 3/2018 | Bennett et al. |
| 10,059,941 B2 | 8/2018 | Krieg et al. |
| 10,174,328 B2 | 1/2019 | Krieg et al. |
| 10,266,822 B2 | 4/2019 | Singh et al. |
| 10,436,802 B2 | 10/2019 | Rigo et al. |
| 2001/0053519 A1 | 12/2001 | Fodor et al. |
| 2003/0077829 A1 | 4/2003 | MacLachlan |
| 2003/0100505 A1 | 5/2003 | Scharschmidt et al. |
| 2003/0119724 A1 | 6/2003 | Ts'o et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2005/0164235 A1 | 7/2005 | Manoharan et al. |
| 2005/0214288 A1 | 9/2005 | Bell et al. |
| 2006/0148740 A1 | 7/2006 | Platenburg |
| 2006/0183886 A1 | 8/2006 | Tso et al. |
| 2007/0031844 A1 | 2/2007 | Khvorova et al. |
| 2007/0292408 A1 | 12/2007 | Singh et al. |
| 2007/0299021 A1 | 12/2007 | Dunckley et al. |
| 2008/0039618 A1 | 2/2008 | Allerson et al. |
| 2008/0045456 A1 | 2/2008 | Greenway et al. |
| 2008/0064084 A1 | 3/2008 | Muller et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Monahan et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2010/0081627 A1 | 4/2010 | Sampath et al. |
| 2010/0087511 A1 | 4/2010 | Singh et al. |
| 2010/0190837 A1 | 7/2010 | Migawa et al. |
| 2010/0197762 A1 | 8/2010 | Swayze et al. |
| 2010/0216238 A1 | 8/2010 | Baker et al. |
| 2010/0240730 A1 | 9/2010 | Beigelman et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0207799 A1 | 8/2011 | Rozema et al. |
| 2011/0269814 A1 | 11/2011 | Manoharan et al. |
| 2011/0269820 A1 | 11/2011 | Singh et al. |
| 2011/0294868 A1 | 12/2011 | Monia et al. |
| 2012/0021515 A1 | 1/2012 | Swayze et al. |
| 2012/0035115 A1 | 2/2012 | Manoharan et al. |
| 2012/0059042 A1 | 3/2012 | Platenburg et al. |
| 2012/0087869 A1 | 4/2012 | Thakker et al. |
| 2012/0095075 A1 | 4/2012 | Manoharan et al. |
| 2012/0101148 A1 | 4/2012 | Akinc et al. |
| 2012/0128760 A1 | 5/2012 | Manoharan et al. |
| 2012/0136042 A1 | 5/2012 | Manoharan et al. |
| 2012/0149756 A1 | 6/2012 | Schumperli et al. |
| 2012/0149757 A1 | 6/2012 | Krainer et al. |
| 2012/0157509 A1 | 6/2012 | Hadwiger et al. |
| 2012/0165393 A1 | 6/2012 | Rozema et al. |
| 2012/0165394 A1 | 6/2012 | Singh et al. |
| 2012/0190728 A1 | 7/2012 | Bennett et al. |
| 2012/0230938 A1 | 9/2012 | Rozema et al. |
| 2013/0004427 A1 | 1/2013 | El-Sayed et al. |
| 2013/0109091 A1 | 5/2013 | Baker et al. |
| 2013/0109817 A1 | 5/2013 | Yurkovetskiy et al. |
| 2013/0121954 A1 | 5/2013 | Wakefield et al. |
| 2013/0130378 A1 | 5/2013 | Manoharan et al. |
| 2013/0178512 A1 | 7/2013 | Manoharan et al. |
| 2013/0203836 A1 | 8/2013 | Rajeev et al. |
| 2013/0236968 A1 | 9/2013 | Manoharan et al. |
| 2013/0289092 A1 | 10/2013 | Rigo et al. |
| 2014/0107330 A1 | 4/2014 | Freier et al. |
| 2014/0128449 A1 | 5/2014 | Liu et al. |
| 2014/0155363 A1 | 6/2014 | Marom et al. |
| 2014/0296323 A1 | 10/2014 | Leumann et al. |
| 2014/0323552 A1 | 10/2014 | Burghes et al. |
| 2014/0329772 A1 | 11/2014 | Linsey et al. |
| 2014/0343127 A1 | 11/2014 | Kammler |
| 2014/0357558 A1 | 12/2014 | Hua et al. |
| 2014/0367278 A1 | 12/2014 | Zaworski et al. |
| 2015/0018540 A1 | 1/2015 | Prakash et al. |
| 2015/0073140 A1 | 3/2015 | Hanson et al. |
| 2015/0164901 A1 | 6/2015 | Rubin et al. |
| 2015/0184153 A1 | 7/2015 | Freier et al. |
| 2015/0191727 A1 | 7/2015 | Migawa et al. |
| 2015/0252364 A1 | 9/2015 | Krieg et al. |
| 2015/0267195 A1 | 9/2015 | Seth et al. |
| 2015/0275212 A1 | 10/2015 | Albaek et al. |
| 2015/0315582 A1 | 11/2015 | Singh et al. |
| 2015/0353929 A1 | 12/2015 | Baker et al. |
| 2016/0002627 A1 | 1/2016 | Bennett et al. |
| 2016/0068838 A1 | 3/2016 | Lorson et al. |
| 2016/0068845 A1 | 3/2016 | Isis et al. |
| 2016/0074474 A1 | 3/2016 | Passini et al. |
| 2017/0015995 A1 | 1/2017 | Bennett et al. |
| 2017/0037397 A1 | 2/2017 | Singh et al. |
| 2017/0044538 A1 | 2/2017 | Rigo et al. |
| 2017/0051277 A1 | 2/2017 | Wilton et al. |
| 2017/0088835 A1 | 3/2017 | Baker et al. |
| 2017/0363643 A1 | 12/2017 | Rigo et al. |
| 2018/0028554 A1 | 2/2018 | Theodora et al. |
| 2018/0273954 A1 | 9/2018 | Linsley et al. |
| 2018/0291376 A1 | 10/2018 | Baker et al. |
| 2018/0298384 A1 | 10/2018 | Krieg et al. |
| 2019/0030058 A1 | 1/2019 | Bennett et al. |
| 2019/0040384 A1 | 2/2019 | Bennett et al. |
| 2019/0211330 A1 | 7/2019 | Hua et al. |
| 2021/0032624 A1 | 2/2021 | Rigo et al. |
| 2021/0315918 A1 | 10/2021 | Prakash et al. |

FOREIGN PATENT DOCUMENTS

| | | |
|---|---|---|
| EP | 2548560 | 6/2015 |
| EP | 3305302 | 9/2018 |
| EP | 3308788 | 10/2018 |
| WO | WO 1994/026887 | 11/1994 |
| WO | WO 1995/022980 | 8/1995 |
| WO | WO 1997/020563 | 6/1997 |
| WO | WO 1997/046098 | 12/1997 |
| WO | WO 1998/013381 | 4/1998 |
| WO | WO 1999/014226 | 3/1999 |
| WO | WO 2001/009311 | 2/2001 |
| WO | WO 2002/038738 | 5/2002 |
| WO | WO 2002/043771 | 6/2002 |
| WO | WO 2003/037909 | 5/2003 |
| WO | WO 2004/024757 | 3/2004 |
| WO | WO 2004/101619 | 11/2004 |
| WO | WO 2004/106356 | 12/2004 |
| WO | WO 2004/113867 | 12/2004 |
| WO | WO 2007/002390 | 1/2007 |

(56) References Cited

FOREIGN PATENT DOCUMENTS

| WO | WO 2007/134181 | 11/2007 |
|---|---|---|
| WO | WO 2008/098788 | 8/2008 |
| WO | WO 2008/101157 | 8/2008 |
| WO | WO 2009/008725 | 1/2009 |
| WO | WO 2009/068689 | 6/2009 |
| WO | WO 2009/082607 | 7/2009 |
| WO | WO 2009/120700 | 10/2009 |
| WO | WO 2009/126933 | 10/2009 |
| WO | WO 2009/134487 | 11/2009 |
| WO | WO 2010/054406 | 5/2010 |
| WO | WO 2010/088537 | 8/2010 |
| WO | WO 2010/091308 | 8/2010 |
| WO | WO 2010/115993 | 10/2010 |
| WO | WO 2010/120820 | 10/2010 |
| WO | WO 2010/123594 | 10/2010 |
| WO | WO 2010/129709 | 11/2010 |
| WO | WO 2010/144740 | 12/2010 |
| WO | WO 2010/148013 | 12/2010 |
| WO | WO 2010/148249 | 12/2010 |
| WO | WO 2011/032109 | 3/2011 |
| WO | WO 2011/038356 | 3/2011 |
| WO | WO 2011/100131 | 8/2011 |
| WO | WO 2011/120053 | 9/2011 |
| WO | WO 2011/133876 | 10/2011 |
| WO | WO 2011/150408 | 12/2011 |
| WO | WO 2011/159836 | 12/2011 |
| WO | WO 2011/163121 | 12/2011 |
| WO | WO 2012/012443 | 1/2012 |
| WO | WO 2012/037254 | 3/2012 |
| WO | WO 2012/058462 | 5/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/138487 | 10/2012 |
| WO | WO 2012/150960 | 11/2012 |
| WO | WO 2012/177947 | 12/2012 |
| WO | WO 2012/178146 | 12/2012 |
| WO | WO 2013/009703 | 1/2013 |
| WO | WO 2013/033230 | 3/2013 |
| WO | WO 2013/053928 | 4/2013 |
| WO | WO 2013/068441 | 5/2013 |
| WO | WO 2013/075035 | 5/2013 |
| WO | WO 2013/082551 | 6/2013 |
| WO | WO 2013/086207 | 6/2013 |
| WO | WO 2013/119916 | 8/2013 |
| WO | WO 2013/165816 | 11/2013 |
| WO | WO 2013/166121 | 11/2013 |
| WO | WO 2013/173638 | 11/2013 |
| WO | WO 2014/059341 | 4/2014 |
| WO | WO 2014/110291 | 7/2014 |
| WO | WO 2014/113540 | 7/2014 |
| WO | WO 2014/169243 | 10/2014 |
| WO | WO 2014/179620 | 11/2014 |
| WO | WO 2015/014838 | 2/2015 |
| WO | WO 2015/023941 | 2/2015 |
| WO | WO 2015/035460 | 3/2015 |
| WO | WO 2015/051283 | 4/2015 |
| WO | WO 2015/106128 | 7/2015 |
| WO | WO 2015/161170 | 10/2015 |
| WO | WO 2015/193651 | 12/2015 |
| WO | WO 2016/040748 | 3/2016 |
| WO | WO 2016/164896 | 10/2016 |
| WO | WO 2017/040271 | 3/2017 |
| WO | WO 2017/053995 | 3/2017 |
| WO | WO 2017/075030 | 5/2017 |
| WO | WO 2017/218454 | 12/2017 |
| WO | WO 2017/218884 | 12/2017 |
| WO | WO 2017/223258 | 12/2017 |
| WO | WO 2018/007475 | 1/2018 |
| WO | WO 2018/014041 | 1/2018 |
| WO | WO 2018/014042 | 1/2018 |
| WO | WO 2018/014043 | 1/2018 |
| WO | WO 2018/055577 | 3/2018 |
| WO | WO 2018/150196 | 8/2018 |
| WO | WO 2018/193428 | 10/2018 |
| WO | WO 2018/215563 | 11/2018 |
| WO | WO 2019/075357 | 4/2019 |
| WO | 2019084050 A1 | 5/2019 |
| WO | WO 2019/168558 | 9/2019 |
| WO | WO 2019/169203 | 9/2019 |
| WO | 2021174019 A1 | 9/2021 |

OTHER PUBLICATIONS

Albaek et al., "Analogues of a Locked Nucleic Acid with Three-Carbon 2',4'-Linkages: Aynthesis by Ring-Closing Metathesis and Influence on Nucleic Acid Duplex Stability and Structure" J. Org. Chem. (2006) 71, 7731-7740.

Avila et al., "Trichostatin A increases SMN expression and survival in a mouse model of spinal muscular atrophy" J. Clin Inves. (2007) 117(3): 659-671.

Batrakova et al., "Mechanism of Pluronic Effect on P-Glycoprotein Efflux System in Blood-Brain Barrier: Contributions of Energy Depletion and Membrane Fluidization" The Journal of Pharmacology and Experimental Therapeutics (2001) 299(2):483-493.

Baughan et al., "Delivery of bifunctional RNAs tha target an intronic repressor and increase SMN levels in an animal model of spinal muscular atrophy" Human Molecular Genetics (2009) 18(9):1600-1611.

Bennett et al., "Anitsense Oligonucleotides as a tool for gene functionalization and target validation" Biochimica et Biophysics Acta (1999) 1489: 19-30.

Biessen et al., "Novel hepatotrophic prodrugs of the antiviral nucleoside 9-(2-phosphonylmethoxyethyl)adenine with improved pharmacokinetics and antiviral activity" Faseb J (2000) 14, 1784-1792.

Biessen et al., "Synthesis of Cluster Galactosides with High Affinity for the Hepatic Asialoglycoprotein Receptor" J Med Chem (1995) 38, 1538-1546.

Biessen et al., "The Cholesterol Derivative of a Triantennary Galactoside with High Affinity for the Hepatic Asialoglycoprotein Receptor: a Potent Cholesterol Lowering Agent" J Med Chem (1995) 38, 1846-1852.

Bosch-Marce et al., "Increased IGF-1 in muscle modulates the phenotype of severe SMA mice," Human Molecular Genetics (2011) 20: 1844-1853.

Braasch et al., "Novel Antisense and Peptide Nucleic Acid Strategies for Controlling Gene Expression" Biochemistry (2002) 41, 4503-4510.

Branch et al., "A good antisense molecule is hard to find," TIBS (1998) 23:45-50.

Brichta et al., "Valproic acid increases the SMN2 protein level: a well-known drug as a potential therapy for spinal muscular atrophy" Human Molecular Genetics (2003) 12(19):2481-2489.

Cartegni et al., "Correction of disease-associated exon skipping by synthetic exon-specific activators" Nat. Struct. Biol. (2003) 10:120-125.

Cartegni et al., "Disruption of an SF2/ASF-dependent exonic splicing enhancer in SMN2 causes spinal muscular atrophy in the absence of SMN1", Nat. Genet., (2002) 30:377-384.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Coady et al.,"Development of a single vector system that enhances trans-splicing of SMN2 transcripts." PLoS ONE (2008) 3(10): e3468.

Connolley et al., "Binding and Endocytosis of Cluster Glycosides by Rabbit Hepatocytes" J Biol Chem (1982) 257, 939-945.

Crooke et al., "Basic Principles of Antisense Therapeutics" Antisense Research and Application (1998) Chapter 1:1-50.

Crooke et al., "Pharmacokinetic Properties of Several Novel Oligonucleotide Analogs in mice" J. Pharmacol. Exp. Ther. (1996) 277, 923-937.

Crooke, "Antisense strategies" Curr. Mol. Med. (2004) 4(5):465-487.

(56) References Cited

OTHER PUBLICATIONS

Crooke, St., et al., "Antisense Drug Technology" Second Edition, CRC Press (2008) Chapters 1-28.
Davis et al. "Potent inhibition of microRNA in vivo without degradation" Nucleic Acids Res (2009) 37: 70-77.
Dokka et al., "Novel non-endocyte delivery of antisense oligonucleotides" Advanced Drug Delivery Reviews (2000) 44:35-49.
Dominski et al., "Restoration of correct splicing in thalassemic pre-mRNA by antisense oligonucleotides" PNAS (1993) 90:8673-8677.
Douglas et al., "Splicing therapy for neuromuscular disease" Mol Cell Neurosci (2013) 56: 169-185.
Duff et al., "Intrabody Tissue-Specific Delivery of Antisense Conjugates in Animals: Ligand-Linker-Antisense Oligomer Conjugates" Methods Enzymol (2000) 313, 297-321.
Dunckley et al., "Modification of splicing in the dystrophin gene in cultured mdx muscle cells by antisense oligoribonucleotides" Human Mol. Genetics (1998) 7(7): 1083-1090.
Dunckley et al., "Modulation of Splicing in the DMD Gene by Antisense Oligoribonucleotides" Nucleosides & Nucleotides (1997) 16(7-9): 1665-1668.
D'ydewalle "Possible functions of SMN-associated long non-coding RNAs" Johns Hopkins Medicine Apr. 10, 2014.
D'ydewalle "The long non-coding RNA SMN-AS1 as therapeutic target for SMA" 2016 FightSMA 25th Anniversary Conference Presentation.
D'ydewalle. LncRNA as therapeutic target for SMA [online] Jan. 30, 2015 [retrieved Aug. 11, 2015 by ISA/US].
D'ydewalle et al., "The Antisense Transcript SMN-AS1 Regulates SMN Expression and Is a Novel Therapeutic Target for Spinal Muscular Atrophy" Neuron (2017) 93: 66-79.
Efimov et al., "Phosphono Peptide Nucleic Acids with a Constrained Hydroxproline-Based Backbone" Nucleosides, Nucleotides & Nucleic Acids (2003) 22(5-8):593-599.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41): 16642-16649.
Forte et al., "Small interfering RNAs and Antisense Oligonucleotides for Treatment of Neurological Diseases" Current Drug Targets (2005) 6:21-29.
Freier et al., "The ups and downs of nucleic acid duplex stability: structure-stability studies on chemically-modified DNA:RNA duplexes" Nucleic Acids Research (1997) 25(22), 4429-4443.
Frieden et al., "Expanding the design horizon of antisense oligonucleotides with alpha-L-LNA" Nucleic Acids Research (2003) 21, 6365-6372.
Friedman et al., "Correction of Aberrant Splicing of the Cystic Fibrosis Transmembrane Conductance Regulator (CFTR) Gene by Antisense Oligonucleotides" J. Biol. Chem. (1999) 274:36193-36199.
Gautschi et al., "Activity of a novel bcl-2/bcl-xLbispecific antisense oligonucleotide against tumors of diverse histologic origins" J. Natl. Cancer Inst. (2001) 93:463-471.
Genbank Accession No. BC045789.1.
GENBANK Accession No. NT 006713.14 truncated from nucleotides 19939708 to 19967777.
Gravrilina et al., "Neuronal SMN expression corrects spinal muscular atrophy in severe SMA mice while muscle-specific SMN expression has no phenotypic effect" Hum Mol Genet (2008) 17(8): 1063-1075.
Heasman, "Morpholino Oligos: Making Sense of Antisense?" Developmental Biology (2002) 243:209-214.
Hofmann et al., "Htra2-beta1 stimulates an exonic splicing enhancer and can restor full-length SMN expression to survival motor neuron 2 (SMN2)" PNAS (2000) 97(17):9618-9623.
Hsieh-Li et al., "A mouse model for spinal muscular atrophy" Nature Genet. (2000) 24, 66-70.

Hua et al., "Antisense correction of SMN2 splicing in the CNS rescues necrosis in a type III SMA mouse model" Genes Dev. (2010) 24:1634-1644.
Hua et al., "Antisense masking of an hnRNP A1/A2 inronic splicing silencer corrects SMN2 splicing in transgenic mice" American Journal of Human Genetics (2008) 82(4):834-848.
Hua et al., "Enhancement of SMN2 exon 7 inclusionby antisense oligonucleotides targeting the exon" PLOS Biology (2007) 5(4):E73.
Hua et al., "Peripheral SMN restoration is essential for long-term rescue of a severe spinal muscular atrophy mouse model," Nature (2011) 478: 123-126.
Inclan et al., "Review of nine cases of chronic progressive muscular atrophy treated with growth hormone by the endoarterial route" Medicina (1958) 26(2): 347-351.
Ittig et al., "Nuclear antisense effects in cyclophilin A pre-mRNA splicing by oligonucleotides: a comparison of tricyclo-DNA with LNA" Nucleic Acids Research (2004) 32(10:346-353.
Jaeger et al., "Transport of Antisense Across the Blood-Brain Barrier" Methods in Molecular Medicine (2005) vol. 106: Antisense Therapeutics, Second Edition, I. Phillips (Ed.) Humana Press, Inc. Totowa, N.J., Cht. 12:237-251.
Jayaprakash et al., "Non-Nucleoside Building Blocks for Copper-Assisted and Copper-Free Click Chemistry for the Efficieny Synthesis of RNA Conjugates" Org Lett (2010) 12, 5410-5413.
Kabanov et al., "A new class of antivirals: antisense oligonucleotides combined with a hydrophobic substituent effectively inhibit influenza virus reproduction and synthesis of virus-specfic proteins in MDCK cells" FEBS Lett. (1990) 259, 327-330.
Kashima et al., "A negative element in SMN2 exon 7 inhibits splicing in spinal muscular atrophy." Nature Genetics (2003) 34(4):460-463.
Kato et al., "N-acetylgalactosamine incorporation into a peptide containing consecutive threonine residues by UDP-N-acetyl-D-galactosaminide:polypeptide N-acetylgalactosaminyltransferases" Glycobiol (2001) 11, 821-829.
Khoo et al., "Splicing therapeutics in SMN2 and APOB" Curr Opin Mol Ther (2009) 11: 108-115.
Khorev et al., "Trivalent, Gal/GalNAc-containing ligands designed for the asialoglycoprotein receptor" Bioorg Med Chem (2008) 16, 5216-5231.
Kim et al., "Oligomeric Glycopeptidomimetics Bearing the Cancer Related TN-Antigen" Tetrahedron Lett (1997) 38, 3487-3490.
Kiraly et al., "Expression of human cationic trypsinogen with an authentic N terminus using intein-mediated splicing in aminopeptidase P (pepP) deficient Escherichia coli" Protein Exp Purif (2006) 48: 104-111.
Kobayashi et al., "Evaluation of peripheral blood mononuclear cell processing and analysis for Survival Motor Neuron protein" PLoS One (2012) 7(11): e50763.
Kobayashi et al., "Utility of Survival Motor Neuron ELISA for Spinal Muscular Atrophy Clinical and Preclinical Analyses," PLoS ONE (2011) 6:e24269 pp. 1-15.
Kole et al., "RNA modulation, repair and remodeling by splice switching oligonucleotides" Acta Biochimica Polonica (2004) 51(2):373-378.
Kole, "Modification ot pre-mRNA splicing by antisense oligonucleotides" Acta Biochimica Polonica (1997) 44(2):231-238.
Koller et al., "Use of a Chemically Modified Antisense Oligonucleotide Library to Identify and Validate Eg5 (Kinesin-Like 1) as a Target for Antineoplastic Drug Development" Cancer Res (2006) 66: 2059-2066.
Kornilova et al., "Development of a fluorescence polarization binding assay for asialoglycoprotein receptor" Analyt Biochem (2012) 425, 43-46.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54, 3607-3630.
Krawczak et al., "The mutational spectrum of single base-pair substitutions in mRNA splice junctions of human genes: causes and consequences." Hum. Genet. (1992) 90:41-54.

(56) References Cited

OTHER PUBLICATIONS

Kramer et al., "Raise the Roof: Boosting the Efficacy of a Spinal Muscular Atrophy Therapy" Neuron (2017) 93: 3-5.
Kumar et al., "Design, synthesis, biophysical and primer extension studies of novel acyclic butyl nucleic acid (BuNA)" Org. Biomol. Chem. (2013) 11, 5853-5865.
Kumar et al., "The First Analogues of LNA (Locked Nucleic Acids): Phosphorothioate-LNA and 2'-thio-LNA" Bioorg. Med. Chem. Lett. (1998) 8, 2219-2222.
Kurreck, "Antisense Technologies Improvement Through Novel Chemical Modifications" European Journal of Biochemistry (2003) 270(8): 1628-1644.
Lacerra et al., "Restoration of hemoglobin A synthesis in erythroid cells from peripheral blood of thalassemic patients" PNAS (2000) 97(17):9591-9596.
Le et al., "SMNdelta7, the major product of the centromeric survival motor neuron (SMN2) gene, exends survival in mice with spinal muscular atrophy and associates with full-length SMN" Human Molecular Genetics (2005) 14(6):845-857.
Lee "Synthesis of some cluster glycosides suitable for attachment to proteins or solid matrices" Carbohydr Res (1978) 67, 509-514.
Lee et al., "Facile Synthesis of a High-Affinity Ligand for Mammalian Hepatic Lectin Containing Three Terminal N-Acetylgalactosamine Residues" Bioconjug Chem (1997) 8, 762-765.
Lee et al., "New and more efficient multivalent glyco-ligands for asialoglycoprotein receptor of mammalian hepatocytes" Bioorg Med Chem (2011) 19, 2494-2500.
LEE et al., "New Synthetic Cluster Ligands for Galactose/N-Acetylgalactosamine-Specific Lectin of Mammalian Liver" Biochem (1984) 23, 4255-4261.
Lee et al., "Preparation of Cluster Glycosides of N-Acetylgalactosamine that have Subnanomolar Binding Constants Towards the Mammalian Hepatic Gal/GalNAc-spccific Receptor" Glycoconjugate J (1987) 4, 317-328.
Lee et al., "Protein microarrays to study cardohydrate-recognition events" Bioorg Med Chem Lett (2006) 16(19), 5132-5135.
Lee et al., "Synthesis of Multivalent Neoglyconjugates of MUC1 by the Conjugation of Carbohydrate-Centered, Triazole-Linked Glycoclusters to MUC1 Peptides Using Click Chemistry" J Org Chem (2012) 77, 7564-7571.
Lee et al., "Synthesis of Peptide-Based Trivalent Scaffold for Preparation of Cluster Glycosides" Methods Enzymol (2003) 362, 38-43.
Lefebvre et al., "The Role of the SMN Gene in Proximal Spinal Muscular Atrophy" Hum. Mol. Genet. (1998) 7(10):1531-1536.
Letsinger et al., "Cholesteryl-conjugated oligonucleotides: Synthesis, properties, and activity as inhibitors of replication of human immunodeficiency virus in cell culture" Proc. Natl. Acad. Sci. USA (1989) 86, 6553-6556.
Leumann "DNA Analogues: From Supramolecular Principles to Biological Properties" CJ. Bioorg. & Med. Chem. (2002) 10, 841-854.
Lim et al., "Modulation of Survival Motor Neuron Pre-mRNA Splicing by Inhibition of Alternative 3'Splice Site Pairing" J. Biol. Chem. (2001) 276(48):45476-45483.
Lorson et al., "A single nucleotide in the SMN gene regulates splicing and is responsible for spinal muscular atrophy" PNAS (1999) 96:6307-6311.
Lu et al., "Systemic delivery of antisense oligoribonucleotide restores dystrophin expression in body-wide skeletal muscles" PNAS (2005) 102(1):198-203.
Madocsai et al., "Correction of SMN2 Pre-mRNA Splicing by Antisense U7 Small Nuclear RNAs" Molecular Therapy (2005) 12(6):1013-1022.
Maher et al., "Comparative hybrid arrest by tandem antisense oligodeoxy ribonucleotides or oligodeoxyribonucleoside methylpbosphonates in a cell-free system" Nucl. Acid. Res. (1988) 16(8): 3341 -3358.

Maier et al., "Synthesis of Antisense Oligonucleotides Conjugated to a Multivalent Carbohydrate Cluster for Cellular Targeting" Bioconjug Chem (2003) 14, 18-29.
Maierhofer et al., "Probing multivalent carbohydrate-lectin interactions by an enzyme-linked lectin assay employing covalently immobilized carbohydrates" Bioorg Med Chem (2007) 15, 7661-7676.
Manoharan et al., "Chemical Modifications to Improve Uptake and Bioavailability of Antisense Oligonucleotides" Ann. N.Y. Acad. Sci. (1992) 660, 306-309.
Manoharan et al., "Cholic Acid-Oligonucleotide Conjugates for Antisense Applications" Bioorg. Med. Chem. Lett. (1994) 4, 1053-1060.
Manoharan et al., "Introduction of a Lipophilic Thioether Tether in the Minor Groove of Nucleic Acids for Antisense Applications" Bioorg. Med. Chem. Lett. (1993) 3, 2765-2770.
Manoharan et al., "Lipidic Nucleic Acids" Tetrahedron Lett. (1995) 36, 3651-3654.
Manoharan et al., "Oligonucleotide Conjugates: Alteration of the Pharmacokinetic Properties of Antisense Agents" Nucleosides & Nucleotides (1995) 14, 969-973.
Manoharan, "Oligonucleotide Conjugates as Potential Antisense Drugs with Improved Uptake, Biodistribution, Targeted Delivery, and Mechanism of Action" Antisense Nucleic Acid Drug Dev (2002) 12, 103-128.
Matsuzawa et al., "Age-related volumetric changes of brain gray and white matter in healthy infants and children," Cereb Cortex (2001) 11(4):335-342.
Mattis et al., "Subcutaneous adminstration of TC007 reduces disease severity in an animal model of SMA" BioMed Central Neuroscience (2009) 10: 1-6.
Merwin et al., "Targeted Delivery of DNA Using YEE(GalNAcAH)3, a Synthetic Glycopeptide Ligand for the Asialoglycoprotein Receptor" Bioconjug Chem (1994) 5, 612-620.
Miller et al., "Gene-Target Therapies for the Central Nervous System" Arch Neurol (2008) 65: 447-451.
Mishra et al., "Improved leishmanicidal effect of phosphorotioate antisense oligonucleotides by LDL-mediated delivery" Biochim. Biophys. Acta (1995) 1264, 229-237.
Miyajima et al., "Identification of a Cis-Acting Element for the Regulation of SMN Exon 7 Splicing" J. Biol. Chem. (2002) 277(26):23271-23277.
Miyaso et al., "An Intronic Splicing Enhancer Element in Survival Motor Neuron (SMN) Pre-mRNA" J. Biol. Chem. (2003) 278(18):15825-15831.
New England Biolabs 1998/99 Catalog (cover page and pp. 121 and 284).
Ngo et al., Computaitonal Complexity, Protein Structure Predication and the Levinthal Paradox. The Protein Folding Problem and Tertiary Structure Prediction (1994) 433-440 nad 492-495.
Nguyen et al., "A two-site ELISA can quantify upregulation of SMN protein by drugs for spinal muscular atrophy" Neurology (2008) 71(22): 1757-1763.
Nishina et al., "Chimeric Antisense Oligonucleotide Conjugated to α-Tocopherol" Molecular Therapy Nucleic Acids (2015) 4, e220.
Nishina et al., "Efficient In Vivo Delivery of siRNA to the Liver by Conjugation of α-Tocopherol" Molecular Therapy (2008) 16, 734-740.
Oberhauser et al., "Effective incorporation of 2'-O-methyl-oligonucleotides into liposomes and enhanced cell association through modification with thiocholesterol" Nucl. Acids Res. (1992) 20, 533-538.
Ouagazzal, Abdel-Mouttalib. "Reducing Gene Expression in the Brain via Antisense Methods." Current Protocols in Neuroscience. Hoboken: John Wiley & Sons, 2001, N.Chapter 5.
Ozaki et al., "Synthesis and Properties of Oligodeoxyribonucleotides Bearing a Ployamino Group at the 2' Position via 2'-O-Carbamoylmethyl and 2'-S-Carbamoylmethyl groups" Nucleosides, Nucleotides, and Nucleic Acids (2009) 28:10, 943-952.
Passini et al., "Antisense Oligonucleotides Delivered to the Mouse CNS Ameliorate Symptoms of Severe Spinal Muscular Atrophy," Science Translational Medicine (2011)72: 72ra18-72ra18.

(56) References Cited

OTHER PUBLICATIONS

Passini et al., "CNS-targeted gene therapy improves survival and motor function in a mouse model of spinal muscular atrophy" J Clin Invest (2010) 120(4): 1253-64.

Pattanayek et al., "Structural rationalization of a large difference in RNA affinity despite a small difference in chemistry between two 2'-O-modified nucleic acid analogues" J Am Chem Soc (2004) 126: 15006-15007.

Pavia et al., "Synthetic TN glycopeptide related to human glycophorin AM" Int J Pep Protein Res (1983) 22, 539-548.

Piepers et al., "Quantification of SMN protein in leucocytes from spinal muscular atrophy patients: effects of treatment with valproic acid" J Neurol Neurosurg Psychiatry (2011) 82(8): 850-852.

Prakash et al., "2'-O-[2-(Amino)-2-oxoethyl] Oligonucleotides" Org. Lett. (2003) 5, 403-6.

Prakash et al., "Comparing In Vitro and In Vivo Activity of 2'-O-[2-(Methylamino)-2-oxoethyl]- and 2'-O-Methoxyethyl-Modified Antisense Oligonucleotides" J. Med. Chem. (2008) 51: 2766-2776.

Prakash et al., "An overview of sugar-modified oligonucleotides for antisense therapeutics" Chem Biodivers (2011) 8: 1616-1641.

Pujol et al., "A Sulfur Tripod Glycoconjugate that Releases a High-Affinity Copper Chelator in Hepatocytes" Angew Chemie Int Ed Engl (2012) 51, 7445-7448.

Rajur et al., "Covalent Protein-Oligonucleotide Conjugates for Efficient Delivery of Antisense Molecules" Bioconjug Chem (1997) 8, 935-940.

Ramos et al., "Age-dependent SMN expression in disease-relevant tissue and implications for SMA treatment" J Clin Invest (2019) 129: 4817-4831.

Rebuffat et al., "Gene delivery by a steroid-peptide nucleic acid conjugate" FASEB J. (2002) 19(11):1426-1428.

Rensen et al., "Design and Synthesis of Novel N-Acetylgalactosamine-Terminated Glycolipids for Targeting of Lipoproteins to the Hepatic Asialoglycoprotein Receptor" J Med Chem (2004) 47, 5798-5808.

Rensen et al., "Determination of the Upper Size Limit for Uptake and Processing of Ligands by the Asialoglycoprotein Receptor on Hepatocytes in Vitro and in Vivo" J Biol Chem (2001) 276, 37577-37584.

Rensen et al., "Stimulation of Liver-Directed Cholesterol Flux in Mice by Novel N-Acetylgalactosamine-Terminated Glycolipids with High Affinity for the Asialoglycoprotein Receptor" Arterioscler Thromb Vasc Biol (2006) 26, 169-175.

Reynolds et al., "Rational siRNA design for RNA interference" Nature Biotechnology (2004) 22(3):326-330.

Riessland et al., "SAHA ameliorates the SMA phenotype in two mouse models for spinal muscular atrophy" Human Molecular Genetics (2010) 19(8): 1492-1506.

Rigo et al., "Pharmacology of a central nervous system delivered 2'-O-methoxyethyl-modified survival of motor neuron splicing oligonucleotide in mice and nonhuman primates" J Pharmacol Exp Ther (2014) 350(1): 46-55.

Saison-Behmoaras et al., "Short modified antisense oligonucleotides directed against Ha-ras point mutation induce selective cleavage of the mRNA and inhibit T24 cells proliferation" EMBO J. (1991) 10, 1111-1118.

Sanghvi et al., "Heterocyclic Base Modifications in Nucleic Acids and Their Applications in Antisense Oligonucleotides" Antisense Research and Applications (1993) pp. 273-288.

Sato et al., "Glycoinsulins: Dendritic Sialyloligosaccharide-Displaying Insulins Showing a Prolonged Blood-Sugar-Lowering Activity" J Am Chem Soc (2004) 126, 14013-14022.

Sazani et al., "Therapeutic potential of antisense oligonucleotides as modulators of alternative splicing" The Journal of Clinical Investigation (2003) 112(4):481-486.

Schmid et al., "Animal models of spinal muscular atrophy" Journal of Child Neurology (2007) 22(8):1004-1012.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Shea et al., "Synthesis, hydridization properties and antiviral activity of lipid-oligodeoxynucleotide conjugates" Nucl. Acids Res. (1990) 18, 3777-3783.

Sheng et al., "Comparison of the efficacy of MOE and PMO modifications of systemic antisense oligonucleotides in a severe SMA mouse model" Nucleic Acids Res (2020) 48: 2853-2865.

Shukla et al., "Quantitative determination of human interleukin 22 (IL-22) in serum using Singulex-Erenna® technology" J Immunol Methods (2013) 390: 30-34.

Sierakowska et al., "Repair of thalassemic human β-globin mRNA in mammalian cells by antisense oligonucleotides" PNAS (1996) 93:12840-12844.

Sierakowska et al., "Restoration of 62-Globin Gene Expression in Mammalian Cells by Antisense Oligonucleotides That Modify the Aberrant Splicing Patierns of Thalassemic Pre-mRNAs" Nucleosides & Nucleotides (1997) 16(7-9):1173-1182.

Singh et al., "A short antisense oligonucleotide masking a unique intronic motif prevents skipping of a critical exon in spinal muscular atrophy" RNA Bio (2009) 6(3):341-350.

Singh et al., "An extended inhibitory context causes skipping of exon 7 of SMN2 in spinal muscular atrophy" Biochem. Biophys. Res. Comm. (2004) 315(2):381-388.

Singh et al., "In vivo selection reveals combinatorial controls that define a critical exon in the spinal muscular atrophy genes" RNA (2004) 10:1291-1305.

Singh et al., "LNA (locked nucleic acids): synthesis and high-affinity nucleic acid recognition" Chem. Commun. (1998) 4, 455-456.

Singh et al., "Splicing of a critical exon of human Survival Motor Neuron is regulated by a unique silencer element located in the last intron" Molecular and Cellular Biology (2006) 26(4): 1333-1346.

Singh et al., "Synthesis of 2'-Amino-LNA: A Novel Conformationally Restricted High-Affinity Oligonucleotide Analogue with a Handle" J. Org. Chem. (1998) 63, 10035-10039.

Skolnick et al., "From genes to protein structure and function: novel applications of computational approaches in the genomic era" Trends in Biotech (2000) 18: 34-39.

Skordis et al., "Bifunctional Antisense Oligonucleotides Provide a Trans-Acting Splicing Enhancer that Stimulated SMN2 Gene Expression in Patient Fibroblasts" PNAS (2003) 100(7):4114-4119.

Sliedregt et al., "Design and Synthesis of Novel Amphiphilic Dendritic Galactosides for Selective Targeting of Liposomes to Hepatic Asialoglycoprotein Receptor" J Med Chem (1999) 42, 609-618.

Sloop et al. "Hepatic and glucagon-like peptide-1-mediated reversal of diabetes by glucagon receptor antisense oligonucleotide inhibitors" J Clinical Invest (2004) 113: 1571-1581.

Smith "Antisense oligonucleotide therapy for neurodegenerative disease" Journal of Clinical Investigation (2006) 116:2290-2296.

Srivastava et al., "Five- and Six-Membered Conformationally Locked 2', 4'-Carbocyclic ribo-Thymidines: Synthesis, Structure, and Biochemical Studies" J. Am. Chem. Soc. (2007) 129, 8362-8379.

Svinarchuk et al., "Inhibition of HIV proliferation in MT-4 cells by antisense oligonucleotide conjugated to lipophilic groups" Biochimie (1993) 75, 49-54.

Swoboda et al., "0.9 First-in-human phase I study to assess safety, tolerability and dose for intrathecal injection of ISIS-SMNRx in SMA patients," Neuromuscular Disorders (2013) 23: 797-798.

Takeshima et al., "Modulation of in vitro splicing of the upstream intron by modifying an intra-exon sequence which is deleted from the dystrophin gene in dystrophin Kobe." J. Clin. Invest. (1995) 95(2):515-520.

Taylor et al., "Induction of endogenous Bcl-xS through the control of Bcl-x pre-mRNA splicing by antisense oligonucleotides" Nat. Biotechnol, (1999) 17:1097-1100.

Todd et al., "Ultrasensitive flow-based immunoassays using single-molecule counting" Clin Chem (2007) 53(11): 1990-1995.

Tokuriki et al., "Stability effects of mutations and protein evolvability" Current Opinion in Structual Biology (2009) 19:596-604.

(56) References Cited

OTHER PUBLICATIONS

Tomiya et al., "Liver-targeting of primaquine-( poly-γ-glutamic acid) and its degradation in rat hepatocytes" Bioorg Med Chem (2013) 21, 5275-5281.
Toyokuni et al., "Synthetic Vaccines: I. Synthesis of Multivalent Tn Antigen Cluster-Lysyllysine Conjugates" *Tetrahedron Lett* (1990) 31, 2673-2676.
Translated abstract from JP 2004-344072.
Tsai et al., "Systemic Administration of a Recombinant AAV1 Vector Encoding IGF-1 Improves Disease Manifestaions in SMA Mice" Molecular Therapy (2014) 22: 1450-1459.
Valentijn et al., "Solid-phase Synthesis of Lysine-Based Cluster Galactosides with High Affinity for the Asialoglycoprotein Receptor" *Tetrahedron* (1997) 53, 759-770.
Van Rossenberg et al., "Stable polyplexes based on arginine-containing oligopeptides for in vivo gene delivery" *Gene Ther* (2004) 11, 457-464.
Veldink et al., "SMN genotypes producing less SMN protein increase susceptibility to and severity of sporadic ALS" Neurology (2005) 65(6):820-825.
Vinogradov et al., "Nanogels for Oligonucleotide Delivery to the Brain" Bioconjugate Chem. (2004) 15:50-60.
Wadman, "Antisense rescues babies from killer disease" Science (2016) 354(6318): 1359-1360.
Wahlesiedt et al., "Potent and nontoxic antisense oligonucleotides containined locked nucleic acids" PNAS (2000) 97(10):5633-5638.
Wang, "Antisense oligodeoxynucleotides selectively suppress expression of the mutant alpha 2(I) collagen allele in type IV osteogenesis imperfecta fibroblasts. A molecular approach to therapeutics of dominant negative disorders." J. Clin. Invest. (1996) 97(2):448-454.
Wells, J.A. "Additivity of Mutational Effects in Proteins" Biochemistry (1990) 29: 8509-8517.
Wenqiang et al. "Mixed-backbone oligonucleotides as second generation antisense agents with reduced phosphorothioate-related side effects" BioOrganic & Medicinal Chemistry Letters (1998) 8(22): 3269-3274.
Westerlind et al., "Ligands of the asialoglycoprotein receptor for targeted gene delivery, part 1: Synthesis of and binding studies with biotinylated cluster glycosides containaing N-acetylgalactosamine" *Glycoconj J* (2004) 21, 227-241.
Wilcox et al. "Immobilization and Utilization of the Recombinant Fusion Proteins Trypsin-Streptavidin and Streptavidin-Transglutaminase for Modification of Whey Protein Isolate Functionality" J Agricult Food Chem (2002) 50: 3723-3730.
Williams et al., "Oligonucleotide-mediated survival of motor neuron protein expression in CNS improves phenotype in a mouse model of Spinal Muscular Atrophy" Journal of Neuroscience (2009) 29(24):7633-7638.
Wilton et al., "Specific removal of the nonsense mutation from the mdx dystrophin mRNA using antisense oligonucleotides" Neuromuscul. Disord (1999) 9:330-338.
Woo et al., "Gene activation of SMN by selective disruption of lncRNA-mediated recruitment of PRC2 for the treatment of spinal muscular atrophy" Proc Natl Acad Sci USA (2017) 114: E1509-E1518.
Woolf et al., "Specificity of antisense oligonucleotides in vivo" PNAS (1992) 89: 7305-7309.
Yamamoto et al., "Antisense drug discovery and development" Future Med Chem (2011) 3: 339-365.
Yeo et al., "Variation in sequence and organization of splicing regulatory elements invertebrate genes." Proc. Natl. Acad. Sci. (2004) 101(44):15700-15705.
Zhang et al., "An in vivo reporter system for measuring increased inclusion of exon 7 in SMN2 mRNA: potential therapy of SMA" Gene Ther (2001) 8(20): 1532-1538.
Zhou, et al., "Fine Tuning of Electrostatics around the Internucleotidic Phosphate through Incorporation of Modified 2',4'-Carbocyclic-LNAs and -ENAs Leads to Significany Modulation of Antisense Properties" J. Org. Chem. (2009) 74, 118-134.
Zhou et al., "Targeting RNA-splicing for SMA Treatment" Molecules and Cells (2012) 33: 223-228.
International Search Report for application PCT/US06/24469 dated Sep. 13, 2007.
International Search Report for application PCT/US10/30940 dated Jul. 13, 2010.
International Search Report for application PCT/US2010/39077 dated Aug. 17, 2010.
International Search Report for application PCT/US2015/026326 dated Nov. 3, 2015.
International Search Report for application PCT/US2016/026928 dated Sep. 27, 2016.
International Search Report for application PCT/US2017/037862 dated Oct. 20, 2017.
International Search Report for application PCT/US2017/042463 dated Nov. 27, 2017.
International Search Report for PCT/US17/042465 dated Oct. 12, 2017.
Partial Search Report for EP 17814164.4 dated Jan. 23, 2020.
Partial EP Search Report for 17828626.6 dated Feb. 17, 2020.
European Search Report for application EP 06773838 dated Aug. 11, 2010.
European Search Report for application EP 10790221 dated Sep. 4, 2013.
European Search Report for application EP 17151519,0 dated Jul. 18, 2017.
European Search Report for application EP 2943225 dated Jun. 10, 2016.
Extended EP Search Report for 17828627.4 dated Feb. 18, 2020.
Extended Search Report for EP 17814164.4 dated Jun. 5, 2020.
Briese et al., "SMN, the product of the spinal muscular atrophy-determining gene, is expressed widely but selectively in the developing human forebrain" J Comp Neurol (2006) 497: 808-816.
Mattis et al., "Detection of human survival motor neuron (SMN) protein in mice containing the SMN2 transgene: applicability to preclinical therapy development for spinal muscular atrophy" J Neurosci Methods (2008) 175: 36-43.
Haynes et al., "Proteme Analysis: Biological Assay or Data Archive" Electrophoresis (1998) 19: 1862-1871.
Kempf et al., "The transforming growth factor-B superfamily member growth differentiation factor-15 protects the heart from ischemia/reperfusion injury" Circulation Research (2006) 98: 351-360.
International Search Report for PCT/US21/019934 dated Aug. 13, 2021, 12 pages.
U.S. Appl. No. 17/187,018, filed Feb. 26, 2021.

US 11,299,737 B1

SEQUENCE LISTING

<160> NUMBER OF SEQ ID NOS: 50

<210> SEQ ID NO 1
<211> LENGTH: 28070
<212> TYPE: DNA
<213> ORGANISM: Homo sapiens

<400> SEQUENCE: 1

```
ccacaaatgt gggagggcga taaccactcg tagaaagcgt gagaagttac tacaagcggt      60
cctcccggcc accgtactgt tccgctccca gaagccccgg gcggcggaag tcgtcactct     120
taagaaggga cggggcccca cgctgcgcac ccgcgggttt gctatggcga tgagcagcgg     180
cggcagtggc ggcggcgtcc cggagcagga ggattccgtg ctgttccggc gcggcacagg     240
ccaggtgagg tcgcagccag tgcagtctcc ctattagcgc tctcagcacc cttcttccgg     300
cccaactctc cttccgcagc ctcgggacag catcaagtcg atccgctcac tggagttgtg     360
gtccgcgttt ttctacgtct tttcccactc cgttccctgc gaaccacatc cgcaagctcc     420
ttcctcgagc agtttgggct ccttgatagc gttgagtgga ggccctgccg cgacttggca     480
gtagcttatt ttgttcactc ctctctggct ggtgtggggg aggtgggggc attaggccag     540
ggtgaagcag gggaaccact taggagtctg ttaagatgat ctgaacttca gaacaagatg     600
ttattaacag agtgaaagta tttggattct gggtatattt tgaaatcgga ggcaacaggt     660
ttttcagata gattcgataa cggaggttat cctgaatagt tgaaaagata aagttgcctt     720
ttgctgaggt gggaaagaga agattgccag tagagcaggt ttctcaggag ttcagtcttg     780
ggcatagcat ggtaggggtg aatttggctg gagtgagttg gagagtagga gaagagaaat     840
ccaaggcaac atttgaccag cctgggcaac atagtgtgac tccgagtctg caaaaattag     900
acgggtgttg tggtgcgcgt ctgtggtctc agctacctgg aaggttcagg ccttggaagg     960
ctcagggagg tggaggctgc agtgatctgt gattgcgcct ctgcactcca gcctgggcga    1020
cagagccaga ccctgtctta aaacaaaata aacggccggg cgcggtggct caagcctgta    1080
atcccagcac tttgggaggc cgaggcggcc ggatcacaag gtcaggagat cgagaccatc    1140
ctggctaaca cggtgaaacc ccgtctctac tacaaataca aaaaattagc cgggcgtggt    1200
gacgggcgcc tgtagtccca gctactcggg aggctgaggc aggagaatgt catgaagccg    1260
ggaggcggag cttgcagtga gccgagatcg cgccactgca ctccagcctg ggcgatagag    1320
```

```
caagactccg tctcaaataa ataaataaat aaataaataa ataataaaaa catcggtagg    1380
catatttcaa ggaattctat ttaaaaaaaa ttttttagga gacaagttcg ctctctgtgg    1440
cccaggctgg agtacagtgg catgatccta gcccatggca gcgttgatct cttggcctca    1500
agcgaccctc ctttggagtc gctgggccta aaggagtgag ccaccacgaa attttattat    1560
aaatggaggg tagagaaatt gggcaataaa tggagggggga agtgagttaa gaggaatttt    1620
aattatgtgt gtgtggtttt aaagagggg ggtcttgctc tgttgcccag gctgctgggg    1680
tgccagtggc gcaatcatga atcactacag ccttggactc ctggcctcaa gctatcctcc    1740
cacctctgcc tcccaaagta ctgggattac tagtgtgagc cactgcacta agataggagc    1800
aacatgtttc agcatgtttg tgggttgata ggaaagatga gaatgggaaa gttgatgtcg    1860
gaaagaagac aatggctaga gcaatgtcct agagtaggta agaagggatg gatttggcct    1920
ttgttggaaa cattagcggt tcttttggtg acagctatat agttaacaca tctatgatac    1980
gtgaatgggc agataggatg gcaggagatt ttgaaagttc tcttgattct tactgttctc    2040
ttagtgaaag aagcaaggtt atcagctaga agctgggatg ggagaggaaa gagaagatgg    2100
gaagtagata gttctcttaga agagtgggca agggttggac tagggaagtt tagtggaaat    2160
attgctaggc aacataaaga gcctacttga gattcgtggt catgagttga aggagaccag    2220
acagcaagat tgtgtatgag ggcacccaca gagtaaatgg agagttgaaa ttaatgcagt    2280
tgtgatttta ccacgtggat atgaagaagt gaggggggaga agtacaaagg agttctctta    2340
atgattgacc atggaattta agctggctaa gaaaggaagt gagaggccgg gcgcggtggc    2400
tcacgcctgt aatcccagca ctttgggaga ctgaggtggg tggattacct gaggtcagga    2460
gtttgagacc aacctggccg atatggcgaa accccatctc taataaaaat acagaaaaat    2520
tagccgggaa tggtggcagg tgcctgtaat cccagctact caagaggctg tggcaggagt    2580
atcccttgga cccaggaggt ggaggttgca gtgagccgag atcacgccac tgtactccag    2640 cctgacgat atagtgagac ttcacctcaa aaaaaaaaa aaagaaagga agtgaggatt    2700 ttaagacccct gagagacagt ttaaaaagtg ggaggatcgg ccgggcgctg tggctgacac    2760
ctgtaatccc agcactttgg gaggccgagt tgggcagatc acaaggtcag gagttcgaga    2820
ccagcctggc caatatggtg aaaccttgtc tctactaaaa atacaaaaat tagccgggca    2880
tggtgtcacg tgtctataat cccagctact cgggaggctg aggcagaaaa attgcttgaa    2940
cctgggaggc agaggttgca gacagctgag atcactccat tgcactccag cctgggcaac    3000
aagagcaaaa ctttgtcttt aaaaaaaaaa aaaaaaaaag aatacaaaaa ttagccgggc    3060
gtggtggcgc gtgcctataa tcccagctac ttgggaggct gaggcaggag aatcagttga    3120
acacgggagg cgaggtttgc agtgagccga gattgcgcca ctgcactcca gcctgggcga    3180
cagagcagga ctcctcttgg aaaaaaaaaa ttagctgggc atggtggcag gtgcctgtag    3240
tctcagctac tagggaggct gaggcaggaa aatcacttga acccgggatg tggagtttgc    3300
agtgacccga gatcgtgcca ctgtactcca tcctgggcga caaaatgaga ctctgcctca    3360
aaaaaaaaaa aaaaaaaaag tgggaggatc aatgtactgc cagtcctaat gaagtggaat    3420
gattgtcccc atcaaatcac tagtaggagt aagttcaga gcctagaagg tgatggttaa    3480
gagagtggga ttcttgaaac tgcatttatg gagaggttgt ggttattggt tataataaat    3540
aaatacagtt gaagtgagtg agtagctgag atttggggat gtatcagttc attcttacac    3600
tgctacaaag acatacctga gaccaggtat ttataaagat aagaggttta atcagctcac    3660
agttctgctg cctgtacagg cttctcttgt ggaggcctaa ggaaacttac agtcatggtg    3720
```

```
gaaggtgaag gggaaacaag cacagtcttc acatggccag caggagagag agagaagggg    3780
gaagtgctac atactttaaa acaaccagat cttgtgagaa cgcttatcag gaaacagcac    3840
ttggggatgg tgctaaatca ttagaaatca cccccatgat ccagtcgcct cctaccatgc    3900
ccacctccaa cactgggat cacaattcag catgagattt gggtaggaac acagagctgc     3960
accacatcag aggatgtaca agattgtggt ggagaggagt ttagagacct gcaaatatag    4020
ggtaattgaa gggatcatct acatggatat ttaaatcacc aaaaattatg acaggagtag    4080
tgttggagag agaactgcga tgtaaacatt aaggaatgag gaagagtgac tcggtaggct    4140
gtaggtgact gcaataggaa acgataatag actgtgagtc tggtgacaag attttccttc    4200 tttcttttt tccccccccc cgagacaggg cctcttttg ttgcccaggt gggagtgcag       4260
tggcgcgatc acggctcact acaacctcct cccaagctca agggattctc ccacttcagc    4320
ctctcaagta gctggaacta caggtgctga ccaccatgcc tggctacttt ttgtcaggat    4380
tttcaaggct gggaattttg agaggggaat ggaggagaat aatctgaaag tgcaagtaag    4440
gagcagggaa gatttctttt ttcttttttt tttttttttt tgagtcggag tctggctcag    4500
tcgcccaggc tggagtgcag tggcgagatc tccgctcact gcaagctccg cctcccgtgt    4560
tcacgccatt ctcctccttc agcctcccga gtagctggga ctacaggcgc ccgccaccac    4620
gcccagctaa ttgtttttt gtattttag tagagacggg gtttcaccgt gttagccagg       4680
atggtctcaa tctcctgact tgtgatccg cccacccgg cctcccaaag cgcttgggat       4740
tacaggcgtg agccaccgcg ccagccagag cagggaagat ttcttcccca catctccagt    4800
aggtacagtg atatgaagtg tgtggaggag aaaagaggaa acatctatca tttgagatgg    4860
ctgcgaaagg aaaaggcatc ctcagggagc tagattttac ttagagcaag aaatgaaggg    4920
atgattcaga ggttaaaaga gtggatttta tgaattactc aagggagcac agtggaagtt    4980
tcaggaagtg gtaggagaag gtagaagatg gcagggtgtt gggaataatt tgagaaatct    5040
gagctactgg aaatgactga gaatcagata taaaggcagt cctggtggtc cgttctggct    5100
gccgttgctg tgtaacgaat ctgccaaaac ttagtggctt gaaacaacaa gaaacatttt    5160
attatctctc attgtttctg tgggttagga atttgtgaga gccgtgctgg gcagttttcg    5220
tgcggctgtc tcgtggttgc acctacatag ttgctagagc tacagtagct ggggactgag    5280
cagctaggga ttggcaggct atctcttttt ttcatgtagt ctcatgaaga tttctttatg    5340
tggtttcaat gtgtgggctg gtttggattt ccttatagca tggtggcctc agttggattg    5400
ctgttttgtg atccttttca tccctccttg tcctgtcccc agacaaccac tgatctactt    5460
tctgtcacca tagattagcc tgcattttta agaatttta taaacgtgga atgatagagt       5520 acctttttg tcacgtttct tttatttatc atagctattt tgattttcat ccatttatt       5580 gctgagtagt atcccattgc atgtatatac tatactgtat tcattcgctt gcttgtgaac    5640
atttgggctt tttccagttt gggactgtta acaagtagag ccactatgaa tattagtgta    5700
taagacttca tatagccaag gctggcagat cgcttgagcc caggagtttg agaccagcct    5760
gggaaacatg gtgaaacctc tatttttatt ttaaaatcaa aaattaaaaa ttttctataa    5820
aaaattttaa agaagacttt gtatagacat acgctttcat ttttcttgag tgaatactta    5880
ggtctcaggg tagatgtatt ttaagtcttt aaggagctgt caaactcttc ctcaaagtgg    5940
tggttgtacc atgttacttt ttaatataac agagattaat tgagcaaaga aaaattcaaa    6000
agttggacag ccccccacaac taaataggtt cagaacagct ccccccatttt gcattttgac   6060
```

```
cagcaatgta tgaaagttcc atttgctcag tgtccctgca acacctggt atggtcagtc    6120 ttttaattt taggcattat aatagatata gtggcttctt gtgattttaa ttagcatttc    6180
ctaatgacca gtgctgctgt tgatcatttc atgagtgtat ttgccatccg tatatctttt    6240
ttggtgaagt gtctattcaa atcatttggg tttttttttt ttttgttttt tttttttgga    6300
gacagtgtct cactctgtca cccaggctgt tgtgcagtgg tgcaatcaca cagcctactg    6360
cagcctccac ctcctgcgct cagtcttctt gtctcagcct tctgagtagc tgaaattacg    6420
agcacacgcc acaatgcctg gctaattttt taaaattttg tagaaacaag gtctcattat    6480
gttgcctggg cttgtcgtga actcctgggc tcaagcaatc ttcctgcctc agcctcccaa    6540
agattgggat tgcaagtatg agccactgca cccggccaac ttacccatct tttaattgaa    6600
tttttttgtt gttgaggttt gagagttctt catgtttgct gggtacaata tcttatcag    6660 ataggtaact tgcatgtatt ttctcccggt ttacactttg gtttttcatt ttgttaacaa    6720
cgtcttttta agaacagaaa atcttaattt tgctgaaatc taattttca gttttttctt    6780 tgatggtttt gagagaggag gtaaaaaaag actaggtaag ccgatagtta gacagagtcc    6840
tcggtagaac ttcccttcta acaaaaagca gcccaagaaa tcacttctct tctaacaagg    6900
agcagcctgg aagatcgggc tgtaaacatg tataaggaag cagctctggc acagagggg    6960 agcttcctgg gtaatcagca agcttcacat acgtaaggtg ggtatgtgaa gtaaacacag    7020
tatgtgaagt aaacacagtg gaccttagta catactcaga taaggaagct ggaagcttgc    7080
atgttgtgag ttgttggggt tgcctgcagc tgcacggaga gaaaggggta cctggggcca    7140
ggcatgtcca ccatggtggc tccacctccc cttatttagc acatgcacaa taggaaagag    7200
ataagcaatg tggagtagct caggccaagg acctgcctgc ataataaaag gttggggtgg    7260
gggatgccag agattcacgc tctgtgcaga tggcaacacc tggtcctaac tggttttttg    7320
ctccctatgt gtagataagc tacccccttc ccattagctc atttataaaa atgcttgcat    7380
ttcactgtgg aatgggaact cttttcagga cctctctctg caggagagag ctagtctctt    7440
tcttttgcct attaaacttc tgctctagcc tcacacccct ggtgtgtcag cgtccttgat    7500
ttcctcagcg tgagaccaag aacctcgggt gccaccccag gcaacaaggc catttcagtt    7560 tgttctttttg ttataggcaa tccatgatca cagatttttc tctctttttt ttttttacac    7620
agtttagagt tttagtttta cacttaggtc tgtaatccat tttgtattaa ttcttatatg    7680
tggctcagtg taggtggaaa tttggtttgt ttttgcataa ggatttccaa tagttttacc    7740
accatttctt gaaactacta tgcttttctct attaaaccac atttgtaact ttagttaaaa    7800
tcagtcacat atatcacagg gctatttctg actctcaatt ctgttacatt gtctattagt    7860
gtatattgat gtcagtacta cacttttaat tactattgct tcagggtatg tcttgtaaac    7920
caaaaataaa attataggcc cccccgccc ctgcacaacc aactgaatgg acccatcctc    7980
tcagccaagg gcattccaaa attaacctga aaaactagtt caagccatga tgggaagggg    8040
gagttggaca tgtctcatca caccctacta ccttttggaa ttactgatag aacagactct    8100
taaagtctga aagaaacat ttacaaccta ccctctctga agcctgctac ctgggagctt    8160
catctgcatg ataaaacctt ggtctccaca accccttatg gtaacccaaa cattcctttc    8220
tgttgataat aactctttca actagttgcc aattagaaaa tctttaaatc ttcctatgac    8280
ctagaaacct ccctacccc actttgagtt gtcctgcctt tcctgacaga actcatgtac    8340
atcttacata tattgattga tgcctcatgt ctccctaaaa tgtataaaac aaagctgtac    8400
cccaccacct tggggacatg tcatcaggac ctcctgtggc tgtgtcatag gagcgtcttt    8460
```

```
aactttggca aaataaactt tctaaattga ttgaaacctg tcttagctac ttctggttta   8520
cagtcttaaa gttagataat gtaaattgtc cagctttggt ttattttgt ccttagtagt    8580
tccatataaa ttttagaatc agcttttcaa tttaatacac tactttcctc ttagatccac   8640
aattaaatat atttgatgct aacaattctg ttttatgttt ttcgttttt ttttttgaga    8700
caagagtttc gctcttgttg cccaggctgg agtgcagtgg cgcgatcttg gctcaccaca   8760
acctccacct cccaggttca agcaattctt ctgcctcagc ctcccgagta gctgggatta   8820
caggcatgcg ccaccacgcc cggctaattt tgtatttta gtagagacgg ggtttcacca    8880
tgttgatcag gctggtcttg aactcctgac ctcaggtgat ccacccacct cggcctccca   8940
aagtgttggg attacaggcg tgaaccacca tgcctggcca gttctgttat ttttaaaacc   9000
caagtttccc tggtcatatc ttggttggat gaagcgtatt ttcaatagat taccctggaa   9060
aggctagtga gtacggtatt cttctacatt ttagactttt cttagtcttg ctacttcaag   9120
gacagctagg ctgcatataa aattcttggc tcatactttt tccccataaa tttctatgag   9180
aaagtctaat gataactgat tttctttatt ttgtaactta gtcttttgc ttagaggctc    9240
tctgaggatg ggaggggtt cttcctccca tccctaggaa tttttctttt ttttaaattc    9300
ctaatcacta gaccaccagg aagattgttt gttttgtttt gttttattc ttcagggacc    9360
ccatttatac atacgttaaa taatactgt ttgccaatgt atcaaccatt ttgcttctta    9420
tttatttttg ttcctttggt tcttttcat ggctttgctt tggtgctcct tagattttca    9480
gtcagatgta tttgtccttg ggtaccttgt aatcagtatt accttttctt ctgtcgcttt   9540
gttttctgtt cgttttgaaa ttacttgttt cctggtctgg caataacagt tgagatatga   9600
ggagtttgag ctgccatctg tctatgtatc ttgctttaag actgcactct tctattgata   9660
tcactggcct tgattttgtg atttctttat ttcttcagga ccacccttca ttttctactg   9720
tttgcttcct tttttttga gatggagtct cactctgtca ctcaggctgg agtgcagtga   9780
tcttggctca ttgcaacctc tgcctcccgg gttccagcaa ttctcctgcc tcagcctccc   9840
aagtatctgg gactacaggt gtgcaccacc atgcccggct aagttttgta tttttaatag   9900
agacggggtt ttgccacatt ggcaggctgg tctcaaactc ctgatgtcaa gtgatccacc   9960
cacccacccc acctctgcat cccaaagtgc tgggattaca ggaatgagct gccgtgccca  10020
gcctccccce tacccccctt tttttctttc gagacagaga ttataggtgt gagccactgg  10080
acccagcctg ttttattcc ttttaccaaa tctccaagga atatcttccc ttccaagtgc   10140
gaatgtaacc ttaagtcagt taacctcttt gtgattactt ttcttatctg caaagtgact  10200
taatgatctt aagtactttt ttttttgag acagggtctc actgtcaccc tggctggagt  10260
gcagtggcac gatctctgat ctccactcac tgcaatctcc tcttccctgg ttcaagcggc  10320
cctcccacct tagccttctg ggtagctggg actacagatg tgaaccacca cgcccagcta  10380
attttttgtac ttttttgtaga gatgggggttt tgccatgttg cccaggctgg gattattaag 10440
tacttttta tcatacagcaa gattgacatt ttatattgga atacatttgt ctctatataa   10500
cggagattaa caggaaaatg acaagcctgg gtgcggtggc tcatgcctgt aatcccagca  10560
ctttgggagg ctgaggtggg aggatcactt gaggtcagga gttcgagacc agttttgcca  10620
agatgatgaa agcccatgtc tactaaaaat acaaaaatta gcccagcttg atggtgggcg  10680
cctataatcc cagctatttg agagactgag gcaggagaat cacttgaacc tgggcagcag  10740
aggttgcagt gagccgagat catgccactg cactccagcc tgggtggcat agcgagactc   10800
```

-continued

```
ttgtctcaag agaaaacaaa acaaaacaaa aaaaaaacag gaaaatgaca aaaagtaata  10860
ttacaactca gtgaatttta taacaaactt ttttggaatt cattgactaa tactatacca  10920
aatccaaaat actctctagt ataccaaatc caactctacc ctatagtata aattggattc  10980
tatttggact tgtctcacta atccctcata cagtgtgttt tattttttat tgaagtaaaa  11040
aaatttgtca ttttaaccat ttttaagtat atagttcagt aatattaagt atgttcatgt  11100
tgttgcgcaa tagatcttcg gaagtttttc gtcttgcaac ctgaaactct acccattagc  11160
aaattcccat ttctccttac acttagccct tggtaatcat cattcttttt tttttttttt  11220
tgagatggag ttttactctt gttgcccagg ctggagtgca atggtgcaat ctcgactcac  11280
cacaacctcc gcctcccagg ttcaagcaat tctacctcag cctcccgagt agctgggatt  11340
acagtcatgc accaccacgc ccggctaatt ttgtattttt agtagagaag ggtttctcc   11400
atgttgaggc tggtctcgaa ctcctgacct caggtgatct gcccacctcg gcctcccaaa  11460
gtgctgggat tacaggcgtg agccactgcg cctggcccat tctttctaat tctataaatt  11520
tgactactta gttaccttac ataaataaat tcttatagtt agtgttattt ttgcttccat  11580
gccttttttg ttgttgttca tgctcttact tggaatgcgt tctattttgt ctacctatgc  11640
acatcctgtt gggttttttt tttttttggg ggttttttt gtttttttt gtttttttt    11700
cccagacaag gtctcaattt gttacccagg ctggagtgca gcggcgccat ctccactcac  11760
tgcatcctca acttcctggg cccaggtgat cctctcgcct cagcccctgc aggtagctgg  11820
gactataggc atgtgccacc atgcccagct aaatttggtt ttttttgtttg tttgttttg  11880
agacagagtc tcactctgtc acccaggctg gagtgcagtg gcacaatctc agctcactgc  11940
aatctctgcc gcccgggttc aagtgattct cctgcctcag cctcccaagc agctgggatt  12000
acaggtgact gccaccacgc cagctaagtt ttgtagtttt agtagagatg gggtttcacc  12060
ttgttggcca tgctggtctc gaactcctga cctcgtgatc tgcctgcttc tgcctcccaa  12120
agtgctggaa ttacaggcat gagccaccac gcccggccag aattttttgta ttttagtag  12180
acacaaggtt cttaccctgt tgcctaggct ggtctggaag tcctggactc aagcaattca  12240
cctgccttgg cctcccaaaa tgctgggatt acaagccacc atgcccggcc taaatcctgt  12300
tgttttgttt tgttttattt tgttttgttt tgttttgttt gttttttgag acagagtctc  12360
gctatgtctc tcaggctgta gtgcagtggc gcgatcttgg ctcactgcca cctctgcctc  12420
ccaggttcaa gtgattctcc tgcctcagcc tcccaagtag ctgggattac aggcatgtgc  12480
tactatgtcc ggctaatttt tgtattttta gtagagacag ggtttcacca tgttggccag  12540
gctggtctcg aactcctgac ctcgtgatcc acccacctcg gcacccaaa gtgctgggat   12600
tacaggcgtg agtggttttt atttcttagg ccggttccct ccatatgatc ttgcagtaga  12660
cattaatttc tttcctttt aattaaaata ctgtttgtat ttcacatttt gatgtttgtt   12720
aagatttgtt ttatattgtt ttttgttttg tcttgtgtga tagtcttaaa tcccctagtta  12780
gataataact ggagagtacc atgtttctat atatctctca gtgacttgca cagtgctagc  12840
agatagtgct aaaaaattat ttattattat tattattttg ttattgttgt tgttgttgtt  12900
agacagggtc ttcctctgtc acccaggcta gagggcaatg gatgatcat agcttactgc    12960
agcctccaac aactgggctc atgtaattct cctgcctcag cttcccaagt agctgggatt  13020
acaggcatga gccaccatgt ctggacaaaa atatttccag gtgcagtggc tcatgcctgt  13080
aattcccaca cttgggaggc cgagcgaggc tggaggatca cttgagccta ggagttcaag  13140
accagcttgg ctaagatggc gagaccccgt ccctacaaaa aattttaaaa actagccagg  13200
```

```
catggtggca tgcacctata ttcccaacta ctcagtgggc tgaggtggga gggtcatttg    13260
aacacaggaa tttgagggga gaaaaaaaga agagagaaag agaagtgaag gaaggaagaa    13320
aggaaggagg gagggagaga agaaagaaac gaaagaaagg aaaagaaaag gaaggaagaa    13380
aaattggtac caggaaagca ggaaagggaa atggaagtaa aaaaataata ataataataa    13440
aatgaaaatt ggttagtcac tattaacaat ttgtatcctt ataatctgga aacattataa    13500
tttcaaaaga aaaaatattc tttggatcat aggttctgag gtcagaacag cattcccgta    13560
gtctagatga agtcaagttt tatctgatct taattgaaat aaatatagct ggccttgaac    13620
aaatctactc atggtatgtg gataggaatt aaattgtagg ggcattcact tgatggcatt    13680
cattcttaga acatttacct atgtctagct tttggagtaa agtcacataa cctctaacca    13740
ggtaagtttc ctgtggcttt atttaggatt ttaaatactc attttcagtg taattttgtt    13800
atgtgtggat taagatgact cttggtacta acatacattt tctgattaaa cctatctgaa    13860
catgagttgt ttttatttct tacccttttcc agagcgatga ttctgacatt tgggatgata    13920
cagcactgat aaaagcatat gataaagctg tggcttcatt taaggtatga aatgcttgct    13980
tagtcgtttt cttatttttct cgttattcat ttggaaagga attgataaca tacgataaag    14040
tgttaaagta catgttattc agttttcatt ttgaagatta gatggtagta tgagttagtt    14100
aaatcaggtg atatcctcct ttagaagttg atagcctata tatgtcatcc tttgtggagg    14160
caatttaaat aaaatttaaa acatttattc ctggctgggt atggtggctc actcctgtaa    14220
tcccagcact ttgagaggct gaggcgggtg gatcacctga ggtcaggagt ttgagaccag    14280
cctggccaac atggtgaaac cccgtcttta ctaaaaatac aaaaattagc caagcatggt    14340
ggcacgtgcc tgtaatccca gctgcttggg acactgaggc aggagaattg cttgaacctg    14400
gggggcagag gttgcaatga ttgcaccact gcactccagc ctgggcgata gagtgagact    14460
ccatctcaga aaacgaacaa acaatgtatt cctttttagta ttttttacatt gtatcaaact    14520 atggaagtcc tctaattgag attaataaga aaaagacaat ctgaattata atttttaaaca    14580 tttaacaagc atgtagtaaa ataatgatga agataaatag cattagtaca gcaattaata    14640
tttgtagcat gctgacagtg ctctgtgtgc gtttcatata ttaaattact ctaatcatcc    14700
caaatcctgt aagttgggta tcaattcaag tgttcctatt gggtaggaat atacagttct    14760
tttaggaaat gtagtatggt tctgtgtctc aaacaggaca cttacacagt tggccaacat    14820
catcaccttc tccattctct gagatgttta gtcttactga gcactaaata tgggtcatca    14880
atagtccaga ctaccttgag caaacaatag tccagactac cttgagcaaa cagagcatat    14940
actcatacag tgtataaaga gcaccaagca tacagatttc atgtctttct catagttact    15000
cttgtaacat gagctaaaga tcagacctct atgtcacctt tgtaactgat ttctagattt    15060
tttttttttt ttgagatggg gtcttgccct gtcacccagg ctggagtgta gtggcgtgat    15120
catgcctcat tggagccttc aactcatgag ctcaaacaat cctcctacct cagcttcctg    15180
agtagttggg accacaggtg tgtgccacca cacccagctc attttttgtat tctttgtaga    15240 gatgcagtct cacccctgttg cccacgctgg cctggaactc ctgagctcaa aagatccctc    15300
cgccttgacc ttcaaagtg ctgggattac aagcatgaac cactgcaccc ggcctagatt    15360
tttaaatgtg ctttccagta tacactgaaa ctagaagtcg actaaagaat taccaagaga    15420
attctataaa atagagattg aaatgggcct cgatgtggga tgggttggtg atattgcagg    15480
gagaagtaat ctgagtaaag gaggaaaaga actgatttgg gaaaacgata gttttagtag    15540
```

```
tgagtttgag tatgaattaa gttgagattg aatttgaatt aagttgaggt tgaatatgaa    15600
ttaagttgag gttgagtttg aggtatgaat taagatgtga aattgatcat tggaaatgtt    15660
agattgagaa aagtcacagc tggattaata gcttcagaag tgtgtttgca gacagttgca    15720
actaaagtaa taagaataga tggccttggc cgggcgcggt ggctcacgcc tgtaatccca    15780
gtactttggg aggctgaggc gagcaaatca cgaggtcagg agttcaagac cagcctggcc    15840
cacatggtga aacccgtctc ttattaaaaa tacaaaaatt agctgtgcac agtggtgcac    15900
gcctgtaatc ccagctactc gggaggctga gacaggagaa tcgcttgaac ctgggaggtg    15960
gaggttgcag tgagctgaga tcagtgtgac tgcactccag cccggtgaca gagtgagact    16020
ctgtgtaaaa aaataaaata aataaaataa tggccgtaag caagtaaaga aggatggcca    16080
gctcttattg ggaatgccta aatctaaggc ttgatcagaa gtaatgaaac cgttggggcc    16140
ctacattgct atgacatcca aagggccatg aatatcagga agaaagataa ttaacagggt    16200
ctaatgttac agagaggttg agagcaagga gatttgatta aagggtctt tagagctgat     16260 gtcaggtgta tgatgccttt aagagcagtt tttatagtgc aggggggtggt caaaagagaa    16320 aataggtgct ttctgaggtg acggagcctt gagactagct tatagtagta actgggttat    16380
gtcgtgactt ttattctgtg caccaccctg taacatgtac attttttattc ctattttcgt   16440 agcatgctct aaagaatggt gacatttgtg aaacttcggg taaaccaaaa accacaccta    16500
aaagaaaacc tgctaagaag aataaaagcc aaaagaagaa tactgcagct tccttacaac    16560
aggttatttt aaaatgttga gatttaactt caaggatgt ctcattagtc cttatttaat     16620
agtgtaaaat gtctttaact taagtgatta gtacagtgtt tctattgaca tatacttata   16680
caacttcaaa acaactatt aaattttctg ttatttagga acatgcatat tagtcatgaa   16740
agtataaaga attagatggg aatgataaat gctaaaatca ggacatgtgt tccatttgtg    16800
aatggaaggc agggagaagg tgccgtttgg aaggagtacc caagagccgt aagctgaatt    16860
ggcagtgttt tacatcttaa gctgagagat agatttttt ttccccttttt tcttttaaaaa   16920 ctctaaaact gttaattcca aggaacccag aagtctaggt agattatttc tgctagttaa    16980
aagcagtagt cctgaaagct gaatattttg gtgtcttttg agccaacttt agtttcatca    17040
ttaccaaggg ggaagagagc taacagttga tgagcacttg ctctaggcca gtccagagtg    17100
ctgggcacca tacgcatttt atctccctcc cgctattcac aacaaatatg ggaggtagtt    17160
tatattatag ccatctaata agatggggaa actaagactc aaagagattc agaaacttgt    17220
ccatgattat aaatgtaaga gagttggaat tcagatttat gtatttagac cccaagcctt    17280
tctcattaca tcattttgcc ttccaaatct ctaccctcta tccttcacct ccccactgat    17340
caaaacgaga tgtagttgg ccctcttcaa aagaaatgtg tgcatgtata tatctttgat     17400
ttcttttgta gtggaaagtt ggggacaaat gttctgccat ttggtcagaa gacggttgca    17460
tttacccagc taccattgct tcaattgatt ttaagagaga aacctgtgtt gtggtttaca    17520
ctggatatgg aaatagagag gagcaaaatc tgtccgatct actttcccca atctgtgaag    17580
tagctaataa tatagaacaa aatgctcaag aggtaaggat acaaaaaaaa aaaaattcaa    17640
tttctggaag cagagactag atgagaaact gttaaacagt atacacagtt gtcagtttga    17700
tccaccgagg cattaatttt ttcttaatca caccttata acaaaaacct gcatattttt     17760 tcttttttaaa gaatgaaaat gaagccaag tttcaacaga tgaaagtgag aactccaggt    17820
ctcctggaaa taaatcagat aacatcaagc ccaaatctgc tccatggaac tcttttctcc    17880
ctccaccacc ccccatgcca gggccaagac tgggaccagg aaaggtaaac cttctatgaa    17940
```

```
agttttccag aaaatagtta atgtcgggac atttaacctc tctgttaact aatttgtagc    18000
tctcccatga aacttttgta gcttaaatac acaagaattt tttgaaaagg aaataagata    18060
atgatgcaaa atagttaatt ttttaaaaaa atgttagaca ctgcagtgga tgcaacaaaa    18120
tactttatat gaaagattta tccagttaac ttttgtggag tattaggtat tagactaata    18180
attagcacac ttacttaagt tagaaagtat aataatgcgc cggacgcggt agctcacgcc    18240
tgtaatccca gcactttggg aggccaaggt gggcggatca caaggtcagg agatcgagac    18300
catcctggct aacacggtga aaccccatct ctactgaaaa tacaaaaaaa tttgccgggc    18360
gtgatggcgg gcacctgtag tcccagctac tcgggaggct gaggcaggag gatggtgtga    18420
accccggagg cagagcttgc agtgagtcaa gatcgtgcca ctgcactcca acctgggcga    18480
cagaatgaga ctccatctca aacaaaaaaa caaaacaaaa caaaaaaaag tgtaataata    18540
atttatcatt agctggatga tatgctgttg tttcccatgt cacctgtata agatatgtaa    18600
aataagaaca cattatttac atctaatata gataaaatcc tgaggcgctc tcagattgtt    18660
ttgtagagtt caaatgtaaa tattgttttc atttatggtc cttttggtta taagtaacag    18720
aaatcaactc taaaaagatt tttattatag gttagattat gtcatggaac cttaaggctt    18780
gtcccttcct agttcttttg tgtaaagcgg tgatttcttc catggaggga atggtattta    18840
ggcaattttt tttttttttt cgagatggag tcttgctctg tcgctcaggc tggagtgcag    18900
tggcaccatt tcagctcact gcaacttcca cctcctgggt tcaagtgatt ctcctgcttc    18960
agcctcccaa gtagctgaga ttacaggcac ccgccaccac acccggctta ttttgtattt    19020
ttagtagaga tggggtttca ccatgttggc caggctggtc ttgaactcct gacctcaagt    19080
gatctcccca ccttggcctt ccaaagtgct aggattacag gcgcctagcc taggcagtca    19140
ttttcaaaaa acaagcatga ctcaccaaaa gttttaagat tttctgtgat aatgttctta    19200
ttgaggctta cattatatta cagtttcttg aatctaaaat gatgtaccct cttagaatat    19260
atacatcatg cttcattggt ctcagggggc tgatttttat aaggagagat ttgctagttt    19320
tcacaatatg tcctctaagt tggcatgtat agctaaacag gctttcataa aaatatacaa    19380
tttagttaat gaaatttggg atatagtctt ttatgattga aataattttg ctaaatagac    19440
tgtctctgat ttattaggta atcaccactc ttatttttgtt ttacttcctt aatgtctaca    19500
tagaaaggaa atgagaaaaa tccagaggtt gtcatttgac ttatgagtct gtttgacttc    19560
aggatttggt acatgaaatt tcacttaatc ttttttgatat gtataaaaca aatattctgg    19620
gtaattattt ttatcctttt ggttttgagt ccttttttatt cctatcatat tgaaattggt    19680
aagttaattt tcctttgaaa tattccttat agccaggtct aaaattcaat ggcccaccac    19740
cgccaccgcc accaccacca ccccacttac tatcatgctg gctgcctcca tttccttctg    19800
gaccaccagt aagtaaaaaa gagtataggt tagattttgc tttcacatac aatttgataa    19860
ttagcagaat agaggattgt aaaatgtcat tgtagaacat cccttgggcc agattctaat    19920
gggtagaaat ttgaactaaa cctctgggtt ttgtttgttt ttaatgcctt tctgttaccc    19980
agatgcagtg ctcttgtagt cccaagtcta agctctaggt tgccttcttt cctggcagaa    20040
gttggtgtct atgccataag gaggtagttc ctgttagaag ggatttaatt ataccttata    20100
taaggaatta gtgtttgccc ttctaggtat agttggatgt tagcttctga tgtaaactgg    20160 atttctttt ctttctctct cttttttttt ttttgttttg gaggcagagt tttgcccttg    20220
taccccaggc tggagtgcag tggtgtgatc tcagctcaca gcaacctccg cctcctgggt    20280
```

```
tcaagcaatt ctgcctcggc ctcccaagta gctgggatta caggcgactg ccaccacacc  20340
cggctaattt ttgttttatt agtagagatg gggtttcacc atgttggcca gactgatctt  20400
gaactcctga cctcaggtga tccacccgcc ttggcctccc aaagcgctgg gattacaggc  20460
gtgagctgcc gcacccagct gtaaactgga tttctaatgg tagattttta ggtattaaca  20520
atagataaaa agatactttt tggcatactg tgtattggga tggggttaga acaggtgttc  20580
tacccaagac atttacttaa aatcgccctc gaaatgctat gtgagctgtg tgtgtgtgtg  20640
tgtgtgtgtg tgtattaagg aaaagcatga aagtatttat gcttgatttt ttttttttac  20700
tcatagcttc atagtggaac agatacatag tctaaatcaa aatgtttaaa cttttatgt  20760 cacttgctgt cttttcgtcc tcgttaaatt taattttgtt ggtcttttgt tgttattggt  20820
tggttttctc caaatgctag ctatgttaag aaatttaagg ccaggtacag tggctcatgc  20880
ctgtaatccc ggcattttag aaggctgagg caggaggatc acttgagctc aggagtttga  20940
gaccagtctg gcaacatag caagacctcg tctttgttta ggggaaaaaa aagaaattta  21000
agtaggagat tatataagca aaaatacaat taatttccag cattcactat ataatataaa  21060
tctccagact ttactttttt gtttactgga tataaacaat atcttttct gtctccagat  21120 aattccccca ccacctccca tatgtccaga ttctcttgat gatgctgatg ctttgggaag  21180
tatgttaatt tcatggtaca tgagtggcta tcatactggc tattatatgg taagtaatca  21240
ctcagcatct tttcctgaca attttttgt agttatgtga ctttgtttg taaattata  21300 aaatactact tgcttctctc tttatattac taaaaataa aaataaaaaa atacaactgt  21360
ctgaggctta aattactctt gcattgtccc taagtataat tttagttaat tttaaaagc  21420 tttcatgcta ttgttagatt attttgatta tacacttttg aattgaaatt actttttc  21480 taaataatgt tttaatctct gatttgaaat tgattgtagg gaatgaaaaa gatgggataa  21540
tttttcataa atgaaaaatg aaattctttt ttttttttt ttttttttga cggagtct  21600 tgctctgttg cccaggctgg agtgcaatgg cgtgatcttg gctcacagca agctctgcct  21660
cctggattca cgccattctc ctgcctcagc ctcagaggta gctgggacta caggtgcctg  21720
ccaccacgcc tgtctaattt tttgtatttt tttgtaaaga cagggtttca ctgtgttagc  21780
caggatggtc tcaatctcct gacccccgtga tccacccgcc tcggccttcc aagagaaatg  21840 aaatttttt aatgcacaaa gatctggggt aatgtgtacc acattgaacc ttggggagta  21900
tggcttcaaa cttgtcactt tatacgttag tctcctacgg acatgttcta ttgtattta  21960 gtcagaacat ttaaaattat tttatttat tttatttttt ttttttttt gagacggagt  22020 ctcgctctgt cacccaggct ggagtacagt ggcgcagtct cggctcactg caagctccgc  22080
ctcccgggtt cacgccattc tcctgcctca gcctctccga gtagctggga ctacaggcgc  22140
ccgccaccac gcccggctaa ttttttttta tttttagtag agacgggggtt tcaccgtggt  22200 ctcgatctcc tgacctcgtg atccacccgc ctcggcctcc caaagtgctg ggattacaag  22260
cgtgagccac cgcgcccggc ctaaaattat ttttaaaagt aagctcttgt gccctgctaa  22320
aattatgatg tgatattgta ggcacttgta tttttagtaa attaatatag aagaaacaac  22380
tgacttaaag gtgtatgttt ttaaatgtat catctgtgtg tgcccccatt aatattctta  22440
tttaaaagtt aaggccagac atggtggctt acaactgtaa tcccaacagt ttgtgaggcc  22500
gaggcaggca gatcacttga ggtcaggagt ttgagaccag cctggccaac atgatgaaac  22560
cttgtctcta ctaaaaatac caaaaaaat ttagccaggc atggtggcac atgcctgtaa  22620
tccgagctac ttgggaggct gtggcaggaa aattgcttta atctgggagg cagaggttgc  22680
```

```
agtgagttga gattgtgcca ctgcactcca cccttggtga cagagtgaga ttccatctca   22740
aaaaaagaaa aaggcctggc acggtggctc acacctataa tcccagtact ttgggaggta   22800
gaggcaggtg gatcacttga ggttaggagt tcaggaccag cctggccaac atggtgacta   22860
ctccatttct actaaataca caaaacttag cccagtggcg ggcagttgta atcccagcta   22920
cttgagaggt tgaggcagga gaatcacttg aacctgggag gcagaggttg cagtgagccg   22980
agatcacacc gctgcactct agcctggcca acagagtgag aatttgcgga gggaaaaaaa   23040
agtcacgctt cagttgttgt agtataacct tggtatattg tatgtatcat gaattcctca   23100
ttttaatgac caaaaagtaa taaatcaaca gcttgtaatt tgttttgaga tcagttatct   23160
gactgtaaca ctgtaggctt ttgtgttttt taaattatga aatatttgaa aaaaatacat   23220
aatgtatata taaagtattg gtataattta tgttctaaat aactttcttg agaaataatt   23280
cacatggtgt gcagtttacc tttgaaagta tacaagttgg ctgggcacaa tggctcacgc   23340
ctgtaatccc agcactttgg gaggccaggc aggtggatc acgaggtcag gagatcgaga   23400
ccatcctggc taacatggtg aaaccccgtc tctactaaaa gtacaaaaac aaattagccg   23460
ggcatgttgg cgggcacctt tgtcccagc tgctcgggag gctgaggcag gagagtggcg   23520
tgaacccagg aggtggagct tgcagtgagc cgagattgtg ccagtgcact ccagcctggg   23580
cgacagagcg agactctgtc tcaaaaaata aaataaaaaa gaaagtatac aagtcagtgg   23640
ttttggtttt cagttatgca accatcacta caatttaaga acattttcat cacccaaaa   23700 agaaaccctg ttaccttcat tttccccagc cctaggcagt cagtacactt tctgtctcta   23760
tgaatttgtc tattttagat attatatata aacggaatta tacgatatgt ggtcttttgt   23820
gtctggcttc tttcacttag catgctattt tcaagattca tccatgctgt agaatgcacc   23880
agtactgcat tccttcttat tgctgaatat tctgttgttt ggttatatca cattttatcc   23940
attcatcagt tcatggacat ttaggttgtt tttattttg ggctataatg aataatgttg   24000
ctatgaacat tcgtttgtgt tcttttttgtt ttttgtttt ttgggttttt ttttgttttg   24060
tttttgtttt tgagacagtc ttgctctgtc tcctaagctg gagtgcagtg gcatgatctt   24120
ggcttactgc aagctctgcc tcccgggttc acaccattct cctgcctcag cccgacaagt   24180
agctgggact acaggcgtgt gccaccatgc acggctaatt ttttgtattt ttagtagaga   24240
tggggtttca ccgtgttagc caggatggtc tcgatctcct gacctcgtga tctgcctgcc   24300
taggcctccc aaagtgctgg gattacaggc gtgagccact gcacctggcc ttaagtgttt   24360
ttaatacgtc attgccttaa gctaacaatt cttaaccttt gttctactga agccacgtgg   24420
ttgagatagg ctctgagtct agcttttaac ctctatcttt ttgtcttaga aatctaagca   24480
gaatgcaaat gactaagaat aatgttgttg aaataacata aaataggtta aactttgat    24540 actcattagt aacaaatctt tcaatacatc ttacggtctg ttaggtgtag attagtaatg   24600
aagtgggaag ccactgcaag ctagtataca tgtagggaaa gatagaaagc attgaagcca   24660
gaagagagac agaggacatt tgggctagat ctgacaagaa aaacaaatgt tttagtatta   24720
atttttgact ttaaatttt ttttatta gtgaatactg gtgtttaatg gtctcatttt      24780
aataagtatg acacaggtag tttaaggtca tatatttat ttgatgaaaa taaggtatag    24840
gccgggcacg gtggctcaca cctgtaatcc cagcactttg ggaggccgag gcaggcggat   24900
cacctgaggt cgggagttag agactagcct caacatggag aaaccccgtc tctactaaaa   24960
aaaatacaaa attaggcggg cgtggtggtg catgcctgta atcccagcta ctcaggaggc   25020
```

```
tgaggcagga gaattgcttg aacctgggag gtggaggttg cggtgagccg agatcacctc    25080
attgcactcc agcctgggca acaagagcaa aactccatct caaaaaaaaa aaaataaggt    25140
ataagcgggc tcaggaacat cattggacat actgaaagaa gaaaaatcag ctgggcgcag    25200
tggctcacgc cggtaatccc aacactttgg gaggccaagg caggcgaatc acctgaagtc    25260
gggagttcca gatcagcctg accaacatgg agaaaccctg tctctactaa aaatacaaaa    25320
ctagccgggc atggtggcgc atgcctgtaa tcccagctac ttgggaggct gaggcaggag    25380
aattgcttga accgagaagg cggaggttgc ggtgagccaa gattgcacca ttgcactcca    25440
gcctgggcaa caagagcgaa actccgtctc aaaaaaaaaa ggaagaaaaa tattttttta    25500
aattaattag tttatttatt ttttaagatg gagttttgcc ctgtcaccca ggctggggtg    25560
caatggtgca atctcggctc actgcaacct ccgcctcctg ggttcaagtg attctcctgc    25620
ctcagcttcc cgagtagctg tgattacagc catatgccac cacgcccagc cagttttgtg    25680
ttttgttttg ttttttgttt ttttttttttg agagggtgtc ttgctctgtc ccccaagctg    25740
gagtgcagcg gcgcgatctt ggctcactgc aagctctgcc tcccaggttc acaccattct    25800
cttgcctcag cctcccgagt agctgggact acaggtgccc gccaccacac ccggctaatt    25860
tttttgtgtt tttagtagag atggggtttc actgtgttag ccaggatggt ctcgatctcc    25920
tgaccttttg atccacccgc ctcagcctcc caagtgctg ggattatagg cgtgagccac    25980
tgtgcccggc ctagtcttgt attttttagta gagtcgggat ttctccatgt tggtcaggct    26040
gttctccaaa tccgacctca ggtgatccgc ccgccttggc ctccaaaagt gcaaggcaag    26100
gcattacagg catgagccac tgtgaccggc aatgttttta aattttttac atttaaattt    26160 tatttttag agaccaggtc tcactctatt gctcaggctg gagtgcaagg gcacattcac    26220
agctcactgc agccttgacc tccagggctc aagcagtcct ctcacctcag tttcccgagt    26280
agctgggact acagtgataa tgccactgca cctggctaat ttttattttt atttatttat    26340
ttttttttga gacagagtct tgctctgtca cccaggctgg agtgcagtgg tgtaaatctc    26400
agctcactgc agcctccgcc tcctgggttc aagtgattct cctgcctcaa cctcccaagt    26460
agctgggatt agaggtcccc accaccatgc ctggctaatt ttttgtactt tcagtagaaa    26520
cggggttttg ccatgttggc caggctgttc tcgaactcct gagctcaggt gatccaactg    26580
tctcggcctc ccaaagtgct gggattacag gcgtgagcca ctgtgcctag cctgagccac    26640
cacgccggcc taattttttaa atttttttgta gagacagggt ctcattatgt tgcccagggt    26700
ggtgtcaagc tccaggtctc aagtgatccc cctacctccg cctcccaaag ttgtgggatt    26760
gtaggcatga gccactgcaa gaaaacctta actgcagcct aataattgtt ttctttggga    26820
taacttttaa agtacattaa aagactatca acttaatttc tgatcatatt ttgttgaata    26880
aaataagtaa aatgtcttgt gaaacaaaat gcttttttaac atccatataa agctatctat    26940
atatagctat ctatatctat atagctattt ttttaacttt cctttatttt ccttacaggg    27000
ttttagacaa aatcaaaaag aaggaaggtg ctcacattcc ttaaattaag gagtaagtct    27060
gccagcatta tgaaagtgaa tcttactttt gtaaactttt atggtttgtg gaaaacaaat    27120 gttttgaac atttaaaaag ttcagatgtt agaaagttga aaggttaatg taaaacaatc    27180
aatattaaag aattttgatg ccaaaactat tagataaaag gttaatctac atccctacta    27240
gaattctcat acttaactgg ttggttgtgt ggaagaaaca tactttcaca ataaagagct    27300
ttaggatatg atgccatttt atatcactag taggcagacc agcagacttt ttttttattgt    27360 gatatgggat aacctaggca tactgcactg tacactctga catatgaagt gctctagtca    27420
```

```
agtttaactg gtgtccacag aggacatggt ttaactggaa ttcgtcaagc ctctggttct    27480
aatttctcat ttgcaggaaa tgctggcata gagcagcact aaatgacacc actaaagaaa    27540
cgatcagaca gatctggaat gtgaagcgtt atagaagata actggcctca tttcttcaaa    27600
atatcaagtg ttgggaaaga aaaaggaag tggaatgggg aactcttctt gattaaaagt    27660
tatgtaataa ccaaatgcaa tgtgaaatat tttactggac tctattttga aaaccatct    27720 gtaaaagact gaggtggggg tgggaggcca gcacggtggt gaggcagttg agaaaatttg    27780
aatgtggatt agattttgaa tgatattgga taattattgg taattttatg agctgtgaga    27840
agggtgttgt agtttataaa agactgtctt aatttgcata cttaagcatt taggaatgaa    27900
gtgttagagt gtcttaaaat gtttcaaatg gtttaacaaa atgtatgtga ggcgtatgtg    27960
gcaaaatgtt acagaatcta actggtggac atggctgttc attgtactgt ttttttctat    28020
cttctatatg tttaaaagta tataataaaa atatttaatt tttttttaaa              28070
```

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 24
<212> TYPE: DNA
<213> ORGANISM: Artificial sequence
<220> FEATURE:
<223> OTHER INFORMATION: Primer

<400> SEQUENCE: 11
gctgatgctt tgggaagtat gtta                                              24

<210> SEQ ID NO 12
<211> LENGTH: 25
<212> TYPE: DNA
<213> ORGANISM: Artificial sequence
<220> FEATURE:
<223> OTHER INFORMATION: Primer

<400> SEQUENCE: 12
caccttcctt cttttgatt ttgtc                                              25

<210> SEQ ID NO 13
<211> LENGTH: 21
<212> TYPE: DNA
<213> ORGANISM: Artificial sequence
<220> FEATURE:
<223> OTHER INFORMATION: Probe

<400> SEQUENCE: 13
tacatgagtg gctatcatac t                                                 21

<210> SEQ ID NO 14
<211> LENGTH: 27
<212> TYPE: DNA
<213> ORGANISM: Artificial sequence
<220> FEATURE:
<223> OTHER INFORMATION: Primer

<400> SEQUENCE: 14
catggtacat gagtggctat catactg                                           27

<210> SEQ ID NO 15
<211> LENGTH: 25
<212> TYPE: DNA
<213> ORGANISM: Artificial sequence
<220> FEATURE:
<223> OTHER INFORMATION: Primer

<400> SEQUENCE: 15
tggtgtcatt tagtgctgct ctatg                                             25

<210> SEQ ID NO 16
<211> LENGTH: 21
<212> TYPE: DNA
<213> ORGANISM: Artificial sequence
<220> FEATURE:
<223> OTHER INFORMATION: Probe

<400> SEQUENCE: 16
ccagcatttc catataatag c                                                 21

```
<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
caggaggatt ccgtgctgtt                                                     20

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
cagtgctgta tcatcccaaa tgtc                                                24

<210> SEQ ID NO 19
<211> LENGTH: 15
<212> TYPE: DNA
<213> ORGANISM: Artificial sequence
<220> FEATURE:
<223> OTHER INFORMATION: Probe

<400> SEQUENCE: 19
acaggccaga gcgat                                                          15

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
attcactttc ataatgctgg                                                     20

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
cactttcata atgctggc                                                       18

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ttcactttca taatgctggc                                                     20

<210> SEQ ID NO 23
<211> LENGTH: 18
<212> TYPE: DNA
<213> ORGANISM: Artificial sequence
<220> FEATURE:
<223> OTHER INFORMATION: Synthetic oligonucleotide
```

-continued

```
<400> SEQUENCE: 23
tcactttcat aatgctgg                                                  18

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24
actttcataa tgctggcag                                                 19

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cactttcata atgctggcag                                                20

<210> SEQ ID NO 26
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 26
cactttcata atgctggca                                                 19

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
tcactttcat aatgctggca                                                20

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
ctttcataat gctggc                                                    16

<210> SEQ ID NO 29
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 29
actttcataa tgctggc                                                   17

<210> SEQ ID NO 30
```

```
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 30
tcactttcat aatgctggc                                                   19

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
actttcataa tgctgg                                                      16

<210> SEQ ID NO 32
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 32
cactttcata atgctgg                                                     17

<210> SEQ ID NO 33
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 33
ttcactttca taatgctgg                                                   19

<210> SEQ ID NO 34
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 34
attcactttc ataatgctg                                                   19

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
agattcactt tcataatgct                                                  20

<210> SEQ ID NO 36
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 36
```

```
tcactttcat aatgctggt                                               19

<210> SEQ ID NO 37
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 37
tcactttcat aatgctgga                                               19

<210> SEQ ID NO 38
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: bases at these positions are RNA

<400> SEQUENCE: 38
tcactttcat aatgctggu                                               19

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
tcactttcat aatgctggaa                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
tcactttcat aatgctggat                                              20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tcactttcat aatgctggac                                              20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
tcactttcat aatgctggtc                                              20
```

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tcactttcat aatgctggtt                                              20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
tcactttcat aatgctggta                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tcactttcat aatgctggcc                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
tcactttcat aatgctggct                                              20

<210> SEQ ID NO 47
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 47
ctcactttca taatgctgg                                               19

<210> SEQ ID NO 48
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 48
atcactttca taatgctgg                                               19

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 49
gattcacttt cataatgctg                                          20
<210> SEQ ID NO 50
<211> LENGTH: 19
<212> TYPE: DNA
<213> ORGANISM: Artificial sequence
<220> FEATURE:
<223> OTHER INFORMATION: Synthetic oligonucleotide
<400> SEQUENCE: 50
gattcacttt cataatgct                                           19
```

COMPOUNDS AND METHODS FOR MODULATING SMN2

SEQUENCE LISTING

The present application is being filed along with a Sequence Listing in electronic format. The Sequence Listing is provided as a file entitled BIOL0367USC1SEQ_ST25.txt, created on Jun. 17, 2021 which is 44 KB in size. The information in the electronic format of the sequence listing is incorporated herein by reference in its entirety.

FIELD

Provided are compounds, methods, and pharmaceutical compositions for modulating SMN2 RNA in a cell or subject. Such compounds, methods, and pharmaceutical compositions are useful to ameliorate at least one symptom of a neurodegenerative disorder. Such symptoms include reduced muscle strength; inability or reduced ability to sit upright, to stand, and/or walk; reduced neuromuscular activity; reduced electrical activity in one or more muscles; reduced respiration; inability or reduced ability to eat, drink, and/or breathe without assistance; loss of weight or reduced weight gain; and/or decreased survival.

BACKGROUND

Proximal spinal muscular atrophy (SMA) is a genetic neurodegenerative disorder characterized by the loss of spinal motor neurons. SMA is an autosomal recessive disease of early onset and is a leading genetic cause of death among infants. The severity of SMA varies among patients and it has thus been classified into four types. Type I SMA is the most severe form with onset at birth or within 6 months, and typically results in death within 2 years. Children with Type I SMA are unable to sit or walk. Type II SMA is the intermediate form and patients are able to sit, but cannot stand or walk. Patients with Type III SMA, a chronic form of the disease, typically develop SMA after 18 months of age (Lefebvre et al., *Hum. Mol. Genet.,* 1998, 7, 1531-1536). Type IV SMA is a milder form and typically has an onset after 18 years of age, sometimes after 10 years of age; patients with Type IV SMA experience limited mild motor impairment, are able to walk in adulthood and generally do not have respiratory or nutritional problems (Farrar et al., *Ann. Neurol.,* 2017, 81, 355-368; D'Amico et al., *Orphanet J. of Rare Diseases,* 2011, 6:71).

The molecular basis of SMA is the loss of both copies of survival motor neuron gene 1 (SMN1), which may also be known as SMN Telomeric, and encodes a protein that is part of a multi-protein complex thought to be involved in snRNP biogenesis and recycling. A nearly identical gene, SMN2, which may also be known as SMN Centromeric, exists in a duplicated region on chromosome 5q13 and modulates disease severity. Although SMN1 and SMN2 have the potential to code for the same protein, expression of the normal SMN1 gene results solely in expression of full-length survival motor neuron (SMN) protein, while expression of the SMN2 gene results in two different protein forms, full-length SMN2 protein, and a truncated SMN2 protein, SMNΔ7 protein. SMN2 contains a translationally silent mutation at position +6 of exon 7, which results in inefficient inclusion of exon 7 in SMN2 transcripts. Thus, the predominant form of SMN2 is a truncated version, lacking exon 7, which is unstable and inactive (Cartegni and Krainer, Nat. Genet., 2002, 30, 377-384). Expression of the SMN2 gene results in approximately 10-20% of the full-length SMN protein and 80-90% of the unstable/non-functional SMNΔ7 protein. SMN protein plays a well-established role in assembly of the spliceosome and may also mediate mRNA trafficking in the axon and nerve terminus of neurons.

It is an object herein to provide compounds, methods, and pharmaceutical compositions for the treatment of SMA.

SUMMARY OF THE INVENTION

Provided herein are compounds, methods, and pharmaceutical compositions for modulating splicing of SMN2 RNA in a cell or subject. In certain embodiments, compounds useful for modulating splicing of SMN2 RNA are oligomeric compounds. In certain embodiments, oligomeric compounds increase the amount of SMN2 RNA including exon 7. In certain embodiments, oligomeric compounds increase full-length SMN2 protein expression. In certain embodiments, the oligomeric compound comprises a modified oligonucleotide. In certain embodiments, the subject has a neurodegenerative disease. In certain embodiments, the subject has Spinal Muscular Atrophy (SMA).

Also provided are methods useful for ameliorating at least one symptom of a neurodegenerative disease. In certain embodiments, the neurodegenerative disease is SMA. In certain embodiments, symptoms include reduced muscle strength; inability or reduced ability to sit upright, to stand, and/or walk; reduced neuromuscular activity; reduced electrical activity in one or more muscles; reduced respiration; inability or reduced ability to eat, drink, and/or breathe without assistance; loss of weight or reduced weight gain; and/or decreased survival. In certain embodiments, provided herein are modified oligonucleotides for treating SMA.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, and GenBank and NCBI reference sequence records are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

As used herein, "2'-deoxyribonucleoside" means a nucleoside comprising a 2'-H(H) deoxyribosyl sugar moiety. In certain embodiments, a 2'-deoxyribonucleoside is a 2'-β-D deoxyribonucleoside and comprises a 2'-β-D-deoxyribosyl sugar moiety, which has the β-D configuration as found in naturally occurring deoxyribonucleic acids (DNA). In certain embodiments, a 2'-deoxyribonucleoside may comprise a modified nucleobase or may comprise an RNA nucleobase (uracil).

As used herein, "2'-MOE" means a 2'-OCH$_2$CH$_2$OCH$_3$ group in place of the 2'-OH group of a ribosyl sugar moiety. A "2'-MOE sugar moiety" is a sugar moiety with a 2'-OCH$_2$CH$_2$OCH$_3$ group in place of the 2'-OH group of a ribosyl sugar moiety. Unless otherwise indicated, a 2'-MOE sugar moiety is in the β-D configuration. "MOE" means O-methoxyethyl.

As used herein, "2'-MOE nucleoside" means a nucleoside comprising a 2'-MOE sugar moiety.

As used herein, "2'-NMA" means a —O—CH$_2$—C(=O)—NH—CH$_3$ group in place of the 2'-OH group of a ribosyl sugar moiety. A "2'-NMA sugar moiety" is a sugar moiety with a 2'-O—CH$_2$—C(=O)—NH—CH$_3$ group in place of the 2'-OH group of a ribosyl sugar moiety. Unless otherwise indicated, a 2'-NMA sugar moiety is in the β-D configuration. "NMA" means 0-N-methyl acetamide.

As used herein, "2'-NMA nucleoside" means a nucleoside comprising a 2'-NMA sugar moiety.

As used herein, "2'-OMe" means a 2'-OCH$_3$ group in place of the 2'-OH group of a ribosyl sugar moiety. A "2'-OMe sugar moiety" is a sugar moiety with a 2'-OCH$_3$ group in place of the 2'-OH group of a ribosyl sugar moiety. Unless otherwise indicated, a 2'-OMe sugar moiety is in the β-D configuration. "OMe" means O-methyl.

As used herein, "2'-OMe nucleoside" means a nucleoside comprising a 2'-OMe sugar moiety. As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to a subject.

As used herein, "ameliorate" in reference to a treatment means improvement in at least one symptom relative to the same symptom in the absence of the treatment. In certain embodiments, amelioration is the reduction in the severity or frequency of a symptom, or the delayed onset or slowing of progression in the severity or frequency of a symptom. In certain embodiments, the symptom is reduced muscle strength; inability or reduced ability to sit upright, to stand, and/or walk; reduced neuromuscular activity; reduced electrical activity in one or more muscles; reduced respiration; inability or reduced ability to eat, drink, and/or breathe without assistance; loss of weight or reduced weight gain; and/or decreased survival.

As used herein, "antisense activity" means any detectable and/or measurable change attributable to the hybridization of an antisense compound to its target nucleic acid.

As used herein, "antisense compound" means an oligomeric compound or oligomeric duplex capable of achieving at least one antisense activity.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the furanosyl moiety is a ribosyl moiety. In certain embodiments, the bicyclic sugar moiety does not comprise a furanosyl moiety.

As used herein, "cerebrospinal fluid" or "CSF" means the fluid filling the space around the brain and spinal cord. "Artificial cerebrospinal fluid" or "aCSF" means a prepared or manufactured fluid that has certain properties of cerebrospinal fluid.

As used herein, "cEt" means a 4' to 2' bridge in place of the 2'OH-group of a ribosyl sugar moiety, wherein the bridge has the formula of 4'-CH(CH$_3$)—O-2', and wherein the methyl group of the bridge is in the S configuration. A "cEt sugar moiety" is a bicyclic sugar moiety with a 4' to 2' bridge in place of the 2'OH-group of a ribosyl sugar moiety, wherein the bridge has the formula of 4'-CH(CH$_3$)—O-2', and wherein the methyl group of the bridge is in the S configuration. "cEt" means constrained ethyl.

As used herein, "cEt nucleoside" means a nucleoside comprising a cEt sugar moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "complementary" in reference to an oligonucleotide means that at least 70% of the nucleobases of the oligonucleotide or one or more portions thereof and the nucleobases of another nucleic acid or one or more portions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) with thymine (T), adenine (A) with uracil (U), cytosine (C) with guanine (G), and 5-methyl cytosine (mC) with guanine (G). Complementary oligonucleotides and/or target nucleic acids need not have nucleobase complementarity at each nucleoside. Rather, some mismatches are tolerated. As used herein, "fully complementary" or "100% complementary" in reference to an oligonucleotide, or a portion thereof, means that the oligonucleotide, or portion thereof, is complementary to another oligonucleotide or target nucleic acid at each nucleobase of the shorter of the two oligonucleotides, or at each nucleoside if the oligonucleotides are the same length.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "internucleoside linkage" means the covalent linkage between contiguous nucleosides in an oligonucleotide. As used herein, "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "motif" means the pattern of unmodified and/or modified sugar moieties, nucleobases, and/or internucleoside linkages, in an oligonucleotide.

As used herein, "non-bicyclic modified sugar moiety" means a modified sugar moiety that comprises a modification, such as a substituent, that does not form a bridge between two atoms of the sugar to form a second ring.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a target nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutical composition" means a mixture of substances suitable for administering to a subject. For example, a pharmaceutical composition may comprise an oligomeric compound and a sterile aqueous solution.

As used herein, "pharmaceutically acceptable carrier or diluent" means any substance suitable for use in administering to a subject. Certain such carriers enable pharmaceutical compositions to be formulated as, for example, tablets, pills, dragees, capsules, liquids, gels, syrups, slurries, suspension, and lozenges for the oral ingestion by a subject. In certain embodiments, a pharmaceutically acceptable carrier or diluent is sterile water, sterile saline, sterile buffer solution, or sterile artificial cerebrospinal fluid.

As used herein, "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein, "RNA" means an RNA transcript and includes pre-mRNA and mature mRNA unless otherwise specified.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "subject" means a human or non-human animal. As used herein, "sugar moiety" means an unmodified sugar moiety or a modified sugar moiety. As used herein, "unmodified sugar moiety" means a 2'-OH(H) β-D ribosyl moiety, as found in RNA (an "unmodified RNA sugar moiety"), or a 2'-H(H) β-D deoxyribosyl moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "standard in vivo assay" means the assay described in Example 2 and reasonable variations thereof.

As used herein, "symptom" means any physical feature or test result that indicates the existence or extent of a disease or disorder. In certain embodiments, a symptom is apparent to a subject or to a medical professional examining or testing the subject.

As used herein, "target nucleic acid" means a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to a subject. For example, a therapeutically effective amount improves a symptom of a disease.

CERTAIN EMBODIMENTS

The present disclosure provides the following non-limiting numbered embodiments:

Embodiment 1. An oligomeric compound comprising a modified oligonucleotide consisting of 16, 17, 18, 19, or 20 linked nucleosides and having a nucleobase sequence comprising at least 15 or at least 16 contiguous nucleobases of any of the nucleobase sequences of SEQ ID NOs: 20-50, wherein the modified oligonucleotide comprises at least one modification selected from a modified sugar moiety and a modified internucleoside linkage.

Embodiment 2. An oligomeric compound comprising a modified oligonucleotide consisting of 17, 18, 19, or 20 linked nucleosides and having a nucleobase sequence comprising at least 15, at least 16, or at least 17 contiguous nucleobases of any of the nucleobase sequences of SEQ ID NOs: 20-27, 29-30, or 32-50, wherein the modified oligonucleotide comprises at least one modification selected from a modified sugar moiety and a modified internucleoside linkage.

Embodiment 3. An oligomeric compound comprising a modified oligonucleotide consisting of 18, 19, or 20 linked nucleosides and having a nucleobase sequence comprising at least 15, at least 16, or at least 17, or at least 18 contiguous nucleobases of any of the nucleobase sequences of SEQ ID NOs: 20-27, 30, or 33-50, wherein the modified oligonucleotide comprises at least one modification selected from a modified sugar moiety and a modified internucleoside linkage.

Embodiment 4. An oligomeric compound comprising a modified oligonucleotide consisting of 19 or 20 linked nucleosides and having a nucleobase sequence comprising at least 15, at least 16, or at least 17, at least 18, or at least 19 contiguous nucleobases of any of the nucleobase sequences of SEQ ID NOs: 20, 22, 24-27, 30, 33-50, wherein the modified oligonucleotide comprises at least one modification selected from a modified sugar moiety and a modified internucleoside linkage.

Embodiment 5. An oligomeric compound comprising a modified oligonucleotide consisting of 20 linked nucleosides and having a nucleobase sequence comprising at least 15, at least 16, or at least 17, at least 18, at least 19, or at least 20 contiguous nucleobases of any of the nucleobase sequences of SEQ ID NOs: 20, 22, 25, 27, 35, 39-46, or 49, wherein the modified oligonucleotide comprises at least one modification selected from a modified sugar moiety and a modified internucleoside linkage.

Embodiment 6. The oligomeric compound of any of embodiments 1-5, wherein the modified oligonucleotide has a nucleobase sequence that is at least 80%, 85%, 87.5%, 88.2%, 89%, 89.4%, 90%, 93.7%, 94%, 94.7%, 95%, or is 100% complementary to the nucleobase sequence of SEQ ID NO: 1 when measured across the entire nucleobase sequence of the modified oligonucleotide.

Embodiment 7. The oligomeric compound of any of embodiments 1-6, wherein the modified oligonucleotide has an internucleoside linkage motif (5' to 3') selected from:

```
sosossssssssssss, ssosssssssssssoss, ssossssosssssoss, ssosssosssosssoss, soossssssssssooss, soooosssssssssooss, soooossssssssooosss, ssssssooosssssss, ssosssssssssssss, sssssosssssssssss, sssssssossssssss, sssssssosssssss, sssssssssossssss, sssssssssssossss, ssssssssssssoss, sosssssssssssoss, sossssssssssosss, sossssssosssssss, sossssosssssssss, sosssosssssssss, ssssosssssssssoss, sssssossssssoss, sssssssossssoss, sssssssssossoss, sssssssssssososs, soosssssssssssss, ssssooossssssssss, sssssoosssssssss, sssssssoossssssss, ssssssssoossssss, ssssssssssooosss, ssssssssssssooss, ssssssssooossssss, ssoooossssssssss, sssssoooossssssss, sssssssoooossssss, sssssssssooooss, sssssssssooooss, sssssoooooossssss, sssssssoooooossss, soooossssssoooss, sssssooooooosssss, sssssssssssssoss, sssssssssssossss, sssssssssssooss, sssssssssssososs, sssssssssssosssss, sssssssssosossss, sssssssssossossss, sssssssssosssssss, sssssssssossosss, sssssssssosssss, sssssssssosssossss, sssssssssossssss, sssssssssoossssss, sssssossssssssss, ssssossssssssss, sossssssssssssss, sossssssossssssss, soossssssssssss, osssssssssssssso, ssssssssssssssss, sssssssssssssoss, sssssssssssssooss, sssssssssssosss, sssssssssosssssss, sssssssssosssssos, sssssssoossssssss, sosssssssssssssss, sossssssssssssoss, sossssssosssssss, sosossssssssssss, sooosssssssssss, sssssssssssssss, sssssssssssssso, osssssssssssssss,
``` ssssssssssssosssso, sssssssssssssssoss, sssssssssssssososs, sssssssosssssssss, sssssssosssssssoss, sosssssssssssssss, sosssssssssssssoss, sosssssosssssssss, sosossssssssssssss, sssssssssoooosss, ssssssssooossss, sssssssooossssss, ssssssoooossssss, ssssssooooossssss, ssssso ooooosssss, sssso oooooosss, sssooooossssssss, sossssssssssoss, ssosssssosssoss, ssosssossssosss, ssosossosssosss, ssososososososs, ssooossssssssss, soosssssssssooss, sooossssssssooss, sooosssssssooss, soooossssssooss, sssssssssoooss, ssssssssoooosss, ssssssooosssss, sssssoooossss, ssssoooosssss, ssssooooosss, sssooooosssss, sssoooooooss, ssssossosssosss, ssosssssssssoss, ssosssossossosss, ssosssososososs, ssososososososs, ssooossssssss, sooosssssssooss, sooosssssssooss, sooossssssooooss,
and sooooosssssooss;

wherein 's' represents a phosphorothioate internucleoside linkage and 'o' represents a phosphodiester internucleoside linkage.

Embodiment 8. The oligomeric compound of any of embodiments 1-6, wherein the modified oligonucleotide has an internucleoside linkage motif selected from: ssssssssssssssxs and sssssssssssssssx, wherein 's' represents a phosphorothioate internucleoside linkage, 'o' represents a phosphodiester internucleoside linkage, and "x" represents a methoxypropylphosphonate internucleoside linkage.

Embodiment 9. The oligomeric compound of any of embodiments 1-6, wherein the modified oligonucleotide has an internucleoside linkage motif selected from zzzzzzzzzzzzzzzz, sssssssssssszzzzz, ssssszzzzzzsssss, zzoooooooooooozz, zzzzooooooooozz, zzzzz-zoooooooozz, zzzzzzzzooooooozz, and ssoooooooooooooss, wherein 's' represents a phosphorothioate internucleoside linkage, 'o' represents a phosphodiester internucleoside linkage, and "z" represents a mesyl phosphoramidate internucleoside linkage.

Embodiment 10. The oligomeric compound of any of embodiments 1-9, wherein the modified oligonucleotide has a sugar motif (5' to 3') selected from:

eeeeeeeeeeeeeeeeee, eeeeeeeeeeeeeeeee, eeeeeeeeeeeeeeeee, eeeeeeeeeeeeeeee, eeeeeeeeeeeeeee, nnnnnnnnnnnnnnn, nnnnnnnnnnnnnnnn, nnnnnnnnnnnnnnnn, nnnnnnnnnnnnnnnnnn, nnnnnnnnnnnnnnnnnnn, nennnnneneennnnnn, nnnnnnnnnnnenneen, nennnneneenenneen, nnnnnnnnnnnnnnnne, nnnnnnnnnnnnnnnnd, nnnnnnnnnnnnnnnny, nnnnnnnnnnnnnnnndd, nnnnnnnnnnnnnnnned, nnnnnnnnnnnnnnnnde, nnnnnnnnnnnnnnnnee, eeeeeeeeeeeeeeedd, eeeeeeeeeeeeeeeed, eeeeeeeeeeeeeeede, nnnnnnnnnnnnnnnnd, nnnnnnnnnnnnnnnne, eeeeeeeeeeeeeeeed, keekeekeekeekeeeek, keeekeeekeeekeeeek, keeeeekeeeekeeeek, keeeeeeekeeeeeeek, keeeeeeeeeeeeeeek, eekeekeekeekeekek, eekeekeekeekeekee, eeeeeekeekeekeekee, eeeeeekeekeeeee, eeeeeekeeeekeeee, keekeekeekeeeeeee, eeeeeeeekeekeekeek, keekeekeeeeeeeeee, eeeeeeeeeekeekeek, keekeeeeeeeeeeee, eeeeeeeeeeeeekeek, keekeekeekeekeeck, keeekeeekeeekeeek, keeeekeeeekeeeek, keeeeeeekeeeeeek, keeeeeeeeeeeeeeek, eekeekeekeekeekek, eekeekeekeekeekee, eeeeekeekeekeekee, eeeeekeekeekeeeee, eeeeekeeeeekeeee, keekeekeekeeeeee, eeeeeekeekeekeek, keekeeeeeeeeeek, eeeeeeeeekeekeek, keekeeeeeeeeeeee, eeeeeeeeeekeek, keekeekeekeekeek, keekeeekeeekeek, keeeekeeeekeeeek, keeeeeeekeeeeek, keeeeeeeeeeeek, kekeekeekeekeeke, eekeekeekeekeeke, eeeeekeekeekeeke, eeeeekeekeekeeee, eeeeekeeeekeeee, keekeekeekeeeee, eeeeeekeekeekeek, keekeekeeeeeeeee, eeeeeeeekeekeek, keekeeeeeeeeee, eeeeeeeeeekeek, eeeeeeeeeeeeeeed, eeeeeeeeeeeeeeey, ennnnnnnnnnnnnnnn,
and ennnnnnnnnnnnnnnne;

wherein 'e' represents a 2'-MOE sugar moiety, 'n' represents a 2'-NMA sugar moiety, 'k' represents a cEt sugar moiety, 'd' represents a 2'β-D-deoxyribosyl sugar moiety, and 'y' represents a 2'-OMe sugar moiety.

Embodiment 11. The oligomeric compound of any of embodiments 1-9, wherein the modified oligonucleotide has a sugar motif (5' to 3') selected from nnnnnnnnnnnnnnnenn and nnnnnnnnnnnnnnnen, wherein 'e' represents a 2'-MOE sugar moiety and 'n' represents a 2'-NMA sugar moiety.

Embodiment 12. The oligomeric compound of any of embodiments 1-9, wherein the modified oligonucleotide has a sugar motif (5' to 3') of qqnqqqqqnqnnqnqqnn wherein in each 'n' represents a 2'-NMA sugar moiety, and each 'q' is independently selected from a 2'-O—(N,N-dimethyl) acetamide sugar moiety, a 2'-O—(N-ethyl) acetamide sugar moiety, a 2'-O—(N-propyl) acetamide sugar moiety, a 2'O—(N-cyclopropyl) acetamide sugar moiety, and a 2'-O—(N-cyclopropylmethyl) acetamide sugar moiety.

Embodiment 13. The oligomeric compound of any of embodiments 1-9, wherein the modified oligonucleotide comprises at least one modified sugar moiety.

Embodiment 14. The oligomeric compound of embodiment 13, wherein the modified oligonucleotide comprises at least one bicyclic sugar moiety.

Embodiment 15. The oligomeric compound of embodiment 14, wherein the bicyclic sugar moiety has a 4'-2' bridge, wherein the 4'-2' bridge is selected from —CH$_2$—O—; and —CH(CH$_3$)—O—.

Embodiment 16. The oligomeric compound of embodiment 13, wherein the modified oligonucleotide comprises at least one non-bicyclic modified sugar moiety.

Embodiment 17. The oligomeric compound of embodiment 16, wherein the non-bicyclic modified sugar moiety is any of a 2'-MOE sugar moiety, a 2'-NMA sugar moiety, a 2'-OMe sugar moiety, or a 2'-F sugar moiety.

Embodiment 18. The oligomeric compound of embodiment 13, wherein the modified oligonucleotide comprises at least one sugar surrogate.

Embodiment 19. The oligomeric compound of embodiment 18, wherein the sugar surrogate is any of morpholino, modified morpholino, PNA, THP, and F-HNA.

Embodiment 20. The oligomeric compound of any of embodiments 1-6 and 10-19, wherein the modified oligonucleotide comprises at least one modified internucleoside linkage.

Embodiment 21. The oligomeric compound of embodiment 20, wherein each internucleoside linkage of the modified oligonucleotide is a modified internucleoside linkage.

Embodiment 22. The oligomeric compound of embodiment 20 or embodiment 21, wherein the modified internucleoside linkage is a phosphorothioate internucleoside linkage.

Embodiment 23. The oligomeric compound of any of embodiments 1-20 or 22, wherein the modified oligonucleotide comprises at least one phosphodiester internucleoside linkage.

Embodiment 24. The oligomeric compound of any of embodiments 20, 22, or 23, wherein each internucleoside linkage is independently selected from a phosphodiester internucleoside linkage and a phosphorothioate internucleoside linkage.

Embodiment 25. The oligomeric compound of any of embodiments 13-19, wherein the modified oligonucleotide has an internucleoside linkage motif (5' to 3') selected from:

sosossssssssssss, sooss ssssssssssss,
sosssosssssssss, sosssssosssssss,
sosssssssosssssss, sssoossssssssss,
sssssssooss ssssss, ssssssssssooss ssss,
and
ssssssssssooss sss;

wherein 's' represents a phosphorothioate internucleoside linkage and 'o' represents a phosphodiester internucleoside linkage.

Embodiment 26. The oligomeric compound of any of embodiments 1-25, wherein the modified oligonucleotide comprises a modified nucleobase.

Embodiment 27. The oligomeric compound of embodiment 26, wherein the modified nucleobase is a 5-methyl cytosine.

Embodiment 28. The oligomeric compound of any of embodiments 1-27, wherein the modified oligonucleotide consists of 16, 17, 18, 19, or 20 linked nucleosides.

Embodiment 29. The oligomeric compound of any of embodiments 1-28, wherein the modified oligonucleotide comprises 1 or 2 non-complementary nucleobases.

Embodiment 30. The oligomeric compound of any of embodiments 1-29, wherein the modified oligonucleotide comprises 1 or 2 cleavable moieties.

Embodiment 31. The oligomeric compound of embodiment 30, wherein the cleavable moiety is a phophodiester internucleoside linkage.

Embodiment 32. The oligomeric compound of any of embodiments 1-31, consisting of the modified oligonucleotide.

Embodiment 33. The oligomeric compound of any of embodiments 1-32, wherein the oligomeric compound is a singled-stranded oligomeric compound.

Embodiment 34. An oligomeric compound comprising a modified oligonucleotide according to the following chemical notation: $^mC_{es} A_{eo} {}^mC_{es} T_{eo} T_{es} T_{es} {}^mC_{es} A_{es} T_{es} A_{es} A_{es} T_{es} G_{es} {}^mC_{es} T_{es} G_{es} G_{es} {}^mC_e$ (SEQ ID NO: 21), wherein:
A=an adenine nucleobase,
$^mC$=a 5-methyl cytosine nucleobase,
G=a guanine nucleobase,
T=a thymine nucleobase,
e=a 2'-MOE sugar moiety,
s=a phosphorothioate internucleoside linkage, and
o=a phosphodiester internucleoside linkage.

Embodiment 35. An oligomeric compound comprising a modified oligonucleotide according to the following chemical notation: $T_{eo} T_{es} {}^mC_{es} A_{es} {}^mC_{es} T_{es} T_{es} T_{es} {}^mC_{es} A_{es} T_{es} A_{es} A_{es} T_{es} G_{es} {}^mC_{es} T_{es} G_{es} G_{eo} {}^mC_e$ (SEQ ID NO: 22), wherein:
A=an adenine nucleobase,
$^mC$=a 5-methyl cytosine nucleobase,
G=a guanine nucleobase,
T=a thymine nucleobase,
e=a 2'-MOE sugar moiety,
s=a phosphorothioate internucleoside linkage, and
o=a phosphodiester internucleoside linkage.

Embodiment 36. An oligomeric compound comprising a modified oligonucleotide according to the following chemical notation: $T_{eo} T_{ns} {}^mC_{ns} A_{ns} {}^mC_{ns} T_{ns} T_{ns} T_{ns} {}^mC_{ns} A_{ns} T_{ns} A_{ns} A_{ns} T_{ns} G_{ns} {}^mC_{ns} T_{ns} G_{ns} G_{no} {}^mC_e$ (SEQ ID NO: 22), wherein:
A=an adenine nucleobase,
$^mC$=a 5-methyl cytosine nucleobase,
G=a guanine nucleobase,
T=a thymine nucleobase, e=a 2′-MOE sugar moiety,
n=a 2′-NMA sugar moiety,
s=a phosphorothioate internucleoside linkage, and
o=a phosphodiester internucleoside linkage.

Embodiment 37. An oligomeric compound comprising a modified oligonucleotide according to the following chemical notation: $^mC_{ns}A_{no}{}^mC_{ns}T_{no}T_{ns}T_{ns}{}^mC_{ns}A_{ns}T_{ns}A_{ns}A_{ns}T_{ns}G_{ns}{}^mC_{ns}T_{ns}G_{ns}G_{ns}{}^mC_n$ (SEQ ID NO: 21), wherein:

A=an adenine nucleobase,
$^mC$=a 5-methyl cytosine nucleobase,
G=a guanine nucleobase,
T=a thymine nucleobase,
n=a 2′-NMA sugar moiety,
s=a phosphorothioate internucleoside linkage, and
o=a phosphodiester internucleoside linkage.

Embodiment 38. A modified oligonucleotide according to the following chemical structure:

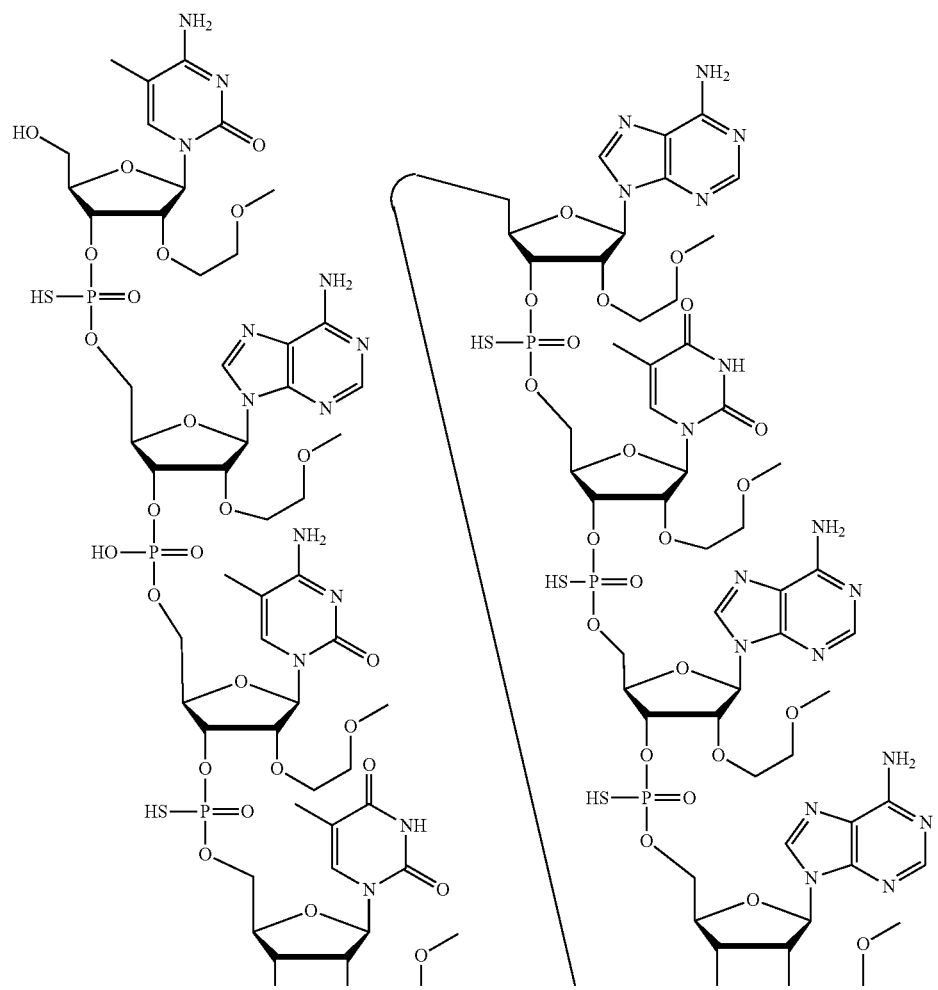

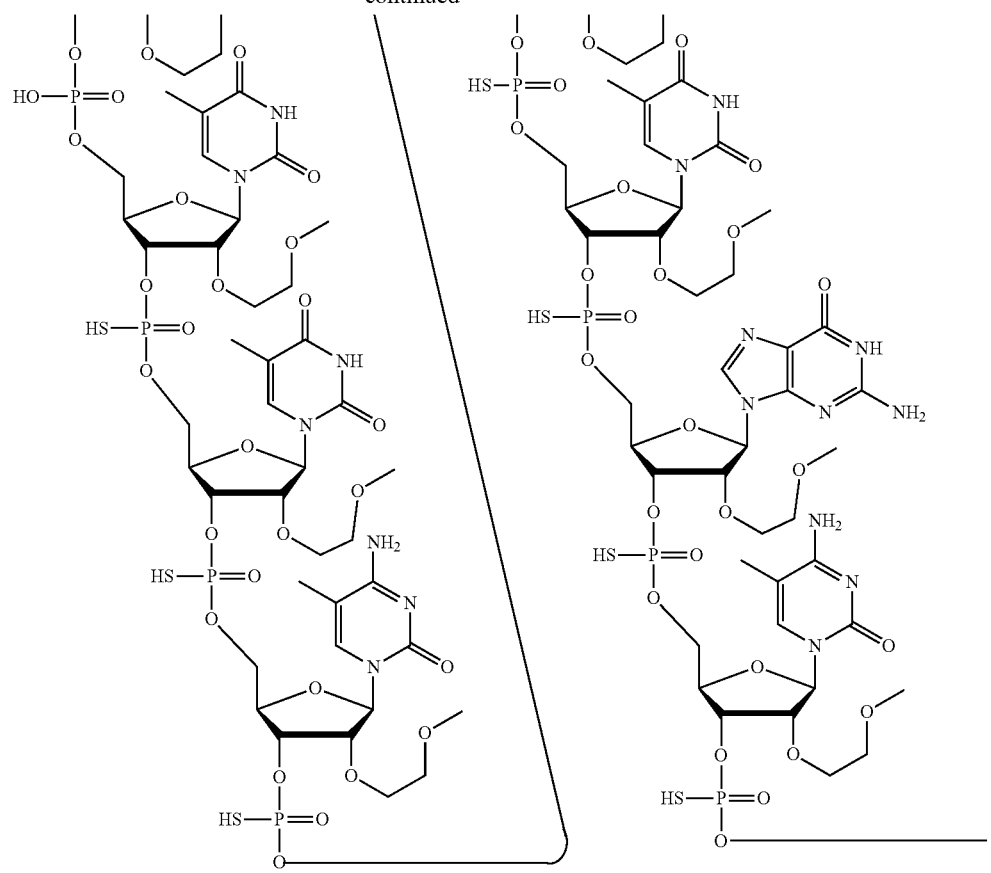
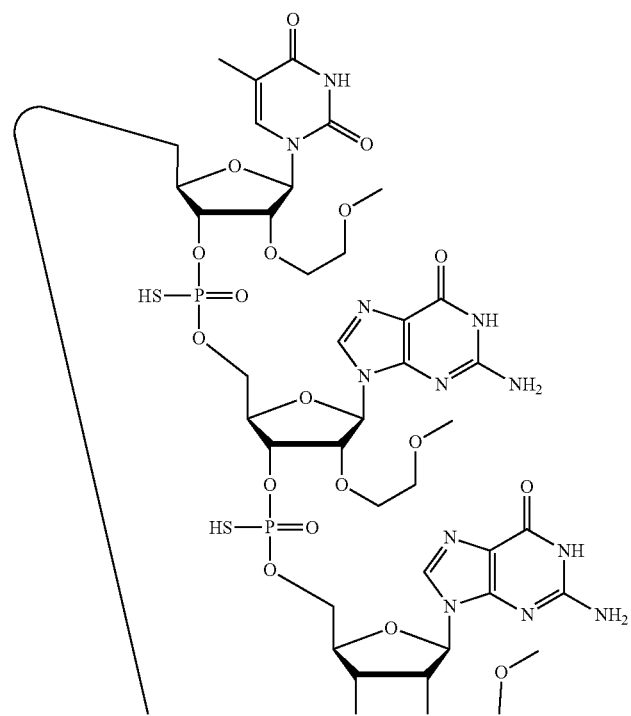

-continued
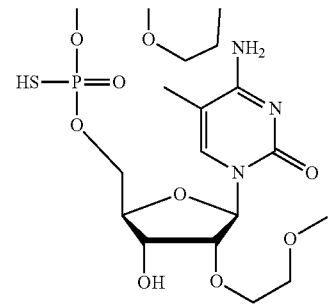
(SEQ ID NO: 21), or a salt thereof.
Embodiment 39. The modified oligonucleotide of embodiment 38, which is the sodium salt or the potassium salt.
Embodiment 40. A modified oligonucleotide according to the following chemical structure:
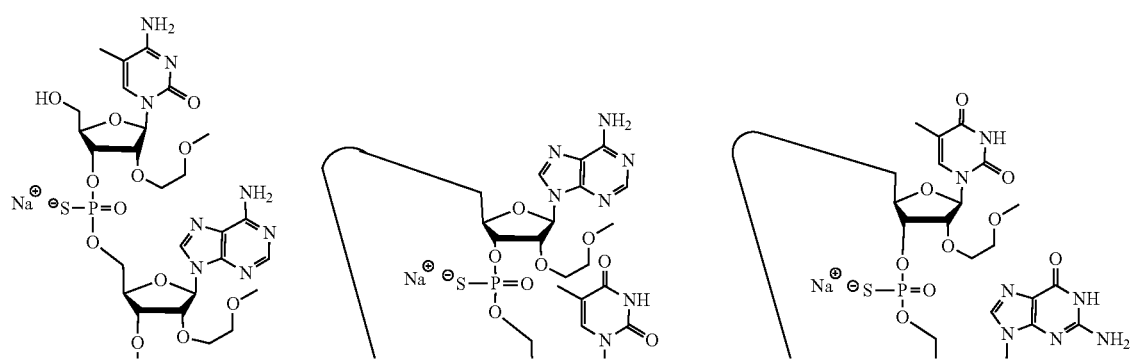

19
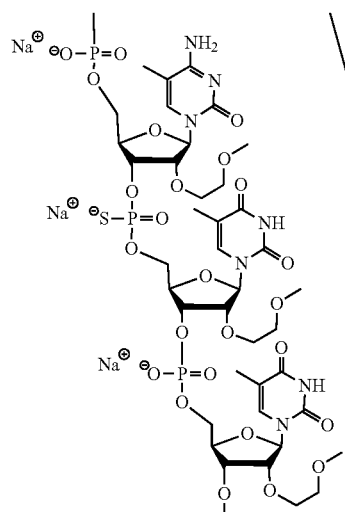
20
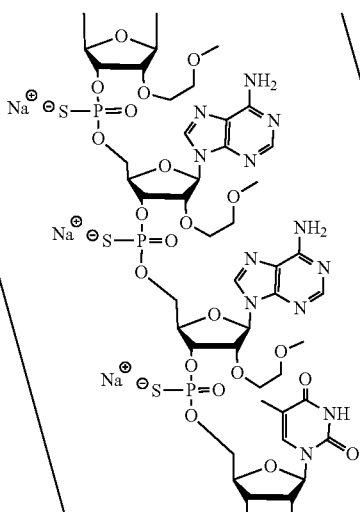
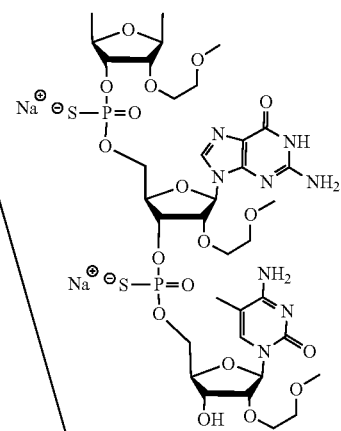
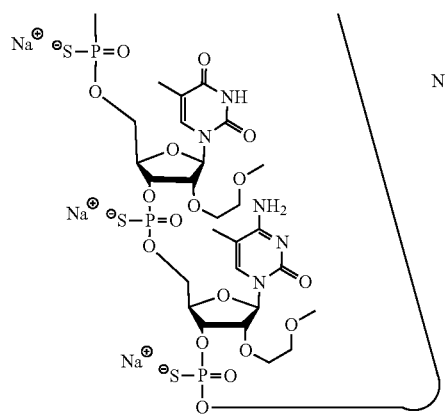
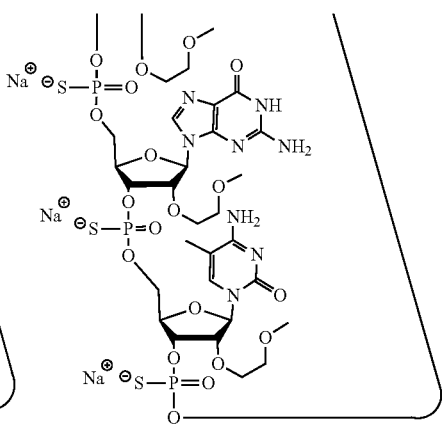
(SEQ ID NO: 21).

Embodiment 41. A modified oligonucleotide according to the following chemical structure:
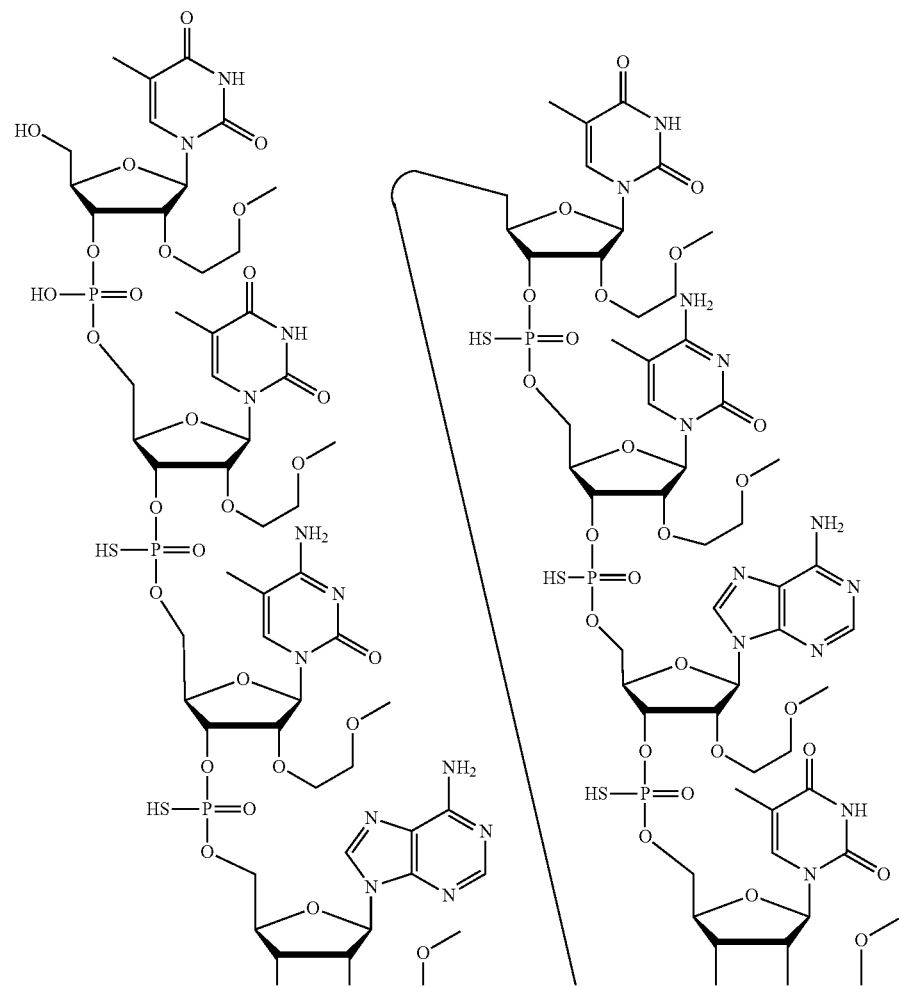

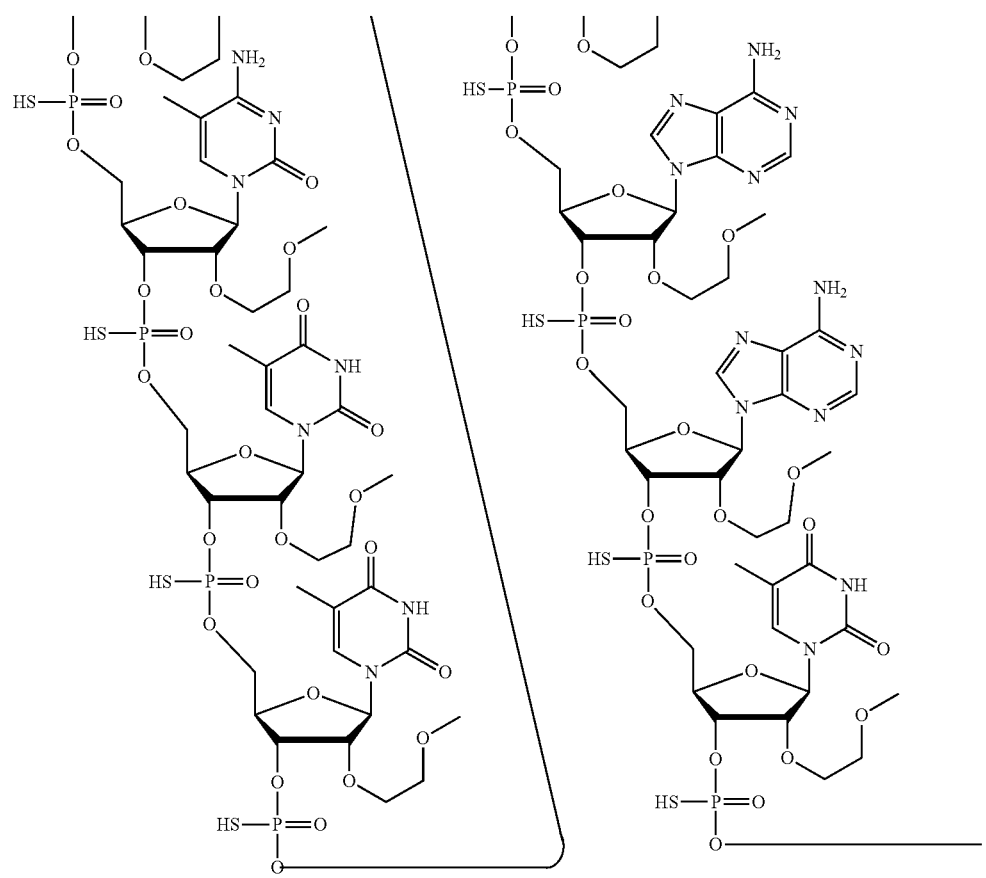

-continued
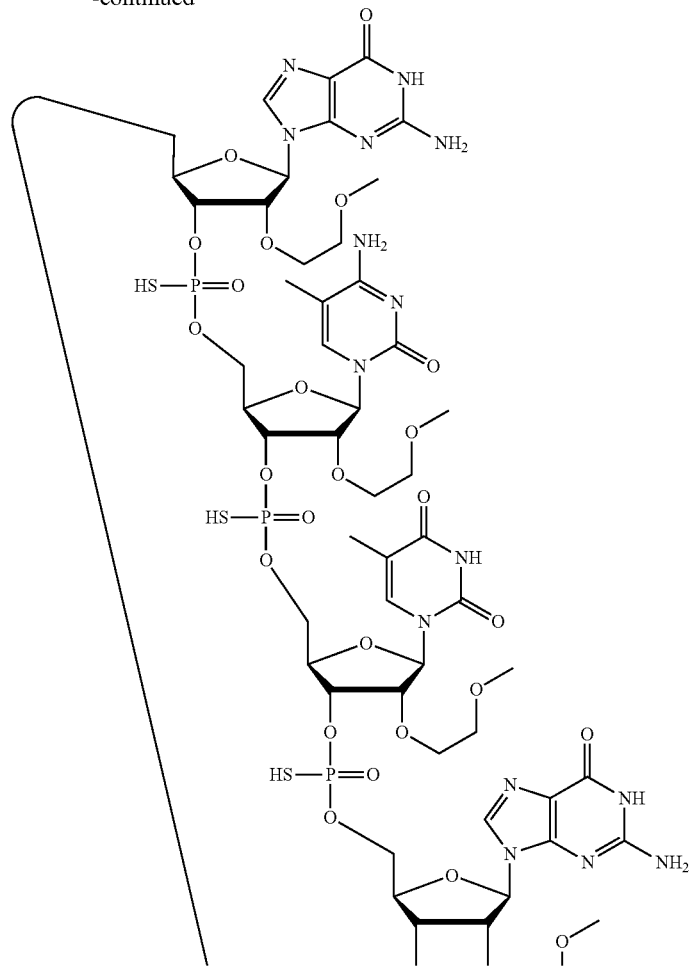
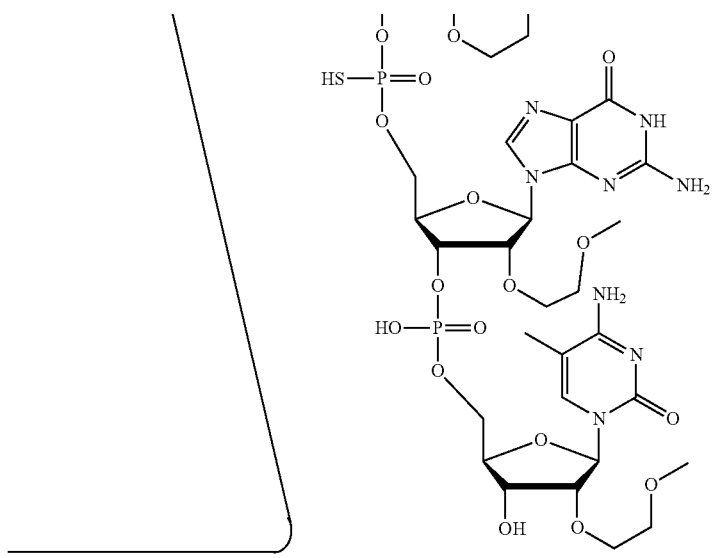
(SEQ ID NO: 22), or a salt thereof.

Embodiment 42. The modified oligonucleotide of embodiment 41, which is the sodium salt or the potassium salt.
Embodiment 43. A modified oligonucleotide according to the following chemical structure:
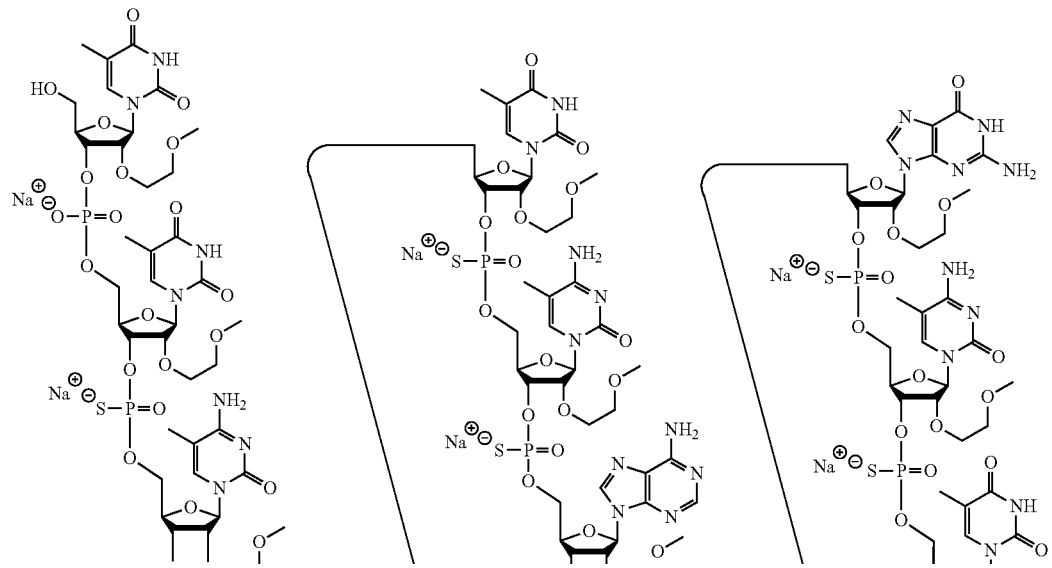
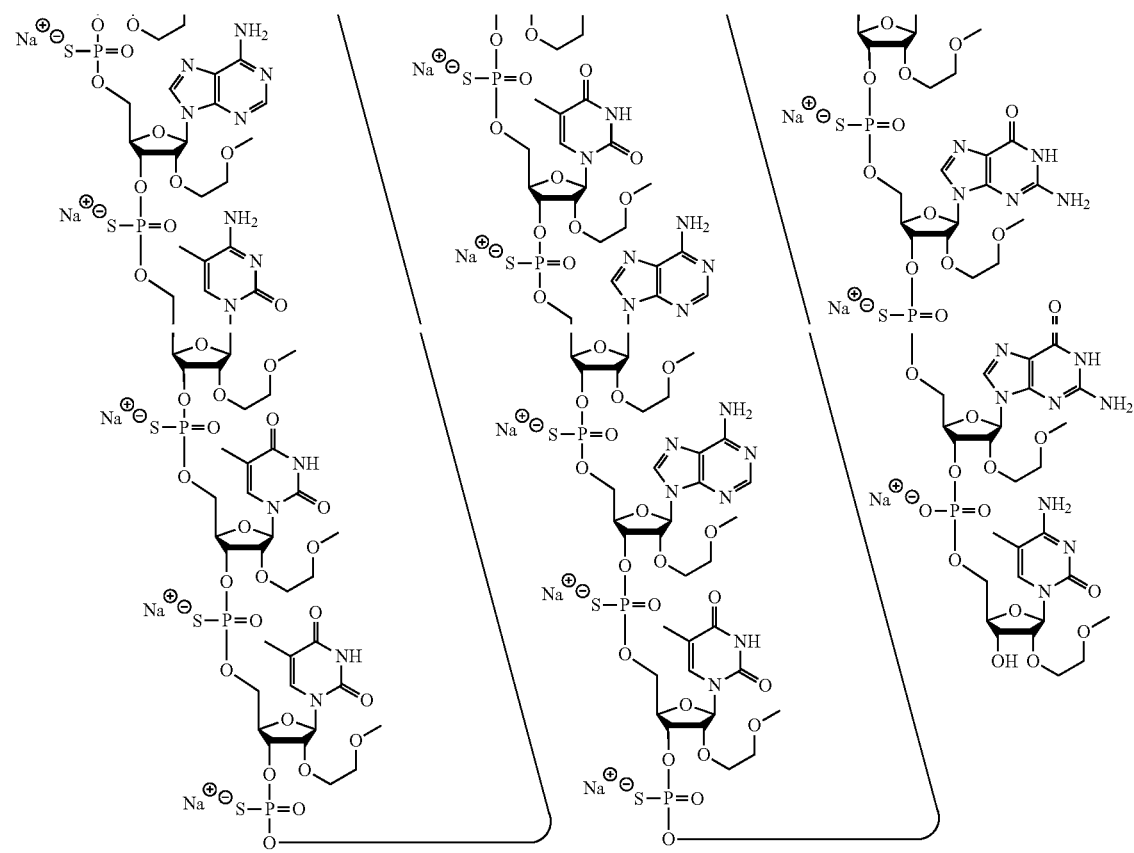
(SEQ ID NO: 22).

Embodiment 44. A modified oligonucleotide according to the following chemical structure:
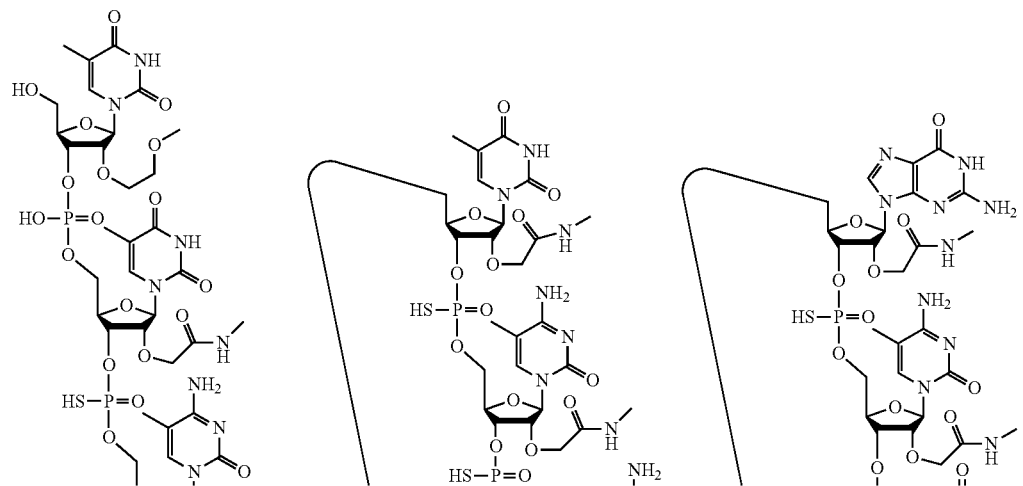
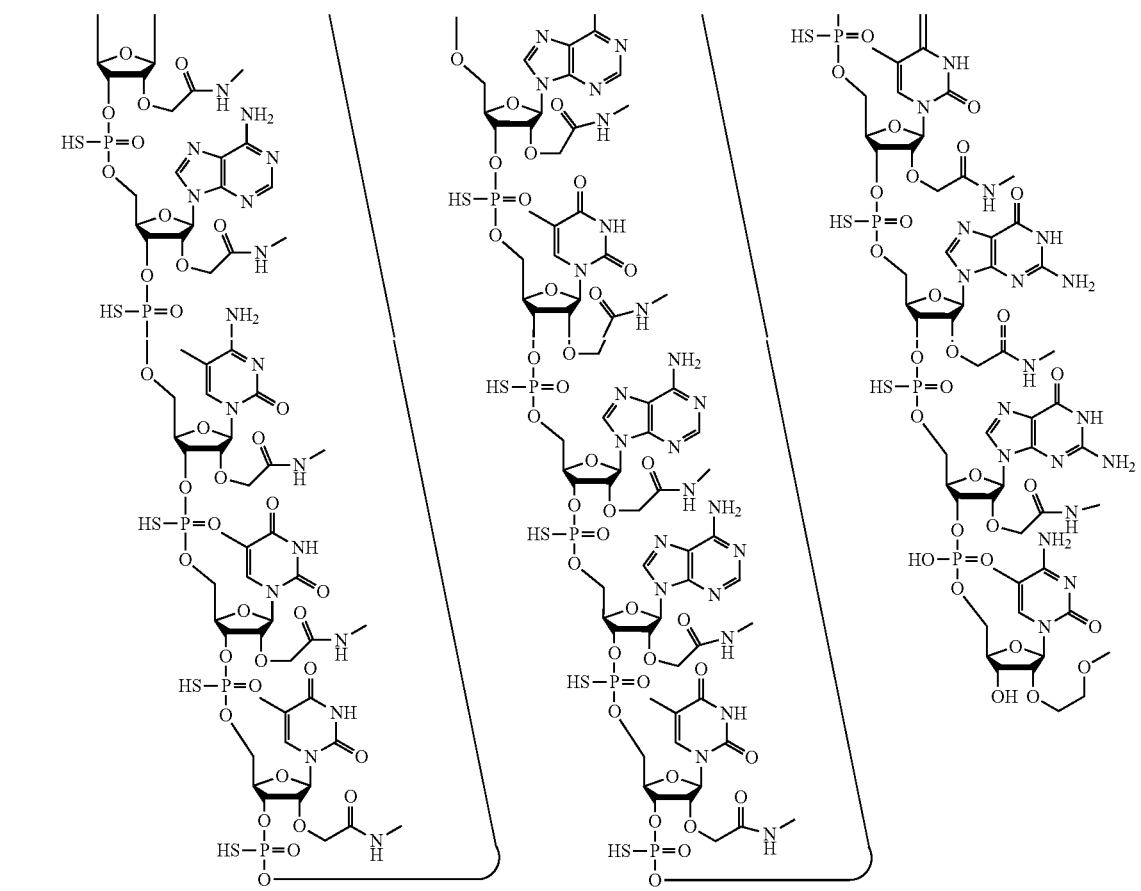
(SEQ ID NO: 22), or a salt thereof.

Embodiment 45. The modified oligonucleotide of embodiment 44, which is the sodium salt or the potassium salt.
Embodiment 46. A modified oligonucleotide corresponding to the following chemical structure:
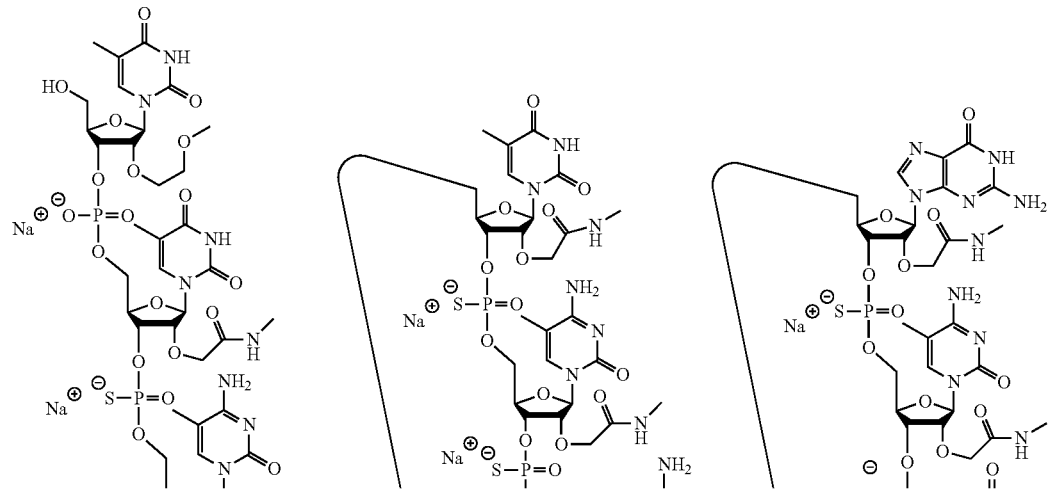
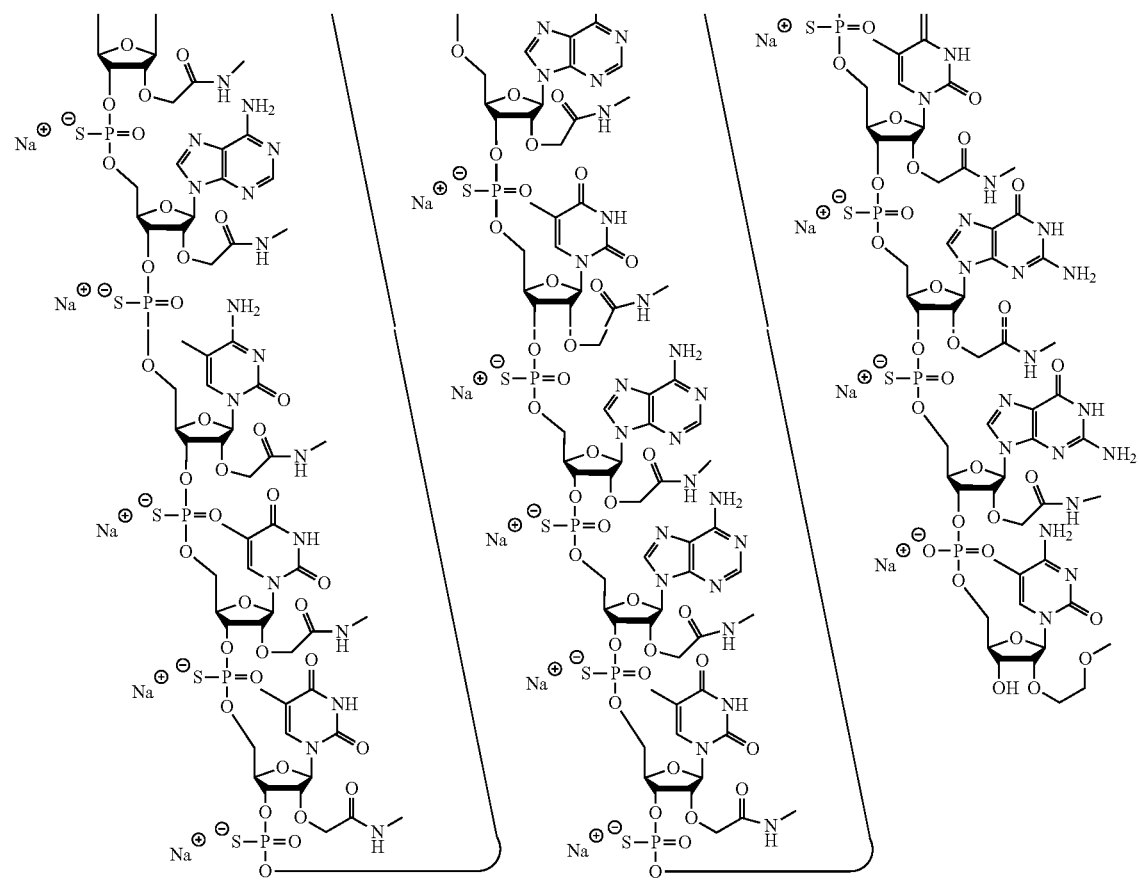
(SEQ ID NO: 22).

Embodiment 47. A modified oligonucleotide according to the following chemical structure:
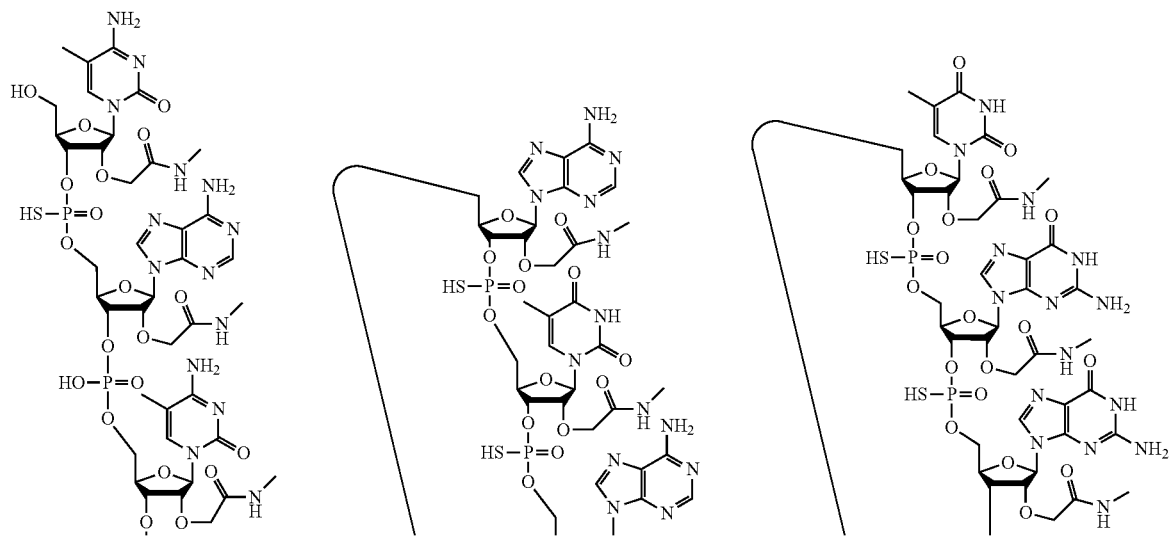
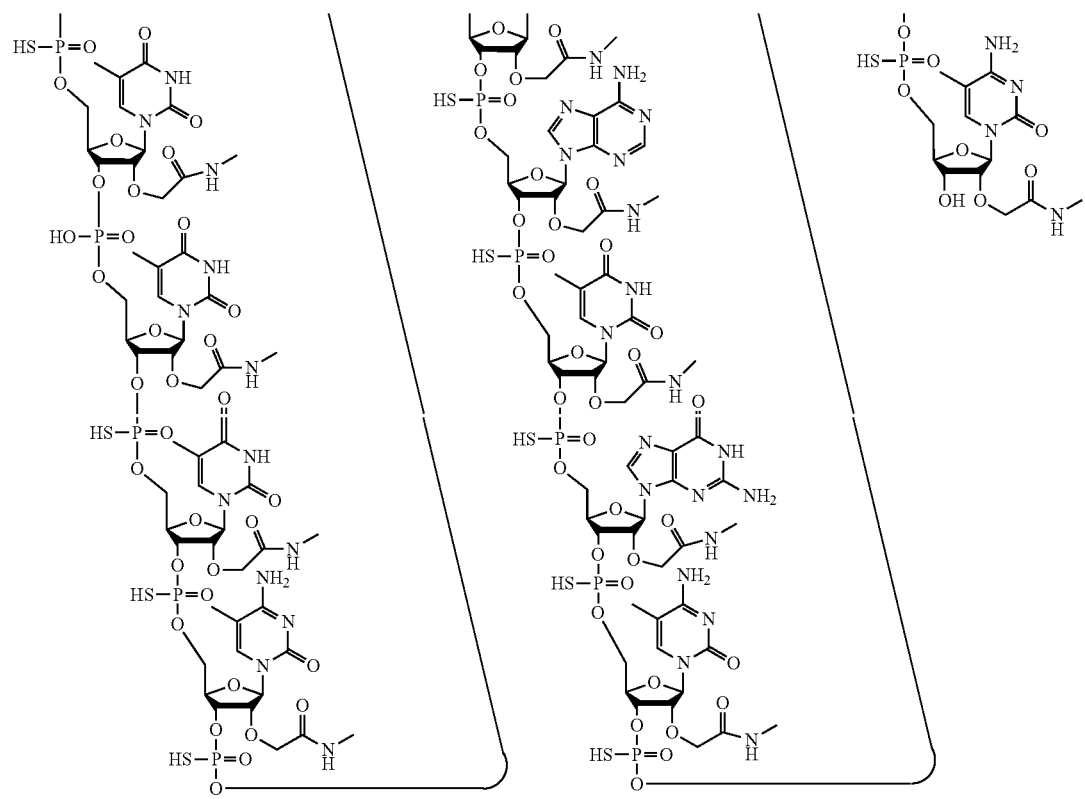
(SEQ ID NO: 21), or a salt thereof.

Embodiment 48. The modified oligonucleotide of embodiment 47, which is the sodium salt or the potassium salt.

Embodiment 49. A modified oligonucleotide according to the following chemical structure:

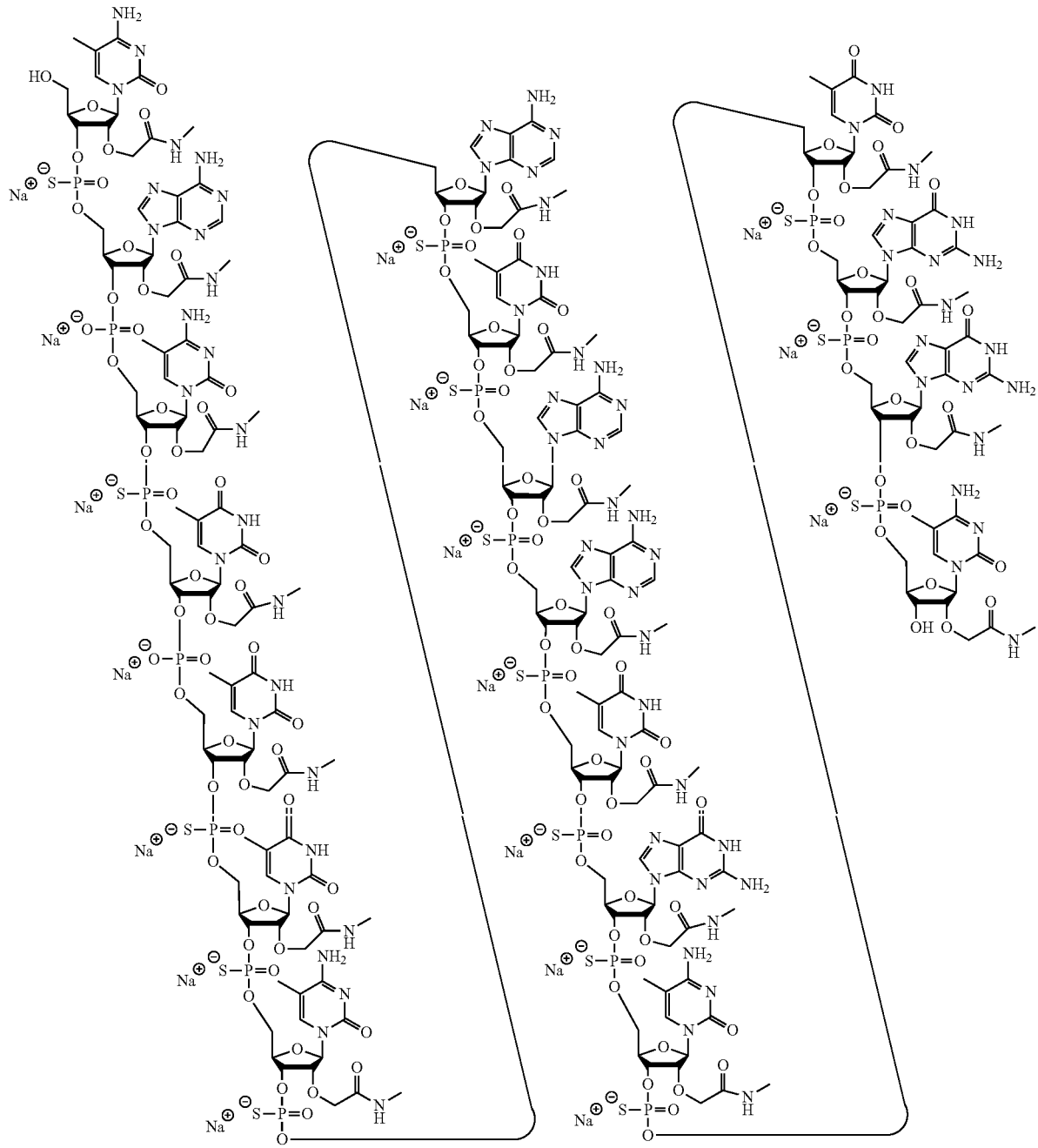

(SEQ ID NO: 21).

Embodiment 50. A pharmaceutical composition comprising the oligomeric compound of any of embodiments 1-36 or the modified oligonucleotide of any of embodiments 38-49, and a pharmaceutically acceptable diluent or carrier.

Embodiment 51. The pharmaceutical composition of embodiment 50, comprising a pharmaceutically acceptable diluent and wherein the pharmaceutically acceptable diluent is artificial CSF (aCSF) or PBS.

Embodiment 52. The pharmaceutical composition of embodiment 51, wherein the pharmaceutical composition consists essentially of the modified oligonucleotide and artificial CSF (aCSF).

Embodiment 53. The pharmaceutical composition of embodiment 51, wherein the pharmaceutical composition consists essentially of the modified oligonucleotide and PBS.

Embodiment 54. A chirally enriched population of modified oligonucleotides of any of embodiments 38-49, wherein the population is enriched for modified oligonucleotides comprising at least one particular phosphorothioate internucleoside linkage having a particular stereochemical configuration.

Embodiment 55. The chirally enriched population of embodiment 54, wherein the population is enriched for modified oligonucleotides comprising at least one particular phosphorothioate internucleoside linkage having the (Sp) configuration.

Embodiment 56. The chirally enriched population of embodiment 54, wherein the population is enriched for modified oligonucleotides comprising at least one particular phosphorothioate internucleoside linkage having the (Rp) configuration.

Embodiment 57. The chirally enriched population of embodiment 54, wherein the population is enriched for modified oligonucleotides having a particular, independently selected stereochemical configuration at each phosphorothioate internucleoside linkage.

Embodiment 58. The chirally enriched population of embodiment 57, wherein the population is enriched for modified oligonucleotides having the (Sp) configuration at each phosphorothioate internucleoside linkage or for modified oligonucleotides having the (Rp) configuration at each phosphorothioate internucleoside linkage.

Embodiment 59. The chirally enriched population of embodiment 57, wherein the population is enriched for modified oligonucleotides having the (Rp) configuration at one particular phosphorothioate internucleoside linkage and the (Sp) configuration at each of the remaining phosphorothioate internucleoside linkages.

Embodiment 60. The chirally enriched population of embodiment 57, wherein the population is enriched for modified oligonucleotides having at least 3 contiguous phosphorothioate internucleoside linkages in the Sp, Sp, and Rp configurations, in the 5' to 3' direction.

Embodiment 61. A population of modified oligonucleotides of any of embodiments 38-49, wherein all of the phosphorothioate internucleoside linkages of the modified oligonucleotide are stereorandom.

Embodiment 62. A method of treating a disease associated with SMN1 or SMN2 comprising administering to a subject having or at risk for developing a disease associated with SMN1 or SMN2 a therapeutically effective amount of a pharmaceutical composition according to any of embodiments 50-53; and thereby treating the disease associated with SMN1 or SMN2.

Embodiment 63. The method of embodiment 62, wherein the disease associated with SMN1 or SMN2 is a neurodegenerative disease.

Embodiment 64. The method of embodiment 63, wherein the neurodegenerative disease is Spinal Muscular Atrophy (SMA).

Embodiment 65. The method of embodiment 64, wherein the SMA is any of Type I SMA, Type II SMA, Type III SMA, or Type IV SMA.

Embodiment 66. The method of embodiment 64 or embodiment 65, wherein at least one symptom of SMA is ameliorated.

Embodiment 67. The method of embodiment 66, wherein the symptom is any of reduced muscle strength; inability or reduced ability to sit upright, to stand, and/or walk; reduced neuromuscular activity; reduced electrical activity in one or more muscles; reduced respiration; inability or reduced ability to eat, drink, and/or breathe without assistance; loss of weight or reduced weight gain; and/or decreased survival.

Embodiment 68. The method of any of embodiments 62-67, wherein the pharmaceutical composition is administered to the central nervous system or systemically.

Embodiment 69. The method of embodiment 68, wherein the pharmaceutical composition is administered to the central nervous system and systemically.

Embodiment 70. The method of any of embodiment 62-67, wherein the pharmaceutical composition is administered any of intrathecally, systemically, subcutaneously, or intramuscularly.

Embodiment 71. A method of increasing SMN2 RNA including exon 7 comprising contacting a cell, tissue, or organ with an oligomeric compound of any of embodiments 1-37, a modified oligonucleotide of any of embodiments 38-49, or a pharmaceutical composition of any of embodiments 50-53.

Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

Certain Modified Nucleosides

Modified nucleosides comprise a modified sugar moiety or a modified nucleobase or both a modified sugar moiety and a modified nucleobase.

Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE" or "O-methoxyethyl"), and 2'-O—N-alkyl acetamide, e.g., 2'-O—N-methyl acetamide ("NMA"), 2'-O—N-dimethyl acetamide, acetamide, or 2'-O—N-propyl acetamide. For example, see U.S. Pat. No. 6,147,200, Prakash et al., 2003, *Org. Lett.*, 5, 403-6. A "2'-O—N-methyl acetamide nucleoside" or "2'-NMA nucleoside" is shown below:

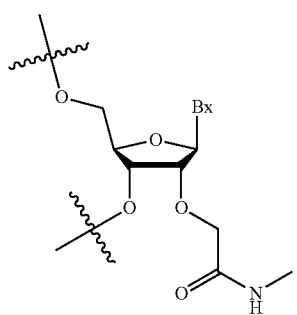

In certain embodiments, 2'-substituent groups are selected from among: halo, allyl, amino, azido, SH, CN, OCN, $CF_3$, $OCF_3$, $O-C_1-C_{10}$ alkoxy, $O-C_1-C_{10}$ substituted alkoxy, $O-C_1-C_{10}$ alkyl, $O-C_1-C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)-N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2$ $ON(R_m)(R_n)$, $O(CH_2)$, $ON(CH_3)_2$, $O(CH_2)_2O$ $(CH_2)_2N(CH_3)_2$, and N-substituted acetamide ($OCH_2C$ $(=O)-N(R_m)(R_n)$), where each $R_m$ and $R_n$ is, independently, H, an amino protecting group, or substituted or unsubstituted $C_1$-$C_{10}$ alkyl, e.g., for example, $OCH_2C$ $(=O)-N(H)CH_3$ ("NMA").

In certain embodiments, a 2'-substituted non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON$ $(CH_3)_2$, $O(CH_2)_2O(CH_2)_2N(CH_3)_2$, and $OCH_2C(=O)-N$ $(H)CH_3$ ("NMA").

In certain embodiments, a 2'-substituted non-bicyclic modified nucleoside comprises a sugar moiety comprising a non-bridging 2'-substituent group selected from: F, $OCH_3$, $OCH_2CH_2OCH_3$, and $OCH_2C(=O)-N(H)CH3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt"), 4'-$CH_2$—O—$CH_2$-2', 4'-$CH_2$—N(R)-2', 4'-$CH$ $(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—$C(H)(CH_3)$-2' (see, e.g., Zhou, et al., J. Org. Chem., 2009, 74, 118-134), 4'-$CH_2$—$C(=CH_2)$-2' and analogs thereof (see e.g., Seth et al., U.S. Pat. No. 8,278,426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O- 2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: $-[C(R_a)(R_b)]_n-$, $-[C(R_a)(R_b)]_n-O-$, $-C(R_a)=C(R_b)-$, $-C(R_a)=N-$, $-C(=NR_a)-$, $-C(=O)-$, $-C(=S)-$, $-O-$, $-Si(R_a)_2-$, $-S(=O)_x-$, and $-N(R_a)-$;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl ($C(=O)$—H), substituted acyl, CN, sulfonyl ($S(=O)_2$-$J_1$), or sulfoxyl ($S(=O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl ($C(=O)$—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

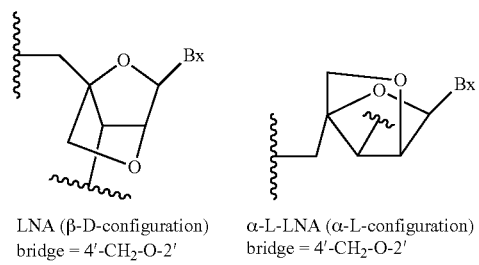

LNA (β-D-configuration)
bridge = 4'-CH$_2$-O-2'

α-L-LNA (α-L-configuration)
bridge = 4'-CH$_2$-O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

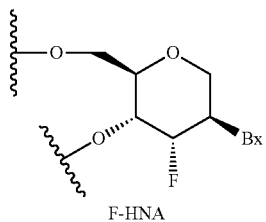

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

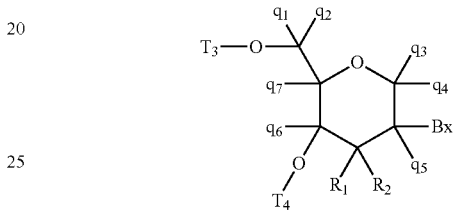

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H.

In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of R1 and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., *Biochemistry*, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

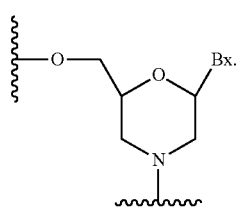

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

Certain Modified Nucleobases

In certain embodiments, modified oligonucleotides comprise one or more nucleosides comprising an unmodified nucleobase. In certain embodiments, modified oligonucleotides comprise one or more nucleosides comprising a modified nucleobase. In certain embodiments, modified oligonucleotides comprise one or more nucleosides that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyl adenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp) Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphodiesters, which contain a phosphodiester bond, P(O$_2$)=O, (also referred to as unmodified or naturally occurring linkages); phosphotriesters; methylphosphonates; methoxypropylphosphonates ("MOP"); phosphoramidates; mesyl phosphoramidates; phosphorothioates (P(O$_2$)=S); and phosphorodithioates (HS—P=S). Representative non-phosphorus containing internucleoside linking groups include but are not limited to methylenemethylimino (—CH$_2$—N(CH$_3$)—O—CH$_2$—); thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate internucleoside linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate internucleoside linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate internucleoside linkage is present in at least 65% of the molecules in the population. In certain embodiments, the particular configuration of the particular phosphorothioate internucleoside linkage is present in at least 70% of the molecules in the population. In certain embodiments, the particular configuration of the particular phosphorothioate internucleoside linkage is present in at least 80% of the molecules in the population. In certain embodiments, the particular configuration of the particular phosphorothioate internucleoside linkage is present in at least 90% of the molecules in the population. In certain embodiments, the particular configuration of the particular phosphorothioate internucleoside linkage is present in at least 99% of the molecules in the population. Such chirally enriched populations of modified oligonucleotides can be generated using synthetic methods known in the art, e.g., methods described in Oka et al., *JACS*, 2003, 125, 8307, Wan et al. *Nuc. Acid. Res.*, 2014, 42, 13456, and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

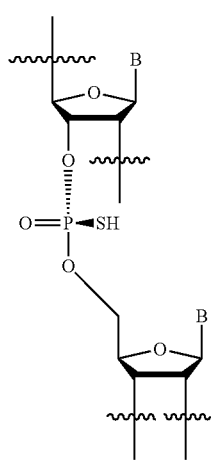

(R$_p$)

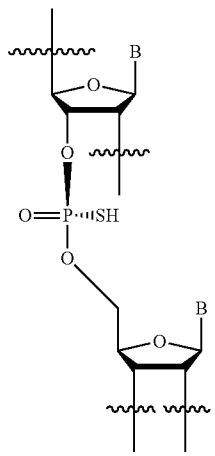

(S$_p$)

Unless otherwise indicated, chiral internucleoside linkages of modified oligonucleotides described herein can be stereorandom or in a particular stereochemical configuration.

In certain embodiments, modified oligonucleotides comprise an internucleoside motif of (5' to 3') sooosssssssssssssss. In certain embodiments, the particular stereochemical configuration of the modified oligonucleotides is (5' to 3') Sp-o-o-o-Sp-Sp-Sp-Rp-Sp-Sp-Rp-Sp-Sp-Sp-Sp-Sp-Sp-Sp-Sp or Sp-o-o-o-Sp-Sp-Sp-Rp-Sp-Sp-Sp-Sp-Sp-Sp-Sp-Sp-Sp-Sp; wherein each 'Sp' represents a phosphorothioate internucleoside linkage in the S configuration; Rp represents a phosphorothioate internucleoside linkage in the R configuration; and 'o' represents a phosphodiester internucleoside linkage.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (see e.g., *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

In certain embodiments, a modified internucleoside linkage is any of those described in WO 2021/030778, incorporated by reference herein.

Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkages. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

Certain Sugar Motifs

In certain embodiments, oligonucleotides comprise one or more type of modified sugar and/or unmodified sugar moiety arranged along the oligonucleotide, or portion thereof, in a defined pattern or sugar motif. In certain instances, such sugar motifs include but are not limited to any of the sugar modifications discussed herein.

In certain embodiments, modified oligonucleotides have a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one, at least two, at least three, at least four, at least five, or at least six nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2'-deoxyribosyl sugar moiety. In certain embodiments, at least one nucleoside of the gap of a gapmer comprises a modified sugar moiety and each remaining nucleoside comprises a 2'-deoxyribosyl sugar moiety.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprise a 2'-deoxyribosyl sugar moiety. Thus, a 5-10-5 MOE gapmer consists of 5 linked 2'-MOE nucleosides in the 5'-wing, 10 linked 2'-deoxyribonucleosides in the gap, and 5 linked 2'-MOE nucleosides in the 3'-wing.

In certain embodiments, each nucleoside of a modified oligonucleotide, or portion thereof, comprises a 2'-substituted sugar moiety, a bicyclic sugar moiety, a sugar surrogate, or a 2'-deoxyribosyl sugar moiety. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, PNA, THP, and F-HNA.

In certain embodiments, modified oligonucleotides comprise at least 12, at least 13, at least 14, at least 15, at least 16, at least 17, at least 18, at least 19, or at least 20 nucleosides comprising a modified sugar moiety. In certain embodiments, the modified sugar moiety is selected independently from a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA.

In certain embodiments, each nucleoside of a modified oligonucleotide comprises a modified sugar moiety ("fully modified oligonucleotide"). In certain embodiments, each nucleoside of a fully modified oligonucleotide comprises a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA. In certain embodiments, each nucleoside of a fully modified oligonucleotide comprises the same modified sugar moiety ("uniformly modified sugar motif"). In certain embodiments, the uniformly modified sugar motif is 7 to 20 nucleosides in length. In certain embodiments, each nucleoside of the uniformly modified sugar motif comprises a 2'-substituted sugar moiety, a bicyclic sugar moiety, or a sugar surrogate. In certain embodiments, the 2'-substituted sugar moiety is selected from a 2'-MOE sugar moiety, a 2'-NMA sugar moiety, a 2'-OMe sugar moiety, and a 2'-F sugar moiety. In certain embodiments, the bicyclic sugar moiety is selected from a cEt sugar moiety and an LNA sugar moiety. In certain embodiments, the sugar surrogate is selected from morpholino, modified morpholino, THP, and F-HNA. In certain embodiments, modified oligonucleotides having at least one fully modified sugar motif may also comprise at least 1, at least 2, at least 3, or at least 4 2'-deoxyribonucleosides.

Certain Nucleobase Motifs

In certain embodiments, oligonucleotides comprise modified and/or unmodified nucleobases arranged along the oligonucleotide, or portion thereof, in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of the nucleoside is a 2'-deoxyribosyl sugar moiety. In certain embodiments, the modified nucleobase is selected from: a 2-thiopyrimidine and a 5-propynepyrimidine.

Certain Internucleoside Linkage Motifs

In certain embodiments, oligonucleotides comprise modified and/or unmodified internucleoside linkages arranged along the oligonucleotide, or portion thereof, in a defined pattern or motif. In certain embodiments, each internucleoside linking group is a phosphodiester internucleoside linkage. In certain embodiments, each internucleoside linking group of a modified oligonucleotide is a phosphorothioate internucleoside linkage. In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester internucleoside linkage is not a terminal internucleoside linkage, and the remaining internucleoside linkages are phosphorothioate internucleoside linkages. In certain such embodiments, all of the phosphorothioate internucleoside linkages are stereorandom. In certain embodiments, all of the phosphorothioate internucleoside linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs. In certain embodiments, one or more internucleoside linkage is a mesyl phosphoramidate internucleoside linkage. In certain embodiments, each internucleoside linkage is independently selected from a phosphodiester internucleoside linkage, a phosphorothioate internucleoside linkage, and a mesyl phosphoramidate internucleoside linkage. In certain embodiments, each internucleoside linkage is independently selected from a phosphorothioate internucleoside linkage and a mesyl phosphoramidate internucleoside linkage. In certain embodiments, one or more internucleoside linkage is a methoxypropylphosphonate internucleoside linkage. In certain embodiments, each internucleoside linkage is independently selected from a phosphodiester internucleoside linkage, a phosphorothioate internucleoside linkage, and a methoxypropylphosphonate internucleoside linkage. In certain embodiments, each internucleoside linkage is independently selected from a phosphorothioate internucleoside linkage and a methoxypropylphosphonate internucleoside linkage.

In certain embodiments, modified oligonucleotides comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or at least 19 phosphodiester internucleoside linkages. In certain embodiments, modified oligonucleotides comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or at least 19 phosphorothioate internucleoside linkages. In certain embodiments, modified oligonucleotides comprise at least 1, at least 2, at least 3, at least 4, or at least 5 phosphodiester internucleoside linkages and the remainder of the internucleoside linkages are phosphorothioate internucleoside linkages.

Certain Lengths

It is possible to increase or decrease the length of an oligonucleotide without eliminating activity. For example, in Woolf et al., *Proc. Natl. Acad. Sci. USA,* 1992, 89, 7305-7309, 1992), a series of oligonucleotides 13-25 nucleobases in length were tested for their ability to induce cleavage of a target nucleic acid in an oocyte injection model. Oligonucleotides 25 nucleobases in length with 8 or 11 mismatch bases near the ends of the oligonucleotides were able to direct specific cleavage of the target nucleic acid, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments, oligonucleotides consist of 16 linked nucleosides. In certain embodiments, oligonucleotides consist of 17 linked nucleosides. In certain embodiments, oligonucleotides consist of 18 linked nucleosides. In certain embodiments, oligonucleotides consist of 19 linked nucleosides. In certain embodiments, oligonucleotides consist of 20 linked nucleosides.

Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a portion of an oligonucleotide has a nucleobase sequence that is complementary to a second oligonucleotide or an identified reference nucleic acid, such as a target nucleic acid. In certain embodiments, the nucleobase sequence of a portion or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge, and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nuci. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, lipophilic groups, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial, or an antibiotic.

Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain oligomeric compounds, a conjugate moiety is attached to an oligonucleotide via a more complex conjugate linker comprising one or more conjugate linker moieties, which are sub-units making up a conjugate linker. In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-calboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxyribonucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate internucleoside linkage. In certain such embodiments, the cleavable moiety is 2'-deoxyadenosine.

Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a portion complementary to a target nucleic acid and a second oligomeric compound having a portion complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce, modulate, or increase the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, provided herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid. In certain embodiments, hybridization of an antisense compound to a target nucleic acid results in exon inclusion. In certain embodiments, hybridization of an antisense compound to a target nucleic acid results in an increase in the amount or activity of a target nucleic acid. In certain embodiments, hybridization of an antisense compound complementary to a target nucleic acid results in alteration of splicing, leading to the inclusion of an exon in the mRNA.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or subject.

Certain Target Nucleic Acids

In certain embodiments, oligomeric compounds comprise or consist of an oligonucleotide comprising a portion that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target nucleic acid is a mature mRNA. In certain embodiments, the target nucleic acid is a pre-mRNA. In certain embodiments, the target region is entirely within an intron. In certain embodiments, the target region spans an intron/exon junction. In certain embodiments, the target region is at least 50% within an intron.

Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a portion that is 100% or fully complementary to a target nucleic acid. In certain embodiments, the portion of full complementarity is 6, 7, 8, 9, 10, 11, 12, 13, 14, 15, 16, 17, 18, 19, or 20 nucleobases in length.

In certain embodiments, oligonucleotides comprise one or more mismatched nucleobases relative to the target nucleic acid. In certain embodiments, the mismatch is at position 1, 2, 3, 4, 5, 6, 7, 8, 9, 10, 11, 12, 13, 14, 15, 16, 17, 18, 19, or 20 from the 5'-end of the oligonucleotide.

SMN2

In certain embodiments, oligomeric compounds comprise or consist of a modified oligonucleotide that is complementary to a target nucleic acid encoding SMN2, or a portion thereof. In certain embodiments, SMN2 has the sequence set forth in SEQ ID NO: 1 (GENBANK Accession No. NT_006713.14 truncated from nucleotides 19939708 to 19967777).

In certain embodiments, contacting a cell with the oligomeric compound complementary to SEQ ID NO: 1 modulates the splicing of SMN2 RNA in a cell. In certain embodiments, contacting a cell with the oligomeric compound complementary to SEQ ID NO: 1 increases the amount of SMN2 RNA including exon 7. In certain embodiments, contacting a cell with the oligomeric compound complementary to SEQ ID NO: 1 increases full-length SMN2 protein expression. In certain embodiments, the oligomeric compound consists of a modified oligonucleotide.

In certain embodiments, contacting a cell in a subject with an oligomeric compound complementary to SEQ ID NO: 1 ameliorates one or more symptom of a neurodegenerative disease. In certain embodiments, the neurodegenerative disease is SMA, including Type I SMA, Type II SMA, Type III SMA, and Type IV SMA. In certain embodiments, the symptom is any of reduced muscle strength; inability or reduced ability to sit upright, to stand, and/or walk; reduced neuromuscular activity; reduced electrical activity in one or more muscles; reduced respiration; inability or reduced ability to eat, drink, and/or breathe without assistance; loss of weight or reduced weight gain; and/or decreased survival.

In certain embodiments, an oligomeric compound complementary to SEQ ID NO: 1 is capable of increasing SMN2 RNA including exon 7 in vivo by at least 1 fold, 2 fold, or 3 fold when administered according to the standard in vivo assay. In certain embodiments, an oligomeric compound complementary to SEQ ID NO: 1 is capable of increasing full-length SMN2 protein in vivo by at least 1 fold, 2 fold, or 3 fold when administered according to the standard in vivo assay.

Certain Target Nucleic Acids in Certain Tissues

In certain embodiments, oligomeric compounds comprise or consist of an oligonucleotide comprising a portion that is complementary to a target nucleic acid, wherein the target nucleic acid is expressed in a pharmacologically relevant tissue. In certain embodiments, the pharmacologically relevant tissues are the cells and tissues that comprise the central nervous system (CNS). Such tissues include brain tissues, such as, spinal cord, cortex, and coronal brain tissue.

Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid ("artificial CSF" or "aCSF"). In certain embodiments, the artificial cerebrospinal fluid is pharmaceutical grade. In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents comprising an oligomeric compound provided herein to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or a salt thereof" expressly includes all such forms that may be fully or partially protonated/de-protonated/in association with a cation. In certain instances, one or more specific cation is identified.

In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or an oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid. For example, where a modified oligonucleotide or an oligomeric compound is in solution comprising sodium (e.g., saline), the modified oligonucleotide or oligomeric compound may be partially or fully de-protonated and in association with Na+ ions. However, the mass of the protons are nevertheless counted toward the weight of the dose, and the mass of the Na+ ions are not counted toward the weight of the dose. Thus, for example, a dose, or dosage unit, of 10 mg of Compound No. 1263789, Compound No. 1287717, Compound No. 1287745, and Compound No. 1358996 equals the number of fully protonated molecules that weighs 10 mg. This would be equivalent to 10.53 mg of solvent-free, sodium acetate-free, anhydrous sodiated Compound No. 1263789, 10.53 mg of solvent-free, sodium acetate-free, anhydrous sodiated Compound No. 1287717, 10.52 mg of solvent-free, sodium acetate-free, anhydrous sodiated Compound No. 1287745, and 10.51 mg of solvent-free, sodium acetate-free, anhydrous sodiated Compound No. 1358996. When an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

Certain Compositions

Compound No: 1263789

In certain embodiments, Compound No. 1263789 is characterized as a modified oligonucleotide having a sequence of (from 5' to 3') CACTTTCATAATGCTGGC (SEQ ID NO: 21), wherein each nucleoside comprises a 2'-MOE sugar moiety, wherein the internucleoside linkages between nucleosides 2 to 3 and 4 to 5 are phosphodiester internucleoside linkages and the internucleoside linkages between nucleosides 1 to 2, 3 to 4, 5 to 6, 6 to 7, 7 to 8, 8 to 9, 9 to 10, 10 to 11, 11 to 12, 12 to 13, 13 to 14, 14 to 15, 15 to 16, 16 to 17, and 17 to 18 are phosphorothioate internucleoside linkages, and wherein each cytosine is a 5-methyl cytosine.

In certain embodiments, Compound No. 1263789 is represented by the following chemical notation (5' to 3'): $^{m}C_{es} A_{eo}\, ^{m}C_{es} T_{eo} T_{es} T_{es}\, ^{m}C_{es} A_{es} T_{es} A_{es} A_{es} T_{es} G_{es}\, ^{m}C_{es} T_{es} G_{es} G_{es}\, ^{m}C_{e}$ (SEQ ID NO: 21), wherein, A=an adenine nucleobase, $^{m}$C=a 5-methyl cytosine nucleobase, G=a guanine nucleobase, T=a thymine nucleobase, e=a 2'-MOE sugar moiety, s=a phosphorothioate internucleoside linkage, and o=a phosphodiester internucleoside linkage.

In certain embodiments, Compound No. 1263789 is represented by the following chemical structure:

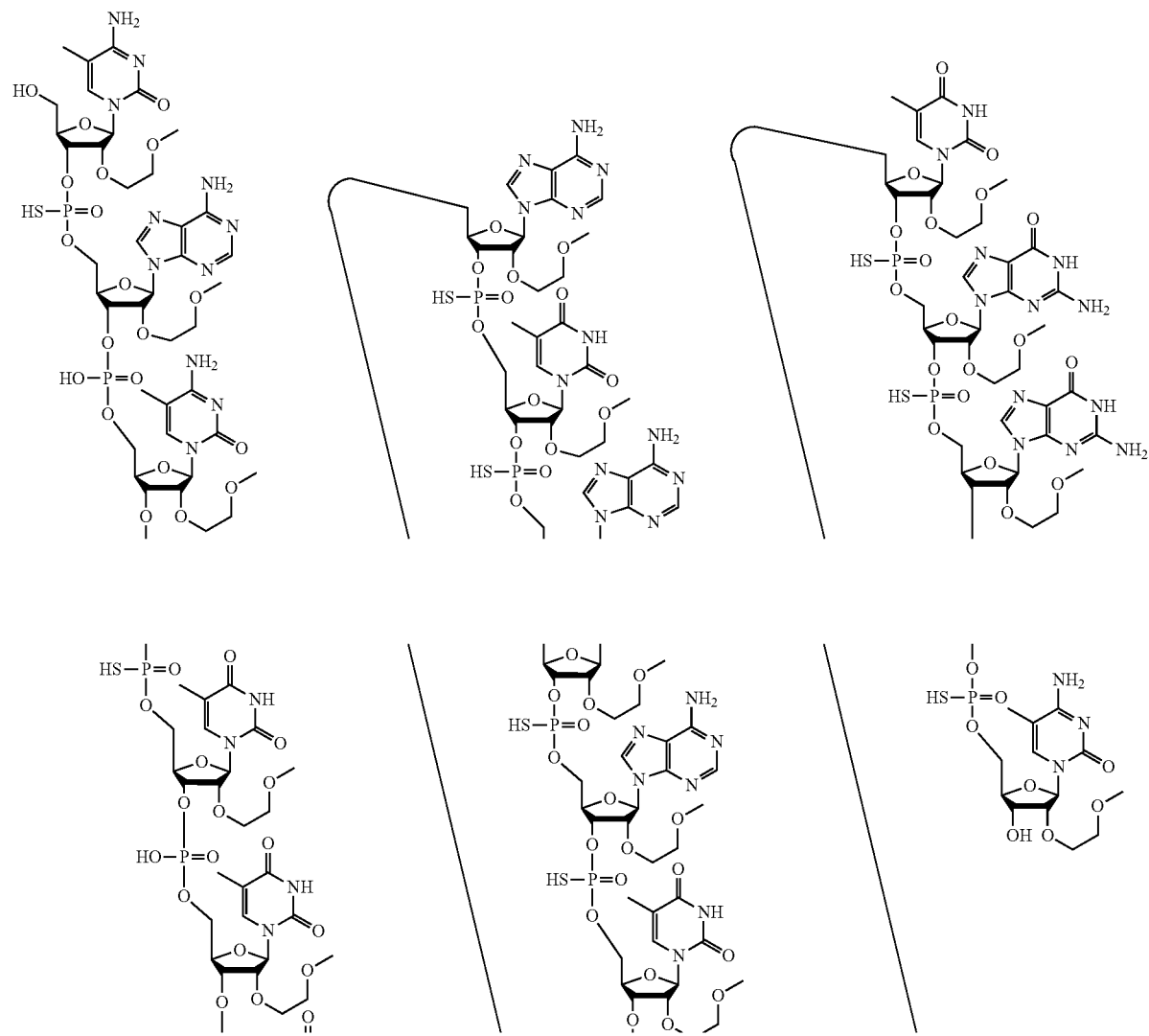

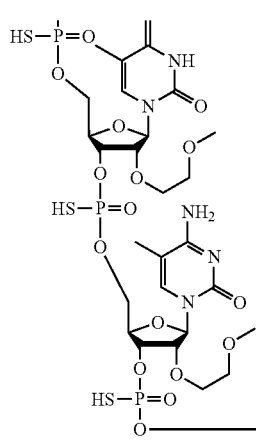
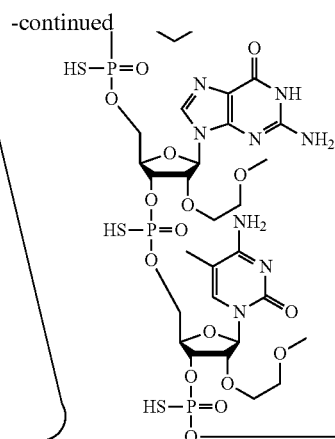
(SEQ ID NO: 21).
Structure 1. Compound No. 1263789
In certain embodiments, the sodium salt of Compound No. 1263789 is represented by the following chemical structure:
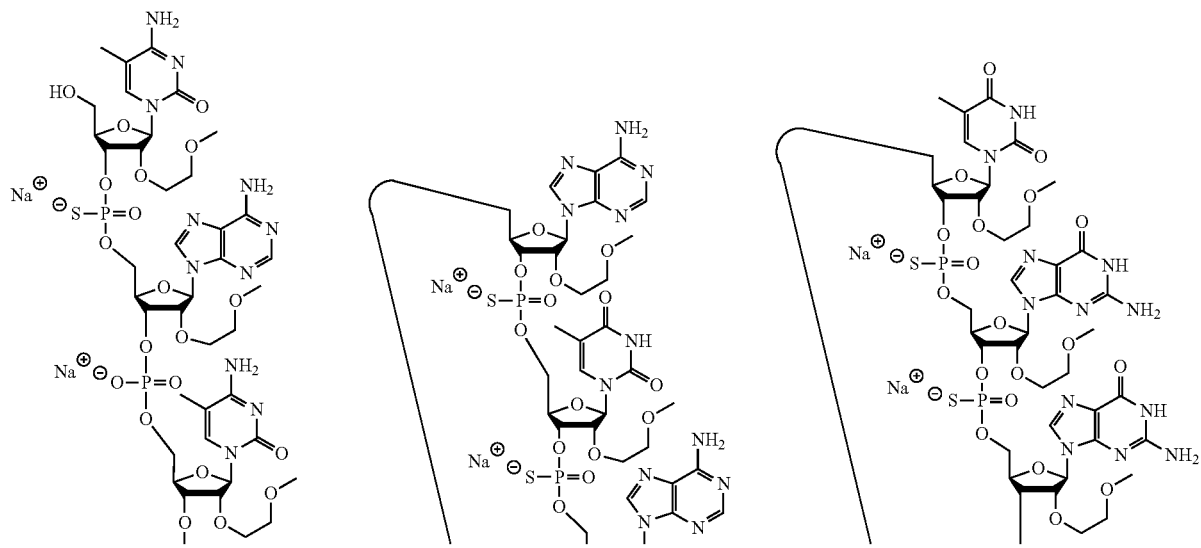
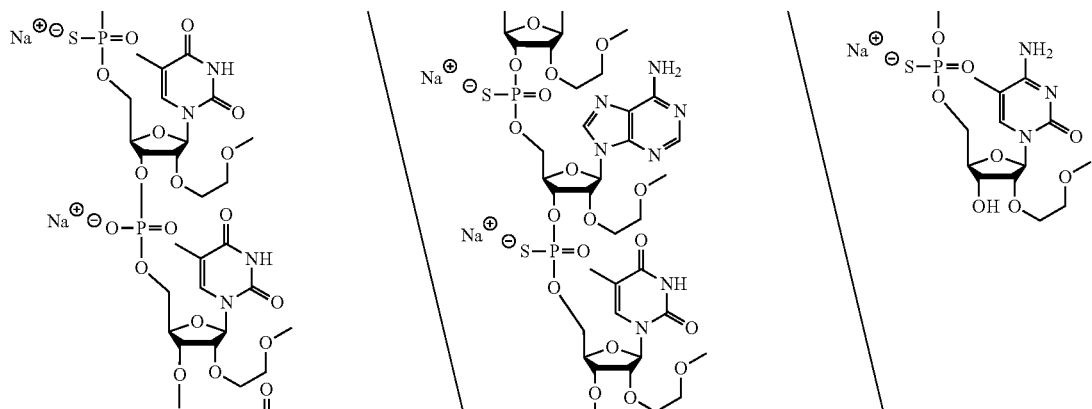

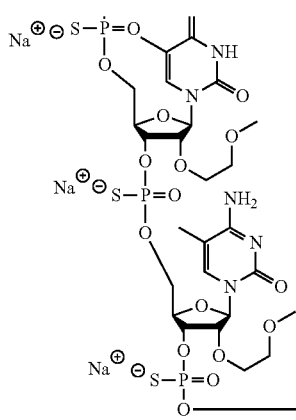
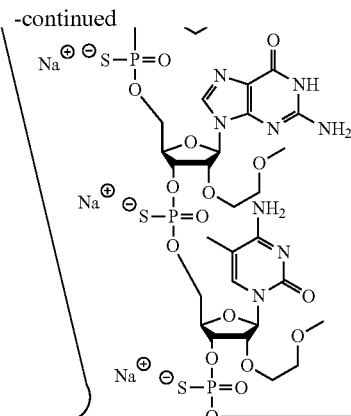

(SEQ ID NO: 21).
Structure 2. The Sodium Salt of Compound No. 1263789

Compound No: 1287717

In certain embodiments, Compound No. 1287717 is characterized as a modified oligonucleotide having a sequence of (from 5' to 3') TTCACTTTCATAATGCTGGC (SEQ ID NO: 22), wherein each nucleoside comprises a 2'-MOE sugar moiety, wherein the internucleoside linkages between nucleosides 1 to 2 and 19 to 20 are phosphodiester internucleoside linkages and the internucleoside linkages between nucleosides 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 are phosphorothioate internucleoside linkages, and wherein each cytosine is a 5-methyl cytosine.

In certain embodiments, Compound No. 1287717 is represented by the following chemical notation (5' to 3'): $T_{eo} T_{es} {}^mC_{es} A_{es} {}^mC_{es} T_{es} T_{es} T_{es} {}^mC_{es} A_{es} T_{es} A_{es} A_{es} T_{es} G_{es} {}^mC_{es} T_{es} G_{es} G_{eo} {}^mC_{e}$ (SEQ ID NO: 22)

wherein,

A=an adenine nucleobase, $^mC$=a 5-methyl cytosine nucleobase,

G=a guanine nucleobase,

T=a thymine nucleobase, e=a 2'-MOE sugar moiety, s=a phosphorothioate internucleoside linkage, and o=a phosphodiester internucleoside linkage.

In certain embodiments, Compound No. 1287717 is represented by the following chemical structure:

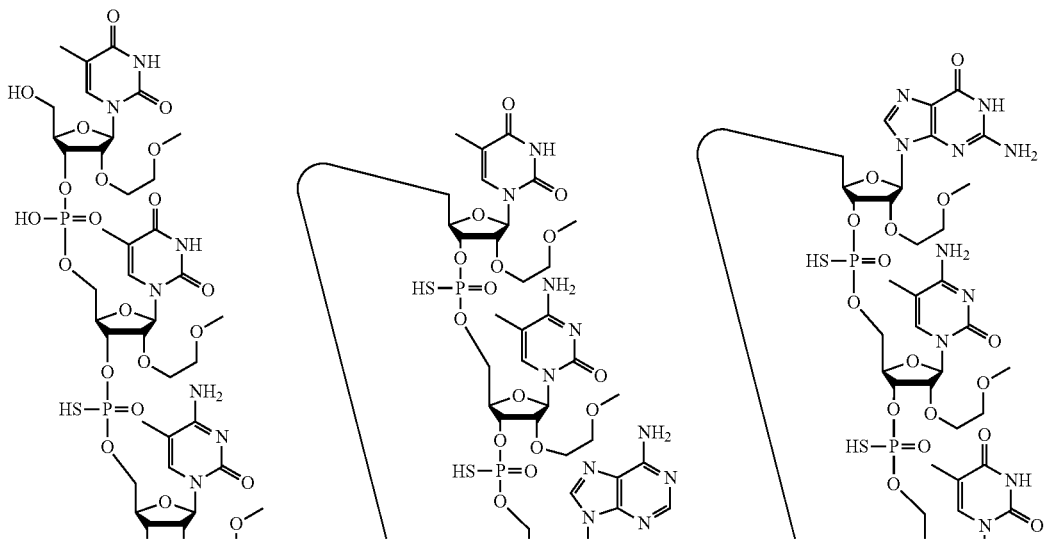

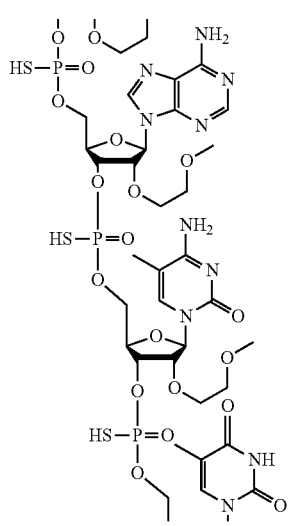
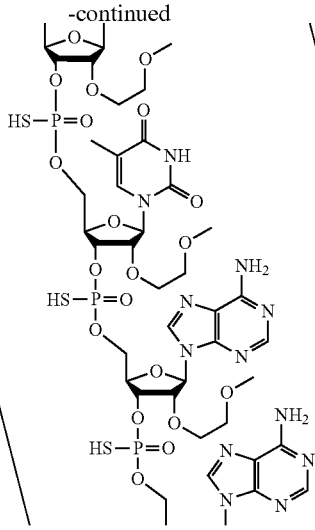
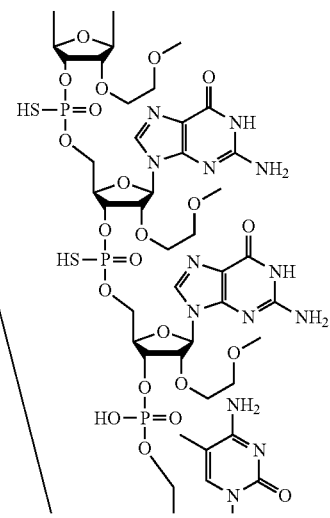
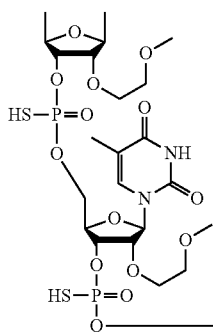
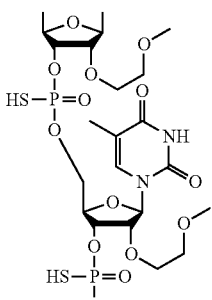
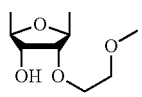
(SEQ ID NO: 22).
Structure 3. Compound No. 1287717
In certain embodiments, the sodium salt of Compound No. 1287717 is represented by the following chemical structure:
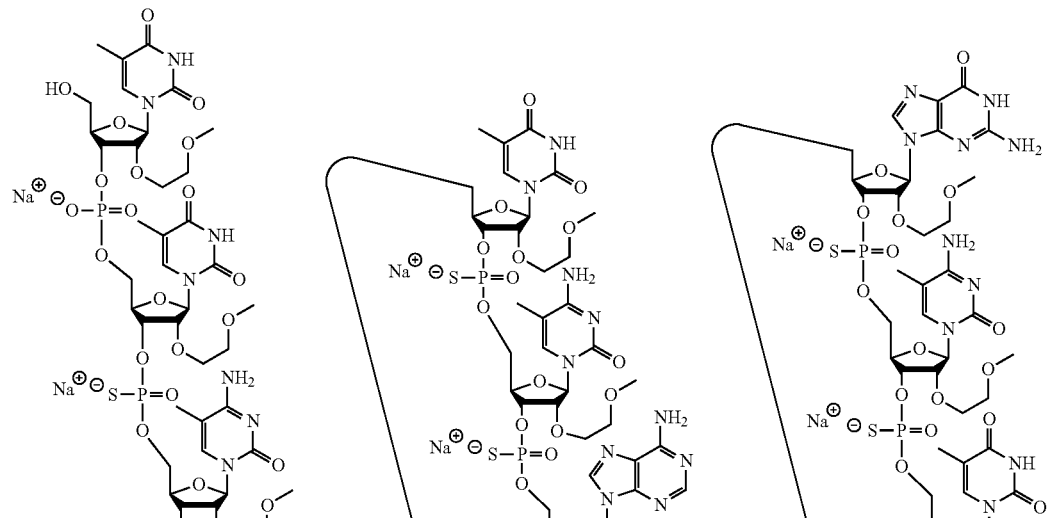

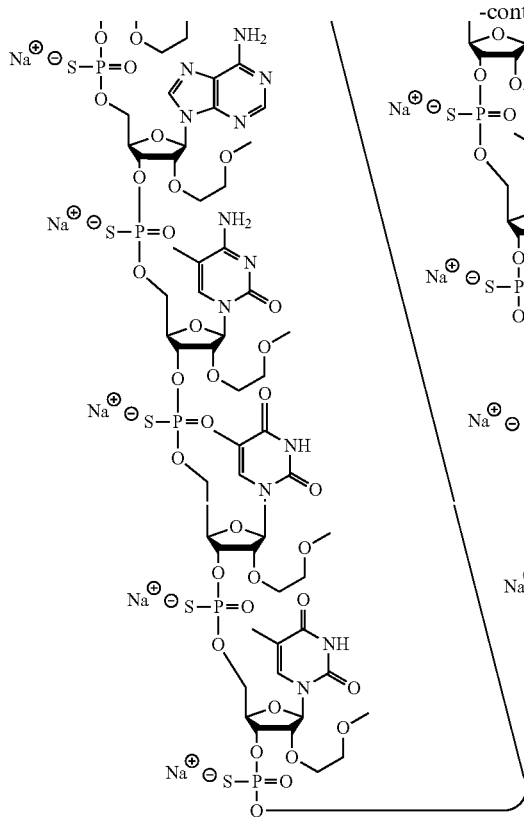
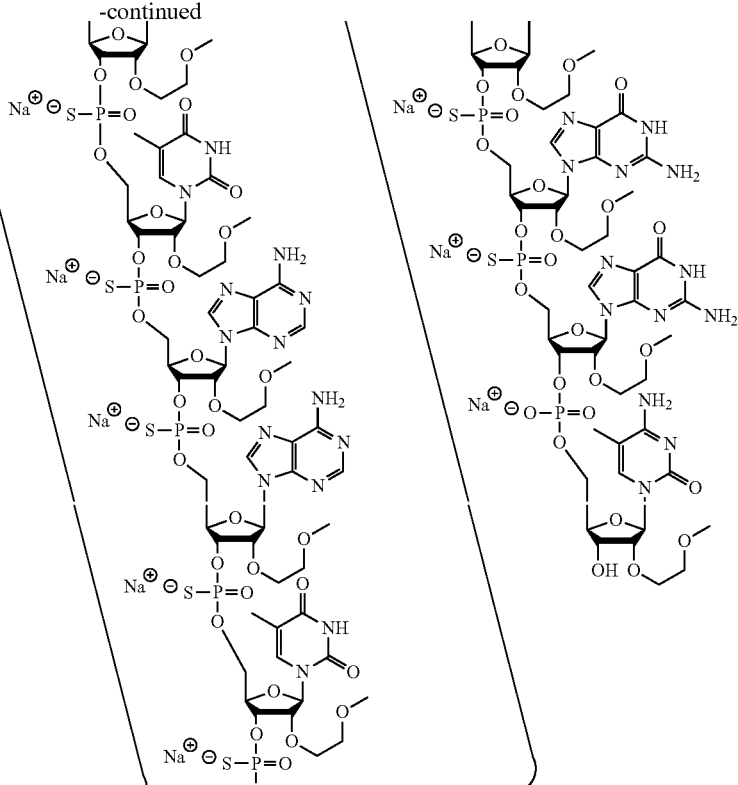

(SEQ ID NO: 22).
Structure 4. The Sodium Salt of Compound No. 1287717
Compound No: 1287745

In certain embodiments, Compound No. 1287745 is characterized as a modified oligonucleotide having a sequence of (from 5' to 3') TTCACTTTCATAATGCTGGC (SEQ ID NO: 22), wherein each of nucleosides 1 and 20 comprises a 2'-MOE sugar moiety, each of nucleosides 2-19 comprises a 2'-NMA sugar moiety, wherein the internucleoside linkages between nucleosides 1 to 2 and 19 to 20 are phosphodiester internucleoside linkages and the internucleoside linkages between nucleosides 2 to 3, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 are phosphorothioate internucleoside linkages, and wherein each cytosine is a 5-methyl cytosine.

In certain embodiments, Compound No. 1287745 is represented by the following chemical notation (5' to 3'): $T_{eo} T_{ns}$ $^mC_{ns} A_{ns} \, ^mC_{ns} T_{ns} T_{ns} T_{ns} \, ^mC_{ns} A_{ns} T_{ns} A_{ns} A_{ns} T_{ns} G_{ns} \, ^mC_{ns}$ $T_{ns} G_{ns} G_{no} \, ^mC_e$ (SEQ ID NO: 22)
wherein,
A=an adenine nucleobase,
$^mC$=a 5-methyl cytosine nucleobase,
G=a guanine nucleobase,
T=a thymine nucleobase,
e=a 2'-MOE sugar moiety,
n=a 2'-NMA sugar moiety,
s=a phosphorothioate internucleoside linkage, and
o=a phosphodiester internucleoside linkage.

In certain embodiments, Compound No. 1287745 is represented by the following chemical structure:

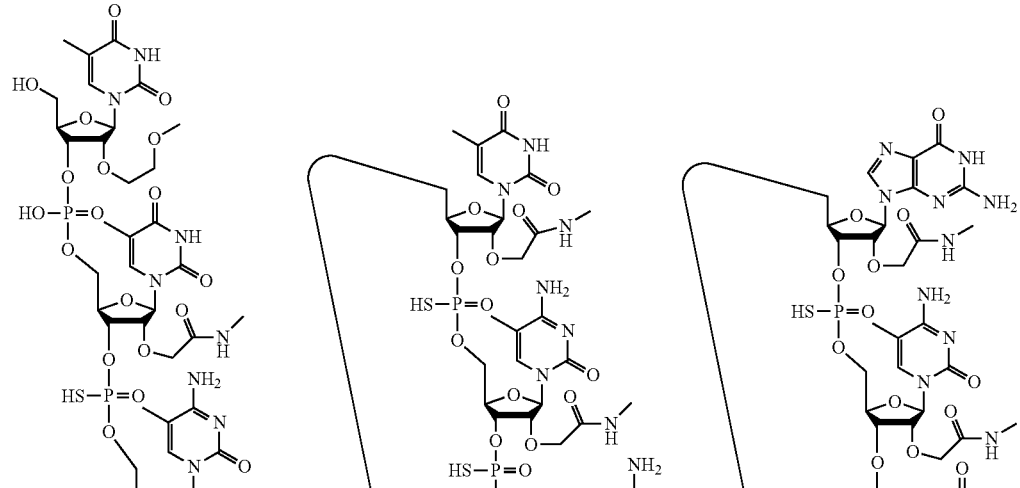

71
-continued
72
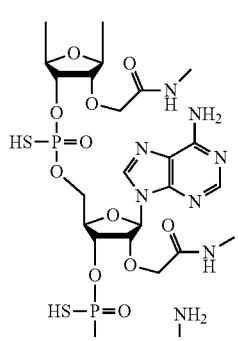
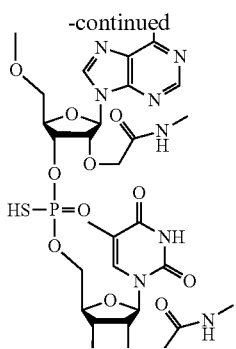
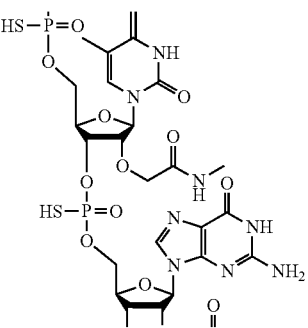
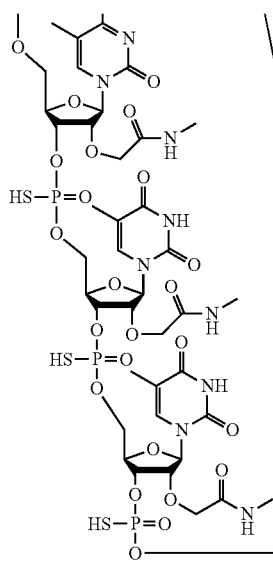
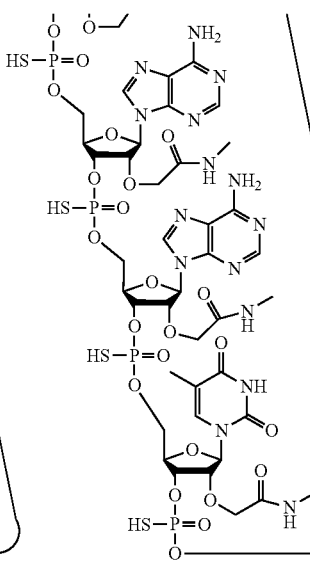
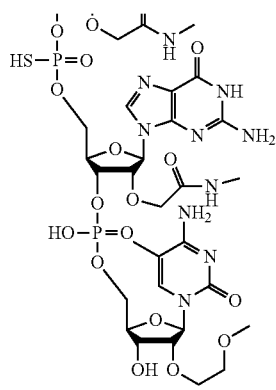
(SEQ ID NO: 22).
Structure 5. Compound No. 1287745
In certain embodiments, the sodium salt of Compound No. 1287745 is represented by the following chemical structure:
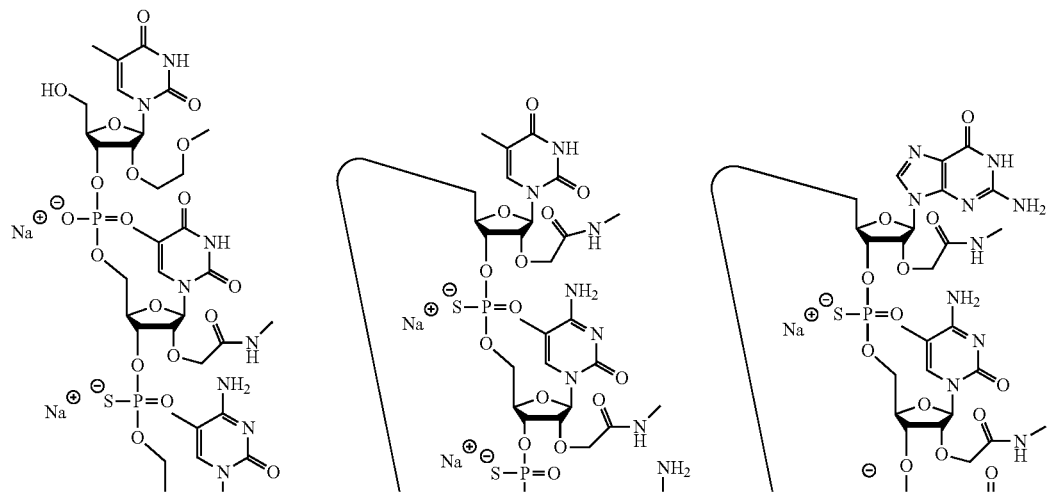

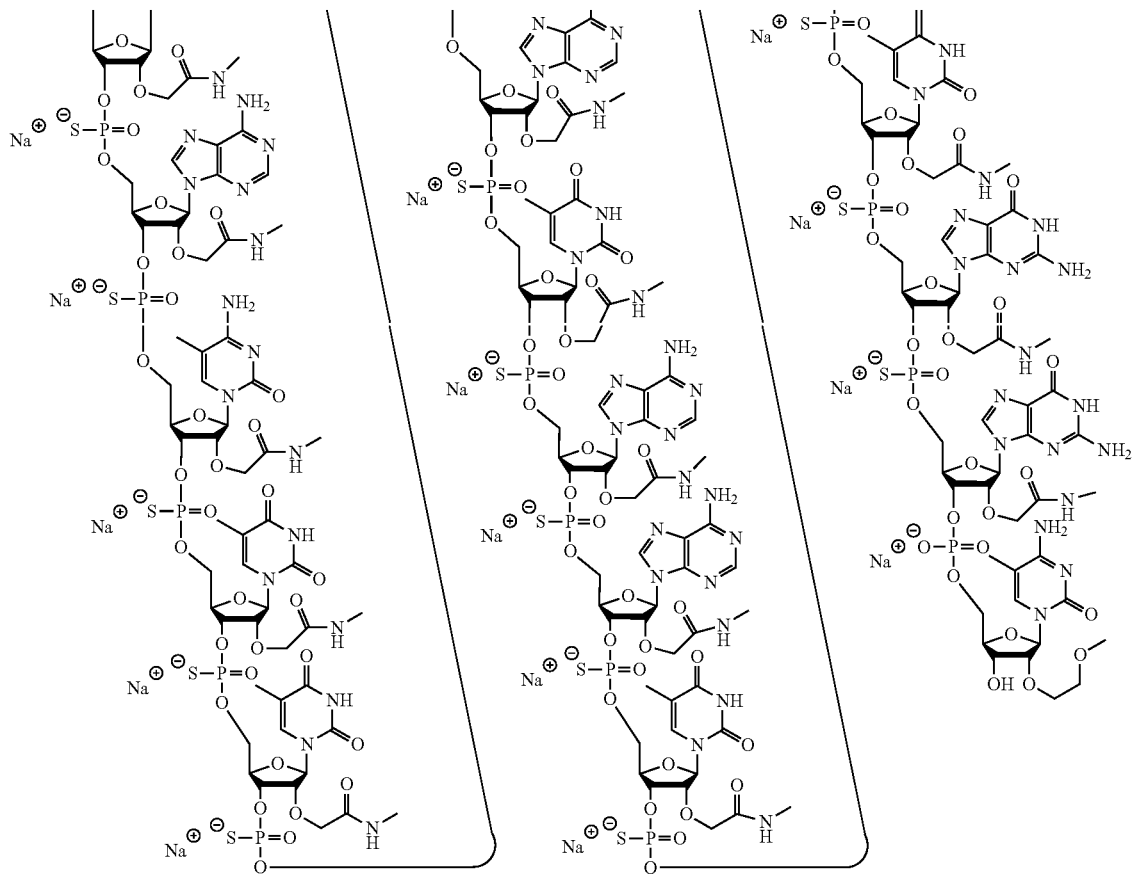

(SEQ ID NO: 22).
Structure 6. The Sodium Salt of Compound No. 1287745
Compound No: 1358996

In certain embodiments, Compound No. 1358996 is characterized as modified oligonucleotide having a sequence of (from 5' to 3') CACTTTCATAATGCTGGC (SEQ ID NO: 21), wherein each nucleoside comprises a 2'-NMA sugar moiety, wherein the internucleoside linkages between nucleosides 2 to 3 and 4 to 5 are phosphodiester internucleoside linkages and the internucleoside linkages between nucleosides 1 to 2, 3 to 4, 5 to 6, 6 to 7, 7 to 8, 8 to 9, 9 to 10, 10 to 11, 11 to 12, 12 to 13, 13 to 14, 14 to 15, 15 to 16, 16 to 17, and 17 to 18 are phosphorothioate internucleoside linkages, and wherein each cytosine is a 5-methyl cytosine.

In certain embodiments, Compound No. 1358996 is represented by the following chemical notation (5' to 3'): $^mC_{ns} A_{no} {}^mC_{ns} T_{no} T_{ns} T_{ns} {}^mC_{ns} A_{ns} T_{ns} A_{ns} A_{ns} T_{ns} G_{ns} {}^mC_{ns} T_{ns} G_{ns} G_{ns} {}^mC_n$ (SEQ ID NO: 21)

wherein,

A=an adenine nucleobase, $^mC$=a 5-methyl cytosine nucleobase,

G=a guanine nucleobase,

T=a thymine nucleobase, n=a 2'-NMA sugar moiety, s=a phosphorothioate internucleoside linkage, and o=a phosphodiester internucleoside linkage.

In certain embodiments, Compound No. 1358996 is represented by the following chemical structure:

75
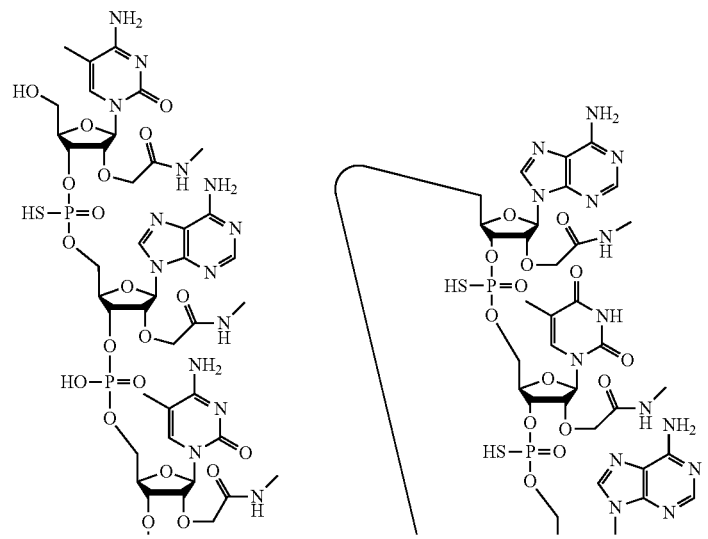
76
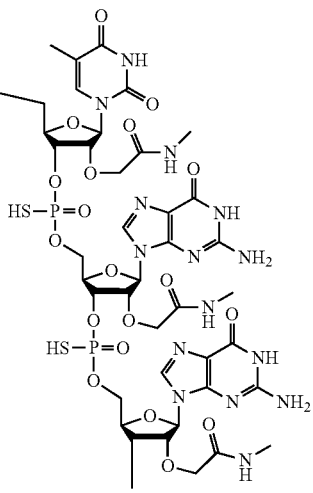
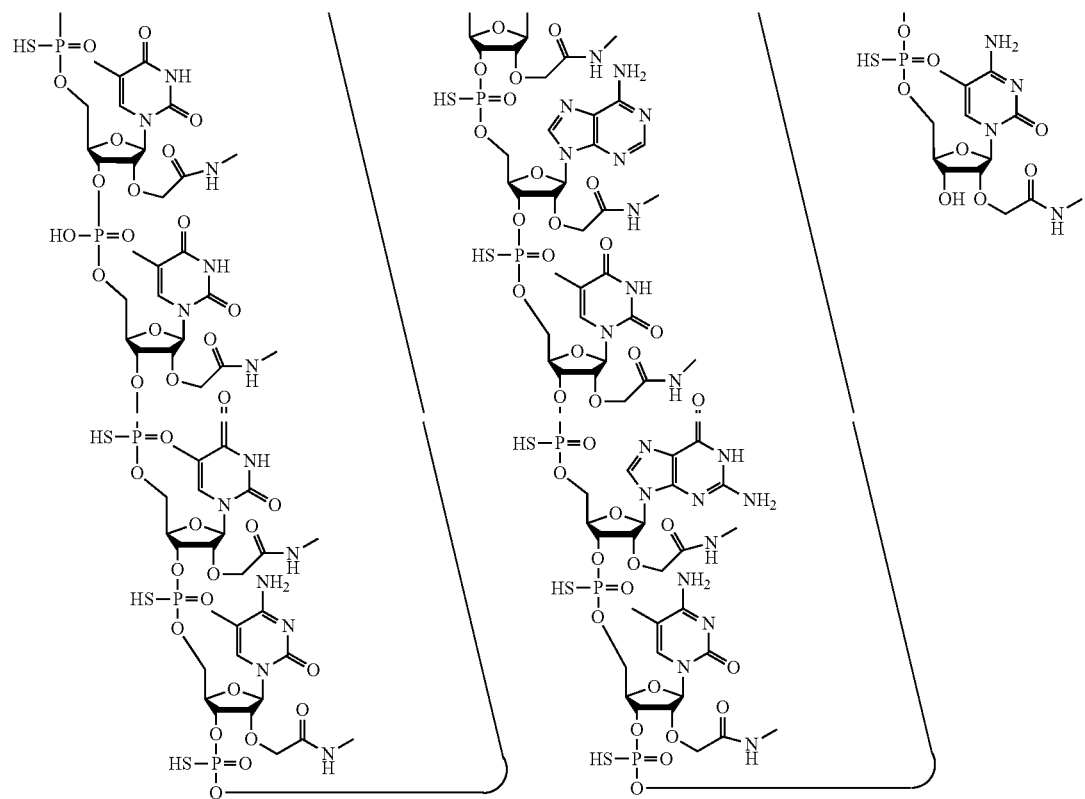
(SEQ ID NO: 21).

Structure 7. Compound No. 1358996

In certain embodiments, the sodium salt of Compound No. 1358996 is represented by the following chemical structure:

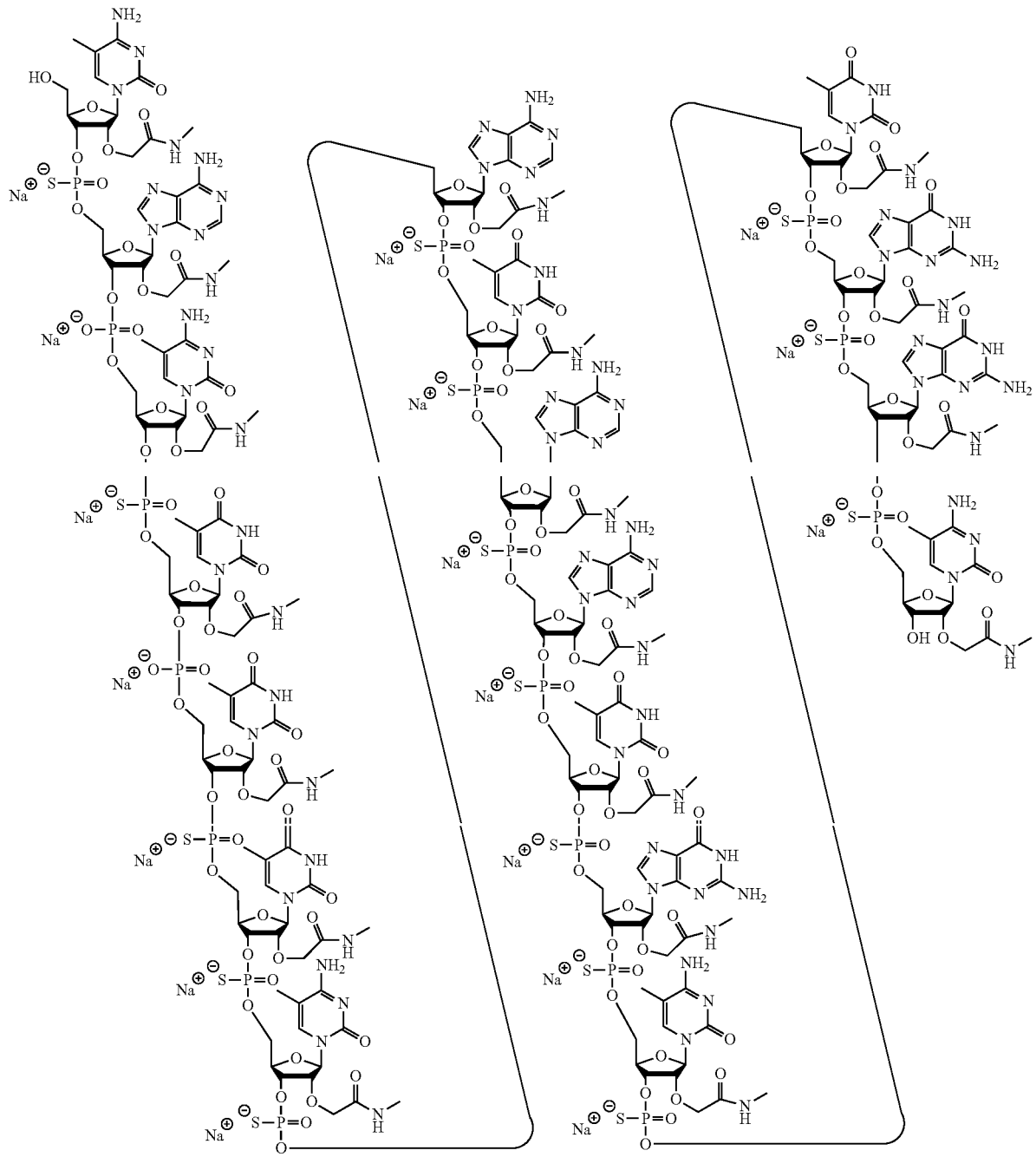

(SEQ ID NO: 21).

Structure 8. The Sodium Salt of Compound No. 1358996

Certain Comparator Compositions

In certain embodiments, Spinraza® (generic name nusinersen; Compound No. 396443), approved for treatment of SMA, is a comparator compound (See, e.g., Chiroboga, et al., Neurology, 86(10): 890-897, 2016; Finkel, et al., Lancet, 338(10063): 3017-3026, 2016; Finkel, et al., N. Engl. J. Med., 377(18):1723-1732 2017; Mercuri, et al., N. Engl. J. Med., 378(7):625-635, 2018; Montes, et al., Muscle Nerve. 60(4): 409-414, 2019; Darras, et al., Neurology, 92(21): e2492-e2506, 2019). Spinraza® was previously described in WO2010120820, incorporated herein by reference, and has a sequence (from 5' to 3') of TCACTTTCATAATGCTGG (SEQ ID NO: 23), wherein each nucleoside comprises a 2'-MOE sugar moiety, each internucleoside linkage is a phosphorothioate internucleoside linkage, and each cytosine is a 5-methyl cytosine.

In certain embodiments, although not approved for human therapy, other previously described compounds, including Compound Nos. 387954, 396442, 443305, and 819735, are comparator compounds Compound No. 387954 was previously described in WO 2014/179620, incorporated herein by reference. Compound No. 387954 has a sequence (from 5' to 3') of ATTCACTTT-CATAATGCTGG (SEQ ID NO: 20), wherein each nucleoside comprises a 2'-MOE sugar moiety, each internucleoside linkage is a phosphorothioate internucleoside linkage, and each cytosine is a 5-methyl cytosine.

Compound No. 396442 was previously described in WO 2010/120820, incorporated herein by reference. Compound No. 396442 has a sequence (from 5' to 3') of CACTTTCAT-AATGCTGGC (SEQ ID NO: 21), wherein each nucleoside comprises a 2'-MOE sugar moiety, each internucleoside linkage is a phosphorothioate internucleoside linkage, and each cytosine is a 5-methyl cytosine.

Compound No. 443305 was previously described in WO 2018/014041, incorporated herein by reference. Compound No. 443305 has a sequence (from 5' to 3') of TCACTTT-CATAATGCTGG (SEQ ID NO: 23), wherein each nucleoside comprises a 2'-NMA sugar moiety, each internucleoside linkage is a phosphorothioate internucleoside linkage, and each cytosine is a 5-methyl cytosine.

Compound No. 819735 was previously described in WO 2018/014041, incorporated herein by reference. Compound No. 819735 has a sequence (from 5' to 3') of CACTTTCAT-AATGCTGGC (SEQ ID NO: 21), wherein each nucleoside comprises a 2'-NMA sugar moiety, each internucleoside linkage is a phosphorothioate internucleoside linkage, and each cytosine is a 5-methyl cytosine.

TABLE 1

Certain Comparator Compositions

| Compound Number | Nucleobase Sequence (5' to 3') | Sugar Motif | Internucleoside Linkage Motif | SEQ ID NO: | Reference Number |
|---|---|---|---|---|---|
| 396443 | TCACTTTCATAATGCTGG | Full 2'-MOE | Full PS | 23 | WO 2010/120820 |
| 387954 | ATTCACTTTCATAATGCTGG | Full 2'-MOE | Full PS | 20 | WO 2014/179620 |
| 396442 | CACTTTCATATGCTGGC | Full 2'-MOE | Full PS | 21 | WO 2010/120820 |
| 443305 | TCACTTTCATAATGCTGG | Full 2'-NMA | Full PS | 23 | WO 2018/014041 |
| 819735 | CACTTTCATATGCTGGC | Full 2'-NMA | Full PS | 21 | WO 2018/014041 |

In certain embodiments, compounds described herein are superior relative to compounds described in WO 2007/002390, WO2010/120820, WO 2015/161170, and WO 2018/014041, because they demonstrate one or more improved properties, such as, potency, efficacy, and tolerability.

For example, Compound No. 1263789, Compound No. 1287745, and Compound No. 1358996 each demonstrated improved potency in vivo as compared to Compound No. 396443. As shown in Example 5, Compound No. 1263789, Compound No. 1287745, and Compound No. 1358996 achieved an $ED_{50}$ in spinal cord of 13.3, 8.8, and 7.4, respectively. In comparison, Compound No. 396443 achieved an $ED_{50}$ in spinal cord of 22.0. Therefore, each of Compound No. 1263789, Compound No. 1287745, and Compound No. 1358996 are more potent than Compound No. 396443 in this assay.

For example, Compound No. 1263789, Compound No. 1287717, Compound No. 1287745, and Compound No. 1358996 each demonstrated improved 3 hour FOB scores as compared to Compound No. 396443, Compound No. 387954, and Compound No. 443305. As shown in Example 6, at 700 µg, Compound No. 1263789, Compound No. 1287717, Compound No. 1287745, and Compound No. 1358996 achieved 3 hour FOB scores of 0, 3.25, 1, and 0, respectively. In comparison, at half the dose (350 µg) Compound No. 396443 achieved a 3 hour FOB score of 4.0; and at the same dose (700 µg) Compound No. 387954 and Compound No. 443305 achieved a 3 hour FOB score of 4.0 and 4.75, respectively. Therefore, each of Compound No. 1263789, Compound No. 1287717, Compound No. 1287745, and Compound No. 1358996 are more tolerable than Compound No. 396443, Compound No. 387954, and Compound No. 443305 in this assay.

For example, Compound No. 1263789, Compound No. 1287717, Compound No. 1287745, and Compound No. 1358996 each demonstrated improved long-term tolerability as compared to Compound No. 396442 and Compound No. 819735. As shown in Example 7, Compound No. 1263789, Compound No. 1287717, Compound No. 1287745, and Compound No. 1358996 demonstrated no adverse events, no Purkinje cell loss, and cortex GFAP mRNA less than 2-fold of control. In comparison, 396442 and 819735 each demonstrated adverse events, Purkinje cell loss, and cortex GFAP mRNA greater than 2-fold of control in certain treated animals Therefore, each of Compound No. 1263789, Compound No. 1287717, Compound No. 1287745, and Compound No. 1358996 are more tolerable than Compound No. 396442 and Compound No. 819735 in this assay.

NONLIMITING DISCLOSURE AND INCORPORATION BY REFERENCE

Each of the literature and patent publications listed herein is incorporated by reference in its entirety. While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar moiety (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "ATmCGAUCG," wherein mC indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, all cis- and trans-isomers and tautomeric forms of the compounds herein are also included unless otherwise indicated. Oligomeric compounds described herein include chirally pure or enriched mixtures as well as racemic mixtures. For example, oligomeric compounds having a plurality of phosphorothioate internucleoside linkages include such compounds in which chirality of the phosphorothioate internucleoside linkages is controlled or is random. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments.

Example 1: Design of Modified Oligonucleotides Complementary to a Human SMN2 Nucleic Acid Modified oligonucleotides complementary to a human SMN2 nucleic acid were designed and synthesized as indicated in the tables below.

The modified oligonucleotides in the tables below are 16, 17, 18, 19, or 20 nucleosides in length, as specified. The modified oligonucleotides comprise 2'-MOE sugar moieties, 2'-NMA sugar moieties, cEt sugar moieties, 2'-OMe sugar moieties, and/or 2'β-D-deoxyribosyl sugar moieties, as specified. Each internucleoside linkage throughout the modified oligonucleotides is either a phosphorothioate internucleoside linkage or a phosphodiester internucleoside linkage, as specified. Cytosines are either non-methylated cytosines or 5-methyl cytosines, as specified.

Each modified oligonucleotide listed in the tables below is 100% complementary to SEQ ID NO: 1 (GENBANK Accession No. NT_006713.14 truncated from nucleotides 19939708 to 19967777), unless specifically stated otherwise. Non-complementary nucleobases are specified in the Nucleobase Sequence column in underlined, bold, italicized font. Each modified oligonucleotide listed in the tables below targets an active site on the SMN2 transcript for inclusion of exon 7. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

Table 2

The modified oligonucleotides in Table 2 below are 16, 17, 18, 19 or 20 nucleosides in length. Each nucleoside comprises a 2'-MOE sugar moiety. The sugar motif for each modified oligonucleotide is provided in the Sugar Motif column, wherein each 'e' represents a 2'-MOE sugar moiety. Each internucleoside linkage is either a phosphorothioate internucleoside linkage or a phosphodiester internucleoside linkage. The internucleoside linkage motif for each modified oligonucleotide is provided in the Internucleoside Linkage Motif column, wherein each 's' represents a phosphorothioate internucleoside linkage, and each 'o' represents a phosphodiester internucleoside linkage. Each cytosine is a 5-methyl cytosine.

Each modified oligonucleotide listed in Table 2 below is 100% complementary to SEQ ID NO: 1 (GENBANK Accession No. NT_006713.14 truncated from nucleotides 19939708 to 19967777), unless specifically stated otherwise. Non-complementary nucleobases are specified in the Nucleobase Sequence column in underlined, bold, italicized font. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 2

2'-MOE modified oligonucleotides with PS or mixed PS/PO internucleoside linkages

| Number Compound | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1287063 | ACTTTCATAATGCTGGCAG | eeeeeeeeeeeeeeeeeee | sssssssssssssssssss | 27059 | 27077 | 24 |
| 1287048 | CACTTTCATAATGCTGGCAG | eeeeeeeeeeeeeeeeeeee | ssssssssssssssssssss | 27059 | 27078 | 25 |

TABLE 2-continued

2'-MOE modified oligonucleotides with PS or mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1287064 | CACTTTCATAATGCTGGCA | eeeeeeeeeeeeeeeeeee | sssssssssssssssssss | 27060 | 27078 | 26 |
| 1287049 | TCACTTTCATAATGCTGGCA | eeeeeeeeeeeeeeeeeeee | ssssssssssssssssssss | 27060 | 27079 | 27 |
| 1210340 | CTTTCATAATGCTGGC | eeeeeeeeeeeeeeee | sssssssssssssss | 27061 | 27076 | 28 |
| 1212868 | CTTTCATAATGCTGGC | eeeeeeeeeeeeeeee | sssssssssooooss | 27061 | 27076 | 28 |
| 1212867 | CTTTCATAATGCTGGC | eeeeeeeeeeeeeeee | ssssssssoooosss | 27061 | 27076 | 28 |
| 1212863 | CTTTCATAATGCTGGC | eeeeeeeeeeeeeeee | sssssoooossssss | 27061 | 27076 | 28 |
| 1212866 | CTTTCATAATGCTGGC | eeeeeeeeeeeeeeee | sssssooooosssss | 27061 | 27076 | 28 |
| 1212861 | CTTTCATAATGCTGGC | eeeeeeeeeeeeeeee | sssssoooosssss | 27061 | 27076 | 28 |
| 1212860 | CTTTCATAATGCTGGC | eeeeeeeeeeeeeeee | ssssoooooosssss | 27061 | 27076 | 28 |
| 1212865 | CTTTCATAATGCTGGC | eeeeeeeeeeeeeeee | ssssooooosssssss | 27061 | 27076 | 28 |
| 1212859 | CTTTCATAATGCTGGC | eeeeeeeeeeeeeeee | ssssoooooossss | 27061 | 27076 | 28 |
| 1212851 | CTTTCATAATGCTGGC | eeeeeeeeeeeeeeee | sssosssossssoss | 27061 | 27076 | 28 |
| 1212850 | CTTTCATAATGCTGGC | eeeeeeeeeeeeeeee | ssossssssssssoss | 27061 | 27076 | 28 |
| 1212852 | CTTTCATAATGCTGGC | eeeeeeeeeeeeeeee | ssossossossosss | 27061 | 27076 | 28 |
| 1212853 | CTTTCATAATGCTGGC | eeeeeeeeeeeeeeee | ssossossosososs | 27061 | 27076 | 28 |
| 1212854 | CTTTCATAATGCTGGC | eeeeeeeeeeeeeeee | ssososososososs | 27061 | 27076 | 28 |
| 1212864 | CTTTCATAATGCTGGC | eeeeeeeeeeeeeeee | ssooossssssssss | 27061 | 27076 | 28 |
| 1212855 | CTTTCATAATGCTGGC | eeeeeeeeeeeeeeee | soosssssssssooss | 27061 | 27076 | 28 |
| 1212856 | CTTTCATAATGCTGGC | eeeeeeeeeeeeeeee | sooossssssooss | 27061 | 27076 | 28 |
| 1212857 | CTTTCATAATGCTGGC | eeeeeeeeeeeeeeee | sooossssssooss | 27061 | 27076 | 28 |
| 1212858 | CTTTCATAATGCTGGC | eeeeeeeeeeeeeeee | sooooosssssooss | 27061 | 27076 | 28 |
| 1210339 | ACTTTCATAATGCTGGC | eeeeeeeeeeeeeeeee | ssssssssssssssss | 27061 | 27077 | 29 |
| 1212849 | ACTTTCATAATGCTGGC | eeeeeeeeeeeeeeeee | ssssssssssooooss | 27061 | 27077 | 29 |
| 1212848 | ACTTTCATAATGCTGGC | eeeeeeeeeeeeeeeee | sssssssoooosssss | 27061 | 27077 | 29 |
| 1212845 | ACTTTCATAATGCTGGC | eeeeeeeeeeeeeeeee | ssssssoooosssss | 27061 | 27077 | 29 |
| 1212844 | ACTTTCATAATGCTGGC | eeeeeeeeeeeeeeeee | sssssoooossssss | 27061 | 27077 | 29 |
| 1212843 | ACTTTCATAATGCTGGC | eeeeeeeeeeeeeeeee | sssssoooosssssss | 27061 | 27077 | 29 |
| 1212842 | ACTTTCATAATGCTGGC | eeeeeeeeeeeeeeeee | sssssooooossssss | 27061 | 27077 | 29 |
| 1212841 | ACTTTCATAATGCTGGC | eeeeeeeeeeeeeeeee | ssssoooooossssss | 27061 | 27077 | 29 |
| 1212847 | ACTTTCATAATGCTGGC | eeeeeeeeeeeeeeeee | ssssoooossssssss | 27061 | 27077 | 29 |
| 1212832 | ACTTTCATAATGCTGGC | eeeeeeeeeeeeeeeee | ssosssssssssssoss | 27061 | 27077 | 29 |
| 1212833 | ACTTTCATAATGCTGGC | eeeeeeeeeeeeeeeee | ssossssossssoss | 27061 | 27077 | 29 |
| 1212834 | ACTTTCATAATGCTGGC | eeeeeeeeeeeeeeeee | ssossossossosss | 27061 | 27077 | 29 |
| 1212835 | ACTTTCATAATGCTGGC | eeeeeeeeeeeeeeeee | ssossossosososs | 27061 | 27077 | 29 |
| 1212836 | ACTTTCATAATGCTGGC | eeeeeeeeeeeeeeeee | ssososososososs | 27061 | 27077 | 29 |
| 1212846 | ACTTTCATAATGCTGGC | eeeeeeeeeeeeeeeee | ssoooosssssssss | 27061 | 27077 | 29 |

TABLE 2-continued

2'-MOE modified oligonucleotides with PS or mixed PS/PO internucleoside linkages

| Number Compound | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1212837 | ACTTTCATAATGCTGGC | eeeeeeeeeeeeeeeee | soosssssssssooss | 27061 | 27077 | 29 |
| 1212838 | ACTTTCATAATGCTGGC | eeeeeeeeeeeeeeeee | sooossssssssooss | 27061 | 27077 | 29 |
| 1212839 | ACTTTCATAATGCTGGC | eeeeeeeeeeeeeeeee | sooossssssoooss | 27061 | 27077 | 29 |
| 1212840 | ACTTTCATAATGCTGGC | eeeeeeeeeeeeeeeee | sooooosssssoooss | 27061 | 27077 | 29 |
| 1263814 | CACTTTCATAATGCTGGC | eeeeeeeeeeeeeeeeee | ssosssssssssssss | 27061 | 27078 | 21 |
| 1263816 | CACTTTCATAATGCTGGC | eeeeeeeeeeeeeeeeee | ssssosssssssssss | 27061 | 27078 | 21 |
| 1263818 | CACTTTCATAATGCTGGC | eeeeeeeeeeeeeeeeee | ssssssosssssssss | 27061 | 27078 | 21 |
| 1263820 | CACTTTCATAATGCTGGC | eeeeeeeeeeeeeeeeee | sssssssosssssss | 27061 | 27078 | 21 |
| 1263822 | CACTTTCATAATGCTGGC | eeeeeeeeeeeeeeeeee | sssssssssosssss | 27061 | 27078 | 21 |
| 1263824 | CACTTTCATAATGCTGGC | eeeeeeeeeeeeeeeeee | sssssssssssosss | 27061 | 27078 | 21 |
| 1263826 | CACTTTCATAATGCTGGC | eeeeeeeeeeeeeeeeee | ssssssssssssoss | 27061 | 27078 | 21 |
| 1210342 | CACTTTCATAATGCTGGC | eeeeeeeeeeeeeeeeee | ssossssssssssoss | 27061 | 27078 | 21 |
| 1263778 | CACTTTCATAATGCTGGC | eeeeeeeeeeeeeeeeee | sossssssssssssoss | 27061 | 27078 | 21 |
| 1263781 | CACTTTCATAATGCTGGC | eeeeeeeeeeeeeeeeee | sosssssssosssss | 27061 | 27078 | 21 |
| 1263783 | CACTTTCATAATGCTGGC | eeeeeeeeeeeeeeeeee | sosssssosssssss | 27061 | 27078 | 21 |
| 1263785 | CACTTTCATAATGCTGGC | eeeeeeeeeeeeeeeeee | sossssosssssssss | 27061 | 27078 | 21 |
| 1263787 | CACTTTCATAATGCTGGC | eeeeeeeeeeeeeeeeee | sosssosssssssss | 27061 | 27078 | 21 |
| 1263789 | CACTTTCATAATGCTGGC | eeeeeeeeeeeeeeeeee | sosossssssssssss | 27061 | 27078 | 21 |
| 1263791 | CACTTTCATAATGCTGGC | eeeeeeeeeeeeeeeeee | sssssssssssssoss | 27061 | 27078 | 21 |
| 1263793 | CACTTTCATAATGCTGGC | eeeeeeeeeeeeeeeeee | ssssssosssssoss | 27061 | 27078 | 21 |
| 1263795 | CACTTTCATAATGCTGGC | eeeeeeeeeeeeeeeeee | sssssssosssssoss | 27061 | 27078 | 21 |
| 1263797 | CACTTTCATAATGCTGGC | eeeeeeeeeeeeeeeeee | sssssssssosssoss | 27061 | 27078 | 21 |
| 1263799 | CACTTTCATAATGCTGGC | eeeeeeeeeeeeeeeeee | ssssssssssssososs | 27061 | 27078 | 21 |
| 1263800 | CACTTTCATAATGCTGGC | eeeeeeeeeeeeeeeeee | soossssssssssss | 27061 | 27078 | 21 |
| 1263802 | CACTTTCATAATGCTGGC | eeeeeeeeeeeeeeeeee | sssoosssssssssss | 27061 | 27078 | 21 |
| 1263804 | CACTTTCATAATGCTGGC | eeeeeeeeeeeeeeeeee | sssssoossssssss | 27061 | 27078 | 21 |
| 1263806 | CACTTTCATAATGCTGGC | eeeeeeeeeeeeeeeeee | ssssssoossssssss | 27061 | 27078 | 21 |
| 1263808 | CACTTTCATAATGCTGGC | eeeeeeeeeeeeeeeeee | sssssssoossssss | 27061 | 27078 | 21 |
| 1263810 | CACTTTCATAATGCTGGC | eeeeeeeeeeeeeeeeee | ssssssssssoosss | 27061 | 27078 | 21 |
| 1263812 | CACTTTCATAATGCTGGC | eeeeeeeeeeeeeeeeee | sssssssssssooss | 27061 | 27078 | 21 |
| 1210343 | CACTTTCATAATGCTGGC | eeeeeeeeeeeeeeeeee | ssosssssosssssoss | 27061 | 27078 | 21 |
| 1212825 | CACTTTCATAATGCTGGC | eeeeeeeeeeeeeeeeee | sssssssooosssssss | 27061 | 27078 | 21 |
| 1212817 | CACTTTCATAATGCTGGC | eeeeeeeeeeeeeeeeee | soossssssssssoss | 27061 | 27078 | 21 |
| 1212824 | CACTTTCATAATGCTGGC | eeeeeeeeeeeeeeeeee | sssssssoooossssss | 27061 | 27078 | 21 |
| 1212826 | CACTTTCATAATGCTGGC | eeeeeeeeeeeeeeeeee | ssooosssssssssss | 27061 | 27078 | 21 |
| 1212827 | CACTTTCATAATGCTGGC | eeeeeeeeeeeeeeeeee | sssoooosssssssss | 27061 | 27078 | 21 |

TABLE 2-continued

2'-MOE modified oligonucleotides with PS or mixed PS/PO internucleoside linkages

| Number Compound | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1212828 | CACTTTCATAATGCTGGC | eeeeeeeeeeeeeeeeee | sssssoooosssssss | 27061 | 27078 | 21 |
| 1212829 | CACTTTCATAATGCTGGC | eeeeeeeeeeeeeeeeee | ssssssoooossssss | 27061 | 27078 | 21 |
| 1212830 | CACTTTCATAATGCTGGC | eeeeeeeeeeeeeeeeee | sssssssoooosssss | 27061 | 27078 | 21 |
| 1212831 | CACTTTCATAATGCTGGC | eeeeeeeeeeeeeeeeee | ssssssssoooossss | 27061 | 27078 | 21 |
| 1212818 | CACTTTCATAATGCTGGC | eeeeeeeeeeeeeeeeee | soooosssssssooss | 27061 | 27078 | 21 |
| 1212823 | CACTTTCATAATGCTGGC | eeeeeeeeeeeeeeeeee | sssssooooossssss | 27061 | 27078 | 21 |
| 1212819 | CACTTTCATAATGCTGGC | eeeeeeeeeeeeeeeeee | sooossssssssooss | 27061 | 27078 | 21 |
| 1212822 | CACTTTCATAATGCTGGC | eeeeeeeeeeeeeeeeee | sssssoooooosssss | 27061 | 27078 | 21 |
| 1212820 | CACTTTCATAATGCTGGC | eeeeeeeeeeeeeeeeee | sooossssssssooss | 27061 | 27078 | 21 |
| 1212821 | CACTTTCATAATGCTGGC | eeeeeeeeeeeeeeeeee | ssssooooooossssss | 27061 | 27078 | 21 |
| 1287065 | TCACTTTCATAATGCTGGC | eeeeeeeeeeeeeeeeeee | sssssssssssssssss | 27061 | 27079 | 30 |
| 1210341 | ACTTTCATAATGCTGG | eeeeeeeeeeeeeeee | sssssssssssssss | 27062 | 27077 | 31 |
| 524403 | CACTTTCATAATGCTGG | eeeeeeeeeeeeeeeee | ssssssssssssssss | 27062 | 27078 | 32 |
| 1287121 | TCACTTTCATAATGCTGG | eeeeeeeeeeeeeeeeee | sssssssssssssoss | 27062 | 27079 | 23 |
| 1287120 | TCACTTTCATAATGCTGG | eeeeeeeeeeeeeeeeee | ssssssssssssosss | 27062 | 27079 | 23 |
| 1287113 | TCACTTTCATAATGCTGG | eeeeeeeeeeeeeeeeee | sssssssssssooss | 27062 | 27079 | 23 |
| 1287110 | TCACTTTCATAATGCTGG | eeeeeeeeeeeeeeeeee | sssssssssssososs | 27062 | 27079 | 23 |
| 1287119 | TCACTTTCATAATGCTGG | eeeeeeeeeeeeeeeeee | sssssssssosssss | 27062 | 27079 | 23 |
| 1364782 | TCACTTTCATAATGCTGG | eeeeeeeeeeeeeeeeee | ssssssssssosososs | 27062 | 27079 | 23 |
| 1364777 | TCACTTTCATAATGCTGG | eeeeeeeeeeeeeeeeee | sssssssssossosss | 27062 | 27079 | 23 |
| 1287118 | TCACTTTCATAATGCTGG | eeeeeeeeeeeeeeeeee | sssssssssosssssss | 27062 | 27079 | 23 |
| 1364783 | TCACTTTCATAATGCTGG | eeeeeeeeeeeeeeeeee | ssssssssosssosss | 27062 | 27079 | 23 |
| 1287109 | TCACTTTCATAATGCTGG | eeeeeeeeeeeeeeeeee | ssssssssossssoss | 27062 | 27079 | 23 |
| 1364784 | TCACTTTCATAATGCTGG | eeeeeeeeeeeeeeeeee | sssssssosssosss | 27062 | 27079 | 23 |
| 1287117 | TCACTTTCATAATGCTGG | eeeeeeeeeeeeeeeeee | sssssssosssssss | 27062 | 27079 | 23 |
| 1287112 | TCACTTTCATAATGCTGG | eeeeeeeeeeeeeeeeee | sssssssoosssssss | 27062 | 27079 | 23 |
| 1287116 | TCACTTTCATAATGCTGG | eeeeeeeeeeeeeeeeee | sssssosssssssss | 27062 | 27079 | 23 |
| 1287115 | TCACTTTCATAATGCTGG | eeeeeeeeeeeeeeeeee | ssssossssssssss | 27062 | 27079 | 23 |
| 1287114 | TCACTTTCATAATGCTGG | eeeeeeeeeeeeeeeeee | sossssssssssssss | 27062 | 27079 | 23 |
| 1287106 | TCACTTTCATAATGCTGG | eeeeeeeeeeeeeeeeee | sosssssssssssoss | 27062 | 27079 | 23 |
| 1287107 | TCACTTTCATAATGCTGG | eeeeeeeeeeeeeeeeee | sosssssosssssss | 27062 | 27079 | 23 |
| 1287108 | TCACTTTCATAATGCTGG | eeeeeeeeeeeeeeeeee | sososssssssssss | 27062 | 27079 | 23 |
| 1287111 | TCACTTTCATAATGCTGG | eeeeeeeeeeeeeeeeee | sooossssssssssss | 27062 | 27079 | 23 |
| 1287066 | TTCACTTTCATAATGCTGG | eeeeeeeeeeeeeeeeeee | sssssssssssssssss | 27062 | 27080 | 33 |
| 1287074 | TTCACTTTCATAATGCTGG | eeeeeeeeeeeeeeeeeee | ssssssssssssssoss | 27062 | 27080 | 33 |
| 1287071 | TTCACTTTCATAATGCTGG | eeeeeeeeeeeeeeeeeee | ssssssssssssososs | 27062 | 27080 | 33 |

TABLE 2-continued

2'-MOE modified oligonucleotides with PS or mixed PS/PO internucleoside linkages

| Number Compound | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1287073 | TTCACTTTCATAATGCTGG | eeeeeeeeeeeeeeeeeee | sssssssssosssssssss | 27062 | 27080 | 33 |
| 1287070 | TTCACTTTCATAATGCTGG | eeeeeeeeeeeeeeeeeee | sssssssssosssssssoss | 27062 | 27080 | 33 |
| 1287072 | TTCACTTTCATAATGCTGG | eeeeeeeeeeeeeeeeeee | sossssssssssssssss | 27062 | 27080 | 33 |
| 1287067 | TTCACTTTCATAATGCTGG | eeeeeeeeeeeeeeeeeee | sossssssssssssssoss | 27062 | 27080 | 33 |
| 1287068 | TTCACTTTCATAATGCTGG | eeeeeeeeeeeeeeeeeee | sossssssosssssssss | 27062 | 27080 | 33 |
| 1287069 | TTCACTTTCATAATGCTGG | eeeeeeeeeeeeeeeeeee | sosossssssssssssss | 27062 | 27080 | 20 |
| 1287060 | ATTCACTTTCATAATGCTGG | eeeeeeeeeeeeeeeeeeee | ssssssssssssssssoss | 27062 | 27081 | 20 |
| 1287057 | ATTCACTTTCATAATGCTGG | eeeeeeeeeeeeeeeeeeee | ssssssssssssssooss | 27062 | 27081 | 20 |
| 1287054 | ATTCACTTTCATAATGCTGG | eeeeeeeeeeeeeeeeeeee | sssssssssssssososs | 27062 | 27081 | 20 |
| 1287059 | ATTCACTTTCATAATGCTGG | eeeeeeeeeeeeeeeeeeee | ssssssssosssssssss | 27062 | 27081 | 20 |
| 1287053 | ATTCACTTTCATAATGCTGG | eeeeeeeeeeeeeeeeeeee | sssssssssossssssoss | 27062 | 27081 | 20 |
| 1287056 | ATTCACTTTCATAATGCTGG | eeeeeeeeeeeeeeeeeeee | sssssssssoosssssss | 27062 | 27081 | 20 |
| 1287058 | ATTCACTTTCATAATGCTGG | eeeeeeeeeeeeeeeeeeee | sossssssssssssssss | 27062 | 27081 | 20 |
| 1287050 | ATTCACTTTCATAATGCTGG | eeeeeeeeeeeeeeeeeeee | sossssssssssssssoss | 27062 | 27081 | 20 |
| 1287051 | ATTCACTTTCATAATGCTGG | eeeeeeeeeeeeeeeeeeee | sossssssosssssssss | 27062 | 27081 | 20 |
| 1287052 | ATTCACTTTCATAATGCTGG | eeeeeeeeeeeeeeeeeeee | sosossssssssssssss | 27062 | 27081 | 20 |
| 1287055 | ATTCACTTTCATAATGCTGG | eeeeeeeeeeeeeeeeeeee | soossssssssssssss | 27062 | 27081 | 20 |
| 1287075 | ATTCACTTTCATAATGCTG | eeeeeeeeeeeeeeeeeee | sssssssssssssssss | 27063 | 27081 | 34 |
| 1287062 | AGATTCACTTTCATAATGCT | eeeeeeeeeeeeeeeeeeee | ssssssssssssssssss | 27064 | 27083 | 35 |
| 1287061 | GATTCACTTTCATAATGCTG | eeeeeeeeeeeeeeeeeeee | ssssssssssssssssss | 27063 | 27082 | 49 |
| 1287076 | GATTCACTTTCATAATGCT | eeeeeeeeeeeeeeeeeee | sssssssssssssssss | 27064 | 27082 | 50 |
| 1287701 | TCACTTTCATAATGCTGGT | eeeeeeeeeeeeeeeeeee | sssssssssssssssss | 27062 | 27079 | 36 |
| 1287702 | TCACTTTCATAATGCTGGA | eeeeeeeeeeeeeeeeeee | sssssssssssssssss | 27062 | 27079 | 37 |

Table 3

The modified oligonucleotides in Table 3 below are 16, 17, 18, 19 or 20 nucleosides in length. Each nucleoside comprises a 2'-NMA sugar moiety. The sugar motif for each modified oligonucleotide is provided in the Sugar Motif column, wherein each 'n' represents a 2'-NMA sugar moiety. Each internucleoside linkage is either a phosphorothioate internucleoside linkage or a phosphodiester internucleoside linkage. The internucleoside linkage motif for each modified oligonucleotide is provided in the Internucleoside Linkage Motif column, wherein each 's' represents a phosphorothioate internucleoside linkage, and each 'o' represents a phosphodiester internucleoside linkage. Each cytosine is a 5-methyl cytosine.

Each modified oligonucleotide listed in Table 3 below is 100% complementary to SEQ ID NO: 1 (GENBANK Accession No. NT_006713.14 truncated from nucleotides 19939708 to 19967777). "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 3

2'-NMA modified oligonucleotides with PS or mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1287127 | CACTTTCATAATGCTGGCA | nnnnnnnnnnnnnnnnnnn | sssssssssssssssssss | 27060 | 27078 | 26 |
| 1287122 | TCACTTTCATAATGCTGGCA | nnnnnnnnnnnnnnnnnnnn | ssssssssssssssssssss | 27060 | 27079 | 27 |
| 1212871 | CTTTCATAATGCTGGC | nnnnnnnnnnnnnnnn | sssssssssssssss | 27061 | 27076 | 28 |
| 1212869 | ACTTTCATAATGCTGGC | nnnnnnnnnnnnnnnnn | ssssssssssssssss | 27061 | 27077 | 29 |
| 1358996 | CACTTTCATAATGCTGGC | nnnnnnnnnnnnnnnnnn | sososssssssssssss | 27061 | 27078 | 21 |
| 1212873 | CACTTTCATAATGCTGGC | nnnnnnnnnnnnnnnnnn | ssosssssssssssoss | 27061 | 27078 | 21 |
| 1212874 | CACTTTCATAATGCTGGC | nnnnnnnnnnnnnnnnnn | ssosssssosssssoss | 27061 | 27078 | 21 |
| 1212875 | CACTTTCATAATGCTGGC | nnnnnnnnnnnnnnnnnn | ssosssosssosssoss | 27061 | 27078 | 21 |
| 1212879 | CACTTTCATAATGCTGGC | nnnnnnnnnnnnnnnnnn | soossssssssssooss | 27061 | 27078 | 21 |
| 1212880 | CACTTTCATAATGCTGGC | nnnnnnnnnnnnnnnnnn | sooossssssssssooss | 27061 | 27078 | 21 |
| 1212881 | CACTTTCATAATGCTGGC | nnnnnnnnnnnnnnnnnn | sooosssssssooosss | 27061 | 27078 | 21 |
| 1212885 | CACTTTCATAATGCTGGC | nnnnnnnnnnnnnnnnnn | sssssoooooosssss | 27061 | 27078 | 21 |
| 1212887 | CACTTTCATAATGCTGGC | nnnnnnnnnnnnnnnnnn | ssssssssoooosssss | 27061 | 27078 | 21 |
| 1287128 | TCACTTTCATAATGCTGGC | nnnnnnnnnnnnnnnnnnn | sssssssssssssssssss | 27061 | 27079 | 30 |
| 1212870 | CACTTTCATAATGCTGG | nnnnnnnnnnnnnnnnn | ssssssssssssssss | 27062 | 27078 | 32 |
| 1287132 | TCACTTTCATAATGCTGG | nnnnnnnnnnnnnnnnnn | sosssssssssssssoss | 27062 | 27079 | 23 |
| 1287133 | TCACTTTCATAATGCTGG | nnnnnnnnnnnnnnnnnn | sssssssosssssssss | 27062 | 27079 | 23 |
| 1332246 | TCACTTTCATAATGCTGG | nnnnnnnnnnnnnnnnnn | ssssssssosssssoss | 27062 | 27079 | 23 |
| 1332265 | TCACTTTCATAATGCTGG | nnnnnnnnnnnnnnnnnn | sssssssssssssosss | 27062 | 27079 | 23 |
| 1364778 | TCACTTTCATAATGCTGG | nnnnnnnnnnnnnnnnnn | sssssssssssossosss | 27062 | 27079 | 23 |
| 1364779 | TCACTTTCATAATGCTGG | nnnnnnnnnnnnnnnnnn | ssssssssssossossss | 27062 | 27079 | 23 |
| 1364780 | TCACTTTCATAATGCTGG | nnnnnnnnnnnnnnnnnn | ssssssssssossossss | 27062 | 27079 | 23 |
| 1364781 | TCACTTTCATAATGCTGG | nnnnnnnnnnnnnnnnnn | ssssssssosssossss | 27062 | 27079 | 23 |
| 1287129 | TTCACTTTCATAATGCTGG | nnnnnnnnnnnnnnnnnnn | sssssssssssssssssss | 27062 | 27080 | 33 |
| 1287130 | TTCACTTTCATAATGCTGG | nnnnnnnnnnnnnnnnnnn | sosssssssssssssoss | 27062 | 27080 | 33 |
| 1287131 | TTCACTTTCATAATGCTGG | nnnnnnnnnnnnnnnnnnn | sssssssossssssssss | 27062 | 27080 | 33 |
| 1332263 | TTCACTTTCATAATGCTGG | nnnnnnnnnnnnnnnnnnn | ssssssssosssssssoss | 27062 | 27080 | 33 |
| 1332264 | TTCACTTTCATAATGCTGG | nnnnnnnnnnnnnnnnnnn | sssssssssssssssssoss | 27062 | 27080 | 33 |

TABLE 3-continued

2'-NMA modified oligonucleotides with PS or mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1332266 | TTCACTTTCATAATGCTGG | nnnnnnnnnnnnnnnnnnn | sssssssssssssssososs | 27062 | 27080 | 33 |
| 1332270 | TTCACTTTCATAATGCTGG | nnnnnnnnnnnnnnnnnnn | sssssssssssssssooss | 27062 | 27080 | 33 |
| 1287124 | ATTCACTTTCATAATGCTGG | nnnnnnnnnnnnnnnnnnnn | ssssssssssssssssssss | 27062 | 27081 | 20 |
| 1287125 | ATTCACTTTCATAATGCTGG | nnnnnnnnnnnnnnnnnnnn | sossssssssssssssssoss | 27062 | 27081 | 20 |
| 1287126 | ATTCACTTTCATAATGCTGG | nnnnnnnnnnnnnnnnnnnn | sssssssssossssssssss | 27062 | 27081 | 20 |
| 1332267 | ATTCACTTTCATAATGCTGG | nnnnnnnnnnnnnnnnnnnn | sssssssssssssssssoss | 27062 | 27081 | 20 |
| 1332268 | ATTCACTTTCATAATGCTGG | nnnnnnnnnnnnnnnnnnnn | sssssssssssssssssooss | 27062 | 27081 | 20 |
| 1332269 | ATTCACTTTCATAATGCTGG | nnnnnnnnnnnnnnnnnnnn | sssssssssssssssssososs | 27062 | 27081 | 20 |
| 1332271 | ATTCACTTTCATAATGCTGG | nnnnnnnnnnnnnnnnnnnn | sssssssssosssssssoss | 27062 | 27081 | 20 |
| 1287123 | TTCACTTTCATAATGCTGGC | nnnnnnnnnnnnnnnnnnnn | ssssssssssssssssssss | 27061 | 27080 | 22 |

Table 4

The modified oligonucleotides in Table 4 below are 18 or 19 nucleosides in length. Each nucleoside comprises either a 2'-MOE sugar moiety or a 2'-NMA sugar moiety. The sugar motif for each modified oligonucleotide is provided in the Sugar Motif column, wherein each 'e' represents a 2'-MOE sugar moiety, and each 'n' represents a 2'-NMA sugar moiety. Each internucleoside linkage is a phosphorothioate internucleoside linkage. The internucleoside linkage motif for each modified oligonucleotide is provided in the Internucleoside Linkage Motif column, wherein each 's' represents a phosphorothioate internucleoside linkage. Each cytosine is a 5-methyl cytosine.

Each modified oligonucleotide listed in Table 4 below is 100% complementary to SEQ ID NO: 1 (GENBANK Accession No. NT_006713.14 truncated from nucleotides 19939708 to 19967777), unless specifically stated otherwise. Non-complementary nucleobases are specified in the Nucleobase Sequence column in underlined, bold, italicized font. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 4

Mixed 2'-MOE/2'-NMA modified oligonucleotides with PS internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1212931 | CACTTTCATAATGCTGGC | nennnneneennnnnn | ssssssssssssssss | 27061 | 27078 | 21 |
| 1212936 | CACTTTCATAATGCTGGC | nnnnnnnnnnnennneen | ssssssssssssssss | 27061 | 27078 | 21 |
| 1212941 | CACTTTCATAATGCTGGC | nennnneneenenneen | ssssssssssssssss | 27061 | 27078 | 21 |
| 1287728 | TCACTTTCATAATGCTGGC | nnnnnnnnnnnnnnnnnne | sssssssssssssssss | 27061 | 27079 | 30 |
| 1287729 | TCACTTTCATAATGCTGG*T* | nnnnnnnnnnnnnnnnnne | sssssssssssssssss | 27062 | 27079 | 36 |
| 1287730 | TCACTTTCATAATGCTGG*A* | nnnnnnnnnnnnnnnnnne | sssssssssssssssss | 27062 | 27079 | 37 |

Table 5 The modified oligonucleotides in Table 5 below are 16, 17, or 18 nucleosides in length. Each nucleoside comprises either a 2'-MOE sugar moiety or a cEt sugar moiety. The sugar motif for each modified oligonucleotide is provided in the Sugar Motif column, wherein each 'e' represents a 2'-MOE sugar moiety, and each 'k' represents a cEt sugar moiety. Each internucleoside linkage is a phosphorothioate internucleoside linkage. The internucleoside linkage motif for each modified oligonucleotide is provided in the Internucleoside Linkage Motif column, wherein each 's' represents a phosphorothioate internucleoside linkage. Each cytosine is a 5-methyl cytosine.

Each modified oligonucleotide listed in Table 5 below is 100% complementary to SEQ ID NO: 1 (GENBANK Accession No. NT_006713.14 truncated from nucleotides 19939708 to 19967777). "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 5

Mixed 2'-MOE/cEt modified oligonucleotides with PS internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1212961 | CACTTTCATAATGCTGGC | keekeekeekeekeeeek | sssssssssssssssss | 27061 | 27078 | 21 |
| 1212962 | CACTTTCATAATGCTGGC | keeekeeekeeekeeek | sssssssssssssssss | 27061 | 27078 | 21 |
| 1212963 | CACTTTCATAATGCTGGC | keeeeekeeeeekeeeek | sssssssssssssssss | 27061 | 27078 | 21 |
| 1212964 | CACTTTCATAATGCTGGC | keeeeeeekeeeeeeeek | sssssssssssssssss | 27061 | 27078 | 21 |
| 1212965 | CACTTTCATAATGCTGGC | keeeeeeeeeeeeeeeek | sssssssssssssssss | 27061 | 27078 | 21 |
| 1212966 | CACTTTCATAATGCTGGC | eekeekeekeekeekek | sssssssssssssssss | 27061 | 27078 | 21 |
| 1212967 | CACTTTCATAATGCTGGC | eekeekeekeekeekee | sssssssssssssssss | 27061 | 27078 | 21 |
| 1212968 | CACTTTCATAATGCTGGC | eeeeekeekeekeekee | sssssssssssssssss | 27061 | 27078 | 21 |
| 1212969 | CACTTTCATAATGCTGGC | eeeeekeekeekeeeee | sssssssssssssssss | 27061 | 27078 | 21 |
| 1212970 | CACTTTCATAATGCTGGC | eeeeekeeeeekeeeee | sssssssssssssssss | 27061 | 27078 | 21 |
| 1212971 | CACTTTCATAATGCTGGC | keekeekeeeeeeeeee | sssssssssssssssss | 27061 | 27078 | 21 |
| 1212972 | CACTTTCATAATGCTGGC | eeeeeeeekeekeekeek | sssssssssssssssss | 27061 | 27078 | 21 |
| 1212973 | CACTTTCATAATGCTGGC | keekeeeeeeeeeeeee | sssssssssssssssss | 27061 | 27078 | 21 |
| 1212974 | CACTTTCATAATGCTGGC | eeeeeeeeekeekeek | sssssssssssssssss | 27061 | 27078 | 21 |
| 1212975 | CACTTTCATAATGCTGGC | keeeeeeeeeeeeeeee | sssssssssssssssss | 27061 | 27078 | 21 |
| 1212976 | CACTTTCATAATGCTGGC | eeeeeeeeeeeeekeek | sssssssssssssssss | 27061 | 27078 | 21 |
| 1212977 | ACTTTCATAATGCTGGC | keekeekeekeekeeek | ssssssssssssssss | 27061 | 27077 | 29 |
| 1212978 | ACTTTCATAATGCTGGC | keeekeeekeeekeeek | ssssssssssssssss | 27061 | 27077 | 29 |
| 1212979 | ACTTTCATAATGCTGGC | keeeeekeeeeekeeek | ssssssssssssssss | 27061 | 27077 | 29 |
| 1212980 | ACTTTCATAATGCTGGC | keeeeeeekeeeeeeek | ssssssssssssssss | 27061 | 27077 | 29 |
| 1212981 | ACTTTCATAATGCTGGC | keeeeeeeeeeeeeeek | ssssssssssssssss | 27061 | 27077 | 29 |
| 1212982 | ACTTTCATAATGCTGGC | eekeekeekeekeekek | ssssssssssssssss | 27061 | 27077 | 29 |
| 1212983 | ACTTTCATAATGCTGGC | eekeekeekeekeekee | ssssssssssssssss | 27061 | 27077 | 29 |

TABLE 5-continued

Mixed 2'-MOE/cEt modified oligonucleotides with PS internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1212984 | ACTTTCATAATGCTGGC | eeeeekeekeekeekee | sssssssssssssss | 27061 | 27077 | 29 |
| 1212985 | ACTTTCATAATGCTGGC | eeeeekeekeekeeeee | sssssssssssssss | 27061 | 27077 | 29 |
| 1212986 | ACTTTCATAATGCTGGC | eeeeekeeeeekeeeee | sssssssssssssss | 27061 | 27077 | 29 |
| 1212987 | ACTTTCATAATGCTGGC | keekeekeekeeeeee | sssssssssssssss | 27061 | 27077 | 29 |
| 1212988 | ACTTTCATAATGCTGGC | eeeeeeekeekeekeek | sssssssssssssss | 27061 | 27077 | 29 |
| 1212989 | ACTTTCATAATGCTGGC | keekeekeeeeeeeee | sssssssssssssss | 27061 | 27077 | 29 |
| 1212990 | ACTTTCATAATGCTGGC | eeeeeeeeekeekeek | sssssssssssssss | 27061 | 27077 | 29 |
| 1212991 | ACTTTCATAATGCTGGC | keekeeeeeeeeeeee | sssssssssssssss | 27061 | 27077 | 29 |
| 1212992 | ACTTTCATAATGCTGGC | eeeeeeeeeeeekeek | sssssssssssssss | 27061 | 27077 | 29 |
| 1212993 | CTTTCATAATGCTGGC | keekeekeekeekeek | sssssssssssssss | 27061 | 27076 | 28 |
| 1212994 | CTTTCATAATGCTGGC | keeeekeekeeeekeek | sssssssssssssss | 27061 | 27076 | 28 |
| 1212995 | CTTTCATAATGCTGGC | keeeekeeeekeeeek | sssssssssssssss | 27061 | 27076 | 28 |
| 1212996 | CTTTCATAATGCTGGC | keeeeeekeeeeeek | sssssssssssssss | 27061 | 27076 | 28 |
| 1212997 | CTTTCATAATGCTGGC | keeeeeeeeeeeeek | sssssssssssssss | 27061 | 27076 | 28 |
| 1212998 | CTTTCATAATGCTGGC | kekeekeekeekeeke | sssssssssssssss | 27061 | 27076 | 28 |
| 1212999 | CTTTCATAATGCTGGC | eekeekeekeekeeke | sssssssssssssss | 27061 | 27076 | 28 |
| 1213000 | CTTTCATAATGCTGGC | eeeeekeekeekeeke | sssssssssssssss | 27061 | 27076 | 28 |
| 1213001 | CTTTCATAATGCTGGC | eeeeekeekeekeeee | sssssssssssssss | 27061 | 27076 | 28 |
| 1213002 | CTTTCATAATGCTGGC | eeeeekeeeeekeeee | sssssssssssssss | 27061 | 27076 | 28 |
| 1213003 | CTTTCATAATGCTGGC | keekeekeekeeeeee | sssssssssssssss | 27061 | 27076 | 28 |
| 1213004 | CTTTCATAATGCTGGC | eeeeekeekeekeeek | sssssssssssssss | 27061 | 27076 | 28 |
| 1213005 | CTTTCATAATGCTGGC | keekeekeeeeeeeee | sssssssssssssss | 27061 | 27076 | 28 |
| 1213006 | CTTTCATAATGCTGGC | eeeeeeeekeekeek | sssssssssssssss | 27061 | 27076 | 28 |
| 1213007 | CTTTCATAATGCTGGC | keekeeeeeeeeeeee | sssssssssssssss | 27061 | 27076 | 28 |
| 1213008 | CTTTCATAATGCTGGC | eeeeeeeeeeeekeek | sssssssssssssss | 27061 | 27076 | 28 |

Table 6

The modified oligonucleotides in Table 6 below are 19 or 20 nucleosides in length. Each nucleoside comprises a 2'-MOE sugar moiety, a 2'-NMA sugar moiety, a 2'-OMe sugar moiety, or a 2'β-D-deoxyribosyl sugar moiety. The sugar motif for each modified oligonucleotide is provided in the Sugar Motif column, wherein each 'e' represents a 2'-MOE sugar moiety, each 'n' represents a 2'-NMA sugar moiety, each 'y' represents a 2'-OMe sugar moiety, and each 'd' represents a 2'β-D-deoxyribosyl sugar moiety. Each internucleoside linkage is either a phosphorothioate internucleoside linkage or a phosphodiester internucleoside linkage. The internucleoside linkage motif for each modified oligonucleotide, provided in the Internucleoside Linkage Motif column, is (from 5' to 3'): sssssssssssssssso; wherein each 's' represents a phosphorothioate internucleoside linkage, and each 'o' represents a phosphodiester internucleoside linkage. Cytosines are either non-methylated cytosines or 5-methyl cytosines, wherein each lowercase 'c' in the Nucleobase Sequence column represents a non-methylated cytosine, and each uppercase 'C' in the Nucleobase Sequence column represents a 5-methyl cytosine.

Each nucleobase in the modified oligonucleotides listed in Table 6 below is complementary to SEQ ID NO: 1 (GENBANK Accession No. NT_006713.14 truncated from nucleotides 19939708 to 19967777), unless specifically stated otherwise. Non-complementary nucleobases are specified in the Nucleobase Sequence column in underlined, bold, italicized font. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 6

Modified oligonucleotides with mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1287707 | TCACTTTCATAATGCTGGC | eeeeeeeeeeeeeeeeeed | sssssssssssssssssso | 27061 | 27079 | 30 |
| 1287708 | TCACTTTCATAATGCTGGc | eeeeeeeeeeeeeeeeeed | sssssssssssssssssso | 27061 | 27079 | 30 |
| 1287709 | TCACTTTCATAATGCTGGT | eeeeeeeeeeeeeeeeeed | sssssssssssssssssso | 27062 | 27079 | 36 |
| 1287710 | TCACTTTCATAATGCTGGA | eeeeeeeeeeeeeeeeeed | sssssssssssssssssso | 27062 | 27079 | 37 |
| 1287711 | TCACTTTCATAATGCTGGc | eeeeeeeeeeeeeeeeeey | sssssssssssssssssso | 27061 | 27079 | 30 |
| 1287712 | TCACTTTCATAATGCTGGU | eeeeeeeeeeeeeeeeeey | sssssssssssssssssso | 27062 | 27079 | 38 |
| 1287713 | TCACTTTCATAATGCTGGA | eeeeeeeeeeeeeeeeeey | sssssssssssssssssso | 27062 | 27079 | 37 |
| 1287731 | TCACTTTCATAATGCTGGC | nnnnnnnnnnnnnnnnnne | sssssssssssssssssso | 27061 | 27079 | 30 |
| 1287732 | TCACTTTCATAATGCTGGc | nnnnnnnnnnnnnnnnnne | sssssssssssssssssso | 27061 | 27079 | 30 |
| 1287733 | TCACTTTCATAATGCTGGT | nnnnnnnnnnnnnnnnnne | sssssssssssssssssso | 27062 | 27079 | 36 |
| 1287734 | TCACTTTCATAATGCTGGA | nnnnnnnnnnnnnnnnnne | sssssssssssssssssso | 27062 | 27079 | 37 |
| 1287735 | TCACTTTCATAATGCTGGC | nnnnnnnnnnnnnnnnnnd | sssssssssssssssssso | 27061 | 27079 | 30 |
| 1287736 | TCACTTTCATAATGCTGGc | nnnnnnnnnnnnnnnnnnd | sssssssssssssssssso | 27061 | 27079 | 30 |
| 1287737 | TCACTTTCATAATGCTGGT | nnnnnnnnnnnnnnnnnnd | sssssssssssssssssso | 27062 | 27079 | 36 |
| 1287738 | TCACTTTCATAATGCTGGA | nnnnnnnnnnnnnnnnnnd | sssssssssssssssssso | 27062 | 27079 | 37 |
| 1287739 | TCACTTTCATAATGCTGGc | nnnnnnnnnnnnnnnnnny | sssssssssssssssssso | 27061 | 27079 | 30 |
| 1287740 | TCACTTTCATAATGCTGGU | nnnnnnnnnnnnnnnnnny | sssssssssssssssssso | 27062 | 27079 | 38 |
| 1287741 | TCACTTTCATAATGCTGGA | nnnnnnnnnnnnnnnnnny | sssssssssssssssssso | 27062 | 27079 | 37 |
| 1287705 | TCACTTTCATAATGCTGGT | eeeeeeeeeeeeeeeeeee | sssssssssssssssssso | 27062 | 27079 | 36 |
| 1287706 | TCACTTTCATAATGCTGGA | eeeeeeeeeeeeeeeeeee | sssssssssssssssssso | 27062 | 27079 | 37 |
| 1287704 | TCACTTTCATAATGCTGGc | eeeeeeeeeeeeeeeeeee | sssssssssssssssssso | 27061 | 27079 | 30 |
| 1287703 | TCACTTTCATAATGCTGGC | eeeeeeeeeeeeeeeeeee | sssssssssssssssssso | 27061 | 27079 | 30 |

Table 7

The modified oligonucleotides in Table 7 below are 19 or 20 nucleosides in length. Each nucleoside comprises a 2'-MOE sugar moiety, a 2'-NMA sugar moiety, or a 2'β-D-deoxyribosyl sugar moiety. The sugar motif for each modified oligonucleotide is provided in the Sugar Motif column, wherein each 'e' represents a 2'-MOE sugar moiety, each 'n' represents a 2'-NMA sugar moiety, and each 'd' represents a 2'β-D-deoxyribosyl sugar moiety. Each internucleoside linkage is either a phosphorothioate internucleoside linkage or a phosphodiester internucleoside linkage. The internucleoside linkage motif for each modified oligonucleotide, provided in the Internucleoside Linkage Motif column, is (from 5' to 3'): sssssssssssssssssoo; wherein each 's' represents a phosphorothioate internucleoside linkage, and each 'o' represents a phosphodiester internucleoside linkage. Each cytosine is a 5-methyl cytosine. Each nucleobase in the modified oligonucleotide listed in Table 6 below is complementary to SEQ ID NO: 1 (GENBANK Accession No. NT_006713.14 truncated from nucleotides 19939708 to 19967777), unless specifically stated otherwise. Non-complementary nucleobases are specified in the Nucleobase Sequence column in underlined, bold, italicized font. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 7

Modified oligonucleotides with mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1318749 | TCACTTTCATAATGCTGG*AA* | nnnnnnnnnnnnnnnnndd | sssssssssssssssssoo | 27062 | 27079 | 39 |
| 1318750 | TCACTTTCATAATGCTGGCA | nnnnnnnnnnnnnnnnned | sssssssssssssssssoo | 27060 | 27079 | 27 |
| 1318751 | TCACTTTCATAATGCTGGCA | nnnnnnnnnnnnnnnnndd | sssssssssssssssssoo | 27060 | 27079 | 27 |
| 1318752 | TCACTTTCATAATGCTGG*AA* | nnnnnnnnnnnnnnnnned | sssssssssssssssssoo | 27062 | 27079 | 39 |
| 1318753 | TCACTTTCATAATGCTGG*AA* | nnnnnnnnnnnnnnnnnde | sssssssssssssssssoo | 27062 | 27079 | 39 |
| 1318754 | TCACTTTCATAATGCTGGCA | nnnnnnnnnnnnnnnnnde | sssssssssssssssssoo | 27060 | 27079 | 27 |
| 1318755 | TCACTTTCATAATGCTGG*AA* | nnnnnnnnnnnnnnnnnee | sssssssssssssssssoo | 27062 | 27079 | 39 |
| 1318756 | TCACTTTCATAATGCTGGCA | nnnnnnnnnnnnnnnnnee | sssssssssssssssssoo | 27060 | 27079 | 27 |
| 1318757 | TCACTTTCATAATGCTGG*AT* | eeeeeeeeeeeeeeeeedd | sssssssssssssssssoo | 27062 | 27079 | 40 |
| 1318758 | TCACTTTCATAATGCTGG*AC* | eeeeeeeeeeeeeeeeedd | sssssssssssssssssoo | 27062 | 27079 | 41 |
| 1318759 | TCACTTTCATAATGCTGG*TC* | eeeeeeeeeeeeeeeeedd | sssssssssssssssssoo | 27062 | 27079 | 42 |
| 1318760 | TCACTTTCATAATGCTGG*AA* | eeeeeeeeeeeeeeeeedd | sssssssssssssssssoo | 27062 | 27079 | 39 |
| 1318761 | TCACTTTCATAATGCTGG*TT* | eeeeeeeeeeeeeeeeedd | sssssssssssssssssoo | 27062 | 27079 | 43 |
| 1318762 | TCACTTTCATAATGCTGG*TA* | eeeeeeeeeeeeeeeeedd | sssssssssssssssssoo | 27062 | 27079 | 44 |
| 1318763 | TCACTTTCATAATGCTGGC*C* | eeeeeeeeeeeeeeeeedd | sssssssssssssssssoo | 27061 | 27079 | 45 |
| 1318764 | TCACTTTCATAATGCTGG*AA* | eeeeeeeeeeeeeeeeeed | sssssssssssssssssoo | 27062 | 27079 | 39 |
| 1318765 | TCACTTTCATAATGCTGG*AC* | eeeeeeeeeeeeeeeeede | sssssssssssssssssoo | 27062 | 27079 | 41 |
| 1318766 | TCACTTTCATAATGCTGGC*T* | eeeeeeeeeeeeeeeeedd | sssssssssssssssssoo | 27061 | 27079 | 46 |
| 1318767 | TCACTTTCATAATGCTGG*TT* | eeeeeeeeeeeeeeeeede | sssssssssssssssssoo | 27062 | 27079 | 43 |
| 1318768 | TCACTTTCATAATGCTGGCA | eeeeeeeeeeeeeeeeedd | sssssssssssssssssoo | 27060 | 27079 | 27 |
| 1318769 | TCACTTTCATAATGCTGGCA | eeeeeeeeeeeeeeeeeed | sssssssssssssssssoo | 27060 | 27079 | 27 |
| 1318770 | TCACTTTCATAATGCTGG*AT* | eeeeeeeeeeeeeeeeede | sssssssssssssssssoo | 27062 | 27079 | 40 |
| 1318771 | TCACTTTCATAATGCTGG*TA* | eeeeeeeeeeeeeeeeede | sssssssssssssssssoo | 27062 | 27079 | 44 |
| 1318772 | TCACTTTCATAATGCTGG*AA* | eeeeeeeeeeeeeeeeede | sssssssssssssssssoo | 27062 | 27079 | 39 |
| 1318773 | TCACTTTCATAATGCTGG*TC* | eeeeeeeeeeeeeeeeede | sssssssssssssssssoo | 27062 | 27079 | 42 |
| 1318774 | TCACTTTCATAATGCTGGC*C* | eeeeeeeeeeeeeeeeede | sssssssssssssssssoo | 27061 | 27079 | 45 |
| 1318775 | TCACTTTCATAATGCTGGC*T* | eeeeeeeeeeeeeeeeede | sssssssssssssssssoo | 27061 | 27079 | 46 |

TABLE 7-continued

Modified oligonucleotides with mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1318776 | TCACTTTCATAATGCTGGCA | eeeeeeeeeeeeeeeeeede | ssssssssssssssssssoo | 27060 | 27079 | 27 |
| 1333508 | TCACTTTCATAATGCTGGC*T* | nnnnnnnnnnnnnnnnnnee | ssssssssssssssssssoo | 27061 | 27079 | 46 |
| 1318777 | TCACTTTCATAATGCTGG*AC* | eeeeeeeeeeeeeeeeeeee | ssssssssssssssssssoo | 27062 | 27079 | 41 |
| 1318778 | TCACTTTCATAATGCTGG*TT* | eeeeeeeeeeeeeeeeeeee | ssssssssssssssssssoo | 27062 | 27079 | 43 |
| 1318779 | TCACTTTCATAATGCTGG*A*A | eeeeeeeeeeeeeeeeeeee | ssssssssssssssssssoo | 27062 | 27079 | 39 |
| 1318780 | TCACTTTCATAATGCTGG*TC* | eeeeeeeeeeeeeeeeeeee | ssssssssssssssssssoo | 27062 | 27079 | 42 |
| 1318781 | TCACTTTCATAATGCTGG*AT* | eeeeeeeeeeeeeeeeeeee | ssssssssssssssssssoo | 27062 | 27079 | 40 |
| 1318782 | TCACTTTCATAATGCTGGC*T* | eeeeeeeeeeeeeeeeeeee | ssssssssssssssssssoo | 27061 | 27079 | 46 |
| 1318783 | TCACTTTCATAATGCTGG*T*A | eeeeeeeeeeeeeeeeeeee | ssssssssssssssssssoo | 27062 | 27079 | 44 |
| 1318784 | TCACTTTCATAATGCTGGC*C* | eeeeeeeeeeeeeeeeeeee | ssssssssssssssssssoo | 27061 | 27079 | 45 |
| 1318748 | TCACTTTCATAATGCTGGCA | eeeeeeeeeeeeeeeeeeee | ssssssssssssssssssoo | 27060 | 27079 | 27 |

Table 8

The modified oligonucleotides in Table 8 below are each 19 nucleosides in length. Each nucleoside comprises a 2'-MOE sugar moiety, a 2'-NMA sugar moiety, or a 2'β-D-deoxyribosyl sugar moiety. The sugar motif for each modified oligonucleotide is provided in the Sugar Motif column, wherein each 'e' represents a 2'-MOE sugar moiety, each represents a 2'-NMA sugar moiety, and each represents a 2'β-D-deoxyribosyl sugar moiety. Each internucleoside linkage is either a phosphorothioate internucleoside linkage or a phosphodiester internucleoside linkage. The internucleoside linkage motif for each modified oligonucleotide, provided in the Internucleoside Linkage Motif column, is (from 5' to 3'): sssssssssssssosossso; wherein each represents a phosphorothioate internucleoside linkage, and each represents a phosphodiester internucleoside linkage. Each cytosine is a 5-methyl cytosine. Each nucleobase in the modified oligonucleotide listed in Table 8 below is complementary to SEQ ID NO: 1 (GENBANK Accession No. NT_006713.14 truncated from nucleotides 19939708 to 19967777), unless specifically stated otherwise. Non-complementary nucleobases are specified in the Nucleobase Sequence column in underlined, bold, italicized font. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 8

Modified oligonucleotides with mixed PS/PO internucleoside linkages

| Compound Number | Nucleobase Sequence (5' to 3') | Sugar Motif (5' to 3') | Internucleoside Linkage Motif (5 to 3') | SEQ ID No: 1 Start Site | SEQ ID No: 1 Stop Site | SEQ ID No. |
|---|---|---|---|---|---|---|
| 1332247 | TCACTTTCATAATGCTGGC | nnnnnnnnnnnnnnnnnnd | sssssssssssssososso | 27061 | 27079 | 30 |
| 1332248 | TCACTTTCATAATGCTGG*A* | nnnnnnnnnnnnnnnnnnd | sssssssssssssososso | 27062 | 27079 | 37 |
| 1332249 | TCACTTTCATAATGCTGG*A* | nnnnnnnnnnnnnnnnnne | sssssssssssssososso | 27062 | 27079 | 37 |
| 1332251 | TCACTTTCATAATGCTGGC | nnnnnnnnnnnnnnnnnne | sssssssssssssososso | 27061 | 27079 | 30 |
| 1332255 | TCACTTTCATAATGCTGGC | eeeeeeeeeeeeeeeeeed | sssssssssssssososso | 27061 | 27079 | 30 |
| 1332257 | TCACTTTCATAATGCTGG*A* | eeeeeeeeeeeeeeeeeed | sssssssssssssososso | 27062 | 27079 | 37 |
| 1332256 | TCACTTTCATAATGCTGG*A* | eeeeeeeeeeeeeeeeeeee | sssssssssssssososso | 27062 | 27079 | 37 |
| 1332258 | TCACTTTCATAATGCTGGC | eeeeeeeeeeeeeeeeeeee | sssssssssssssososso | 27061 | 27079 | 30 |

Table 9

The modified oligonucleotides in Table 9 below are each 19 nucleosides in length. Each nucleoside comprises a 2'-MOE sugar moiety, a 2'-NMA sugar moiety, or a 2'β-D-deoxyribosyl sugar moiety. The sugar motif for each modified oligonucleotide is provided in the Sugar Motif column, wherein each 'e' represents a 2'-MOE sugar moiety, each 'n' represents a 2'-NMA sugar moiety, and each 'd' represents a 2'β-D-deoxyribosyl sugar moiety. Each internucleoside linkage is either a phosphorothioate internucleoside linkage or a phosphodiester internucleoside linkage. The internucleoside linkage motif for each modified oligonucleotide, provided in the Internucleoside Linkage Motif column, is (from 5' to 3'): sssssssssssssssosso; wherein each 's' represents a phosphorothioate internucleoside linkage, and each 'o' represents a phosphodiester internucleoside linkage. Each cytosine is a 5-methyl cytosine. Each nucleobase in the modified oligonucleotide listed in Table 9 below is complementary to SEQ ID NO: 1 (GENBANK Accession No. NT_006713.14 truncated from nucleotides 19939708 to 19967777), unless specifically stated otherwise. Non-complementary nucleobases are specified in the Nucleobase Sequence column in underlined, bold, italicized font. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 9

Modified oligonucleotides with mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1332250 | TCACTTTCATAATGCTGG*A* | nnnnnnnnnnnnnnnnnnd | sssssssssssssssosso | 27062 | 27079 | 37 |
| 1332252 | TCACTTTCATAATGCTGGC | nnnnnnnnnnnnnnnnnnd | sssssssssssssssosso | 27061 | 27079 | 30 |
| 1332253 | TCACTTTCATAATGCTGG*A* | nnnnnnnnnnnnnnnnnne | sssssssssssssssosso | 27062 | 27079 | 37 |
| 1332254 | TCACTTTCATAATGCTGGC | nnnnnnnnnnnnnnnnnne | sssssssssssssssosso | 27061 | 27079 | 30 |
| 1332259 | TCACTTTCATAATGCTGG*A* | eeeeeeeeeeeeeeeeeed | sssssssssssssssosso | 27062 | 27079 | 37 |
| 1332260 | TCACTTTCATAATGCTGGC | eeeeeeeeeeeeeeeeeed | sssssssssssssssosso | 27061 | 27079 | 30 |
| 1332261 | TCACTTTCATAATGCTGG*A* | eeeeeeeeeeeeeeeeeee | sssssssssssssssosso | 27062 | 27079 | 37 |
| 1332262 | TCACTTTCATAATGCTGGC | eeeeeeeeeeeeeeeeeee | sssssssssssssssosso | 27061 | 27079 | 30 |

Table 10

The modified oligonucleotides in Table 10 below are each 19 nucleosides in length. Each nucleoside comprises a 2'-MOE sugar moiety or a 2'-NMA sugar moiety. The sugar motif for each modified oligonucleotide is provided in the Sugar Motif column, wherein each 'e' represents a 2'-MOE sugar moiety, and each 'n' represents a 2'-NMA sugar moiety. Each internucleoside linkage is either a phosphorothioate internucleoside linkage or a phosphodiester internucleoside linkage. The internucleoside linkage motif for each modified oligonucleotide, provided in the Internucleoside Linkage Motif column, is (from 5' to 3'): osssssssssssssssss; wherein each 's' represents a phosphorothioate internucleoside linkage, and each 'o' represents a phosphodiester internucleoside linkage. Each cytosine is a 5-methyl cytosine.

Each nucleobase in the modified oligonucleotide listed in Table 10 below is complementary to SEQ ID NO: 1 (GENBANK Accession No. NT_006713.14 truncated from nucleotides 19939708 to 19967777), unless specifically stated otherwise. Non-complementary nucleobases are specified in the Nucleobase Sequence column in underlined, bold, italicized font. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 10

Modified oligonucleotides with mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1287742 | CTCACTTTCATAATGCTGG | ennnnnnnnnnnnnnnnnn | osssssssssssssssss | 27062 | 27079 | 47 |
| 1287743 | TTCACTTTCATAATGCTGG | ennnnnnnnnnnnnnnnnn | osssssssssssssssss | 27062 | 27080 | 33 |
| 1287744 | ATCACTTTCATAATGCTGG | ennnnnnnnnnnnnnnnnn | osssssssssssssssss | 27062 | 27079 | 48 |
| 1287714 | CTCACTTTCATAATGCTGG | eeeeeeeeeeeeeeeeeee | osssssssssssssssss | 27062 | 27079 | 47 |
| 1287716 | ATCACTTTCATAATGCTGG | eeeeeeeeeeeeeeeeeee | osssssssssssssssss | 27062 | 27079 | 48 |
| 1287715 | TTCACTTTCATAATGCTGG | eeeeeeeeeeeeeeeeeee | osssssssssssssssss | 27062 | 27080 | 33 |

Table 11

The modified oligonucleotides in Table 11 below are each 20 nucleosides in length. Each nucleoside comprises a 2'-MOE sugar moiety or a 2'-NMA sugar moiety. The sugar motif for each modified oligonucleotide is provided in the Sugar Motif column, wherein each 'e' represents a 2'-MOE sugar moiety, and each 'n' represents a 2'-NMA sugar moiety. Each internucleoside linkage is either a phosphorothioate internucleoside linkage or a phosphodiester internucleoside linkage. The internucleoside linkage motif for each modified oligonucleotide, provided in the Internucleoside Linkage Motif column, is (from 5' to 3'): osssssssssssssssso; wherein each 's' represents a phosphorothioate internucleoside linkage, and each 'o' represents a phosphodiester internucleoside linkage. Each cytosine is a 5-methyl cytosine.

Each modified oligonucleotide listed in Table 11 below is 100% complementary to SEQ ID NO: 1 (GENBANK Accession No. NT_006713.14 truncated from nucleotides 19939708 to 19967777). "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

TABLE 11

Modified oligonucleotides with mixed PS/PO internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1287745 | TTCACTTTCATAATGCTGGC | ennnnnnnnnnnnnnnnnnne | ossssssssssssssssso | 27061 | 27080 | 22 |
| 1287717 | TTCACTTTCATAATGCTGGC | eeeeeeeeeeeeeeeeeeee | ossssssssssssssssso | 27061 | 27080 | 22 |

Example 2: Activity of Modified Oligonucleotides Complementary to Human SMN2 in Transgenic Mice, Single Dose (35 µg)

Activity of selected modified oligonucleotides described above was tested in human SMN2 transgenic mice. Taiwan strain of SMA Type III mice were obtained from The Jackson Laboratory (Bar Harbor, Me.). These mice lack mouse SMN and are homozygous for human SMN2 (mSMN−/−; hSMN2+/+; FVB.Cg-Tg(SMN2)2HungSMN1tm1Hung/J, stock number 005058; Bar Harbor, Me.), or are heterozygous for mouse SMN and heterozygous for human SMN2(mSMN+/−; hSMN2+/−; FVB.Cg-Tg(SMN2)$_2$HungSMN1tm1Hung/J) obtained by breeding HOM/HOM (stock #00005058) to FVB/NJ (Stock #001800).

Treatment

Homozygous or heterozygous transgenic mice were divided into groups of 4 mice each. Each mouse received a single ICV bolus of 35 µg of modified oligonucleotide. Comparator Compound Nos. 387954, 396442, and 396443 were also tested in this assay. A group of 4 mice received PBS as a negative control.

RNA Analysis

Two weeks post treatment, mice were sacrificed and RNA was extracted from cortical brain tissue and spinal cord for real-time qPCR analysis of SMN2 RNA. Primer probe set hSMN2vd #4_LTS00216_MGB (forward sequence: GCTGATGCTTTGGGAAGTATGTTA (SEQ ID NO: 11); reverse sequence CACCTTCCTTCTTTTTGATTTTGTC, designated herein as SEQ ID NO: 12; probe sequence TACATGAGTGGCTATCATACT (SEQ ID NO: 13)) was used to determine the amount of SMN2 RNA including exon 7 (exon 7$^+$). Primer probe set hSMN2_Sumner68_PPS50481 (forward sequence: CATGGTACATGAGTGGCTATCATACTG (SEQ ID NO: 14); reverse sequence: TGGTGTCATTTAGTGCTGCTCTATG (SEQ ID NO: 15); probe sequence CCAGCATTTCCATATAATAGC (SEQ ID NO: 16) was used to determine the amount of SMN2 RNA excluding exon 7 (exon 7$^−$). Total SMN2 RNA levels were measured using primer probe set hSMN2_LTS00935 (forward sequence: CAGGAGGATTCCGTGCTGTT (SEQ ID NO: 17); reverse sequence CAGTGCTGTATCATCCCAAATGTC, (SEQ ID NO: 18); probe sequence: ACAGGCCAGAGCGAT (SEQ ID NO: 19)).

Results are presented as fold change in RNA levels relative to PBS control, normalized to total SMN2 levels. Each of Tables 12-18 represents a different experiment.

TABLE 12

Effect of modified oligonucleotides on human SMN2 RNA splicing in homozygous transgenic mice

| Compound No. | Dose (µg) | CORTEX exon 7$^+$ | CORTEX exon 7$^-$ | SPINAL CORD exon 7$^+$ | SPINAL CORD exon 7$^-$ |
|---|---|---|---|---|---|
| PBS | — | 1 | 1 | 1 | 1 |
| 396442 | 35 | 3.3 | 0.3 | 3.4 | 0.3 |
| 396443 | 35 | 3.0 | 0.5 | 2.3 | 0.5 |
| 524403 | 35 | 3.3 | 0.4 | 2.5 | 0.5 |
| 1210339 | 35 | 2.5 | 0.5 | 3.0 | 0.3 |
| 1210340 | 35 | 2.1 | 0.6 | 2.6 | 0.4 |
| 1210341 | 35 | 1.8 | 0.7 | 2.0 | 0.6 |
| 1210342 | 35 | 2.5 | 0.5 | 2.9 | 0.3 |
| 1210343 | 35 | 3.0 | 0.4 | 2.4 | 0.5 |
| 1212817 | 35 | 2.4 | 0.6 | 2.2 | 0.6 |
| 1212818 | 35 | 2.4 | 0.5 | 2.1 | 0.6 |
| 1212823 | 35 | 2.0 | 0.6 | 2.0 | 0.6 |
| 1212824 | 35 | 2.1 | 0.6 | 2.1 | 0.6 |
| 1212825 | 35 | 2.9 | 0.4 | 2.5 | 0.5 |
| 1212826 | 35 | 2.5 | 0.6 | 2.2 | 0.7 |
| 1212827 | 35 | 2.5 | 0.6 | 2.6 | 0.5 |
| 1212828 | 35 | 2.9 | 0.5 | 2.4 | 0.6 |
| 1212830 | 35 | 2.8 | 0.7 | 2.1 | 0.8 |
| 1212831 | 35 | 2.5 | 0.7 | 2.3 | 0.7 |
| 1212832 | 35 | 2.9 | 0.6 | 2.9 | 0.5 |
| 1212833 | 35 | 2.4 | 0.7 | 2.7 | 0.5 |
| 1212837 | 35 | 2.5 | 0.6 | 2.7 | 0.5 |
| 1212838 | 35 | 2.1 | 0.7 | 2.5 | 0.6 |
| 1212844 | 35 | 2.6 | 0.6 | 2.4 | 0.7 |
| 1212845 | 35 | 2.3 | 0.7 | 2.5 | 0.7 |
| 1212846 | 35 | 2.8 | 0.6 | 2.6 | 0.6 |
| 1212849 | 35 | 2.1 | 0.7 | 2.3 | 0.6 |
| 1212850 | 35 | 1.8 | 0.8 | 2.2 | 0.7 |
| 1212855 | 35 | 2.0 | 0.7 | 2.1 | 0.8 |

TABLE 13

Effect of modified oligonucleotides on human SMN2 RNA splicing in homozygous transgenic mice

| Compound No. | Dose (µg) | CORTEX exon 7$^+$ | CORTEX exon 7$^-$ | SPINAL CORD exon 7$^+$ | SPINAL CORD exon 7$^-$ |
|---|---|---|---|---|---|
| PBS | — | 1.0 | 1.0 | 1.0 | 1.0 |
| 396443 | 35 | 2.7 | 0.3 | 1.9 | 0.5 |
| 1210342 | 35 | 2.4 | 0.5 | 2.5 | 0.4 |
| 1212961 | 35 | 1.8 | 0.7 | 1.7 | 0.6 |
| 1212962 | 35 | 2.0 | 0.6 | 1.9 | 0.5 |
| 1212963 | 35 | 2.3 | 0.5 | 2.5 | 0.3 |
| 1212966 | 35 | 1.6 | 0.8 | 2.0 | 0.5 |
| 1212967 | 35 | 1.9 | 0.6 | 1.9 | 0.4 |
| 1212971 | 35 | 1.6 | 0.5 | 2.0 | 0.4 |
| 1212972 | 35 | 1.8 | 0.6 | 2.2 | 0.5 |
| 1212977 | 35 | 2.1 | 0.5 | 2.2 | 0.4 |
| 1212978 | 35 | 2.1 | 0.6 | 2.2 | 0.4 |
| 1212979 | 35 | 2.1 | 0.5 | 2.6 | 0.3 |
| 1212982 | 35 | 2.0 | 0.7 | 1.8 | 0.6 |
| 1212983 | 35 | 1.9 | 0.6 | 1.7 | 0.5 |
| 1212984 | 35 | 1.9 | 0.6 | 1.9 | 0.5 |
| 1212987 | 35 | 2.4 | 0.4 | 2.5 | 0.4 |
| 1212988 | 35 | 1.8 | 0.7 | 1.8 | 0.5 |
| 1212995 | 35 | 2.5 | 0.5 | 2.5 | 0.4 |
| 1212998 | 35 | 1.8 | 0.6 | 1.8 | 0.7 |
| 1212999 | 35 | 2.0 | 0.6 | 2.0 | 0.5 |
| 1213003 | 35 | 1.9 | 0.7 | 2.3 | 0.5 |
| 1213004 | 35 | 1.8 | 0.7 | 2.3 | 0.6 |

TABLE 14

Effect of modified oligonucleotides on human SMN2 RNA splicing in homozygous transgenic mice

| Compound No. | Dose (µg) | CORTEX exon 7$^+$ | CORTEX exon 7$^-$ | SPINAL CORD exon 7$^+$ | SPINAL CORD exon 7$^-$ |
|---|---|---|---|---|---|
| PBS | — | 1.0 | 1.0 | 1.0 | 1.0 |
| 396443 | 35 | 2.6 | 0.5 | 3.1 | 0.5 |
| 1212964 | 35 | 2.5 | 0.6 | 3.6 | 0.4 |
| 1212965 | 35 | 2.9 | 0.5 | 3.3 | 0.4 |
| 1212968 | 35 | 2.2 | 0.6 | 2.3 | 0.6 |
| 1212973 | 35 | 2.6 | 0.5 | 3.2 | 0.4 |

TABLE 14-continued

Effect of modified oligonucleotides on human SMN2 RNA splicing in homozygous transgenic mice

| Compound No. | Dose (µg) | CORTEX exon 7+ | CORTEX exon 7− | SPINAL CORD exon 7+ | SPINAL CORD exon 7− |
|---|---|---|---|---|---|
| 1212974 | 35 | 2.3 | 0.6 | 2.8 | 0.5 |
| 1212975 | 35 | 2.9 | 0.3 | 3.1 | 0.4 |
| 1212976 | 35 | 2.5 | 0.5 | 2.8 | 0.5 |
| 1212980 | 35 | 2.6 | 0.5 | 3.2 | 0.4 |
| 1212981 | 35 | 2.9 | 0.4 | 3.6 | 0.3 |
| 1212985 | 35 | 2.4 | 0.6 | 2.9 | 0.5 |
| 1212986 | 35 | 2.8 | 0.4 | 3.3 | 0.4 |
| 1212989 | 35 | 3.3 | 0.3 | 3.6 | 0.2 |
| 1212990 | 35 | 1.8 | 0.8 | 2.1 | 0.7 |
| 1212991 | 35 | 3.2 | 0.3 | 3.8 | 0.3 |
| 1212992 | 35 | 2.4 | 0.5 | 2.2 | 0.6 |
| 1212996 | 35 | 2.2 | 0.6 | 3.2 | 0.5 |
| 1212997 | 35 | 2.9 | 0.4 | 3.9 | 0.4 |
| 1213001 | 35 | 2.1 | 0.5 | 2.8 | 0.6 |
| 1213002 | 35 | 2.0 | 0.6 | 2.9 | 0.6 |
| 1213005 | 35 | 2.8 | 0.5 | 3.2 | 0.3 |
| 1213006 | 35 | 1.9 | 0.9 | 2.0 | 0.8 |
| 1213007 | 35 | 3.3 | 0.2 | 2.9 | 0.5 |
| 1213008 | 35 | 2.3 | 0.7 | 2.2 | 0.7 |

TABLE 15

Effect of modified oligonucleotides on human SMN2 RNA splicing in heterozygous transgenic mice

| Compound No. | Dose (µg) | CORTEX exon 7+ | CORTEX exon 7− | SPINAL CORD exon 7+ | SPINAL CORD exon 7− |
|---|---|---|---|---|---|
| PBS | — | 1.0 | 1.0 | 1.0 | 1.0 |
| 387954 | 35 | 2.3 | 0.6 | 2.2 | 0.5 |
| 396443 | 35 | 2.5 | 0.5 | 2.4 | 0.5 |
| 1287048 | 35 | 2.2 | 0.5 | 2.2 | 0.5 |
| 1287049 | 35 | 2.3 | 0.6 | 2.5 | 0.4 |
| 1287061 | 35 | 2.4 | 0.5 | 2.2 | 0.4 |
| 1287062 | 35 | 3.0 | 0.3 | 2.3 | 0.4 |
| 1287050 | 35 | 2.8 | 0.5 | 2.3 | 0.4 |
| 1287054 | 35 | 2.2 | 0.5 | 2.3 | 0.4 |
| 1287063 | 35 | 1.8 | 0.7 | 1.7 | 0.6 |
| 1287064 | 35 | 2.6 | 0.3 | 2.4 | 0.4 |
| 1287065 | 35 | 2.5 | 0.4 | 2.3 | 0.4 |
| 1287066 | 35 | 2.2 | 0.5 | 2 | 0.5 |
| 1287075 | 35 | 2.3 | 0.6 | 1.8 | 0.7 |
| 1287076 | 35 | 2.6 | 0.4 | 1.9 | 0.6 |
| 1287067 | 35 | 2.7 | 0.4 | 1.9 | 0.6 |
| 1287070 | 35 | 2.5 | 0.5 | 1.8 | 0.7 |
| 1287071 | 35 | 2.6 | 0.4 | 1.8 | 0.7 |
| 1287074 | 35 | 2.6 | 0.5 | 2 | 0.6 |
| 1287109 | 35 | 2.7 | 0.6 | 2.4 | 0.5 |
| 1287110 | 35 | 2.6 | 0.5 | 2.3 | 0.5 |
| 1287701 | 35 | 2.6 | 0.6 | 2.8 | 0.3 |
| 1287702 | 35 | 3 | 0.5 | 2.8 | 0.4 |
| 1287703 | 35 | 2.3 | 0.6 | 2.4 | 0.4 |
| 1287704 | 35 | 2.7 | 0.5 | 2.3 | 0.4 |
| 1287717 | 35 | 3.3 | 0.3 | 2.4 | 0.6 |

TABLE 16

Effect of modified oligonucleotides on human SMN2 RNA splicing in heterozygous transgenic mice

| Compound No. | Dose (µg) | CORTEX exon 7+ | CORTEX exon 7− | SPINAL CORD exon 7+ | SPINAL CORD exon 7− |
|---|---|---|---|---|---|
| PBS | — | 1 | 1 | 1 | 1 |
| 396442 | 35 | 2.5 | 0.6 | 3.2 | 0.3 |
| 396443 | 35 | 3 | 0.5 | 2.8 | 0.5 |

TABLE 16-continued

Effect of modified oligonucleotides on human SMN2 RNA splicing in heterozygous transgenic mice

| Compound No. | Dose (µg) | CORTEX exon 7+ | CORTEX exon 7− | SPINAL CORD exon 7+ | SPINAL CORD exon 7− |
|---|---|---|---|---|---|
| 1263783 | 35 | 3 | 0.3 | 2.6 | 0.5 |
| 1263785 | 35 | 3.1 | 0.4 | 2.9 | 0.5 |
| 1263787 | 35 | 2.4 | 0.6 | 2.9 | 0.4 |
| 1263789 | 35 | 3.8 | 0.2 | 2.6 | 0.5 |
| 1263800 | 35 | 3.6 | 0.2 | 2.6 | 0.5 |
| 1263802 | 35 | 3.4 | 0.3 | 2.9 | 0.4 |
| 1263806 | 35 | 3.5 | 0.2 | 2.7 | 0.5 |
| 1263808 | 35 | 3.2 | 0.4 | 2.7 | 0.5 |
| 1263810 | 35 | 2.8 | 0.5 | 2.4 | 0.5 |

TABLE 17

Effect of modified oligonucleotides on human SMN2 RNA splicing in heterozygous transgenic mice

| Compound No. | Dose (µg) | CORTEX exon 7+ | CORTEX exon 7− | SPINAL CORD exon 7+ | SPINAL CORD exon 7− |
|---|---|---|---|---|---|
| PBS | — | 1 | 1 | 1 | 1 |
| 396443 | 35 | 2.5 | 0.6 | 2.9 | 0.4 |
| 1364784 | 35 | 2.3 | 0.7 | 2.8 | 0.5 |
| 1364783 | 35 | 2.9 | 0.5 | 2.4 | 0.5 |
| 1364777 | 35 | 2.7 | 0.6 | 2.3 | 0.5 |
| 1364782 | 35 | 2.7 | 0.6 | 2.6 | 0.5 |

TABLE 18

Effect of modified oligonucleotides on human SMN2 RNA splicing in heterozygous transgenic mice

| Compound No. | Dose (µg) | CORTEX exon 7+ | CORTEX exon 7− | SPINAL CORD exon 7+ | SPINAL CORD exon 7− |
|---|---|---|---|---|---|
| PBS | — | 1 | 1 | 1 | 1 |
| 396443 | 35 | 2 | 0.7 | 2.7 | 0.5 |
| 1318748 | 35 | 2.1 | 0.7 | 2.5 | 0.6 |
| 1318782 | 35 | 2.2 | 0.8 | 2.5 | 0.6 |
| 1332262 | 35 | 3.3 | 0.4 | 2.9 | 0.5 |
| 1332258 | 35 | 2.4 | 0.7 | 2.3 | 0.6 |

Example 3: Activity of Modified Oligonucleotides Complementary to Human SMN2 in Transgenic Mice, Single Dose (15 µg)

Activity of selected modified oligonucleotides described above was tested in human SMN2 transgenic mice essentially as described above in Example 2. Comparator Compound Nos. 396443 and 819735 were also tested in this assay. The transgenic mice were divided into groups of 4 mice each. Each mouse received a single ICV bolus of 15 µg of modified oligonucleotide. A group of 4 mice received PBS as a negative control. Two weeks post treatment, mice were sacrificed and RNA was extracted from cortical brain tissue and spinal cord for real-time qPCR analysis of SMN2 RNA. Results are presented as fold change in RNA levels relative to PBS control, normalized to total SMN2 levels. Each of Tables 19-23 represents a different experiment.

TABLE 19

Effect of modified oligonucleotides on human SMN2 RNA splicing in homozygous transgenic mice

| Compound No. | Dose (μg) | CORTEX exon 7+ | CORTEX exon 7− | SPINAL CORD exon 7+ | SPINAL CORD exon 7− |
|---|---|---|---|---|---|
| PBS | — | 1.0 | 1.0 | 1.0 | 1.0 |
| 819735 | 15 | 2.4 | 0.4 | 3.3 | 0.3 |
| 1212869 | 15 | 2.4 | 0.4 | 3.2 | 0.4 |
| 1212870 | 15 | 2.1 | 0.5 | 2.8 | 0.4 |
| 1212873 | 15 | 2.2 | 0.4 | 2.0 | 0.6 |
| 1212874 | 15 | 2.1 | 0.5 | 2.4 | 0.6 |
| 1212875 | 15 | 2.1 | 0.5 | 2.3 | 0.5 |
| 1212880 | 15 | 1.7 | 0.6 | 2.0 | 0.6 |
| 1212881 | 15 | 1.8 | 0.6 | 2.3 | 0.6 |
| 1212885 | 15 | 2.3 | 0.4 | 2.4 | 0.5 |
| 1212887 | 15 | 2.0 | 0.5 | 2.2 | 0.5 |
| 1212931 | 15 | 2.9 | 0.2 | 2.9 | 0.3 |
| 1212936 | 15 | 2.9 | 0.3 | 3.3 | 0.3 |
| 1212941 | 15 | 3.0 | 0.1 | 3.4 | 0.2 |

TABLE 20

Effect of modified oligonucleotides on human SMN2 RNA splicing in heterozygous transgenic mice

| Compound No. | Dose (μg) | CORTEX exon 7+ | CORTEX exon 7− | SPINAL CORD exon 7+ | SPINAL CORD exon 7− |
|---|---|---|---|---|---|
| PBS | — | 1.0 | 1.0 | 1.0 | 1.0 |
| 396443 | 15 | 2.2 | 0.5 | 2.2 | 0.7 |
| 819735 | 15 | 2.7 | 0.5 | 3.1 | 0.5 |
| 1287122 | 15 | 2.9 | 0.5 | 2.3 | 0.6 |
| 1287123 | 15 | 3.0 | 0.4 | 3.0 | 0.4 |
| 1287124 | 15 | 3.0 | 0.4 | 3.2 | 0.3 |
| 1287125 | 15 | 3.0 | 0.4 | 3.0 | 0.4 |
| 1287126 | 15 | 2.8 | 0.4 | 2.8 | 0.4 |
| 1287127 | 15 | 2.7 | 0.5 | 3.0 | 0.5 |
| 1287128 | 15 | 2.6 | 0.5 | 3.2 | 0.5 |
| 1287129 | 15 | 2.9 | 0.4 | 2.9 | 0.5 |
| 1287130 | 15 | 3.7 | 0.1 | 3.1 | 0.5 |
| 1287131 | 15 | 2.2 | 0.6 | 2.7 | 0.4 |
| 1287132 | 15 | 3.2 | 0.3 | 2.2 | 0.6 |
| 1287133 | 15 | 2.9 | 0.4 | 2.8 | 0.4 |
| 1287728 | 15 | 2.8 | 0.6 | 3.4 | 0.3 |
| 1287729 | 15 | 3.1 | 0.4 | 3.0 | 0.3 |
| 1287730 | 15 | 3.1 | 0.3 | 2.7 | 0.4 |
| 1287731 | 15 | 3.3 | 0.3 | 2.8 | 0.5 |
| 1287735 | 15 | 2.9 | 0.5 | 2.6 | 0.5 |
| 1287738 | 15 | 3.7 | 0.2 | 3.2 | 0.3 |
| 1287739 | 15 | 3.3 | 0.4 | 3.2 | 0.4 |
| 1287743 | 15 | 3.6 | 0.4 | 3.8 | 0.4 |
| 1287745 | 15 | 3.1 | 0.5 | 3.8 | 0.5 |

TABLE 21

Effect of modified oligonucleotides on human SMN2 RNA splicing in heterozygous transgenic mice

| Compound No. | Dose (μg) | CORTEX exon 7+ | CORTEX exon 7− | SPINAL CORD exon 7+ | SPINAL CORD exon 7− |
|---|---|---|---|---|---|
| PBS | — | 1 | 1 | 1 | 1.0 |
| 396443 | 15 | 1.9 | 0.6 | 1.7 | 0.7 |
| 819735 | 15 | 2.3 | 0.5 | 1.9 | 0.6 |

TABLE 22

Effect of modified oligonucleotides on human SMN2 RNA splicing in heterozygous transgenic mice

| Compound No. | Dose (μg) | CORTEX exon 7+ | CORTEX exon 7− | SPINAL CORD exon 7+ | SPINAL CORD exon 7− |
|---|---|---|---|---|---|
| PBS | — | 1 | 1 | 1 | 1 |
| 1364781 | 15 | 2.5 | 0.6 | 2.7 | 0.4 |
| 1364780 | 15 | 2.8 | 0.5 | 2.6 | 0.5 |
| 1364779 | 15 | 2.7 | 0.5 | 2.6 | 0.5 |
| 1364778 | 15 | 3 | 0.5 | 2.7 | 0.4 |

TABLE 23

Effect of modified oligonucleotides on human SMN2 RNA splicing in heterozygous transgenic mice

| Compound No. | Dose (μg) | CORTEX exon 7+ | CORTEX exon 7− | SPINAL CORD exon 7+ | SPINAL CORD exon 7− |
|---|---|---|---|---|---|
| PBS | — | 1 | 1 | 1 | 1 |
| 819735 | 15 | 2.8 | 0.5 | 2.4 | 0.6 |
| 1332265 | 15 | 2.1 | 0.7 | 2.6 | 0.6 |
| 1332269 | 15 | 2.5 | 0.6 | 2.7 | 0.5 |
| 1332268 | 15 | 2.9 | 0.5 | 2.3 | 0.6 |
| 1318756 | 15 | 2.2 | 0.7 | 2.4 | 0.6 |
| 1333508 | 15 | 2 | 0.6 | 2.2 | 0.6 |
| 1332251 | 15 | 2.9 | 0.5 | 1.9 | 0.7 |
| 1332249 | 15 | 2.3 | 0.7 | 2.3 | 0.7 |

Example 4: Activity of Modified Oligonucleotides Complementary to Human SMN2 in Transgenic Mice, Single Dose (70 μg)

Activity of modified oligonucleotides was tested in human SMN2 transgenic mice essentially as described above in Example 2. The transgenic mice were divided into groups of 4 mice each. Each mouse received a single ICV bolus of 70 μg modified oligonucleotide. A group of 4 mice received PBS as a negative control. Two weeks post treatment, mice were sacrificed and RNA was extracted from cortical brain tissue and spinal cord for real-time qPCR analysis of SMN2 RNA. Results are presented as fold change in RNA levels relative to PBS control, normalized to total SMN2 levels.

TABLE 24

Effect of modified oligonucleotides on human SMN2 RNA splicing in homozygous transgenic mice

| Compound No. | Dose (μg) | CORTEX exon 7+ | CORTEX exon 7− | SPINAL CORD exon 7+ | SPINAL CORD exon 7− |
|---|---|---|---|---|---|
| PBS | — | 1 | 1 | 1 | 1 |
| 1212969 | 70 | 2.5 | 0.4 | 2.4 | 0.3 |
| 1212970 | 70 | 2.7 | 0.3 | 2.6 | 0.3 |

Example 5: Activity of Modified Oligonucleotides Complementary to Human SMN2 in Transgenic Mice, Multiple Dose Activity of selected modified oligonucleotides described above was tested in human SMN2 transgenic mice essentially as described above in Example 2. Comparator Compound No. 396443 was also tested in this assay. The transgenic mice were divided into groups of 4 mice each. Each mouse received a single ICV bolus of modified oligonucleotide at multiple doses as indicated in the tables below. A group of 4 mice received PBS as a negative control. Two weeks post treatment, mice were sacrificed and RNA was extracted from coronal brain and spinal cord for real-time qPCR analysis of SMN2 RNA. Results are presented as fold change in RNA levels relative to PBS control, normalized to total SMN2 levels. $ED_{50}$ for exon inclusion (exon $7^+$) was calculated in GraphPad Prism 7 using nonlinear regression, 4-parameter dose response curve [Y=Bottom+(Top−Bottom)/(1+(10^log EC50/X)^HillSlope)].

TABLE 25

Effect of modified oligonucleotides on human SMN2 RNA splicing in homozygous transgenic mice

| Compound No. | Dose (µg) | CORONAL BRAIN exon $7^+$ | CORONAL BRAIN exon $7^-$ | ED50 (µg) | SPINAL CORD exon $7^+$ | SPINAL CORD exon $7^-$ | ED50 (µg) |
|---|---|---|---|---|---|---|---|
| PBS | — | 1.0 | 1.0 | | 1.0 | 1.0 | |
| 396443 | 3 | 1.4 | 0.9 | 32.5 | 1.3 | 0.9 | 22.1 |
| | 10 | 1.8 | 0.8 | | 2.0 | 0.7 | |
| | 30 | 2.6 | 0.5 | | 2.6 | 0.4 | |
| | 100 | 3.5 | 0.4 | | 3.2 | 0.3 | |
| | 300 | 4.2 | 0.1 | | 3.6 | 0.2 | |
| 1263789 | 3 | 1.5 | 0.9 | 38.3 | 1.5 | 0.8 | 13.3 |
| | 10 | 2.0 | 0.7 | | 2.2 | 0.6 | |
| | 30 | 2.3 | 0.6 | | 3.0 | 0.4 | |
| | 100 | 3.4 | 0.3 | | 3.4 | 0.3 | |
| | 300 | 3.9 | 0.1 | | 3.7 | 0.2 | |
| 1287717 | 3 | 1.3 | 0.8 | 38.7 | 1.3 | 0.9 | 20.5 |
| | 10 | 1.8 | 0.7 | | 1.9 | 0.7 | |
| | 30 | 2.4 | 0.7 | | 2.7 | 0.5 | |
| | 100 | 3.5 | 0.4 | | 3.3 | 0.3 | |
| | 300 | 4.1 | 0.1 | | 3.8 | 0.2 | |
| 1358996 | 3 | 1.6 | 0.9 | 16.6 | 1.7 | 0.8 | 7.4 |
| | 10 | 2.5 | 0.6 | | 2.6 | 0.5 | |
| | 30 | 3.0 | 0.4 | | 3.5 | 0.2 | |
| | 100 | 4.0 | 0.2 | | 3.6 | 0.2 | |
| | 300 | 4.0 | 0.1 | | 3.9 | 0.1 | |
| 1287745 | 3 | 1.5 | 0.8 | 22.8 | 1.7 | 0.7 | 8.8 |
| | 10 | 2.1 | 0.6 | | 2.4 | 0.5 | |
| | 30 | 3.0 | 0.3 | | 3.3 | 0.3 | |
| | 100 | 3.6 | 0.1 | | 3.5 | 0.2 | |
| | 300 | 4.2 | 0.1 | | 3.8 | 0.1 | |

Example 6: Tolerability of Modified Oligonucleotides Complementary to SMN2 in Wild-Type Mice, 3 Hour Study Modified oligonucleotides described above were tested in wild-type female C57/Bl6 mice to assess tolerability. Wild-type female C57/Bl6 mice each received a single ICV dose of 700 µg of modified oligonucleotide listed in the tables below. Comparator Compound No. 396443 was also tested in this assay with a dose of 350 µg. Comparator Compound Nos. 387954, 396442, 443305, and 819735 were also tested in this assay with a dose of 700 µg. Each treatment group consisted of 4 mice. A group of 4 mice received PBS as a negative control for each experiment (identified in separate tables below). At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed and averaged within each treatment group. The results are presented in the tables below. Each of Tables 26-49 represents a different experiment.

TABLE 26

Tolerability scores in mice at 350 µg dose

| Compound Number | 3 hr FOB |
|---|---|
| PBS | 0 |
| 396443 | 4.0 |

TABLE 27

Tolerability scores in mice at 700 µg dose

| Compound Number | 3 hr FOB |
|---|---|
| PBS | 0.00 |
| 443305 | 4.75 |

TABLE 28

Tolerability scores in mice at 700 µg dose

| Compound Number | 3 hr FOB |
|---|---|
| PBS | 0 |
| 396442 | 2.5 |
| 524403 | 3.25 |
| 1210339 | 1.25 |
| 1210340 | 2.25 |
| 1210341 | 3.75 |
| 1210342 | 0 |
| 1210343 | 0 |
| 1212817 | 0 |
| 1212818 | 0 |
| 1212819 | 0 |
| 1212820 | 0 |
| 1212821 | 0 |
| 1212822 | 0 |
| 1212823 | 0 |
| 1212824 | 0 |
| 1212825 | 1 |
| 1212826 | 0 |
| 1212827 | 0 |
| 1212828 | 0 |
| 1212829 | 0 |
| 1212830 | 0 |
| 1212831 | 0 |

TABLE 29

Tolerability scores in mice at 700 µg dose

| Compound Number | 3 hr FOB |
|---|---|
| PBS | 0.00 |
| 396442 | 2.50 |
| 1210340 | 3.50 |
| 1212850 | 0.50 |
| 1212851 | 0.75 |
| 1212852 | 0.00 |
| 1212853 | 0.00 |

TABLE 29-continued

Tolerability scores in mice at 700 μg dose

| Compound Number | 3 hr FOB |
| --- | --- |
| 1212854 | 0.25 |
| 1212855 | 0.25 |
| 1212856 | 0.00 |
| 1212857 | 0.00 |
| 1212858 | 0.00 |
| 1212859 | 0.00 |
| 1212860 | 0.75 |
| 1212861 | 1.00 |
| 1212863 | 2.00 |
| 1212864 | 0.00 |
| 1212866 | 0.75 |
| 1212867 | 0.00 |
| 1212868 | 0.00 |

TABLE 30

Tolerability scores in mice at 700 μg dose

| Compound Number | 3 hr FOB |
| --- | --- |
| PBS | 0.00 |
| 396442 | 3.25 |
| 1212961 | 0.00 |
| 1212963 | 1.00 |
| 1212964 | 2.00 |
| 1212965 | 1.25 |
| 1212966 | 1.25 |
| 1212968 | 0.00 |
| 1212971 | 1.00 |
| 1212972 | 3.25 |
| 1212973 | 0.50 |
| 1212974 | 2.00 |
| 1212975 | 0.50 |
| 1212976 | 1.75 |

TABLE 31

Tolerability scores in mice at 700 μg dose

| Compound Number | 3 hr FOB |
| --- | --- |
| PBS | 0.00 |
| 1212977 | 0.75 |
| 1212978 | 0.00 |
| 1212979 | 1.75 |
| 1212980 | 1.50 |
| 1212981 | 0.00 |
| 1212982 | 0.50 |
| 1212983 | 0.75 |
| 1212984 | 2.75 |
| 1212985 | 0.00 |
| 1212986 | 1.00 |
| 1212987 | 1.75 |
| 1212988 | 4.50 |
| 1212989 | 1.75 |
| 1212990 | 4.50 |
| 1212991 | 1.25 |
| 1212992 | 3.75 |

TABLE 32

Tolerability scores in mice at 700 μg dose

| Compound Number | 3 hr FOB |
| --- | --- |
| PBS | 0.00 |
| 1212993 | 7.00 |
| 1212994 | 6.50 |
| 1212995 | 4.25 |
| 1212996 | 3.25 |
| 1212997 | 4.00 |
| 1212998 | 2.00 |
| 1212999 | 1.00 |
| 1213000 | 1.25 |
| 1213001 | 3.00 |
| 1213002 | 2.00 |
| 1213003 | 4.00 |
| 1213004 | 3.00 |
| 1213005 | 3.75 |
| 1213006 | 4.00 |
| 1213007 | 4.00 |
| 1213008 | 3.50 |

TABLE 33

Tolerability scores in mice at 700 μg dose

| Compound Number | 3 hr FOB |
| --- | --- |
| PBS | 0.00 |
| 1212832 | 0.00 |
| 1212833 | 0.00 |
| 1212834 | 0.00 |
| 1212835 | 0.00 |
| 1212836 | 0.00 |
| 1212837 | 0.00 |
| 1212838 | 0.00 |
| 1212839 | 0.00 |
| 1212840 | 0.00 |
| 1212841 | 0.00 |
| 1212842 | 0.00 |
| 1212843 | 0.00 |
| 1212844 | 0.25 |
| 1212845 | 1.00 |
| 1212846 | 0.00 |
| 1212847 | 0.00 |
| 1212848 | 0.00 |
| 1212849 | 0.00 |

TABLE 34

Tolerability scores in mice at 700 μg dose

| Compound Number | 3 hr FOB |
| --- | --- |
| PBS | 0.00 |
| 396442 | 1.75 |
| 1210339 | 1.00 |
| 1212865 | 1.00 |
| 1212962 | 0.00 |
| 1212967 | 0.50 |
| 1212969 | 0.50 |
| 1212970 | 1.25 |

TABLE 35

Tolerability scores in mice at 700 µg dose

| Compound Number | 3 hr FOB |
|---|---|
| PBS | 0.00 |
| 819735 | 2.00 |
| 1212869 | 2.00 |
| 1212870 | 4.75 |
| 1212871 | 1.00 |
| 1212873 | 0.00 |
| 1212874 | 0.00 |
| 1212875 | 0.00 |
| 1212879 | 3.00 |
| 1212880 | 0.00 |
| 1212881 | 4.00 |
| 1212885 | 1.00 |
| 1212887 | 2.25 |
| 1212931 | 2.00 |
| 1212936 | 2.00 |
| 1212941 | 1.25 |

TABLE 36

Tolerability scores in mice at 700 µg dose

| Compound Number | 3 hr FOB |
|---|---|
| PBS | 0.00 |
| 1263778 | 0.00 |
| 1263781 | 0.00 |
| 1263783 | 0.00 |
| 1263785 | 1.00 |
| 1263787 | 0.00 |
| 1263789 | 0.00 |
| 1263791 | 0.00 |
| 1263793 | 0.00 |
| 1263795 | 0.00 |
| 1263797 | 0.00 |
| 1263799 | 0.00 |
| 1263800 | 0.00 |
| 1263802 | 0.00 |
| 1263804 | 0.00 |
| 1263806 | 0.00 |
| 1263808 | 1.00 |
| 1263810 | 0.00 |
| 1263812 | 0.00 |
| 1263814 | 1.00 |
| 1263816 | 0.50 |
| 1263818 | 0.00 |
| 1263820 | 0.00 |
| 1263822 | 0.25 |
| 1263824 | 0.00 |

TABLE 37

Tolerability scores in mice at 700 µg dose

| Compound Number | 3 hr FOB |
|---|---|
| PBS | 0.00 |
| 1263826 | 0.00 |

TABLE 38

Tolerability scores in mice at 700 µg dose

| Compound Number | 3 hr FOB |
|---|---|
| PBS | 0.00 |
| 387954 | 4.00 |
| 1287048 | 0.00 |
| 1287049 | 0.00 |
| 1287050 | 2.00 |
| 1287051 | 3.25 |
| 1287052 | 3.50 |
| 1287053 | 2.75 |
| 1287054 | 2.00 |
| 1287055 | 3.25 |
| 1287056 | 4.00 |
| 1287057 | 3.00 |
| 1287058 | 4.00 |
| 1287059 | 4.00 |
| 1287060 | 4.00 |
| 1287061 | 4.00 |
| 1287062 | 3.50 |

TABLE 39

Tolerability scores in mice at 700 µg dose

| Compound Number | 3 hr FOB |
|---|---|
| PBS | 0.00 |
| 1287106 | 3.50 |
| 1287107 | 4.00 |
| 1287108 | 3.75 |
| 1287109 | 3.25 |
| 1287110 | 3.00 |
| 1287111 | 4.75 |
| 1287112 | 4.00 |
| 1287113 | 3.50 |
| 1287114 | 3.25 |
| 1287115 | 3.50 |
| 1287116 | 4.00 |
| 1287117 | 4.25 |
| 1287118 | 3.00 |
| 1287119 | 3.50 |
| 1287120 | 3.75 |
| 1287121 | 2.75 |

TABLE 40

Tolerability scores in mice at 700 µg dose

| Compound Number | 3 hr FOB |
|---|---|
| PBS | 0.00 |
| 1287063 | 0.00 |
| 1287064 | 0.00 |
| 1287065 | 1.00 |
| 1287066 | 3.75 |
| 1287067 | 1.00 |
| 1287068 | 2.50 |
| 1287069 | 2.25 |
| 1287071 | 1.00 |
| 1287072 | 3.00 |
| 1287073 | 3.75 |
| 1287074 | 1.75 |
| 1287075 | 3.50 |
| 1287076 | 2.00 |

TABLE 41

Tolerability scores in mice at 700 μg dose

| Compound Number | 3 hr FOB |
|---|---|
| PBS | 0.00 |
| 1287070 | 2.00 |
| 1287701 | 2.50 |
| 1287702 | 3.75 |
| 1287703 | 3.75 |
| 1287705 | 4.00 |
| 1287706 | 4.00 |
| 1287707 | 4.00 |
| 1287709 | 4.75 |
| 1287710 | 4.00 |
| 1287711 | 4.75 |
| 1287712 | 4.00 |
| 1287713 | 4.00 |
| 1287714 | 3.50 |
| 1287715 | 4.00 |
| 1287716 | 4.00 |
| 1287717 | 3.25 |

TABLE 42

Tolerability scores in mice at 700 μg dose

| Compound Number | 3 hr FOB |
|---|---|
| PBS | 0.00 |
| 1287728 | 1.00 |
| 1287729 | 1.25 |
| 1287730 | 2.00 |
| 1287731 | 2.50 |
| 1287732 | 3.00 |
| 1287733 | 3.25 |
| 1287734 | 3.00 |
| 1287735 | 0.50 |
| 1287736 | 2.50 |
| 1287737 | 4.00 |
| 1287738 | 3.00 |
| 1287739 | 2.50 |
| 1287740 | 2.75 |
| 1287741 | 3.75 |
| 1287742 | 3.00 |
| 1287743 | 2.75 |
| 1287744 | 2.25 |
| 1287745 | 1.00 |

TABLE 43

Tolerability scores in mice at 700 μg dose

| Compound Number | 3 hr FOB |
|---|---|
| PBS | 0.00 |
| 1287122 | 0.00 |
| 1287123 | 0.00 |
| 1287124 | 3.50 |
| 1287125 | 3.00 |
| 1287126 | 3.00 |
| 1287127 | 0.00 |
| 1287128 | 0.00 |
| 1287129 | 4.00 |
| 1287130 | 2.75 |
| 1287131 | 2.50 |
| 1287132 | 2.75 |
| 1287133 | 3.25 |
| 1287704 | 3.50 |
| 1287708 | 3.50 |

TABLE 44

Tolerability scores in mice at 700 μg dose

| Compound Number | 3 hr FOB |
|---|---|
| PBS | 0.00 |
| 1318748 | 2.00 |
| 1318765 | 4.00 |
| 1318767 | 4.25 |
| 1318770 | 3.75 |
| 1318771 | 4.50 |
| 1318772 | 4.25 |
| 1318773 | 4.25 |
| 1318774 | 3.50 |
| 1318775 | 3.75 |
| 1318776 | 3.75 |
| 1318777 | 4.00 |
| 1318778 | 4.00 |
| 1318779 | 4.00 |
| 1318780 | 4.00 |
| 1318781 | 4.00 |
| 1318782 | 1.00 |
| 1318783 | 4.00 |
| 1318784 | 2.00 |

TABLE 45

Tolerability scores in mice at 700 μg dose

| Compound Number | 3 hr FOB |
|---|---|
| PBS | 0.00 |
| 1318757 | 4.00 |
| 1318758 | 4.25 |
| 1318759 | 3.75 |
| 1318760 | 3.75 |
| 1318761 | 4.00 |
| 1318762 | 4.00 |
| 1318763 | 4.00 |
| 1318764 | 3.75 |
| 1318766 | 3.75 |
| 1318768 | 4.00 |
| 1318769 | 4.00 |

TABLE 46

Tolerability scores in mice at 700 μg dose

| Compound Number | 3 hr FOB |
|---|---|
| PBS | 0.00 |
| 1318749 | 4.25 |
| 1318750 | 2.25 |
| 1318751 | 4.00 |
| 1318752 | 3.75 |
| 1318753 | 2.25 |
| 1318754 | 3.00 |
| 1318755 | 3.75 |
| 1318756 | 0.00 |

TABLE 47

Tolerability scores in mice at 700 μg dose

| Compound Number | 3 hr FOB |
|---|---|
| PBS | 0.00 |
| 1332247 | 1.75 |
| 1332248 | 0.25 |
| 1332249 | 0.00 |

TABLE 47-continued

Tolerability scores in mice at 700 µg dose

| Compound Number | 3 hr FOB |
|---|---|
| 1332250 | 3.75 |
| 1332251 | 0.00 |
| 1332252 | 3.00 |
| 1332263 | 2.00 |
| 1332265 | 1.50 |
| 1332266 | 1.00 |
| 1332267 | 3.75 |
| 1332268 | 2.75 |
| 1332269 | 1.25 |
| 1332270 | 2.25 |
| 1332271 | 2.50 |
| 1333508 | 0.00 |

TABLE 48

Tolerability scores in mice at 700 µg dose

| Compound Number | 3 hr FOB |
|---|---|
| PBS | 0.00 |
| 1332255 | 1.00 |
| 1332256 | 2.00 |
| 1332257 | 1.25 |
| 1332258 | 1.25 |
| 1332259 | 2.25 |
| 1332260 | 2.25 |
| 1332261 | 2.50 |
| 1332262 | 2.00 |

TABLE 49

Tolerability scores in mice at 700 µg dose

| Compound Number | 3 hr FOB |
|---|---|
| PBS | 0.00 |
| 1358996 | 0.00 |
| 1364777 | 2.00 |
| 1364778 | 3.00 |
| 1364779 | 3.50 |
| 1364780 | 3.50 |
| 1364781 | 5.25 |
| 1364782 | 2.50 |
| 1364783 | 3.50 |
| 1364784 | 3.50 |

Example 7: Tolerability of Modified Oligonucleotides Complementary to Human SMN2 in Rats, Long-Term Assessment In separate studies run under the same conditions, selected modified oligonucleotides described above were tested in Sprague Dawley rats to assess long-term tolerability. Comparator Compound Nos. 396442 and 819735 were also tested in this assay. Sprague Dawley rats each received a single intrathecal (IT) delivered dose of 3 mg of oligonucleotide or PBS. Beginning 1 week post-treatment, each animal was weighed and evaluated weekly by a trained observer for adverse events. Adverse events were defined as neurological dysfunction not typical in PBS-treated control animals, including, but not limited to: abnormal limb splay, abnormal gait, tremors, abnormal respiration, paralysis, and spasticity. The onset of the adverse event is defined as the week post-dosing when the dysfunction was first recorded. If no adverse event was achieved, there is no onset (–). The onset of adverse events typically correlates with a failure to thrive as defined by a lack of body weight gain/maintenance similar to PBS-treated animals Similar tolerability assessments were described in Oestergaard et al., *Nucleic Acids Res.*, 2013 November, 41(21), 9634-9650 and Southwell et al., *Mol Ther.*, 2014 December, 22(12), 2093-2106.

At the end of the study, the rats were sacrificed and tissues were collected. Histopathology was performed on sections of cerebellum using calbindin stain. Purkinje cell loss was observed in calbindin stained cerebellum sections as indicated in the table below. Cerebellum and spinal cord were also evaluated using an antibody specific for modified oligonucleotides. Animals demonstrating no oligonucleotide uptake were excluded from histopathology analysis. Histology was not completed for animals that were sacrificed early due to adverse events. Additionally, cortical GFAP, a marker of astrogliosis (Abdelhak, et al., *Scientific Reports*, 2018, 8, 14798), was measured using RT-PCR, and average elevations >2-fold are noted below.

TABLE 50

Long-term tolerability in rats at 3 mg dose

| Compound Number | Adverse event onset, weeks post-treatment, individual animals | Purkinje cell loss (# animals with loss/# animals tested) | Cortex GFAP mRNA >2-fold PBS Control |
|---|---|---|---|
| PBS | No | Not observed | N/A |
| 396442 | 6, 6, 2 | 2/3 | Yes |
| 819735 | 4, 6, 6, — | 1/4 | Yes |
| 1263789 | —, —, — | 0/3 | No |
| 1287717 | —, —, —, —, —, —, —, — | 0/8 | No |
| 1287745 | —, —, —, —, —, —, — | 0/7 | No |
| 1358996 | —, —, —, — | 0/4 | No |
| 1263783 | —, —, —, — | 0/4 | No |
| 1263785 | —, —, — | 0/3 | No |
| 1263787 | —, —, —, — | 0/4 | No |
| 1263800 | —, — | 0/2 | No |
| 1263802 | —, —, — | 0/3 | No |
| 1263806 | —, —, — | 0/3 | No |
| 1263808 | —, —, — | 0/3 | No |
| 1263810 | —, —, — | 0/3 | No |

Example 8: Tolerability and Pharmacokinetics of Modified Oligonucleotides in Non-Human Primates, Single or Repeat Dosing Cynomolgus monkeys are treated with modified oligonucleotides to determine the local and systemic tolerability and pharmacokinetics of the modified oligonucleotides. Each group receives either artificial CSF or modified oligonucleotide as a single intrathecal lumbar bolus dose injection (IT), or, for repeat-dosing groups, an IT bolus dose on day 1 of the study, followed by IT bolus doses at later time points. Tissues are collected 1 week after the final injection. In a single dose study, monkeys are administered a single dose of modified oligonucleotide and tolerability is assessed. Representative doses for single-dose studies in adult cynomolgus monkeys include 1 mg, 3 mg, 7 mg, and 35 mg.

In a repeat-dosing study, monkeys are administered an IT bolus dose on day 1 of the study, followed by weekly (e.g., days 8, 15, and 22 for a four-week study) or monthly (e.g., days 29, 57, and 84 for a 13 week study) IT bolus dosing. Representative doses for repeat-dose studies in adult cynomolgus studies include 1 mg, 3 mg, 7 mg, and 35 mg.

Assessment of tolerability is based on clinical observations, body weights, food consumption, physical and neurological examinations including sensorimotor reflexes, cerebral reflexes and spinal reflexes, coagulation, hematology, clinical chemistry (blood and cerebral spinal fluid (CSF)), cell count, and anatomic pathology evaluations. Complete necropsies are performed with a recording of any macroscopic abnormality. Organ weights are taken and microscopic examinations are conducted. Blood is collected for complement analysis. In addition, blood, CSF, and tissues (at necropsy) are collected for toxicokinetic evaluations.

Tolerability of modified oligonucleotides is analyzed in brain and spinal cord tissue by measuring Aif1 and Gfap levels in cynomolgus monkeys treated with the modified oligonucleotide or the control. Brain and spinal cord samples are collected and flash frozen in liquid nitrogen and stored frozen (−60° C. to −90° C.). At time of sampling, 2 mm biopsy punches are used to collect samples from frozen tissues for RNA analysis. Punches are taken from multiple brain and spinal cord regions.

Example 9: Phase Ia Human Clinical Trial with Compound No. 1263789, 1287717, 1287745, or 1358996

Safety, tolerability, pharmacokinetics, pharmacodynamics and efficacy of modified oligonucleotide complementary to human SMN2 is evaluated in a clinical trial setting. Single and/or multiple doses of modified oligonucleotide are evaluated in patients with confirmed SMA, such as Type I SMA, Type II SMA, Type III SMA, or Type IV SMA.

Patient safety is monitored closely during the study. Safety and tolerability evaluations include: physical examination and standard neurological assessment (including fundi), vital signs (HR, BP, orthostatic changes, weight), ECG, AEs and concomitant medications, Columbia Suicide Severity Rating Scale (C-SSRS), CSF safety labs (cell counts, protein, glucose), plasma laboratory tests (clinical chemistry, hematology), and urinalysis.

Efficacy evaluations are selected that are age and Type appropriate and include, for example, the Hammersmith Motor Function Scale-Expanded (HFMSE), which is a reliable and validated tool used to assess motor function in children with SMA; the Pediatric Quality of Life Inventory (PedsQL™) Measurement 4.0 Generic Core Scale; the Pediatric Quality of Life Inventory 3.0 Neuromuscular Modules; the Compound Muscle Action Potential (CMAP); the Motor Unit Number Estimation (MUNE); the Upper Limb Module (ULM); and the 6-Minute Walk Test (6MWT) (Darras, et al., Neurology, 2019, 92: e2492-e2506).

Example 10: Design of Modified Oligonucleotides Complementary to a Human SMN2 Nucleic Acid Modified oligonucleotides complementary to a human SMN2 nucleic acid were designed and synthesized as indicated in the tables below.

Each modified oligonucleotide listed in the tables below is 100% complementary to SEQ ID NO: 1 (GENBANK Accession No. NT_006713.14 truncated from nucleotides 19939708 to 19967777). "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence.

The modified oligonucleotides in the table below are 18 nucleosides in length. Each nucleoside comprises either a 2'-MOE sugar moiety or a 2'-NMA sugar moiety. The sugar motif for each modified oligonucleotide is provided in the Sugar Motif column, wherein each 'e' represents a 2'-MOE sugar moiety, and each 'n' represents a 2'-NMA sugar moiety. Each internucleoside linkage is either a phosphorothioate internucleoside linkage, a phosphodiester internucleoside linkage, a methoxypropyl phosphonate internucleoside linkage, or a mesyl phosphoramidate (MsP) internucleoside linkage. The internucleoside linkage motif for each modified oligonucleotide, is provided in the Internucleoside Linkage Motif column, wherein each 's' represents a phosphorothioate internucleoside linkage, each 'o' represents a phosphodiester internucleoside linkage, each 'x' represents a methoxypropyl phosphonate internucleoside linkage, and each 'z' represents a mesyl phosphoramidate (MsP) internucleoside linkage. Each cytosine is a 5-methyl cytosine. Modified oligonucleotide 449320 has been previously described in WO2015/161170 A2.

TABLE 51

MOE and NMA modified oligonucleotides with mixed PO/PS, PO/MsP, uniform MsP, or PS/MOP internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 449320 | TCACTTTCATAATGCTGG | eeeeeeeeeeeeeeeeee | ssoooooooooooooooss | 27062 | 27079 | 23 |
| 1287723 | TCACTTTCATAATGCTGG | nnnnnnnnnnnnnnnenn | ssssssssssssssssxs | 27062 | 27079 | 23 |
| 1287724 | TCACTTTCATAATGCTGG | nnnnnnnnnnnnnnnnen | ssssssssssssssssssx | 27062 | 27079 | 23 |
| 1287727 | CACTTTCATAATGCTGGC | nnnnnnnnnnnnnnnenn | sssssssssssssssssx | 27061 | 27078 | 21 |
| 1405549 | TCACTTTCATAATGCTGG | eeeeeeeeeeeeeeeeee | zzzzzzzzzzzzzzzzzz | 27062 | 27079 | 23 |
| 1405552 | TCACTTTCATAATGCTGG | eeeeeeeeeeeeeeeeee | ssssssssssszzzzzz | 27062 | 27079 | 23 |
| 1405553 | TCACTTTCATAATGCTGG | eeeeeeeeeeeeeeeeee | ssssszzzzzzssssss | 27062 | 27079 | 23 |
| 1545359 | TCACTTTCATAATGCTGG | nnnnnnnnnnnnnnnnnn | ssoooooooooooooooss | 27062 | 27079 | 23 |

TABLE 51-continued

MOE and NMA modified oligonucleotides with mixed PO/PS, PO/MsP, uniform MsP, or PS/MOP internucleoside linkages

| Compound Number | Nucleobase Sequence (5' to 3') | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|---|
| 1547773 | TCACTTTCATAATGCTGG | eeeeeeeeeeeeeeeeee | zzooooooooooooooozz | 27062 | 27079 | 23 |
| 1549028 | TCACTTTCATAATGCTGG | eeeeeeeeeeeeeeeeee | zzzzooooooooooooozz | 27062 | 27079 | 23 |
| 1549029 | TCACTTTCATAATGCTGG | eeeeeeeeeeeeeeeeee | zzzzzzooooooooooozz | 27062 | 27079 | 23 |
| 1549030 | TCACTTTCATAATGCTGG | eeeeeeeeeeeeeeeeee | zzzzzzzzooooooooozz | 27062 | 27079 | 23 |

The modified oligonucleotides in the table below all consist of the sequence (from 5' to 3'): TCACTTTCATAATGCTGG (SEQ ID NO: 23). Each modified oligonucleotide listed in the tables below is 100% complementary to SEQ ID NO: 1 (described herein above). "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. The modified oligonucleotides in the table below are 18 nucleosides in length. Each nucleoside comprises either a 2'-MOE sugar moiety or a 2'-NMA sugar moiety. The sugar motif for each modified oligonucleotide is provided in the Sugar Motif column, wherein each 'e' represents a 2'-MOE sugar moiety, and each 'n' represents a 2'-NMA sugar moiety. Each internucleoside linkage is either a phosphorothioate internucleoside linkage, a phosphodiester internucleoside linkage, or a mesyl phosphoramidate (MsP) internucleoside linkage. The internucleoside linkage motif for each modified oligonucleotide, is provided in the Internucleoside Linkage Motif column, wherein each 's' represents a phosphorothioate internucleoside linkage, each 'o' represents a phosphodiester internucleoside linkage, and each 'z' represents a mesyl phosphoramidate (MsP) internucleoside linkage. Each cytosine is a 5-methyl cytosine. The modified oligonucleotides in the table below are conjugated to a 6-palmitamidohexyl phosphate conjugate group attached to the 5'-OH of the oligonucleotide. The structure for the conjugate group is:

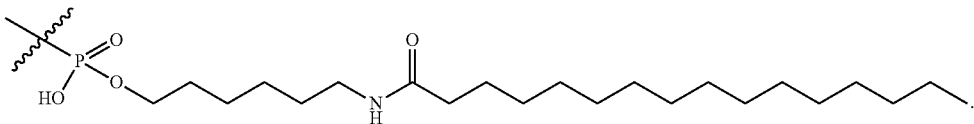 [SMILES: *P(=O)(O)OCCCCCCNC(=O)CCCCCCCCCCCCCCC]

TABLE 52

6-palmitamidohexyl conjugated MOE and NMA modified oligonucleotides with mixed PO/PS, PO/MsP, or uniform MsP internucleoside linkages

| Compound Number | Sugar Motif (5' to 3') | Internucleoside Linkage Motif (5' to 3') | SEQ ID No: 1 Start Site | SEQ ID No: 1 Stop Site | SEQ ID No. |
|---|---|---|---|---|---|
| 1545361 | eeeeeeeeeeeeeeeeee | ssooooooooooooooss | 27062 | 27079 | 23 |
| 1545362 | nnnnnnnnnnnnnnnnnn | ssooooooooooooooss | 27062 | 27079 | 23 |
| 1547772 | eeeeeeeeeeeeeeeeee | zzzzzzzzzzzzzzzzzz | 27062 | 27079 | 23 |
| 1547774 | eeeeeeeeeeeeeeeeee | zzooooooooooooooozz | 27062 | 27079 | 23 |
| 1549031 | eeeeeeeeeeeeeeeeee | zzzzooooooooooooozz | 27062 | 27079 | 23 |
| 1549032 | eeeeeeeeeeeeeeeeee | zzzzzzooooooooooozz | 27062 | 27079 | 23 |
| 1549033 | eeeeeeeeeeeeeeeeee | zzzzzzzzooooooooozz | 27062 | 27079 | 23 |

The modified oligonucleotides in the table below all consist of the sequence (from 5' to 3'): TCACTTTCATAATGCTGG (SEQ ID NO: 23), with a start site of 27062, and a stop site of 27079 on SEQ ID No: 1 (described herein above), wherein "start site" indicates the 5'-most nucleoside to which the modified oligonucleotide is complementary in the target nucleic acid sequence, and wherein "stop site" indicates the 3'-most nucleoside to which the modified oligonucleotide is complementary in the target nucleic acid sequence.

The modified oligonucleotides in the table below are 18 nucleosides in length. The sugar and internucleoside linkage motifs for each modified oligonucleotide are provided in the Sequence and Chemistry Notation column, wherein each subscript 'n' represents a 2'-NMA sugar moiety, each subscript [DMA]' represents a 2'-O—(N,N-dimethyl) acetamide moiety, each subscript [NEA]' represents a 2'-O—(N-ethyl) acetamide moiety, each subscript [NPA]' represents a 2'-O—(N-propyl) acetamide moiety, each subscript [NcPA]' represents a 2'O—(N-cyclopropyl) acetamide moiety, each subscript [McPA]' represents a 2'-O—(N-cyclopropylmethyl) acetamide moiety, and each subscript 's' represents a phosphorothioate internucleoside linkage. Each cytosine is a 5-methyl cytosine, wherein the superscript 'm' before the cytosine residue ($^m$C) represents a 5-methyl cytosine. The structures for each of the sugars represented in the table below are:

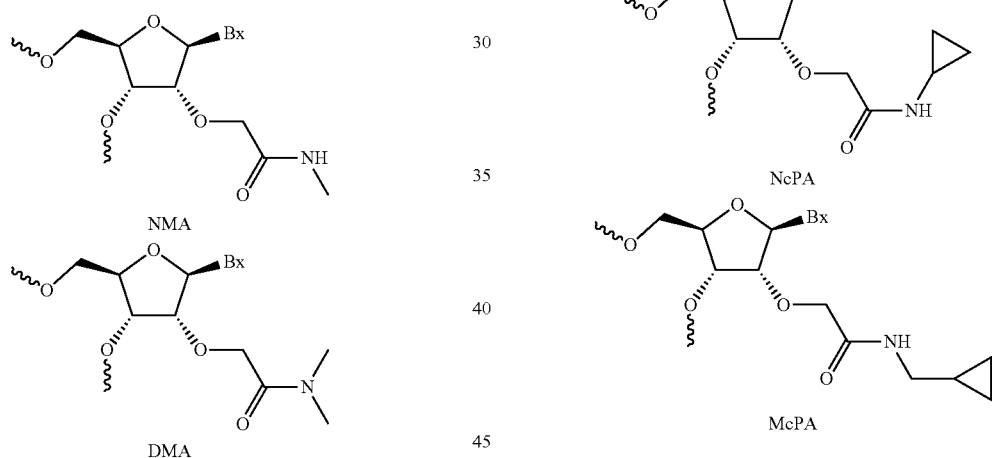

TABLE 53

NMA and NMA analog modified oligonucleotides with uniform PS internucleoside linkages

| Compound Number | Sequence and Chemistry Notation (5' to 3') | SEQ ID No. |
|---|---|---|
| 1355763 | T$_{[DMA]}$s$^m$C$_{[DMA]}$sA$_{ns}$$^m$C$_{[DMA]}$sT$_{[DMA]}$sT$_{[DMA]}$sT$_{[DMA]}$s$^m$C$_{[DMA]}$sA$_{ns}$T$_{[DMA]}$sA$_{[BA]}$ns T$_{[DMA]}$sG$_{ns}$$^m$C$_{[DMA]}$sT$_{[DMA]}$sG$_{ns}$G$_n$ | 23 |
| 1359463 | T$_{[NEA]}$s$^m$C$_{[NEA]}$sAns$^m$C$_{[NEA]}$sT$_{[NEA]}$sT$_{[NEA]}$sT$_{[NEA]}$s$^m$C$_{[NEA]}$sA$_{ns}$T$_{[NEA]}$sA$_{ns}$A$_{ns}$ T$_{[NEA]}$sG$_{ns}$$^m$C$_{[NEA]}$sT$_{[NEA]}$sG$_{ns}$G$_n$ | 23 |
| 1358995 | T$_{[NPA]}$s$^m$C$_{[NPA]}$sAns$^m$C$_{[NPA]}$sT$_{[NPA]}$sT$_{[NPA]}$sT$_{[NPA]}$smC$_{[NPA]}$sA$_{ns}$T$_{[NPA]}$sA$_{ns}$A$_{ns}$ T$_{[NPA]}$sG$_{ns}$$^m$C$_{[NPA]}$sT$_{[NPA]}$sG$_{ns}$G$_n$ | 23 |
| 1355776 | T$_{[NcPA]}$s$^m$C$_{[NcPA]}$sA$_{ns}$$^m$C$_{[NcPA]}$sT$_{[NcPA]}$sT$_{[NcPA]}$sT$_{[NcPA]}$s$^m$C$_{[NcPA]}$sA$_{ns}$T$_{[NcPA]}$sA$_{ns}$A$_{ns}$ T$_{[NcPA]}$sG$_{ns}$$^m$C$_{[NcPA]}$sT$_{[NcPA]}$sG$_{ns}$G$_n$ | 23 |
| 1355777 | T$_{[McPA]}$s$^m$C$_{[McPA]}$sA$_{ns}$$^m$C$_{[McPA]}$sT$_{[McPA]}$sT$_{[McPA]}$sT$_{[McPA]}$s$^m$C$_{[McPA]}$sA$_{ns}$ T$_{[McPA]}$sA$_{ns}$A$_{ns}$T$_{[McPA]}$sG$_{ns}$$^m$C$_{[McPA]}$sT$_{[McPA]}$sG$_{ns}$G$_n$ | 23 |

Example 11: Activity of Modified Oligonucleotides Complementary to Human SMN2 in Transgenic Mice, Single Dose (35 µg)

Activity of selected modified oligonucleotides described above was tested in human SMN2 transgenic mice essentially as described above in Example 2.

Treatment

The transgenic mice were divided into groups of 4 mice each. Each mouse received a single ICV bolus of modified oligonucleotide at doses as indicated in the tables below. A group of 4 mice received PBS as a negative control. Two weeks post treatment, mice were sacrificed and RNA was extracted from coronal brain and spinal cord for real-time qPCR analysis of SMN2 RNA. Results are presented as fold change in RNA levels relative to PBS control, normalized to total SMN2 levels. $ED_{50}$ for exon inclusion (exon 7$^+$) was calculated in GraphPad Prism 7 using nonlinear regression, 4-parameter dose response curve [Y=Bottom+(Top−Bottom)/(1+(10^log EC50/X)^HillSlope)].

RNA Analysis

Two weeks post treatment, mice were sacrificed and RNA was extracted from cortical brain tissue and spinal cord for real-time qPCR analysis of SMN2 RNA. Primer probe set hSMN2vd #4_LTS00216_MGB was used to determine the amount of SMN2 RNA including exon 7 (exon 7$^+$). Primer probe set hSMN2_Sumner68_PPS50481 was used to determine the amount of SMN2 RNA excluding exon 7 (exon 7$^-$). Total SMN2 RNA levels were measured using primer probe set hSMN2_LTS00935. Results are presented as fold change in RNA levels relative to PBS control, normalized to total SMN2 levels.

TABLE 54

Effect of modified oligonucleotides on human SMN2 RNA splicing in heterozygous transgenic mice

| Compound No. | Dose (µg) | CORTEX exon 7$^+$ | CORTEX exon 7$^-$ | SPINAL CORD exon 7$^+$ | SPINAL CORD exon 7$^-$ |
|---|---|---|---|---|---|
| PBS | — | 1 | 1 | 1 | 1 |
| 396443 | 35 | 3 | 0.6 | 3 | 0.5 |
| 1405549 | 35 | 1.6 | 0.9 | 1.2 | 0.9 |
| 1405552 | 35 | 3.2 | 0.6 | 2.1 | 0.7 |
| 1405553 | 35 | 2.4 | 0.7 | 1.7 | 0.8 |

TABLE 55

Effect of modified oligonucleotides on human SMN2 RNA splicing in heterozygous transgenic mice

| Compound No. | Dose (µg) | CORTEX exon 7$^+$ | CORTEX exon 7$^-$ | SPINAL CORD exon 7$^+$ | SPINAL CORD exon 7$^-$ |
|---|---|---|---|---|---|
| PBS | — | 1 | 1 | 1 | N/A |
| 396443 | 35 | 2.7 | 0.5 | 3 | N/A |
| 1405549 | 35 | 1.5 | 0.8 | 1.9 | N/A |
| 1547772 | 35 | 1.8 | 0.8 | 1.8 | N/A |
| 1547773 | 35 | 1.6 | 0.9 | 1.9 | N/A |
| 1547774 | 35 | 1.6 | 1 | 1.6 | N/A |
| 1549028 | 35 | 1.5 | 1 | 1.5 | N/A |
| 1549029 | 35 | 1.4 | 1 | 1.7 | N/A |
| 1549030 | 35 | 1.4 | 1 | 1.4 | N/A |
| 1549031 | 35 | 1.7 | 0.8 | 1.6 | N/A |
| 1549032 | 35 | 1.4† | 0.9† | 1.7† | N/A |
| 1549033 | 35 | 1.4 | 1 | 1.3 | N/A |

†indicates fewer than four samples available

Example 12: Activity of Modified Oligonucleotides Complementary to Human SMN2 in Transgenic Mice, Single Dose (15 µg)

Activity of selected modified oligonucleotides described above was tested in human SMN2 transgenic mice essentially as described above in Example 2.

Treatment

The transgenic mice were divided into groups of 4 mice each. Each mouse received a single ICV bolus of modified oligonucleotide at doses as indicated in the tables below. A group of 4 mice received PBS as a negative control. Two weeks post treatment, mice were sacrificed and RNA was extracted from coronal brain and spinal cord for real-time qPCR analysis of SMN2 RNA. Results are presented as fold change in RNA levels relative to PBS control, normalized to total SMN2 levels. $ED_{50}$ for exon inclusion (exon 7$^+$) was calculated in GraphPad Prism 7 using nonlinear regression, 4-parameter dose response curve [Y=Bottom+(Top−Bottom)/(1+(10^log EC50/X)^HillSlope)].

RNA Analysis

Two weeks post treatment, mice were sacrificed and RNA was extracted from cortical brain tissue and spinal cord for real-time qPCR analysis of SMN2 RNA. Primer probe set hSMN2vd #4_LTS00216_MGB was used to determine the amount of SMN2 RNA including exon 7 (exon 7$^+$). Primer probe set hSMN2_Sumner68_PPS50481 was used to determine the amount of SMN2 RNA excluding exon 7 (exon 7$^-$). Total SMN2 RNA levels were measured using primer probe set hSMN2_LTS00935. Results are presented as fold change in RNA levels relative to PBS control, normalized to total SMN2 levels.

TABLE 56

Effect of modified oligonucleotides on human SMN2 RNA splicing in heterozygous transgenic mice

| Compound No. | Dose (µg) | CORTEX exon 7$^+$ | CORTEX exon 7$^-$ | SPINAL CORD exon 7$^+$ | SPINAL CORD exon 7$^-$ |
|---|---|---|---|---|---|
| PBS | — | 1 | 1 | 1 | 1 |
| 443305 | 15 | 3.4 | 0.4 | 3.3 | 0.3 |
| 1287723 | 15 | 3.9 | 0.3 | 3.3 | 0.3 |
| 1287724 | 15 | 4.2 | 0.2 | 3.7 | 0.2 |
| 1287727 | 15 | 4.5 | 0.2 | 3.4 | 0.2 |

Example 13: Activity of Modified Oligonucleotides Complementary to Human SMN2 in Transgenic Mice, Multiple Dose Activity of selected modified oligonucleotides described above was tested in human SMN2 transgenic mice essentially as described above in Example 2.

Treatment

The transgenic mice were divided into groups of 4 mice each. Each mouse received a single ICV bolus of modified oligonucleotide at multiple doses as indicated in the tables below. A group of 4 mice received PBS as a negative control. Two weeks post treatment, mice were sacrificed and RNA was extracted from coronal brain and spinal cord for real-time qPCR analysis of SMN2 RNA. Results are presented as fold change in RNA levels relative to PBS control, normalized to total SMN2 levels. $ED_{50}$ for exon inclusion (exon 7$^+$) was calculated in GraphPad Prism 7 using nonlinear regression, 4-parameter dose response curve [Y=Bottom+(Top−Bottom)/(1+(10^log EC50/X)^HillSlope)].

RNA Analysis

Two weeks post treatment, mice were sacrificed and RNA was extracted from cortical brain tissue and spinal cord for real-time qPCR analysis of SMN2 RNA. Primer probe set hSMN2vd #4_LTS00216_MGB was used to determine the amount of SMN2 RNA including exon 7 (exon 7$^+$). Primer probe set hSMN2_Sumner68_PPS50481 was used to determine the amount of SMN2 RNA excluding exon 7 (exon 7$^-$). Total SMN2 RNA levels were measured using primer probe set hSMN2_LTS00935. Results are presented as fold change in RNA levels relative to PBS control, normalized to total SMN2 levels.

TABLE 57

Effect of modified oligonucleotides on human SMN2 RNA splicing in heterozygous transgenic mice

| Compound No. | Dose (μg) | CORTEX exon 7$^+$ | exon 7$^-$ | ED50 (μg) | SPINAL CORD exon 7$^+$ | exon 7$^-$ | ED50 (μg) |
|---|---|---|---|---|---|---|---|
| PBS | — | 1 | 1 | — | 1 | 1 | — |
| 396443 | 10 | 2.1 | 0.7 | 26 | 1.9 | 0.8 | 22 |
|  | 30 | 2.8 | 0.5 |  | 2.6 | 0.7 |  |
|  | 100 | 3.2 | 0.3 |  | 2.8 | 0.4 |  |
| 449320 | 10 | 1.2 | 1.0 | >100 | 1.2 | 1.2 | >100 |
|  | 30 | 1.5 | 1.0 |  | 1.3 | 1.2 |  |
|  | 100 | 1.5 | 0.9 |  | 1.3 | 0.9 |  |
| 1545361 | 10 | 1.4 | 1.0 | >100 | 1.2 | 1.1 | >100 |
|  | 30 | 1.8 | 1.1 |  | 1.6 | 1.3 |  |
|  | 100 | 1.3 | 0.9 |  | 1.4 | 0.9 |  |
| 443305 | 10 | 2.4 | 0.6 | 14 | 2.6 | 0.5 | 9 |
|  | 30 | 3.5 | 0.3 |  | 3.0 | 0.4 |  |
|  | 100 | 3.7 | 0.1 |  | 3.3 | 0.1 |  |
| 1545359 | 10 | 1.4 | 1.0 | >100 | 1.4 | 1.1 | >100 |
|  | 30 | 2.0 | 0.9 |  | 1.7 | 1.1 |  |
|  | 100 | 2.3 | 0.6 |  | 1.7 | 0.8 |  |
| 1545362 | 10 | 1.4 | 0.9 | 95 | 1.3 | 1.1 | 51 |
|  | 30 | 1.9 | 0.8 |  | 2.4 | 1.0 |  |
|  | 100 | 2.7 | 0.5 |  | 2.6 | 0.6 |  |

TABLE 58

Effect of modified oligonucleotides on human SMN2 RNA splicing in heterozygous transgenic mice

| Compound No. | Dose (μg) | CORTEX exon 7$^+$ | exon 7$^-$ | ED50 (μg) | SPINAL CORD exon 7$^+$ | exon 7$^-$ | ED50 (μg) |
|---|---|---|---|---|---|---|---|
| PBS | — | 1 | 1 | — | 1 | 1 | — |
| 1263789 | 3 | 1.5 | 0.9 | 35 | 1.6 | 0.8 | 16 |
|  | 10 | 1.9 | 0.8 |  | 2.2 | 0.6 |  |
|  | 30 | 2.7 | 0.6 |  | 2.9 | 0.5 |  |
|  | 100 | 3.8 | 0.3 |  | 3.5 | 0.3 |  |
|  | 300 | 4.3 | 0.2 |  | 3.9 | 0.2 |  |
| 1287703 | 3 | 1.5 | 0.7 | 43 | 1.5 | 0.8 | 28 |
|  | 10 | 1.6 | 0.7 |  | 2.0 | 0.7 |  |
|  | 30 | 2.7 | 0.5 |  | 2.6 | 0.5 |  |
|  | 100 | 3.7 | 0.3 |  | 3.2 | 0.4 |  |
|  | 300 | 4.0 | 0.2 |  | 3.5 | 0.2 |  |
| 1287717 | 3 | 1.4 | 0.8 | 31 | 1.4 | 0.9 | 30 |
|  | 10 | 1.7 | 0.7 |  | 1.8 | 0.7 |  |
|  | 30 | 3.1 | 0.4 |  | 2.4† | 0.5† |  |
|  | 100 | 3.8 | 0.3 |  | 3.3 | 0.3 |  |
|  | 300 | 4.3 | 0.2 |  | 3.8 | 0.2 |  |
| 1318768 | 3 | 1.3 | 0.8 | 49 | 1.2 | 0.8 | 32 |
|  | 10 | 1.8 | 0.7 |  | 1.8 | 0.8 |  |
|  | 30 | 2.4 | 0.6 |  | 2.4 | 0.6 |  |
|  | 100 | 3.5 | 0.3 |  | 3.3 | 0.4 |  |
|  | 300 | 4.1 | 0.2 |  | 3.9 | 0.2 |  |
| 1287731 | 3 | 1.5 | 0.8 | 29 | 1.5 | 1.0 | 13 |
|  | 10 | 2.0 | 0.6 |  | 2.4 | 0.6 |  |
|  | 30 | 2.7 | 0.4 |  | 3.2 | 0.4 |  |
|  | 100 | 4.3 | 0.2 |  | 3.8 | 0.2 |  |
|  | 300 | 4.2 | 0.1 |  | 3.7 | 0.1 |  |

TABLE 58-continued

Effect of modified oligonucleotides on human SMN2 RNA splicing in heterozygous transgenic mice

| Compound No. | Dose (μg) | CORTEX exon 7$^+$ | exon 7$^-$ | ED50 (μg) | SPINAL CORD exon 7$^+$ | exon 7$^-$ | ED50 (μg) |
|---|---|---|---|---|---|---|---|
| 1287735 | 3 | 1.7 | 0.7 | 22 | 1.5 | 0.8 | 15 |
|  | 10 | 2.4 | 0.6 |  | 2.2 | 0.6 |  |
|  | 30 | 3.0 | 0.3 |  | 3.1 | 0.3 |  |
|  | 100 | 4.0 | 0.2 |  | 3.5 | 0.2 |  |
|  | 300 | 4.2 | 0.1 |  | 3.9 | 0.1 |  |
| 1287745 | 3 | 1.5 | 0.7 | 35 | 1.4 | 0.8 | 13 |
|  | 10 | 2.0 | 0.6 |  | 2.4 | 0.6 |  |
|  | 30 | 2.9 | 0.4 |  | 3.2 | 0.4 |  |
|  | 100 | 3.7 | 0.2 |  | 3.6 | 0.2 |  |
|  | 300 | 3.7 | 0.2 |  | 3.8 | 0.2 |  |
| 396443 | 3 | 1.7 | 0.7 | 47 | 1.5 | 0.9 | 22 |
|  | 10 | 1.4 | 0.7 |  | 1.6 | 0.8 |  |
|  | 30 | 2.8 | 0.5 |  | 3.1 | 0.4 |  |
|  | 100 | 3.3 | 0.4 |  | 3.3 | 0.5 |  |
|  | 300 | 4.3 | 0.2 |  | 4.0 | 0.2 |  |

† indicates fewer than four samples available

TABLE 59

Effect of modified oligonucleotides on human SMN2 RNA splicing in heterozygous transgenic mice

| Compound No. | Dose (μg) | CORTEX exon 7$^+$ | exon 7$^-$ | ED50 (μg) | SPINAL CORD exon 7$^+$ | exon 7$^-$ | ED50 (μg) |
|---|---|---|---|---|---|---|---|
| PBS | — | 1 | 1 | — | 1 | 1 | — |
| 396443 | 3 | 1.1 | 0.9 | 39 | 1.2 | 0.9 | 33 |
|  | 30 | 2.0 | 0.6 |  | 2.3 | 0.5 |  |
|  | 100 | 2.3 | 0.4 |  | 2.7 | 0.3 |  |
| 443305 | 3 | 1.4 | 0.7 | 13 | 1.6 | 0.7 | 10 |
|  | 30 | 2.4 | 0.3 |  | 3.0 | 0.2 |  |
|  | 100 | 2.9 | 0.2 |  | 3.1 | 0.2 |  |
| 1355763 | 3 | 1.1 | 0.8 | 54 | 1.1 | 0.8 | 45 |
|  | 30 | 1.7 | 0.6 |  | 2.1 | 0.5 |  |
|  | 100 | 2.4 | 0.4 |  | 2.6 | 0.3 |  |
| 1359463 | 3 | 1.3 | 0.8 | 18 | 1.3 | 0.7 | 19 |
|  | 30 | 2.3 | 0.3 |  | 2.7 | 0.3 |  |
|  | 100 | 2.9 | 0.2 |  | 2.7 | 0.2 |  |
| 1358995 | 3 | 1.2 | 0.8 | 45 | 1.0 | 0.8 | 59 |
|  | 30 | 2.0 | 0.4 |  | 1.8 | 0.4 |  |
|  | 100 | 2.2 | 0.4 |  | 2.6 | 0.3 |  |
| 1355776 | 3 | 1.1 | 0.8 | 25 | 1.3 | 0.7 | 24 |
|  | 30 | 2.2 | 0.4 |  | 2.4 | 0.4 |  |
|  | 100 | 2.6 | 0.3 |  | 2.9 | 0.3 |  |
| 1355777 | 3 | 1.0 | 0.9 | 107 | 0.9 | 0.9 | 72 |
|  | 30 | 1.6 | 0.7 |  | 1.8 | 0.6 |  |
|  | 100 | 1.7 | 0.5 |  | 2.2 | 0.6 |  |

Example 15: Tolerability of Modified Oligonucleotides Complementary to SMN2 in Wild-Type Mice Modified oligonucleotides described above were tested in wild-type female C57/Bl6 mice to assess the tolerability of the oligonucleotides. Wild-type female C57/Bl6 mice each received a single ICV dose of 700 μg of modified oligonucleotide listed in the table below. Each treatment group consisted of 4 mice. A group of 4 mice received PBS as a negative control for each experiment (identified in separate tables below). At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group. The results are presented in the tables below.

TABLE 60

Tolerability scores in mice at 700 µg dose

| Compound Number | 3 hr FOB |
|---|---|
| PBS | 0.00 |
| 1287723 | 2.00 |
| 1287724 | 1.00 |
| 1287727 | 2.00 |

The invention claimed is:
1. A modified oligonucleotide according to the following chemical structure:
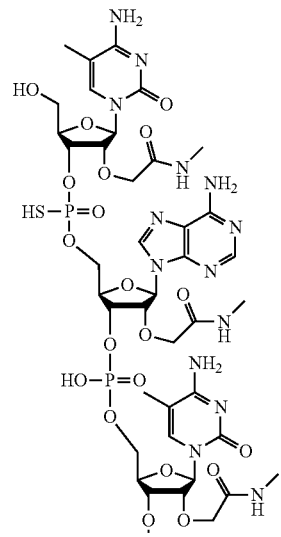
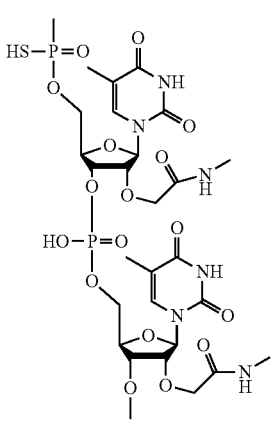
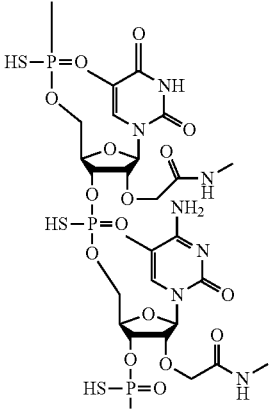
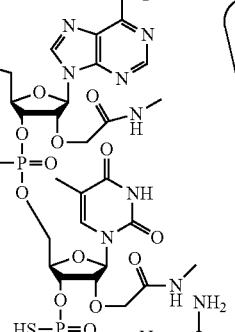
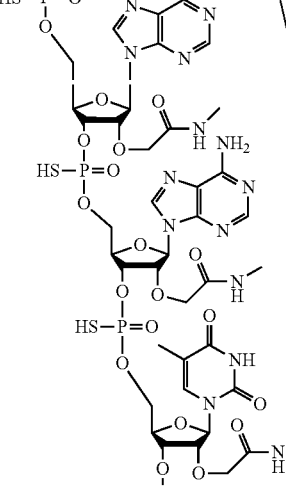

(SEQ ID NO: 21), or a salt thereof.

2. The modified oligonucleotide of claim 1, which is the sodium salt or the potassium salt.

3. A modified oligonucleotide according to the following chemical structure:

177
-continued

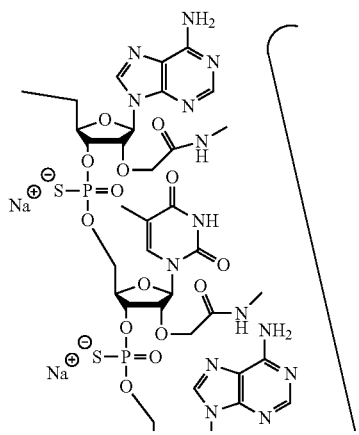

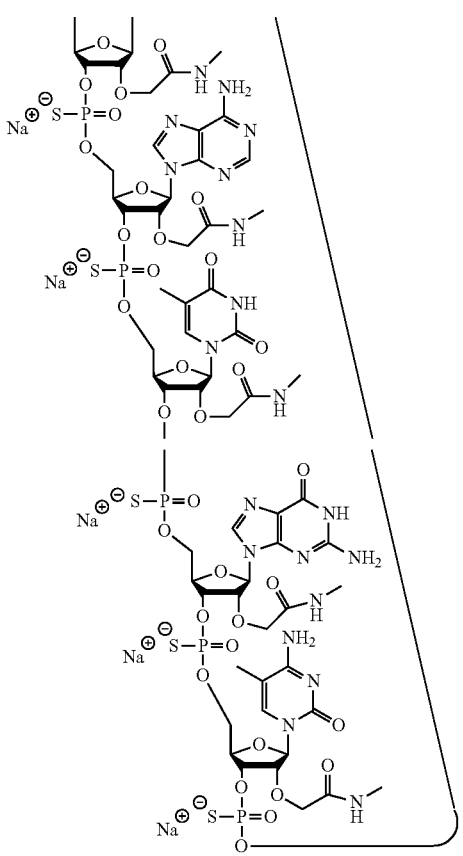

178
-continued

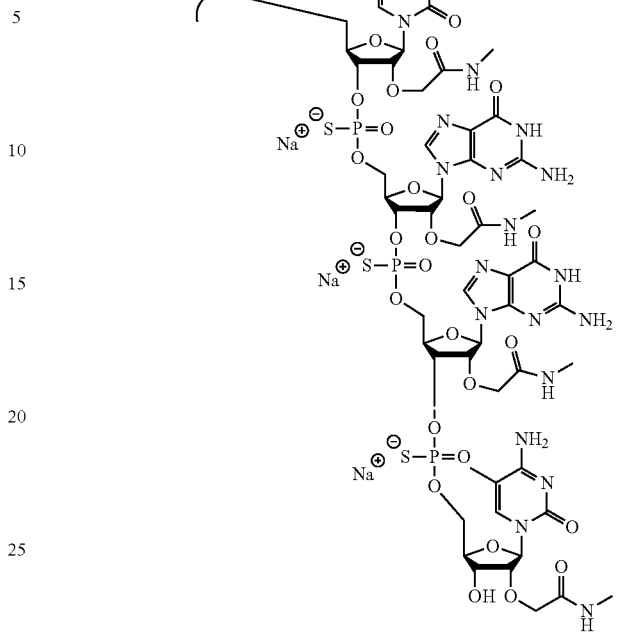

(SEQ ID NO: 21).

4. An oligomeric compound comprising a modified oligonucleotide according to the following chemical notation:
$^{m}C_{ns} A_{no}\,^{m}C_{ns} T_{no} T_{ns} T_{ns}\,^{m}C_{ns} A_{ns} T_{ns} A_{ns} A_{ns} T_{ns} G_{ns}\,^{m}C_{ns} T_{ns} G_{ns} G_{ns}\,^{m}C_{n}$ (SEQ ID NO: 21),
wherein:
A=an adenine nucleobase,
$^{m}C$=a 5-methyl cytosine nucleobase,
G=a guanine nucleobase,
T=a thymine nucleobase,
n=a 2'-NMA sugar moiety,
s=a phosphorothioate internucleoside linkage, and
o=a phosphodiester internucleoside linkage.

5. A population of modified oligonucleotides of claim 1, wherein all of the phosphorothioate internucleoside linkages of the modified oligonucleotide are stereorandom.

6. A population of modified oligonucleotides of claim 3, wherein all of the phosphorothioate internucleoside linkages of the modified oligonucleotide are stereorandom.

7. A population of oligomeric compounds of claim 4, wherein all of the phosphorothioate internucleoside linkages of the modified oligonucleotide are stereorandom.

8. A pharmaceutical composition comprising the modified oligonucleotide of claim 1 and a pharmaceutically acceptable diluent.

9. The pharmaceutical composition of claim 8, wherein the pharmaceutically acceptable diluent is artificial CSF (aCSF) or PBS.

10. The pharmaceutical composition of claim 9, wherein the pharmaceutical composition consists essentially of the modified oligonucleotide and artificial CSF (aCSF) or PBS.

11. A pharmaceutical composition comprising the modified oligonucleotide of claim 3 and a pharmaceutically acceptable diluent.

12. The pharmaceutical composition of claim 11, wherein the pharmaceutically acceptable diluent is artificial CSF (aCSF) or PBS.

13. The pharmaceutical composition of claim 12, wherein the pharmaceutical composition consists essentially of the modified oligonucleotide and artificial CSF (aCSF) or PBS.

14. A pharmaceutical composition comprising the oligomeric compound of claim 4 and a pharmaceutically acceptable diluent.

15. The pharmaceutical composition of claim 14, wherein the pharmaceutically acceptable diluent is artificial CSF (aCSF) or PBS.

16. The pharmaceutical composition of claim 15, wherein the pharmaceutical composition consists essentially of the oligomeric compound and artificial CSF (aCSF) or PBS.

17. A pharmaceutical composition comprising the population of modified oligonucleotides of claim 5 and a pharmaceutically acceptable diluent.

18. The pharmaceutical composition of claim 17, wherein the pharmaceutically acceptable diluent is artificial CSF (aCSF) or PBS.

19. The pharmaceutical composition of claim 18, wherein the pharmaceutical composition consists essentially of the population of modified oligonucleotides and artificial CSF (aCSF) or PBS.

20. A pharmaceutical composition comprising the population of modified oligonucleotides of claim 6 and a pharmaceutically acceptable diluent.

21. The pharmaceutical composition of claim 20, wherein the pharmaceutically acceptable diluent is artificial CSF (aCSF) or PBS.

22. The pharmaceutical composition of claim 21, wherein the pharmaceutical composition consists essentially of the population of modified oligonucleotides and artificial CSF (aCSF) or PBS.

23. A pharmaceutical composition comprising the population of oligomeric compounds of claim 7 and a pharmaceutically acceptable diluent.

24. The pharmaceutical composition of claim 23, wherein the pharmaceutically acceptable diluent is artificial CSF (aCSF) or PBS.

25. The pharmaceutical composition of claim 24, wherein the pharmaceutical composition consists essentially of the population of oligomeric compounds and artificial CSF (aCSF) or PBS.

26. A pharmaceutical composition comprising the modified oligonucleotide of claim 2 and a pharmaceutically acceptable diluent.

27. The pharmaceutical composition of claim 26, wherein the pharmaceutically acceptable diluent is artificial CSF (aCSF) or PBS.

28. The pharmaceutical composition of claim 27, wherein the pharmaceutical composition consists essentially of the modified oligonucleotide and artificial CSF (aCSF) or PBS.

29. A population of modified oligonucleotides of claim 2, wherein all of the phosphorothioate internucleoside linkages of the modified oligonucleotide are stereorandom.

30. A pharmaceutical composition comprising the population of modified oligonucleotides of claim 29 and a pharmaceutically acceptable diluent.

31. The pharmaceutical composition of claim 30, wherein the pharmaceutically acceptable diluent is artificial CSF (aCSF) or PBS.

32. The pharmaceutical composition of claim 31, wherein the pharmaceutical composition consists essentially of the population of modified oligonucleotides and artificial CSF (aCSF) or PBS.

* * * * *

UNITED STATES PATENT AND TRADEMARK OFFICE
CERTIFICATE OF CORRECTION

PATENT NO. : 11,299,737 B1
APPLICATION NO. : 17/356961
DATED : April 12, 2022
INVENTOR(S) : Frank Rigo It is certified that error appears in the above-identified patent and that said Letters Patent is hereby corrected as shown below:

In the Specification

At Column 13, Line 19, through Column 18, Line 36, the structure should read:

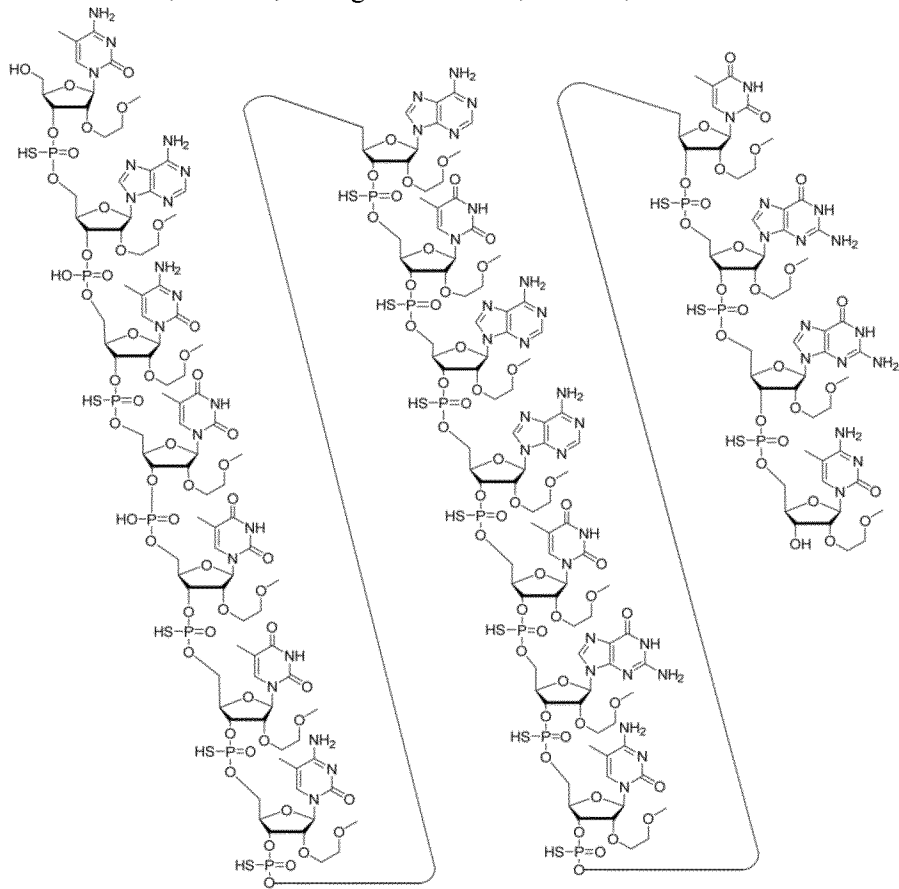

Signed and Sealed this
Fifth Day of July, 2022

Katherine Kelly Vidal
*Director of the United States Patent and Trademark Office*

At Column 17, Line 42, through Column 20, the structure should read:
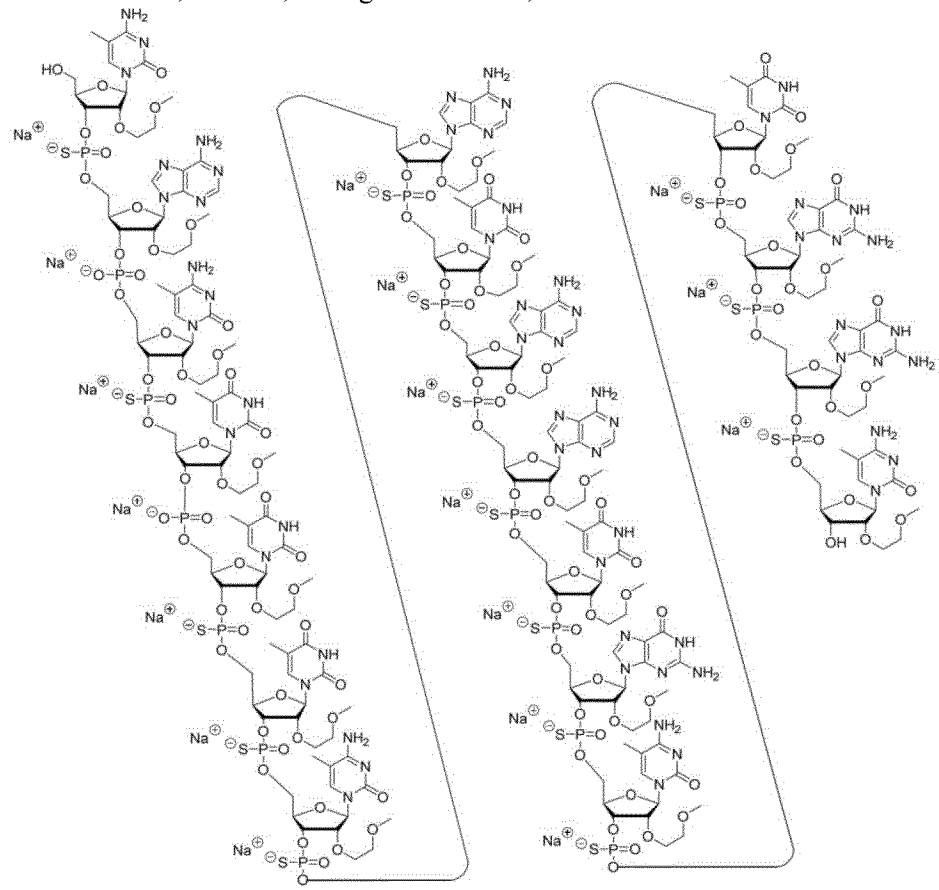

CERTIFICATE OF CORRECTION (continued)
U.S. Pat. No. 11,299,737 B1

At Column 21, Line 3, through Column 26, the structure should read:

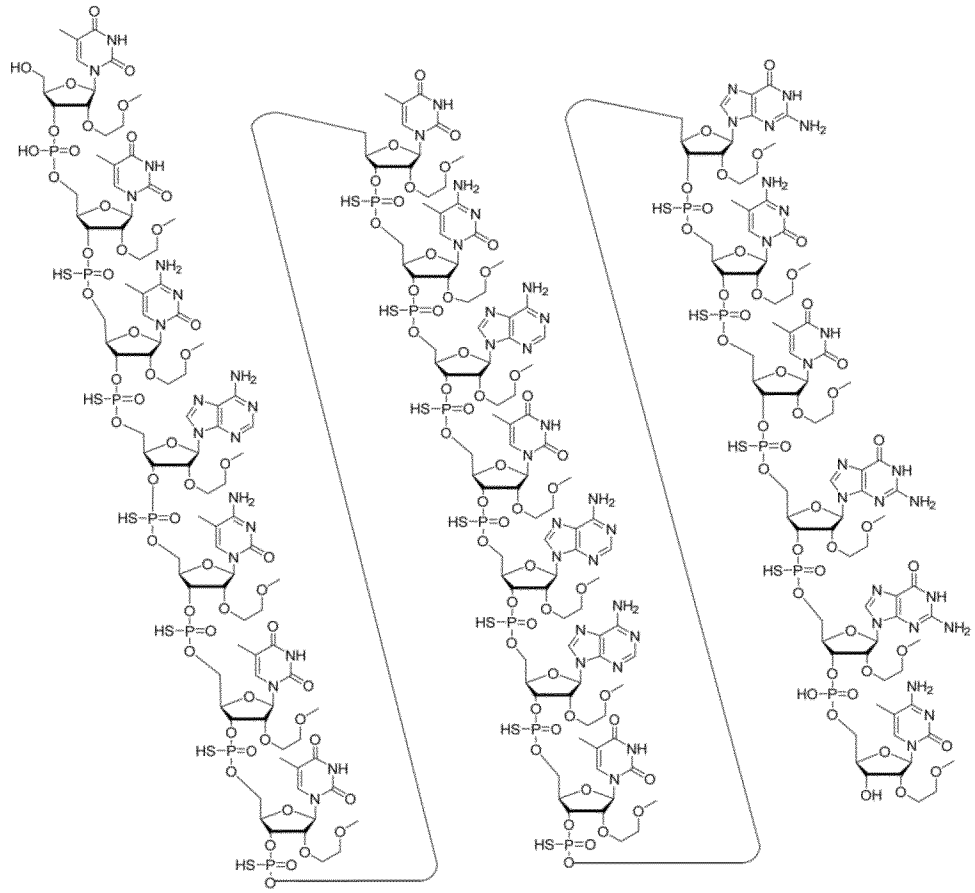

CERTIFICATE OF CORRECTION (continued)
U.S. Pat. No. 11,299,737 B1

At Column 27, Line 5, through Column 28, the structure should read:

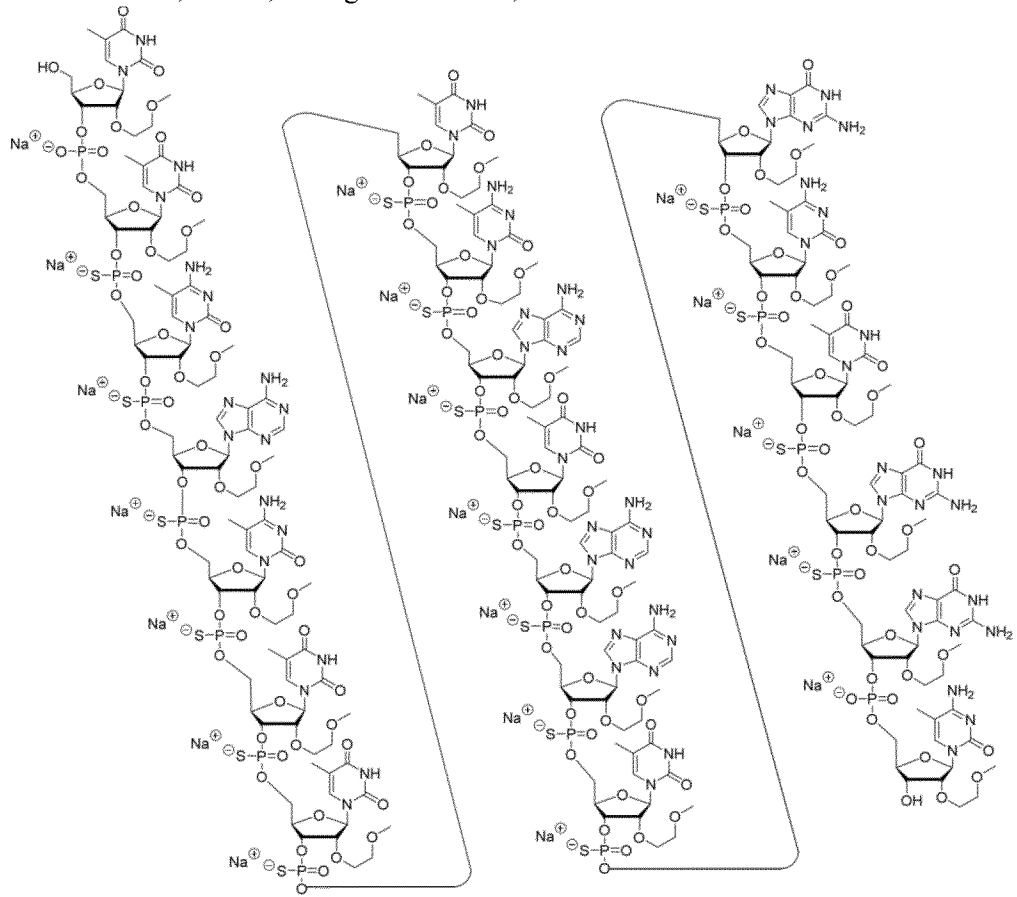

CERTIFICATE OF CORRECTION (continued)
U.S. Pat. No. 11,299,737 B1

At Column 29, Line 2, through Column 30, the structure should read:

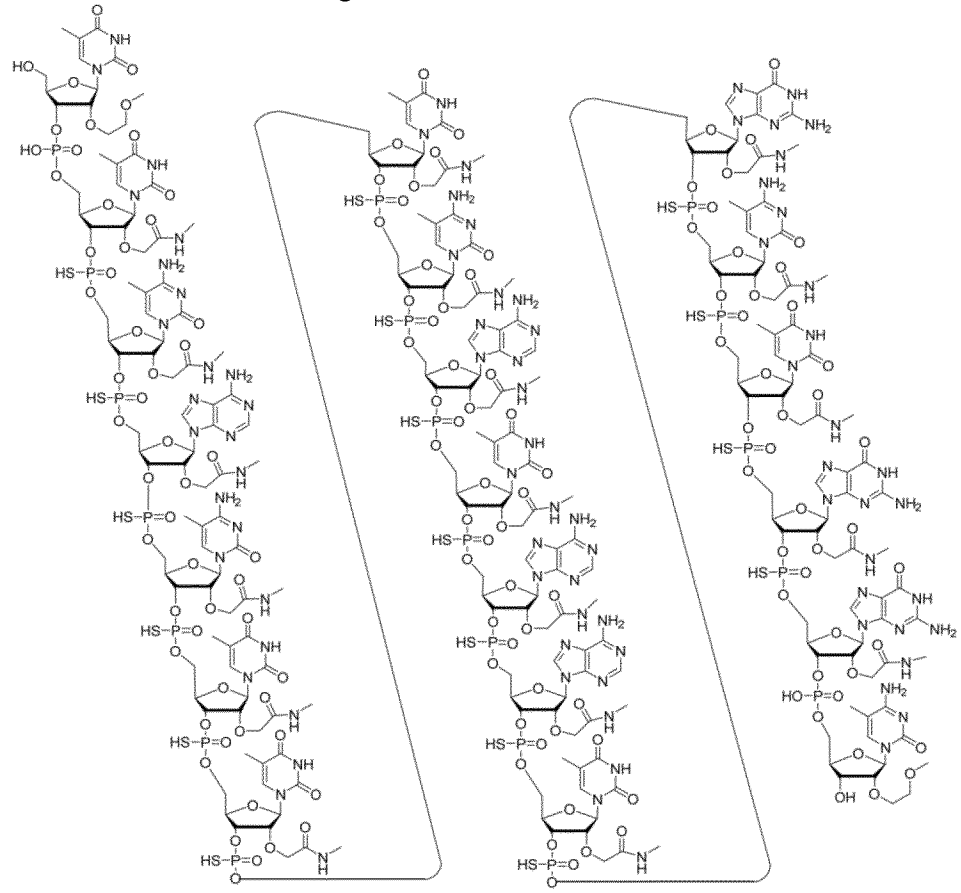

At Column 31, Line 5, through Column 32, the structure should read:
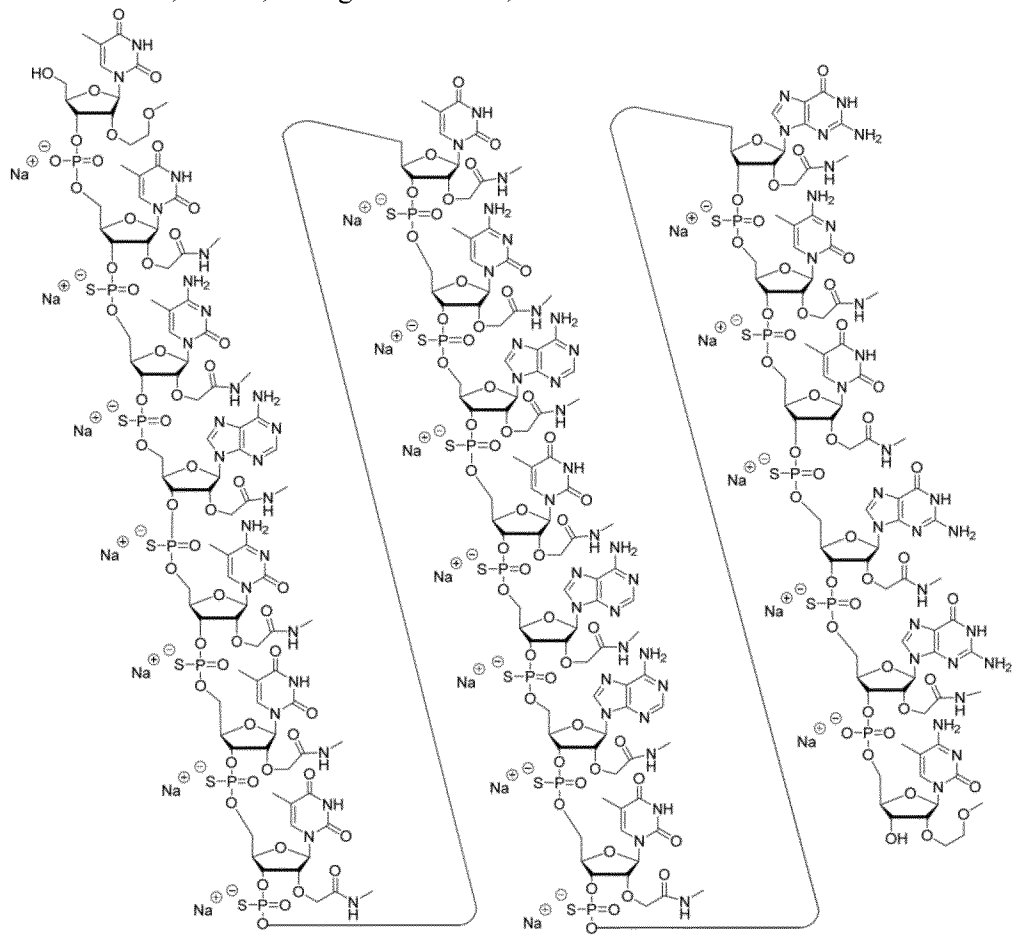

CERTIFICATE OF CORRECTION (continued)
U.S. Pat. No. 11,299,737 B1

At Column 33, Line 3, through Column 34, the structure should read:

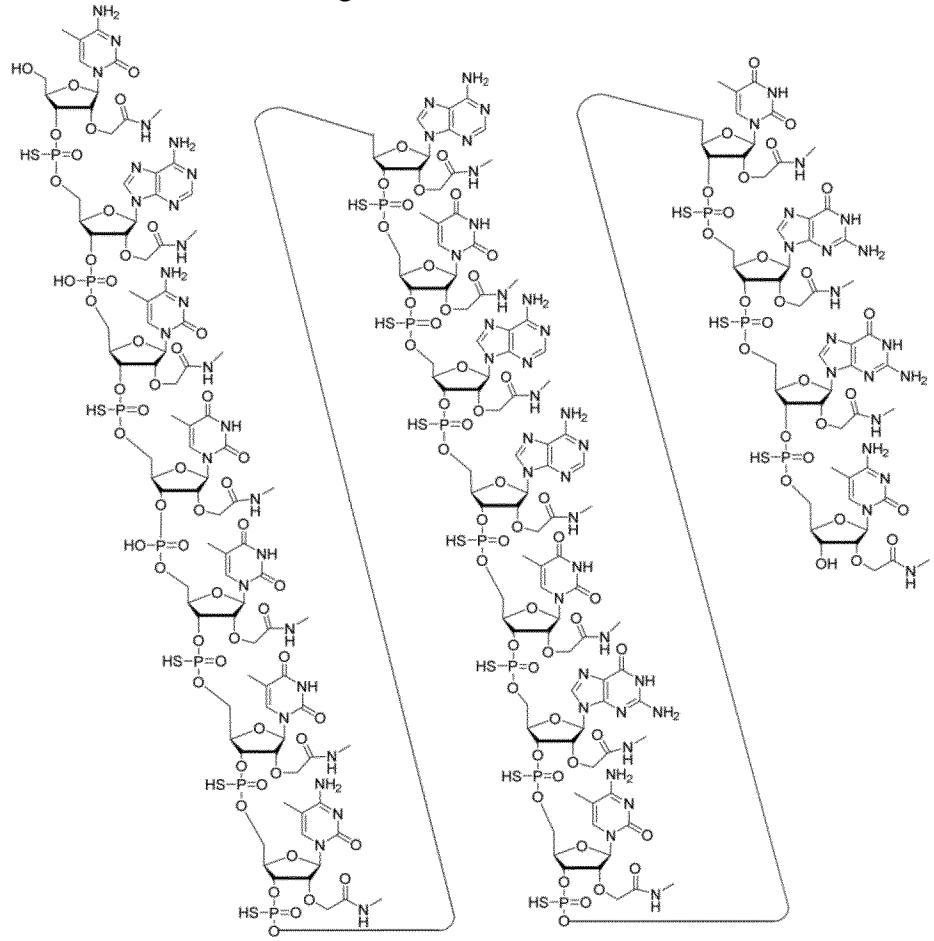

CERTIFICATE OF CORRECTION (continued)
U.S. Pat. No. 11,299,737 B1

At Column 61, Line 25, through Column 64, Line 18, the structure should read:

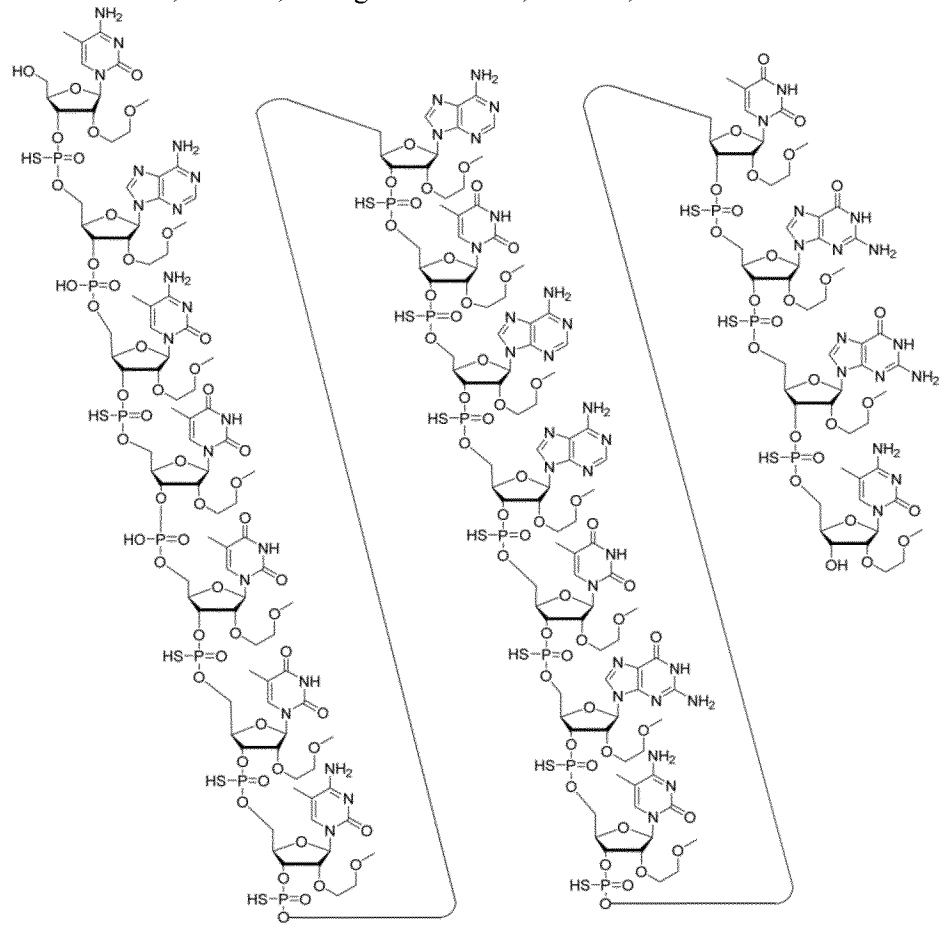

At Column 63, Line 26, through Column 66, Line 18, the structure should read:
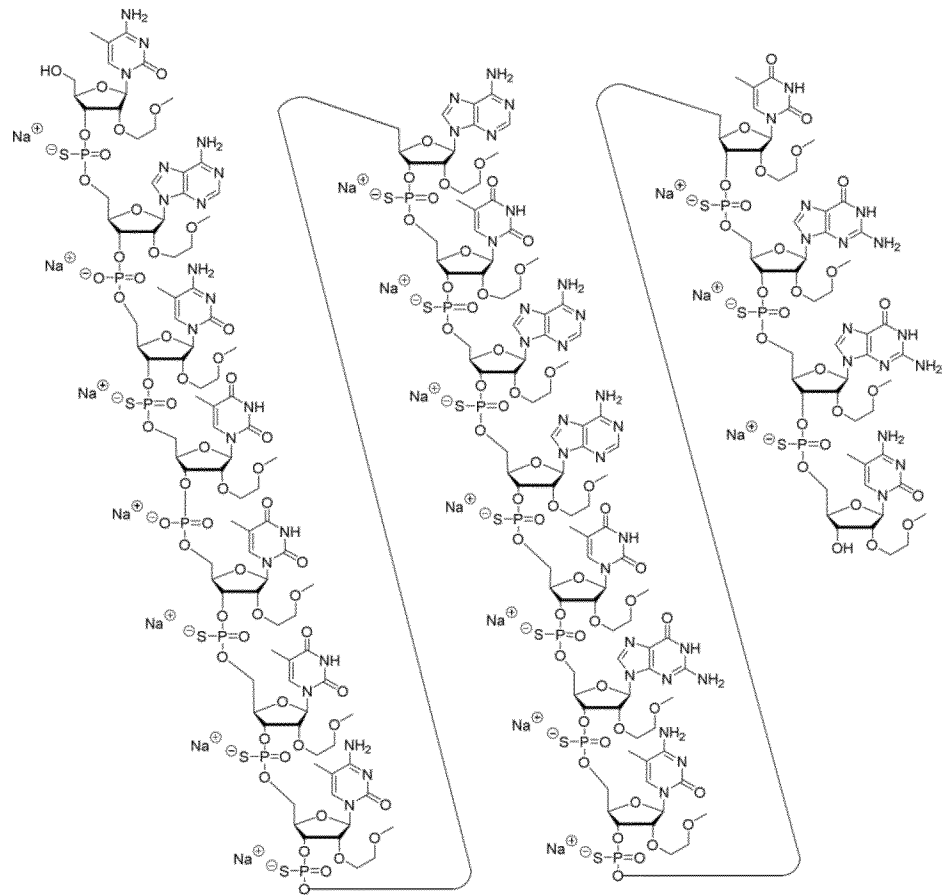

CERTIFICATE OF CORRECTION (continued)
U.S. Pat. No. 11,299,737 B1

At Column 65, Line 37, through Column 68, Line 39, the structure should read:

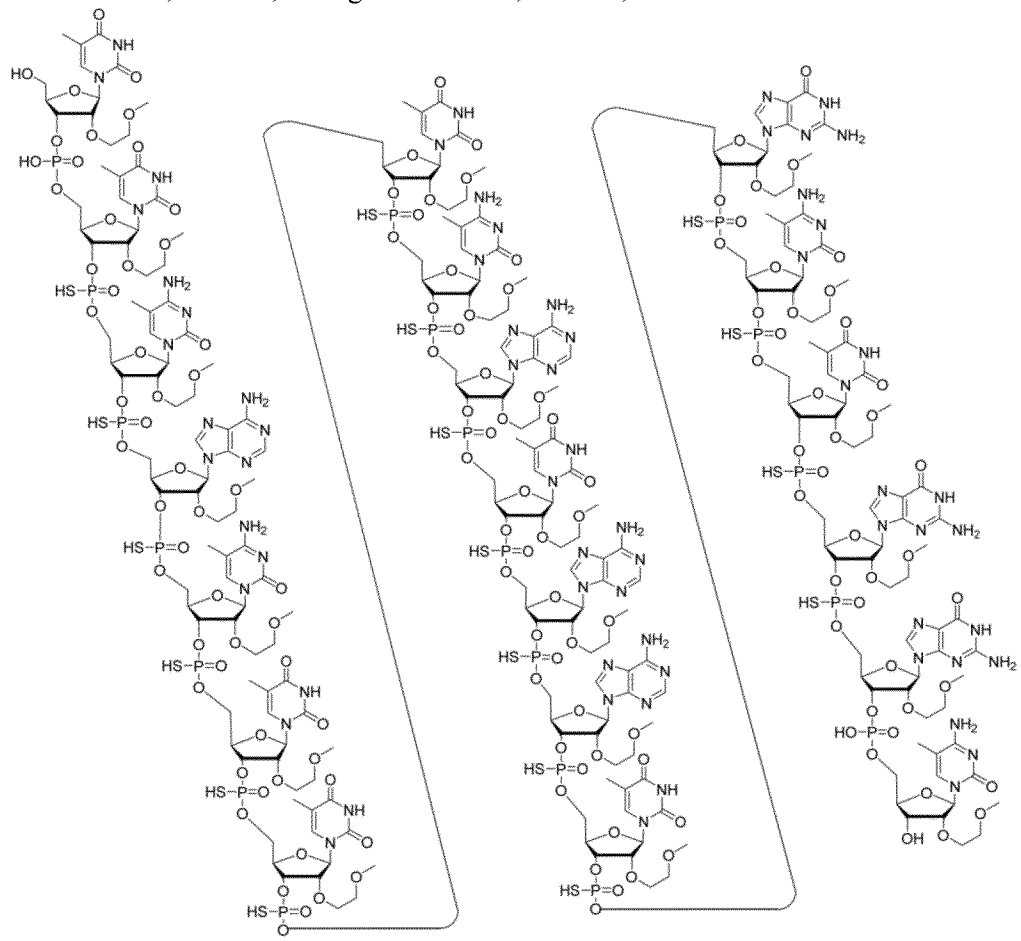

At Column 67, Line 45, through Column 70, Line 33, the structure should read:
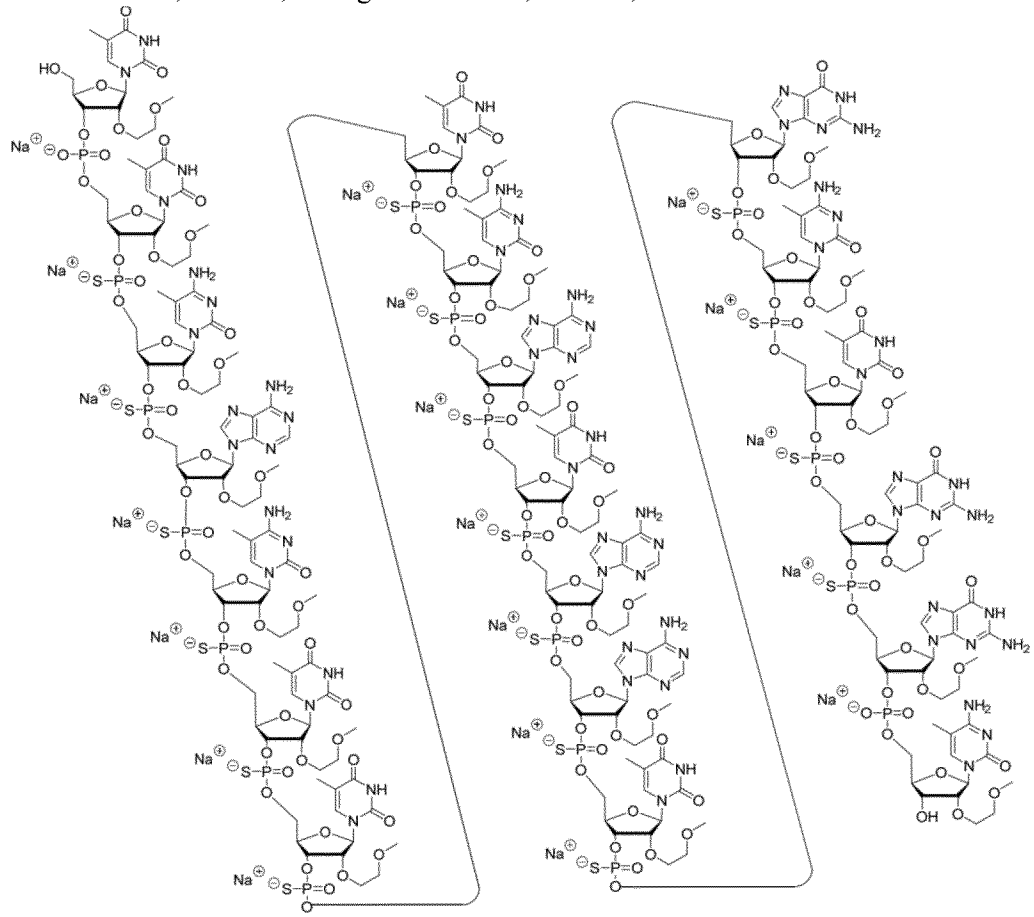

CERTIFICATE OF CORRECTION (continued)
U.S. Pat. No. 11,299,737 B1

At Column 69, Line 49, through Column 72, Line 40, the structure should read:

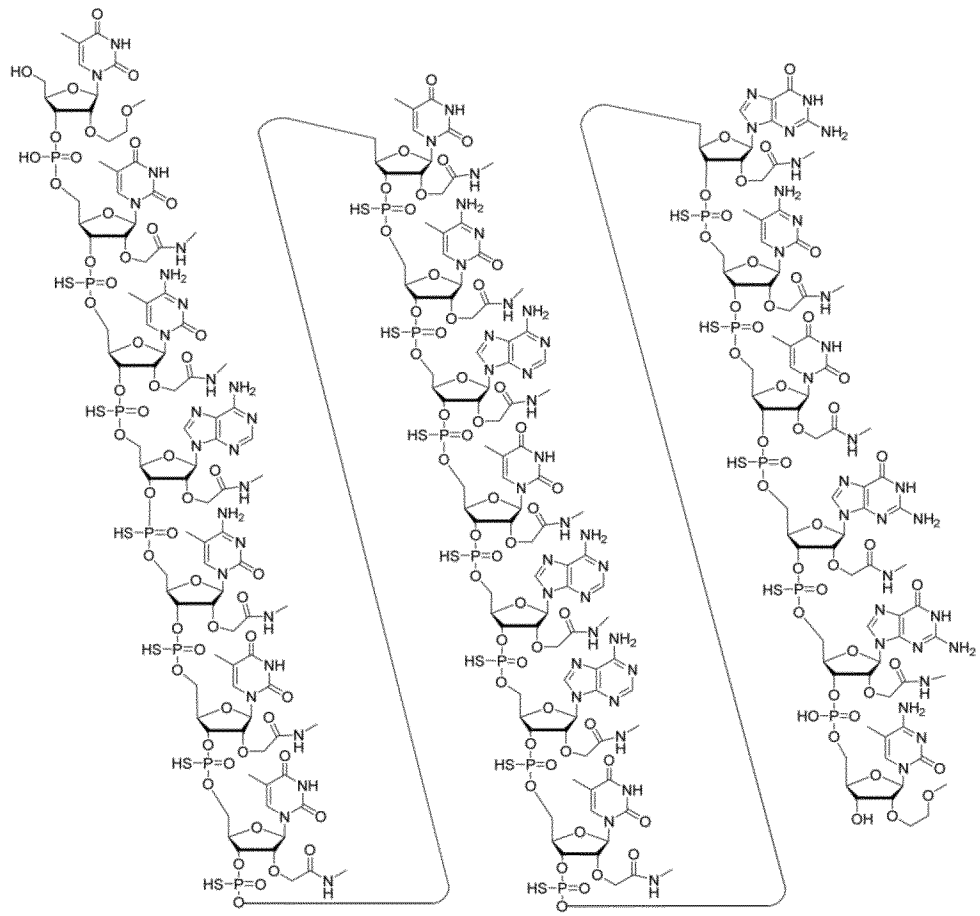

CERTIFICATE OF CORRECTION (continued)
U.S. Pat. No. 11,299,737 B1

At Column 71, Line 46, through Column 74, Line 48, the structure should read:

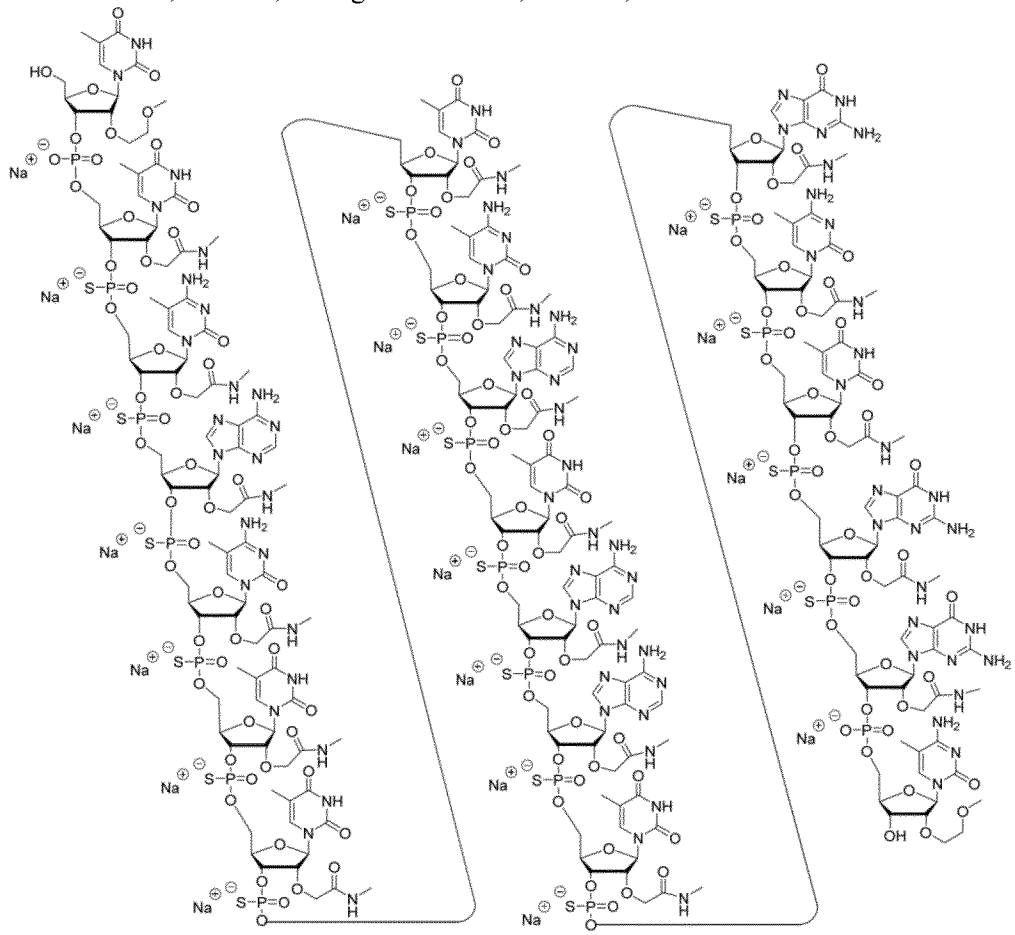

At Column 75 through Column 76, the structure should read:
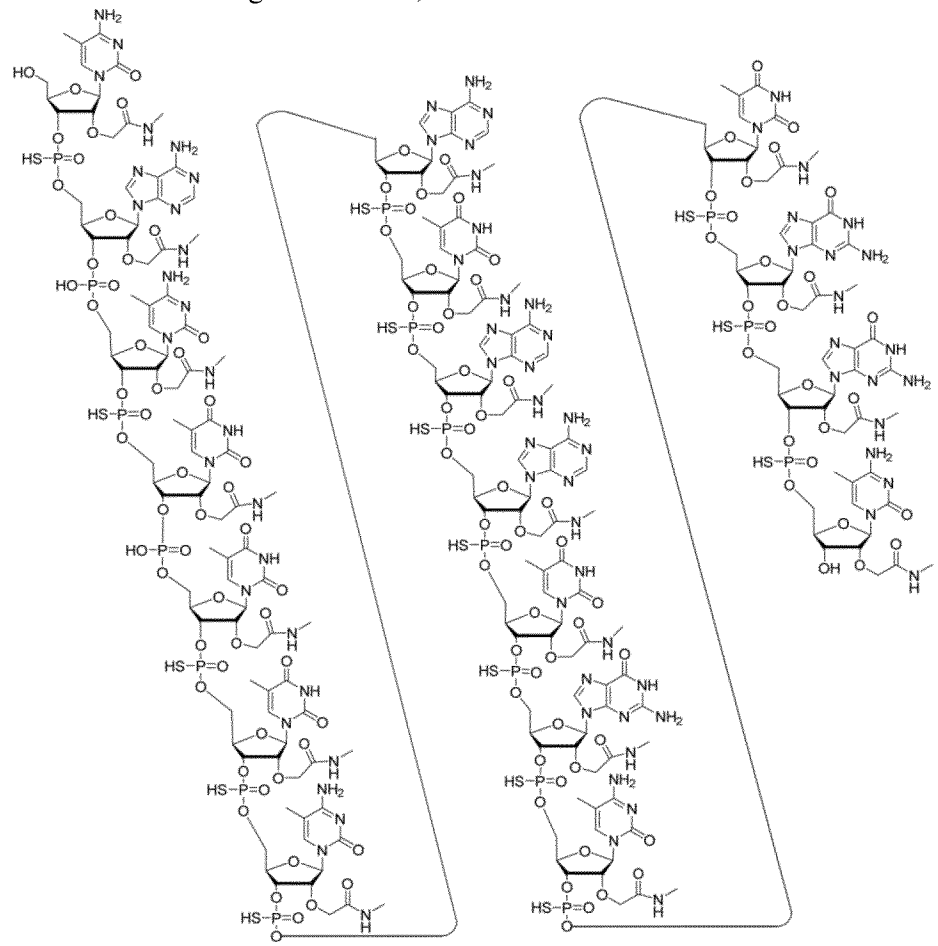

CERTIFICATE OF CORRECTION (continued)
U.S. Pat. No. 11,299,737 B1

At Column 77, Line 5, through Column 78, Line 58, the structure should read:

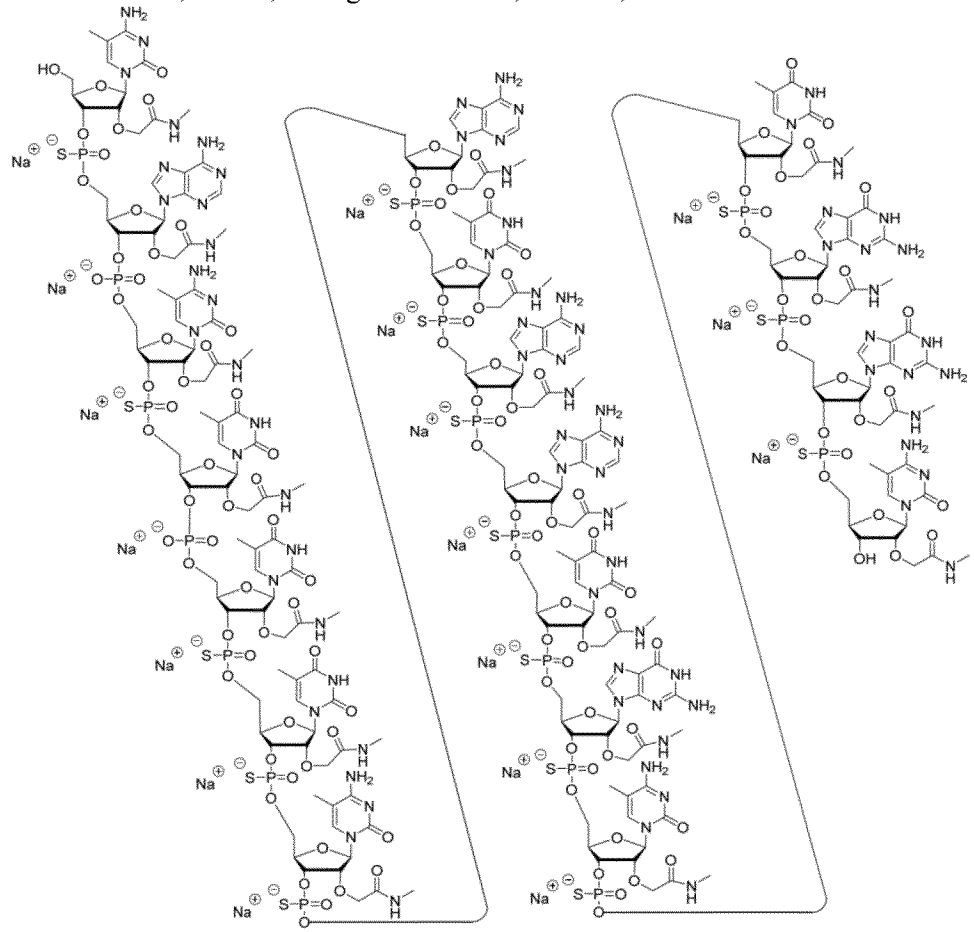

CERTIFICATE OF CORRECTION (continued)

U.S. Pat. No. 11,299,737 B1

In the Claims

In Claim 1, Column 173, Line 22, to Column 175, Line 62, the structure should read:

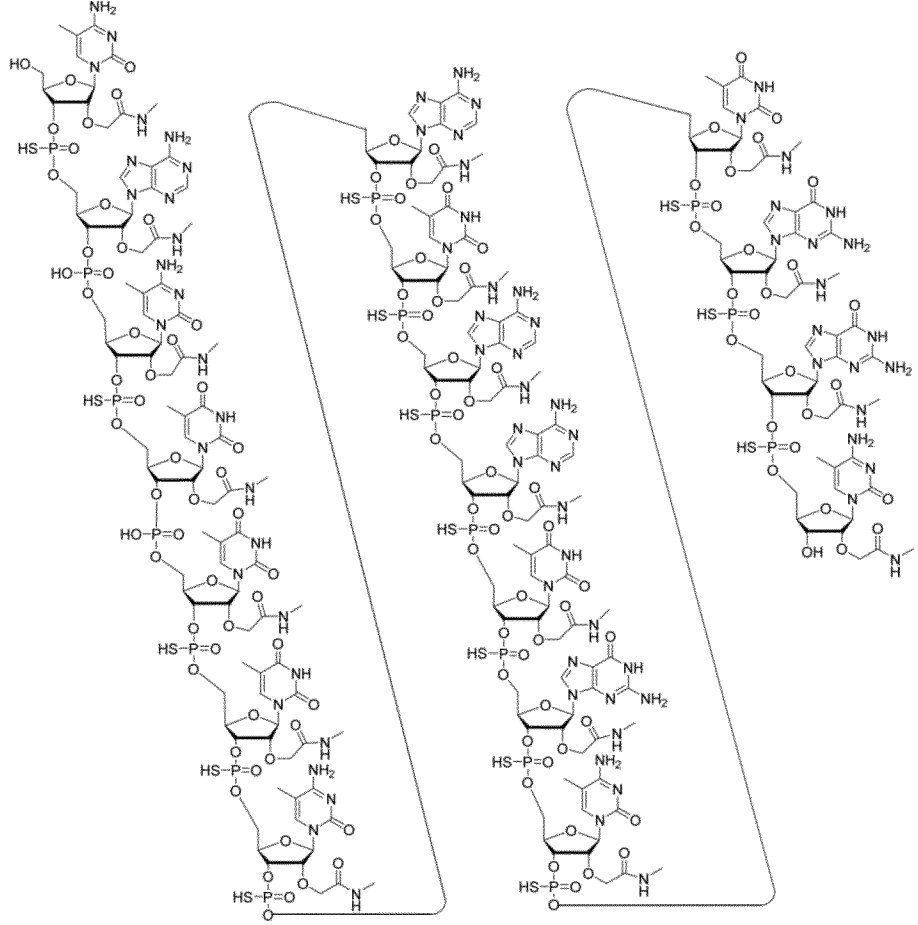

CERTIFICATE OF CORRECTION (continued)

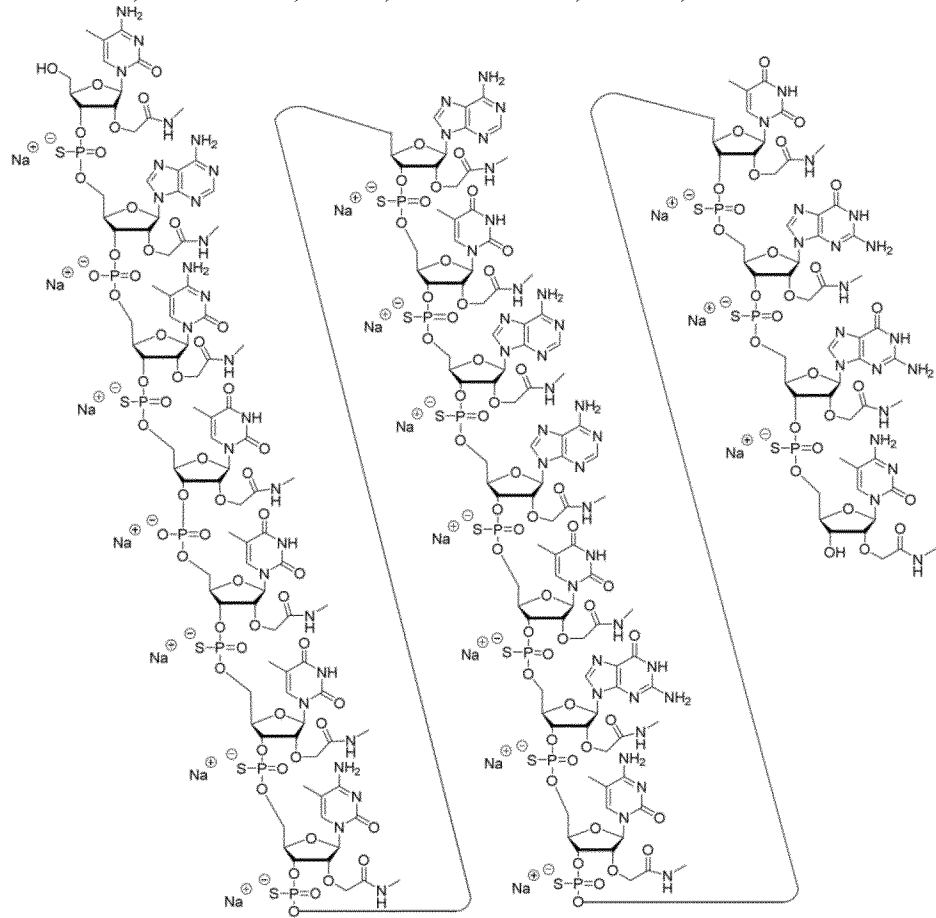

In Claim 3, Column 176, Line 4, to Column 178, Line 29, the structure should read: